(12) United States Patent
Duracher et al.

(10) Patent No.: US 10,463,717 B2
(45) Date of Patent: Nov. 5, 2019

(54) COMPOSITIONS IN THE FORM OF AN INJECTABLE AQUEOUS SOLUTION COMPRISING AMYLIN, AN AMYLIN RECEPTOR AGONIST OR AN AMYLIN ANALOG, AND A CO-POLYAMINO ACID

(71) Applicant: ADOCIA, Lyons (FR)

(72) Inventors: David Duracher, Lyons (FR); Gregory Meiffren, Meyzieu (FR); Remi Soula, Meyzieu (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 15/855,496

(22) Filed: Dec. 27, 2017

(65) Prior Publication Data

US 2018/0193421 A1 Jul. 12, 2018

(30) Foreign Application Priority Data

Dec. 27, 2016 (FR) .................. 16 63438
Dec. 7, 2017 (FR) .................. 17 61806

(51) Int. Cl.

| | |
|---|---|
| *A61K 38/22* | (2006.01) |
| *A61K 47/34* | (2017.01) |
| *A61P 3/10* | (2006.01) |
| *A61K 9/00* | (2006.01) |
| *A61K 38/28* | (2006.01) |
| *A61K 47/18* | (2017.01) |
| *A61K 47/22* | (2006.01) |
| *A61K 9/08* | (2006.01) |

(52) U.S. Cl.
CPC ............ *A61K 38/22* (2013.01); *A61K 9/0019* (2013.01); *A61K 9/08* (2013.01); *A61K 38/28* (2013.01); *A61K 47/183* (2013.01); *A61K 47/22* (2013.01); *A61K 47/34* (2013.01); *A61P 3/10* (2018.01)

(58) Field of Classification Search
CPC ........ A61K 47/34; A61K 9/08; A61K 9/0019; A61K 47/36; A61K 38/28
See application file for complete search history.

(56) References Cited

U.S. PATENT DOCUMENTS

| | | | |
|---|---|---|---|
| 5,124,314 A | 6/1992 | Cooper | |
| 5,234,906 A | 8/1993 | Young et al. | |
| 5,686,411 A | 11/1997 | Gaeta et al. | |
| 6,114,304 A | 9/2000 | Kolterman et al. | |
| 6,410,511 B2 | 6/2002 | L'Italien et al. | |
| 2006/0099264 A1* | 5/2006 | Chan ...................... | A61K 8/678 424/486 |
| 2007/0248686 A1 | 10/2007 | Touraud et al. | |
| 2016/0001002 A1 | 1/2016 | Yodfat et al. | |
| 2016/0074518 A1 | 3/2016 | Soula | |

FOREIGN PATENT DOCUMENTS

| | | |
|---|---|---|
| WO | 2007/104786 A1 | 9/2007 |
| WO | 2013/067022 A1 | 5/2013 |

OTHER PUBLICATIONS

Gerich; "Control of glycaemia;" Bailliere's Clinical Endocrinology and Metabolism; Jul. 1993; pp. 551-586; vol. 7, No. 3.
Schmitz et al.; "Amylin Agonists: A Novel Approach in the Treatment of Diabetes;" Diabetes; Dec. 2004; p. S233-S238; vol. 53, Supplement 3.
Goldsbury et al.; "Polymorphic Fibrillar Assembly of Human Amylin;" Journal of Structural Biology; 1997; pp. 17-27; vol. 119.
Naiki et al; "Fluorometric Determination of Amyloid Fibrils in Vitro Using the Fluorescent Dye, Thioflavine T1;" Analytical Biochemistry; 1989; pp. 244-249; vol. 177.
Levine III; "Quantification of ß-Sheet Amyloid Fibril Structures with Thioflavin T;" Methods in Enzymology; 1999; pp. 274-284; vol. 309.
Lu et al.; "Hexamethyldisilazane-Mediated Controlled Polymerization of α-Amino Acid N-Carboxyanhydrides;" J. Am. Chem. Soc.; 2007; pp. 14114-14115; vol. 129.
Lu et al.; "N-Trimethylsilyl Amines for Controlled Ring-Opening Polymerization of Amino Acid N-Carboxyanhydrides and Facile End Group Functionalization of Polypeptides;" J. Am. Chem. Soc.; 2008; pp. 12562-12563; vol. 130.
Yan et al.; "Design of a mimic of nonamyloidogenic and bioactive human islet amyloid polypeptide (IAPP) as nanomolar affinity inhibitor of IAPP cytotoxic fibrillogenesis;" PNAS; Feb. 14, 2006; pp. 2046-2051; vol. 103, No. 7.
Ruiz et al.; "Effect of Insulin Feedback on Closed-Loop Glucose Control: A Crossover Study;" Journal of Diabetes Science and Technology; Sep. 2012; pp. 1123-1130; vol. 6, No. 5.
Atlas et al; "MD-Logic Artificial Pancreas System; A pilot study in adults with type 1 diabetes;" Diabetes Care; May 2010; pp. 1072-1076; vol. 33, No. 5.
Hovorka et al; "Nonlinear model predictive control of glucose concentration in subjects with type 1 diabetes;" Physiological Measurement; 2004; pp. 905-920; vol. 25.
Jacobs et al.; Automated Control of an Adaptive Bihormonal, Dual-Sensor Artificial Pancreas Evaluation During Inpatient Studies; IEEE Transactions on Biomedical Engineering; Oct. 10, 2014; pp. 2569-2581; vol. 61, No. 10.
Gonzales-Aramundiz et al.; "Polypeptides and polyaminoacids in drug delivery;" Expert Opinion—Drug Delivery; 2012; pp. 183-201; vol. 9, No. 3.

* cited by examiner

*Primary Examiner* — Sudhakar Katakam
(74) *Attorney, Agent, or Firm* — Oliff PLC

(57) ABSTRACT

The invention relates to a composition in the form of an injectable aqueous solution, of which the pH is from 6.0 to 8.0, comprising at least:
  a) amylin, an amylin receptor agonist or an amylin analog;
  b) a co-polyamino acid bearing carboxylate charges and hydrophobic radicals Hy, said co-polyamino acid consisting of glutamic or aspartic units and said hydrophobic radicals Hy having the following formula I:

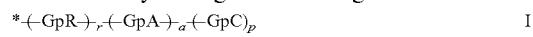

characterized in that the composition does not comprise a basal insulin of which the isoelectric point pI is from 5.8 to 8.5.
It also relates to a composition characterized in that it moreover comprises a prandial insulin.

12 Claims, 2 Drawing Sheets

COMPOSITIONS IN THE FORM OF AN INJECTABLE AQUEOUS SOLUTION COMPRISING AMYLIN, AN AMYLIN RECEPTOR AGONIST OR AN AMYLIN ANALOG, AND A CO-POLYAMINO ACID

The invention relates to therapies by injection of amylin, amylin receptor agonist or amylin analog for treating diabetes.

The invention relates to a composition in the form of an injectable aqueous solution, of which the pH is from 6.0 to 8.0, comprising at least amylin, an amylin receptor agonist or an amylin analog, and a co-polyamino acid bearing carboxylate charges and hydrophobic radicals according to the invention, and to compositions comprising moreover an insulin (excluding basal insulins of which the isoelectric point pI is from 5.8 to 8.5). The invention also relates to pharmaceutical formulations comprising the compositions according to the invention. Finally, the invention also relates to a use of the co-polyamino acids bearing carboxylate charges and hydrophobic radicals according to the invention for stabilizing compositions of amylin, amylin receptor agonist or amylin analog as well as compositions of amylin, amylin receptor agonist or amylin analog comprising moreover an insulin.

Type 1 diabetes is an autoimmune disease which leads to the destruction of the beta cells of the pancreas. These cells are known to produce insulin whose primary function is to regulate the use of glucose in the peripheral tissues (Gerich 1993 Control of glycaemia). Consequently, type 1 diabetes patients suffer from chronic hyperglycemia and have to self-administer exogenous insulin in order to limit this hyperglycemia. Insulin therapy has made it possible to drastically change the life expectancy of these patients. However, the glycemia control ensured by exogenous insulin is not optimal, in particular after the ingestion of a meal. This is connected with the fact that these patients produce glucagon after the ingestion of a meal, which leads to the removal from storage of a portion of the glucose stored in the liver, which is not the case in healthy persons. This glucagon-mediated production of glucose worsens the problem of glycemia regulation in these patients.

It has been demonstrated that amylin, another hormone produced by the beta cells of the pancreas and thus also deficient in type 1 diabetes patients, plays a key role in the regulation of post-prandial glycemia. Amylin, also known under the name of "islet amyloid polypeptide" or IAPP, is a 37 aminoacids peptide which is co-stored and co-secreted with insulin (Schmitz 2004 Amylin Agonists). It is known that this peptide blocks the production of glucagon by the alpha cells of the pancreas. Thus, insulin and amylin have complementary and synergistic functions, since insulin makes it possible to reduce the glucose concentration in the blood, while amylin makes it possible to reduce the entry of endogenous glucose into the blood by inhibiting the production (secretion) of endogenous glucagon.

These problems of post-prandial glycemia regulation are quite similar for type 2 diabetes patients who are treated with insulin to the extent that their disease has led to a very significant loss of their beta cell mass and consequently of their ability to produce insulin and amylin.

Human amylin has properties which are not compatible with the pharmaceutical requirements in terms of solubility and stability (Goldsbury C S et al., Polymorphic fibrillar assembly of human amylin. J Struct Biol 119: 17-27, 1997). Amylin is known to form amyloid fibers which lead to the formation of water-insoluble plaques. Although amylin is the natural hormone, it was necessary to develop an analog in order to solve these solubility problems.

The physico-chemical properties of amylin thus make its use impossible: amylin is stable for only about fifteen minutes at acidic pH and for less than a minute at neutral pH.

The company Amylin developed an amylin analog, pramlintide, in order to remedy the lack of stability of human amylin. This product, which is marketed under the name of Symlin®, was approved in 2005 by the FDA for the treatment of type 1 and type 2 diabetes. It has to be administered by the subcutaneous route three times daily, within the hour preceding the meal, in order to improve the control of post-prandial glycemia. This peptide is formulated at acidic pH and has been described as forming fibrils when the pH of the solution is higher than 5.5. Analog variants are described in U.S. Pat. No. 5,686,411.

This analog is thus not satisfactory with regard to stability when a formulation at neutral pH is considered.

To date, no means exists enabling one to stabilize human amylin in order to make a pharmaceutical product from it. However, it would be advantageous for the patients to have access to the human form of this physiological hormone. It would also be advantageous to be able to formulate an amylin analog or an amylin receptor agonist at neutral pH.

In addition, it would be of interest to be able to mix the amylin, an amylin analog or an amylin receptor agonist in an aqueous solution with a prandial insulin, since these two products are to be administered before the meal. This would additionally mimic the physiology, since these two hormones are co-secreted by the beta cells in response to a meal, in order to improve the control of post-prandial glycemia.

However, taking into account the fact that the solutions of prandial insulins have a pH close to neutrality for reasons having to do with chemical stability, it is not possible to obtain an aqueous solution which meets the pharmaceutical requirements in terms of solubility and stability.

For this reason, the patent application US2016/001002 of the company ROCHE describes a pump containing two separate reservoirs in order to make possible the co-administration of these two hormones using a single medical device. However, this patent does not solve the problem of the mixing of these two hormones in a solution, which would make it possible to administer them with conventional pumps which are already available on the market and which comprise only one reservoir.

The patent application WO2013067022 of the company XERIS provides a solution to the problem of stability of the amylin and the problem of its compatibility with insulin by using an organic solvent instead of water. The absence of water seems to solve the stability problems, but the use of an organic solvent raises safety problems in chronic use for diabetic patients and also problems of compatibility with the usual medical devices, in terms of the tubing, the seals and the plasticizers used.

The patent application WO2007104786 of the company NOVO NORDISK describes a method which makes it possible to stabilize a solution of pramlintide, which is an amylin analog, and of insulin by the addition of a phospholipid derived from glycerophosphoglycerol, in particular dimyristoyl glycerophosphoglycerol (DMPG). But this solution requires the use of large quantities of DMPG, which can pose a local tolerance problem.

To the knowledge of the applicant, no satisfactory means exists which would make it possible to combine a prandial insulin and human amylin, an amylin receptor agonist or an amylin analog in an aqueous solution so as to enable administration using conventional devices.

The acidic formulation pH and the rapid fibril formation impede the obtention of a pharmaceutical formulation at neutral pH based on amylin and pramlintide, but also the combining of amylin or pramlintide with other active pharmaceutical ingredients, in particular peptides or proteins.

The applicant has noted that, surprisingly, the co-polyamino acids according to the invention stabilize compositions of amylin, amylin receptor agonist or amylin analog at a pH from 6 to 8. In fact, compositions comprising amylin, an amylin receptor agonist or an amylin analog in combination with a co-polyamino acid according to the invention have an increased stability over time, which is of great interest for pharmaceutical development.

The applicant also observed that the co-polyamino acids according to the invention moreover make it possible to obtain a composition comprising prandial insulin and amylin, amylin receptor agonist or amylin analog, said composition being clear and having an improved stability with regard to fibril formation.

A conventional method for measuring the stabilities of the proteins or peptides consists in measuring the formation of fibrils with the aid of Thioflavin T, also referred to as ThT. This method makes it possible to measure, under temperature and stirring conditions which enable an acceleration of the phenomenon, the latency time before the formation of fibrils by measuring the increase in fluorescence. The compositions according to the invention have a latency time before the formation of fibrils which is clearly greater than that of amylin, an amylin receptor agonist or an amylin analog at the pH of interest.

The compositions according to the invention have a physical stability, and possibly a chemical stability, which is satisfactory at the desired pH.

In an embodiment, the invention relates to a composition in the form of an injectable aqueous solution, of which the pH is from 6.0 to 8.0, comprising at least:
  a) amylin, an amylin receptor agonist or an amylin analog;
  b) a co-polyamino acid bearing carboxylate charges and hydrophobic radicals Hy, said co-polyamino acid consisting of glutamic or aspartic units and said hydrophobic radicals Hy having the following formula I:

in which
GpR is a radical of formula II or II':

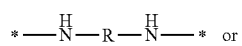

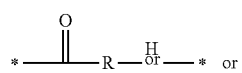

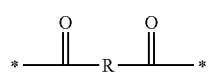

GpA is a radical of formula III or III':

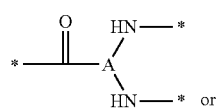

GpC is a radical of formula IV:

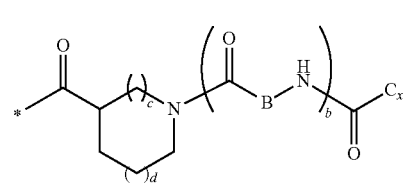

the * indicate the sites of attachment of the different groups;
a is a whole number equal to 0 or to 1;
b is a whole number equal to 0 or to 1;
p is a whole number equal to 1 or 2 and
  if p is equal to 1 then a is equal to 0 or to 1 and GpA is a radical of formula III', and
  if p is equal to 2 then a is equal to 1, and GpA is a radical of formula III;
c is a whole number equal to 0 or to 1, and if c is equal to 0 then d is equal to 1 or to 2;
d is a whole number equal to 0, to 1 or to 2;
r is a whole number equal to 0 or to 1, and
  if r is equal to 0 then the hydrophobic radical of formula I is attached to the co-polyamino acid via a covalent bond between a carbonyl of the hydrophobic radical and a nitrogen atom in N-terminal position of the co-polyamino acid, thus forming an amide function originating from the reaction of an amine function in N-terminal position of the precursor of the co-polyamino acid and an acid function borne by the precursor of the hydrophobic radical, and
  if r is equal to 1 then the hydrophobic radical of formula I is attached to the co-polyamino acid:
    via a covalent bond between a nitrogen atom of the hydrophobic radial and a carbonyl of the copolyamino acid, thus forming an amide function originating from the reaction of an amine function of the precursor of the hydrophobic radical and an acid function borne by the precursor of the co-polyamino acid, or
    via a covalent bond between a carbonyl of the hydrophobic radical and a nitrogen atom in N-terminal position of the co-polyamino acid, thus forming an amide function originating from the reaction of an acid function of the precursor of the hydrophobic radical and an amine function in N-terminal position borne by the precursor of the co-polyamino acid;
R is a radical selected from the group consisting of:
  a linear or branched divalent alkyl radical comprising 2 to 12 carbon atoms if GpR is a radical of formula II or 1 to 11 carbon atoms if GpR is a radical of formula II' or II";
  a linear or branched divalent alkyl radical comprising 2 to 11 carbon atoms if GpR is a radical of formula II or 1 to 11 carbon atoms if GpR is a radical of formula II' or II", 1 to 11 carbon atoms, said alkyl radical bearing one or more —CONH2 functions, and an unsubstituted ether or polyether radical comprising 4 to 14 carbon atoms and 1 to 5 oxygen atoms;

A is a linear or branched alkyl radical comprising 1 to 6 carbon atoms;

B is a linear or branched alkyl radical, optionally comprising an aromatic ring, comprising 1 to 9 carbon atoms;

Cx is a linear or branched monovalent alkyl radical, in which x indicates the number of carbon atoms and:
if p is equal to 1, x is from 11 to 25 ($11 \leq x \leq 25$):
if p is equal to 2, x is from 9 to 15 ($9 \leq x \leq 15$), the ratio i between the number of hydrophobic radicals and the number of glutamic or aspartic units being from 0 to 0.5 ($0 < i \leq 0.5$);

when several hydrophobic radicals are borne by a co-polyamino acid, then they are identical or different, the degree of polymerization DP of glutamic or aspartic units is from 5 to 250;

the free acid functions being in the form of a salt of an alkali cation selected from the group consisting of Na+ and K+;

characterized in that the composition does not comprise a basal insulin of which the isoelectric point pI is from 5.8 to 8.5.

In an embodiment, Hy comprises more than 30 carbon atoms.

In an embodiment, the composition is characterized in that the pH is from 6.6 to 7.8.

In an embodiment, the composition is characterized in that the pH is from 7.0 to 7.8.

In an embodiment, the composition is characterized in that the pH is from 6.8 to 7.4.

In the formulas, the * indicate the sites of attachment of the different elements represented.

In the formulas, the * indicate the sites of attachment of the hydrophobic radicals to the co-polyamino acid. The radicals Hy are attached to the co-polyamino acid via amide functions.

In formulas VII and VIIa, the * indicate the sites of attachment of GpR:
to the co-polyamino acid and
to GpA if a=1 or to GPC if a=0.

In formulas III and III', the * indicate, from left to right respectively, the sites of attachment of GpA:
to GpR if r=1 or to the co-polyamino acid if r=0 and to GpC.

In formula IV, the * indicates the site of attachment of GpC:
to GpA if a=1, GpR if r=1 and a=0 or
to the co-polyamino acid if r=0 and a=0.

All the attachments between the different groups GpR, GpA, GpL, GpG and GpC are amide functions.

The radicals Hy, GpR, GpA, GpL, GpG and GpC, and D are each independently identical or different from one monomeric unit to another.

The compositions in the form of an injectable aqueous solution according to the invention are clear solutions.

"Clear solution" is understood to mean compositions which satisfy the criteria described in the American and European pharmacopoeias concerning injectable solutions. In the American pharmacopoeia, the solutions are defined in part <1151> referring to injection (<1>) (referring to <788> according to USP 35 and specified in <788> according to USP 35 and in <787>, <788> and <790> USP 38 (starting from Aug. 1, 2014), according to USP 38). In the European pharmacopoeia, the injectable solutions have to meet the criteria given in sections 2.9.19 and 2.9.20.

In an embodiment, the composition is characterized in that said hydrophobic radicals are selected from the hydrophobic radicals of formula I in which, if p is equal to 1 (p=1) and if x is less than or equal to 14 ($x \leq 14$), then r=0 or r=1.

In an embodiment, the composition is characterized in that said hydrophobic radicals are selected from the hydrophobic radicals of formula I in which, if p is equal to 1 (p=1) and if x is from 15 to 16 ($15 \leq x \leq 16$), then r=1.

In an embodiment, the composition is characterized in that said hydrophobic radicals are selected from the hydrophobic radicals of formula I in which, if p is equal to 1 (p=1) and if x is greater than 17 ($17 \leq x$), then r=1 and R is an ether or polyether radical.

In an embodiment, the composition is characterized in that said hydrophobic radicals are selected from the hydrophobic radicals of formula I in which, if p is equal to 1 (p=1), then x is from 17 to 25 ($17 \leq x \leq 25$).

In an embodiment, the composition is characterized in that the hydrophobic radicals are selected from the hydrophobic radicals of formula I in which p=1, represented by the following formula V:

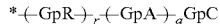  formula V

GpR, GpA, GpC, r and a have the definitions given above.

In an embodiment, the composition is characterized in that the hydrophobic radical is a radical of formula V in which: r is equal to 1 (r=1) and a is equal to 0 (a=0).

In an embodiment, the composition is characterized in that the hydrophobic radical is a radical of formula V in which r is equal to 1 (r=1) and a is equal to 1 (a=1).

In an embodiment, the composition is characterized in that the hydrophobic radical is a radical of formula V in which GpR is a radical of formula II.

In an embodiment, the composition is characterized in that the hydrophobic radical is a radical of formula V in which GpR is a radical of formula II in which R is a divalent linear alkyl radical comprising 2 to 12 carbon atoms.

In an embodiment, the composition is characterized in that the hydrophobic radical is a radical of formula V in which GpR is a radical of formula II in which R is a divalent alkyl radical comprising 2 to 6 carbon atoms.

In an embodiment, the composition is characterized in that the hydrophobic radical is a radical of formula V in which GpR is a radical of formula II in which R is a divalent linear alkyl radical comprising 2 to 6 carbon atoms.

In an embodiment, the composition is characterized in that the hydrophobic radical is a radical of formula V in which GpR is a radical of formula II in which R is a divalent alkyl radical comprising 2 to 4 carbon atoms.

In an embodiment, the composition is characterized in that the hydrophobic radical is a radical of formula V in which GpR is a radical of formula II in which R is a divalent linear alkyl radical comprising 2 to 4 carbon atoms.

In an embodiment, the composition is characterized in that the hydrophobic radical is a radical of formula V in which GpR is a radical of formula II in which R is a divalent alkyl radical comprising 2 carbon atoms.

In an embodiment, the composition is characterized in that the hydrophobic radical is a radical of formula V in which GpR is a radical of formula II'.

In an embodiment, the composition is characterized in that the hydrophobic radical is a radical of formula V in which GpR is a radical of formula II' in which R is a divalent linear alkyl radical comprising 1 to 11 carbon atoms.

In an embodiment, the composition is characterized in that the hydrophobic radical is a radical of formula V in which GpR is a radical of formula II' in which R is a divalent alkyl radical comprising 1 to 6 carbon atoms.

In an embodiment, the composition is characterized in that the hydrophobic radical is a radical of formula V in which GpR is a radical of formula II or II', in which R is a divalent alkyl radical, comprising 2 to 5 carbon atoms and bearing one or more amide functions (—CONH$_2$).

In an embodiment, the composition is characterized in that the hydrophobic radical is a radical of formula V in which GpR is a radical of formula II' or II, in which R is a divalent linear alkyl radical, comprising 2 to 5 carbon atoms and bearing one or more amide functions (—CONH$_2$).

In an embodiment, the composition is characterized in that the hydrophobic radical is a radical of formula V in which GpR is a radical of formula II or II' in which R is a radical selected from the group consisting of the radicals represented by the formulas below:

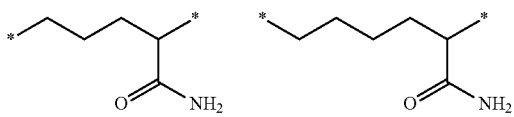

In an embodiment, the composition is characterized in that the radical R is attached to the co-polyamino acid via an amide function borne by the carbon in delta or epsilon position (or in position 4 or 5) with respect to the amide function (—CONH$_2$).

In an embodiment, the composition is characterized in that the hydrophobic radical is a radical of formula V in which GpR is a radical of formula II or II', in which R is an unsubstituted linear ether or polyether radical comprising 4 to 14 carbon atoms and 1 to 5 oxygen atoms.

In an embodiment, the composition is characterized in that the hydrophobic radical is a radical of formula V in which GpR is a radical of formula II or II', in which R is an ether radical.

In an embodiment, the composition is characterized in that the hydrophobic radical is a radical of formula V in which GpR is a radical of formula II or II', in which R is an ether radical comprising 4 to 6 carbon atoms.

In an embodiment, the composition is characterized in that the hydrophobic radical is a radical of formula V in which GpR is a radical of formula II or II' in which R is an ether radical represented by the formula

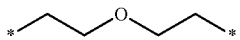

In an embodiment, the composition is characterized in that the hydrophobic radical is a radical of formula V in which GpR is a radical of formula II or II', in which R is a polyether radical.

In an embodiment, the composition is characterized in that the hydrophobic radical is a radical of formula V in which GpR is a radical of formula II or II', in which R is a linear polyether radical comprising 6 to 10 carbon atoms and 2 to 3 oxygen atoms.

In an embodiment, the composition is characterized in that the hydrophobic radical of formula V in which GpR is a radical of formula II or II', in which R is a polyether radical selected from the group consisting of the radicals represented by the formulas below:

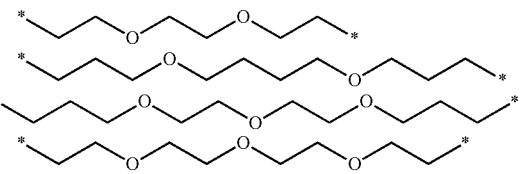

In an embodiment, the composition is characterized in that the hydrophobic radical of formula V in which GpR is a radical of formula II in which R is a polyether radical selected from the group consisting of the radicals represented by the formulas below:

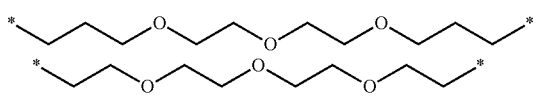

In an embodiment, the composition is characterized in that the hydrophobic radical is a radical of formula V in which a is equal to 0 (a=0) and r is equal to 0 (r=0).

In an embodiment, the composition is characterized in that the hydrophobic radical is a radical of formula V in which a is equal to 1 (a=1) and the radical GpA is a radical of formula III' in which A is selected from the group consisting of the radicals represented by the formulas below:

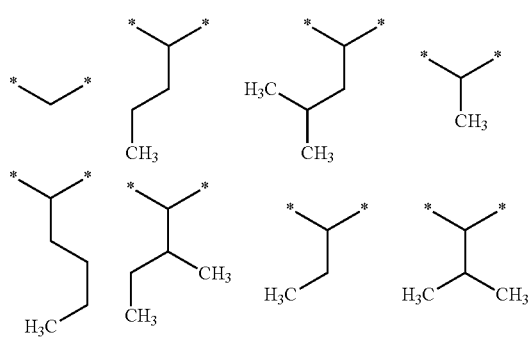

In an embodiment, the composition is characterized in that the hydrophobic radical is a radical of formula V in which the radical GpC of formula IV is selected from the group consisting of the radicals of formula IVa, IVb or IVc represented hereafter:

Formula IVa

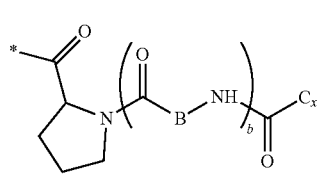

Formula IVb

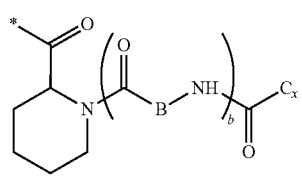

-continued

Formula IVc

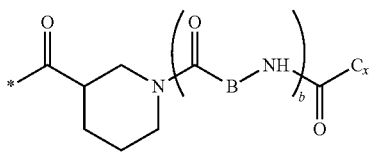

In an embodiment, the composition is characterized in that the hydrophobic radical is a radical of formula V in which the radical GpC is of formula IVa.

In an embodiment, the composition is characterized in that the hydrophobic radical is a radical of formula V in which the radical GpC of formula IV is selected from the group consisting of the radicals of formula IVa, IVb or IVc in which b is equal to 0, corresponding to formulas IVd, IVe and IVf, respectively, represented hereafter:

Formula IVd

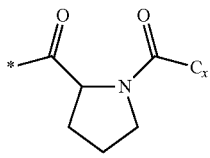

Formula IVe

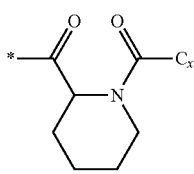

Formula IVf

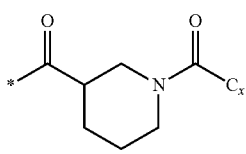

In an embodiment, the composition is characterized in that the hydrophobic radical is a radical of formula V in which the radical GpC corresponds to formula IV or IVa in which b=0 and to formula IVd.

In an embodiment, the composition is characterized in that the hydrophobic radical is a radical of formula V in which the radical GpC of formula IV in which b=1 is selected from the group consisting of the radicals in which B is an amino acid residue selected from the group consisting of the radicals represented by the formulas below:

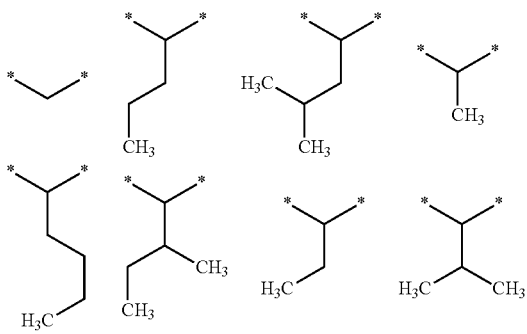

-continued

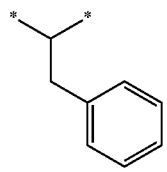

In an embodiment, the composition is characterized in that the hydrophobic radical is a radical of formula V in which the radical GpC of formula IV or IVa in which b=1 is selected from the group consisting of the radicals in which B is an amino acid residue selected from the group consisting of the radicals represented by the formulas below:

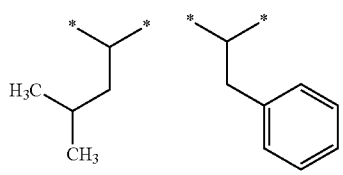

In an embodiment, the composition is characterized in that the hydrophobic radical is a radical of formula V in which the radical GpC of formula IV is selected from the group consisting of the radicals in which Cx is selected from the group consisting of the linear alkyl radicals.

In an embodiment, the composition is characterized in that the hydrophobic radical is a radical of formula V in which the radical GpC of formula IV is selected from the group consisting of the radicals in which Cx is selected from the group consisting of the branched alkyl radicals.

In an embodiment, the composition is characterized in that the hydrophobic radical is a radical of formula V in which the radical GpC of formula IV is selected from the group consisting of the radicals in which Cx is selected from the group consisting of the alkyl radicals comprising from 11 to 14 carbon atoms.

In an embodiment, the composition is characterized in that the hydrophobic radical is a radical of formula V in which the radical GpC of formula IV is selected from the group consisting of the radicals in which Cx is selected from the group consisting of the radicals represented by the formulas below:

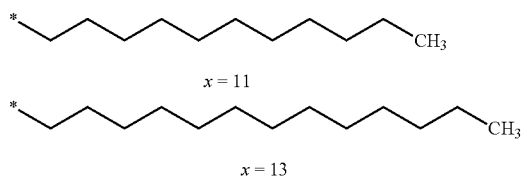

In an embodiment, the composition is characterized in that the hydrophobic radical is a radical of formula V in which the radical GpC of formula IV is selected from the group consisting of the radicals in which Cx is selected from the group consisting of the alkyl radicals comprising from 15 to 16 carbon atoms.

In an embodiment, the composition is characterized in that the hydrophobic radical is a radical of formula V in which the radical GpC of formula IV is selected from the group consisting of the radicals in which Cx is selected from the group consisting of the radicals represented by the formulas below:

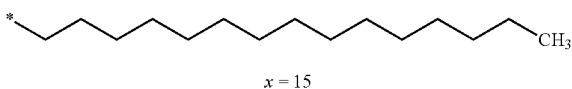

x = 15

In an embodiment, the composition is characterized in that the hydrophobic radical is a radical of formula V in which the radical GpC of formula IV is selected from the group consisting of the radicals in which Cx is selected from the group consisting of the radicals represented by the formulas below:

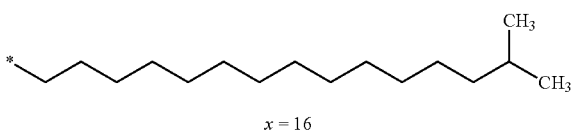

x = 16

In an embodiment, the composition is characterized in that the hydrophobic radical is a radical of formula V in which the radical GpC of formula IV is selected from the group consisting of the radicals in which Cx is selected from the group consisting of the alkyl radicals comprising from 17 to 25 carbon atoms.

In an embodiment, the composition is characterized in that the hydrophobic radical is a radical of formula V in which the radical GpC of formula IV is selected from the group consisting of the radicals in which Cx is selected from the group consisting of the alkyl radicals comprising from 17 to 18 carbon atoms.

In an embodiment, the composition is characterized in that the hydrophobic radical is a radical of formula V in which the radical GpC of formula IV is selected from the group consisting of the radicals in which Cx is selected from the group consisting of the alkyl radicals represented by the formulas below:

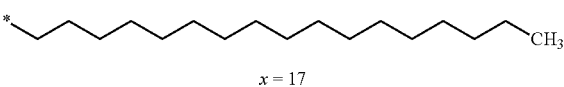

x = 17

In an embodiment, the composition is characterized in that the hydrophobic radical is a radical of formula V in which the radical GpC of formula IV is selected from the group consisting of the radicals in which Cx is selected from the group consisting of the alkyl radicals comprising from 18 to 25 carbon atoms.

In an embodiment, the composition is characterized in that the hydrophobic radical is a radical of formula V in which the radical GpC of formula IV is selected from the group consisting of the radicals in which Cx is selected from the group consisting of the alkyl radicals represented by the formulas below:

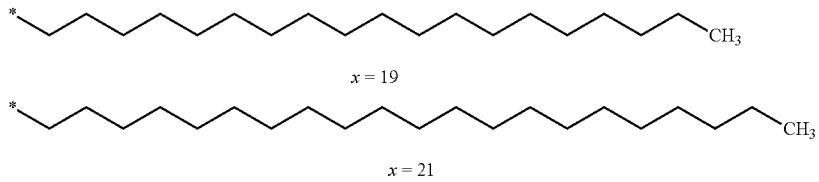

In an embodiment, the composition is characterized in that said hydrophobic radicals are selected from the hydrophobic radicals of formula I in which a=1 and p=2, represented by the following formula VI:

$$*-(GpR)_r-GpA-(GpC)_2 \qquad \text{Formula VI}$$

in which
GpR, GpA, GpC and r have the definitions given above.

In an embodiment, the composition is characterized in that the hydrophobic radical is a radical of formula VI in which GpR is a radical of formula II.

In an embodiment, the composition is characterized in that the hydrophobic radical is a radical of formula VI in which GpR is a radical of formula II in which R is a divalent linear alkyl radical comprising 2 to 12 carbon atoms.

In an embodiment, the composition is characterized in that the hydrophobic radical is a radical of formula VI in which GpR is a radical of formula II in which R is a divalent alkyl radical comprising 2 to 6 carbon atoms.

In an embodiment, the composition is characterized in that the hydrophobic radical is a radical of formula VI in which GpR is a radical of formula II in which R is a divalent linear alkyl radical comprising 2 to 6 carbon atoms.

In an embodiment, the composition is characterized in that the hydrophobic radical is a radical of formula VI in which GpR is a radical of formula II in which R is an alkyl radical comprising 2 to 4 carbon atoms.

In an embodiment, the composition is characterized in that the hydrophobic radical is a radical of formula VI in which GpR is a radical of formula II in which R is a divalent linear alkyl radical comprising 2 to 4 carbon atoms.

In an embodiment, the composition is characterized in that the hydrophobic radical is a radical of formula VI in which GpR is a radical of formula II in which R is a divalent linear alkyl radical comprising 2 carbon atoms.

In an embodiment, the composition is characterized in that the hydrophobic radical is a radical of formula VI in which GpR is a radical of formula II'.

In an embodiment, the composition is characterized in that the hydrophobic radical is a radical of formula VI in which GpR is a radical of formula II' in which R is a divalent linear alkyl radical comprising 1 to 11 carbon atoms.

In an embodiment, the composition is characterized in that the hydrophobic radical is a radical of formula VI in which GpR is a radical of formula II' in which R is a divalent alkyl radical comprising 1 to 6 carbon atoms.

In an embodiment, the composition is characterized in that the hydrophobic radical is a radical of formula VI in which GpR is a radical of formula II or II' in which R is a divalent alkyl radical comprising 2 to 5 carbon atoms and bearing one or more amide functions (—$CONH_2$).

In an embodiment, the composition is characterized in that the hydrophobic radical is a radical of formula VI in which GpR is a radical of formula II or II' in which R is a divalent linear alkyl radical comprising 2 to 5 carbon atoms and bearing one or more amide functions (—$CONH_2$).

In an embodiment, the composition is characterized in that the hydrophobic radical is a radical of formula VI in which GpR is a radical of formula II or II' in which R is a radical selected from the group consisting of the radicals represented by the formulas below:

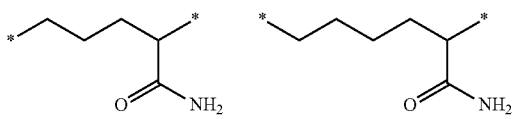

In an embodiment, the composition is characterized in that the hydrophobic radical is a radical of formula VI in which the amine function of the radical GpR involved in the formation of the amide function which binds said radical GpR to the co-polyamino acid is borne by a carbon in delta or epsilon position (or in position 4 or 5) with respect to the amide function (—$CONH_2$).

In an embodiment, the composition is characterized in that the hydrophobic radical is a radical of formula VI in which GpR is a radical of formula II or II', in which R is an unsubstituted linear ether or polyether radical comprising 4 to 14 carbon atoms and 1 to 5 oxygen atoms.

In an embodiment, the composition is characterized in that the hydrophobic radical is a radical of formula VI in which GpR is a radical of formula II or II' in which R is an ether radical.

In an embodiment, the composition is characterized in that the ether radical R is a radical comprising 4 to 6 carbon atoms.

In an embodiment, the composition is characterized in that the ether radical is

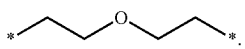

In an embodiment, the composition is characterized in that the hydrophobic radical is a radical of formula VI in which GpR is a radical of formula II or II' in which R is a polyether radical.

In an embodiment, the composition is characterized in that the hydrophobic radical is a radical of formula VI in which GpR is a radical of formula II or II' in which R is a linear polyether radical comprising 6 to 10 carbon atoms and 2 to 3 oxygen atoms.

In an embodiment, the composition is characterized in that the hydrophobic radical is a radical of formula VI in which GpR is a radical of formula II or II' in which R is a linear polyether radical selected from the group consisting of the radicals represented by the formulas below:

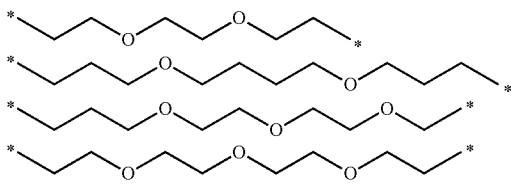

In an embodiment, the composition is characterized in that the hydrophobic radical is a radical of formula VI in which the radical GpA of formula III is selected from the group consisting of the radicals of formulas IIIa and IIIb represented hereafter:

Formula IIIa
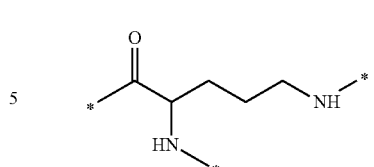

Formula IIIb
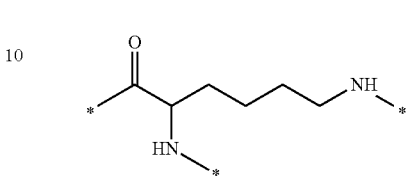

In an embodiment, the composition is characterized in that the hydrophobic radical is a radical of formula VI in which the radical GpA of formula III is a radical of formula IIIb represented hereafter:

Formula IIIb
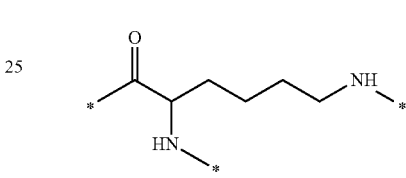

In an embodiment, the composition is characterized in that the hydrophobic radical is a radical of formula VI in which the radical GpC of formula IV is selected from the group consisting of the radicals of formulas IVa, IVb and IVc represented hereafter:

Formula IVa
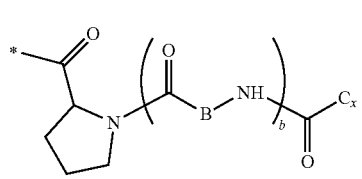

Formula IVb
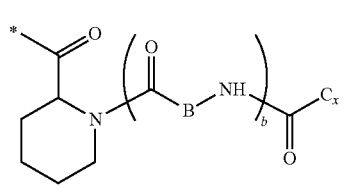

Formula IVc
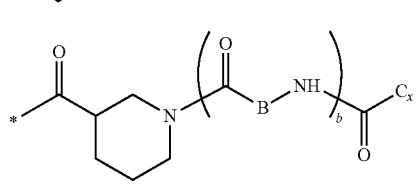

In an embodiment, the composition is characterized in that the hydrophobic radical is a radical of formula VI in which the radical GpC is of formula IVa.

In an embodiment, the composition is characterized in that the hydrophobic radical is a radical of formula VI in which the radical GpC of formula IV is selected from the group consisting of the radicals of formulas IVa, IVb or IVc in which b is equal to 0 (b=0), corresponding to formulas IVd, IVe, and IVf, respectively, represented hereafter:

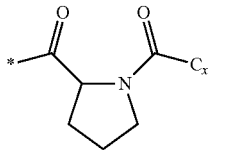

Formula IVd

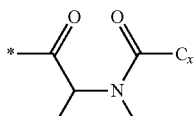

Formula IVe

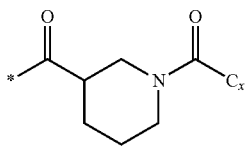

Formula IVf

In an embodiment, the composition is characterized in that the hydrophobic radical is a radical of formula VI in which the radical GpC corresponds to formula IV or IVa in which b=0 and to formula IVd.

In an embodiment, the composition is characterized in that the hydrophobic radical is a radical of formula VI in which the radical GpC of formula IV is selected from the group consisting of the radicals in which Cx is selected from the group consisting of the linear alkyl radicals comprising from 9 to 15 carbon atoms.

In an embodiment, the composition is characterized in that the hydrophobic radical is a radical of formula VI in which the radical GpC of formula IV is selected from the group consisting of the radicals in which Cx is selected from the group consisting of the branched alkyl radicals comprising from 9 to 15 carbon atoms.

In an embodiment, the composition is characterized in that the hydrophobic radical is a radical of formula VI in which the radical GpC of formula IV is selected from the group consisting of the radicals in which Cx is selected from the group consisting of the alkyl radicals comprising 9 or 10 carbon atoms.

In an embodiment, the composition is characterized in that the hydrophobic radical is a radical of formula VI in which the radical GpC of formula IV is selected from the group consisting of the radicals in which Cx is selected from the group consisting of the alkyl radicals comprising from 11 to 15 carbon atoms.

In an embodiment, the composition is characterized in that the hydrophobic radical is a radical of formula VI in which the radical GpC of formula IV is selected from the group consisting of the radicals in which Cx is selected from the group consisting of the alkyl radicals comprising from 11 to 13 carbon atoms.

In an embodiment, the composition is characterized in that the hydrophobic radical is a radical of formula VI in which the radical GpC of formula IV is selected from the group consisting of the radicals in which Cx is selected from the group consisting of the radicals represented by the formulas below:

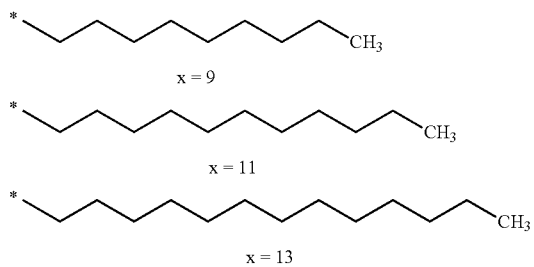

In an embodiment, the composition is characterized in that the hydrophobic radical is a radical of formula VI in which the radical GpC of formula IV is selected from the group consisting of the radicals in which Cx is selected from the group consisting of the alkyl radicals comprising 14 or 15 carbon atoms.

In an embodiment, the composition is characterized in that the hydrophobic radical is a radical of formula VI in which the radical GpC of formula IV is selected from the group consisting of the radicals in which Cx is selected from the group consisting of the radicals represented by the formulas below:

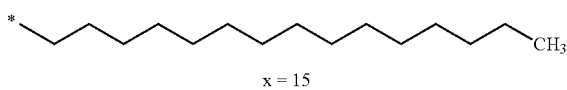

In an embodiment, the composition is characterized in that the co-polyamino acid bearing carboxylate charges and hydrophobic radicals is selected from the co-polyamino acids having the following formula VII:

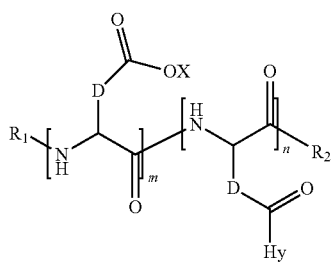

VII in which,
D represents, independently, either a —CH$_2$— group (aspartic unit) or a —CH$_2$—CH$_2$— group (glutamic unit),
Hy is a hydrophobic radical selected from the hydrophobic radicals of formula I, V or VI in which r=1 and GpR is a radical of formula II,
R$_1$ is a hydrophobic radical selected from the hydrophobic radicals of formula I, V or VI in which r=0 or r=1 and GpR is a radical of formula II', or a radical selected from the group consisting of an H, a linear C2 to C10 acyl group, a branched C3 to C10 acyl group, benzyl, a terminal "amino acid" unit, and a pyroglutamate,
R$_2$ is a hydrophobic radical selected from the hydrophobic radicals of formula I, V or VI in which r=1 and GpR is a radical of formula II, or a —NR'R" radical, R' and R", which may be identical or different, being selected from the group consisting of H, the linear or branched or cyclic C2 to C10 alkyls, benzyl, and said alkyls R' and R" optionally forming together one or more saturated, unsaturated and/or aromatic carbon rings and/or optionally comprising heteroatoms selected from the group consisting of O, N and S, X represents an H or a cationic entity selected from the group comprising the metal cations;

n+m represents the degree of polymerization DP of the co-polyamino acid, that is to say the average number of monomeric units per co-polyamino acid chain, and $5 \leq n+m \leq 250$.

The co-polyamino acid bearing carboxylate charges and at least one hydrophobic radical of formula I can also be referred to as "co-polyamino acid" in the present description.

"Statistical co-polyamino acid" refers to a co-polyamino acid bearing carboxylate charges and at least one hydrophobic radical, a co-polyamino acid of formula VIIa.

In an embodiment, the composition is characterized in that the co-polyamino acid bearing carboxylate charges and hydrophobic radicals is selected from the co-polyamino acids of formula VII, in which $R_1=R'_1$ and $R_2=R'_2$, having the following formula VIIa:

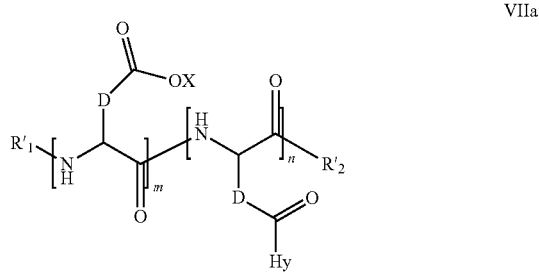

VIIa in which, m, n, X, D and Hy have the definitions given above;

$R'_1$ is a radical selected from the group consisting of an H, a linear C2 to C10 acyl group, a branched C3 to C10 acyl group, benzyl, a terminal "amino acid" unit, and a pyroglutamate;

$R'_2$ is a —NR'R" radical, R' and R", which may be identical or different, being selected from the group consisting of H, the linear or branched or cyclic C2 to C10 alkyls, benzyl, and said alkyls R' and R" optionally forming together one or more saturated, unsaturated and/or aromatic carbon rings and/or optionally comprising heteroatoms selected from the group consisting of O, N and S.

"Defined co-polyamino acid" refers to a co-polyamino acid bearing carboxylate charges and at least one hydrophobic radical, a co-polyamino acid of formula VIIb.

In an embodiment, the composition is characterized in that the co-polyamino acid bearing carboxylate charges and hydrophobic charges is selected from the co-polyamino acids of formula VII in which n=0 having the following formula VIIb:

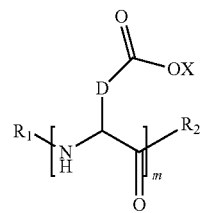

VIIb in which m, X, D, $R_1$ and $R_2$ have the definitions given above and at least $R_1$ or $R_2$ is a hydrophobic radical of formula I, V or VI.

In an embodiment, the composition is characterized in that the co-polyamino acid bearing carboxylate charges and hydrophobic charges is selected from the co-polyamino acids of formula VII in which n=0 of formula VIIb and $R_1$ or $R_2$ is a hydrophobic radical of formula I, V or VI.

In an embodiment, the composition is characterized in that the co-polyamino acid bearing carboxylate charges and hydrophobic radicals is selected from the co-polyamino acids of formula VIIb in which $R_1$ is a hydrophobic radical of formula I, V or VI in which r=0 or r=1 and GpR is of formula II'.

In an embodiment, the composition is characterized in that the co-polyamino acid bearing carboxylate charges and hydrophobic radicals is selected from the co-polyamino acids of formulas VIIb in which $R_2$ is a hydrophobic radical of formula I, V or VI in which r=1 and GpR is of formula II.

In an embodiment, the composition is characterized in that $R_1$ is a radical selected from the group consisting of a linear $C_2$ to $C_{10}$ acyl radical, a branched $C_3$ to $C_{10}$ acyl group, a benzyl, a terminal "amino acid" unit, and a pyroglutamate.

In an embodiment, the composition is characterized in that $R_1$ is a radical selected from the group consisting of a linear $C_2$ to $C_{10}$ acyl group or a branched $C_3$ to $C_{10}$ acyl group.

In an embodiment, the composition is characterized in that the co-polyamino acid bearing carboxylate charges and hydrophobic radicals is selected from the co-polyamino acids of formula VII, VIIa or VIIb in which the group D is a —$CH_2$— group (aspartic unit).

In an embodiment, the composition is characterized in that the co-polyamino acid bearing carboxylate charges and hydrophobic radicals is selected from the co-polyamino acids of formula VII, VIIa or VIIb in which the group D is a —$CH_2$—$CH_2$— group (glutamic unit).

In an embodiment, the composition is characterized in that the ratio i between the number of hydrophobic radicals and the number of glutamic or aspartic acids is from 0.007 to 0.3.

In an embodiment, the composition is characterized in that the ratio i between the number of hydrophobic radicals and the number of glutamic or aspartic acids is from 0.01 to 0.3.

In an embodiment, the composition is characterized in that the ratio i between the number of hydrophobic radicals and the number of glutamic or aspartic acids is from 0.02 to 0.2.

In an embodiment, the composition is characterized in that the hydrophobic radical corresponds to formula VI and the ratio i between the number of hydrophobic radicals and the number of glutamic or aspartic units is from 0.007 to 0.15.

In an embodiment, the composition is characterized in that the hydrophobic radical corresponds to formula VI and the ratio i between the number of hydrophobic radicals and the number of glutamic or aspartic units is from 0.01 to 0.1.

In an embodiment, the composition is characterized in that the hydrophobic radical corresponds to formula VI and the ratio i between the number of hydrophobic radicals and the number of glutamic or aspartic units is from 0.02 to 0.08.

In an embodiment, the composition is characterized in that the hydrophobic radical corresponds to formula VI in which the radical Cx comprises between 9 and 10 carbon atoms and the ratio i between the number of hydrophobic radicals and the number of glutamic or aspartic units is from 0.03 to 0.15.

In an embodiment, the composition is characterized in that the hydrophobic radical corresponds to formula VI in which the radical Cx comprises between 11 and 12 carbon atoms and the ratio i between the number of hydrophobic radicals and the number of glutamic or aspartic units is from 0.015 to 0.1.

In an embodiment, the composition is characterized in that the hydrophobic radical corresponds to formula VI in which the radical Cx comprises from 11 to 12 carbon atoms and the ratio i between the number of hydrophobic radicals and the number of glutamic or aspartic units is from 0.02 to 0.08.

In an embodiment, the composition is characterized in that the hydrophobic radical corresponds to formula VI in which the radical Cx comprises from 13 to 15 carbon atoms and the ratio i between the number of hydrophobic radicals and the number of glutamic or aspartic units is from 0.01 to 0.1.

In an embodiment, the composition is characterized in that the hydrophobic radical corresponds to formula VI in which the radical Cx comprises from 13 to 15 carbon atoms and the ratio i between the number of hydrophobic radicals and the number of glutamic or aspartic units is from 0.01 to 0.06.

In an embodiment, the composition is characterized in that the hydrophobic radical corresponds to formula V and the ratio i between the number of hydrophobic radicals and the number of glutamic or aspartic units is from 0.007 to 0.3.

In an embodiment, the composition is characterized in that the hydrophobic radical corresponds to formula V and the ratio i between the number of hydrophobic radicals and the number of glutamic or aspartic units is from 0.01 to 0.3.

In an embodiment, the composition is characterized in that the hydrophobic radical corresponds to formula V and the ratio i between the number of hydrophobic radicals and the number of glutamic or aspartic units is from 0.015 to 0.2.

In an embodiment, the composition is characterized in that the hydrophobic radical corresponds to formula V in which the radical Cx comprises from 11 to 14 carbon atoms and the ratio i between the number of hydrophobic radicals and the number of glutamic or aspartic units is from 0.1 to 0.2.

In an embodiment, the composition is characterized in that the hydrophobic radical corresponds to formula V in which the radical Cx comprises from 15 to 16 carbon atoms and the ratio i between the number of hydrophobic radicals and the number of glutamic or aspartic units is from 0.04 to 0.15.

In an embodiment, the composition is characterized in that the hydrophobic radical corresponds to formula V in which the radical Cx comprises from 17 to 18 carbon atoms and the ratio i between the number of hydrophobic radicals and the number of glutamic or aspartic units is from 0.02 to 0.06.

In an embodiment, the composition is characterized in that the hydrophobic radical corresponds to formula V in which the radical Cx comprises from 19 to 25 carbon atoms and the ratio i between the number of hydrophobic radicals and the number of glutamic or aspartic units is from 0.01 to 0.06.

In an embodiment, the composition is characterized in that the hydrophobic radical corresponds to formula V in which the radical Cx comprises from 19 to 25 carbon atoms and the ratio i between the number of hydrophobic radicals and the number of glutamic or aspartic units is from 0.01 to 0.05.

In an embodiment, the composition according to the invention is characterized in that n+m is from 10 to 250.

In an embodiment, the composition according to the invention is characterized in that n+m is from 10 to 200.

In an embodiment, the composition according to the invention is characterized in that n+m is from 15 to 150.

In an embodiment, the composition according to the invention is characterized in that n+m is from 15 to 100.

In an embodiment, the composition according to the invention is characterized in that n+m is from 15 to 80.

In an embodiment, the composition according to the invention is characterized in that n+m is from 15 to 65.

In an embodiment, the composition according to the invention is characterized in that n+m is from 20 to 60.

In an embodiment, the composition according to the invention is characterized in that n+m is from 20 to 50.

In an embodiment, the composition according to the invention is characterized in that n+m is from 20 to 40.

The invention also relates to said co-polyamino acids bearing carboxylate charges and hydrophobic radicals of formula I and to the precursors of said hydrophobic radicals.

The co-polyamino acids bearing carboxylate charges and hydrophobic radicals of formula X are soluble in water distilled at a pH from 6 to 8, at a temperature of 25° C. and at a concentration of less than 60 mg/mL.

In an embodiment, the invention also relates to the precursors of said hydrophobic radicals of formula X.

"Soluble" is understood to mean suitable for making it possible to prepare a solution which is clear and free of particles at a concentration of less than 100 mg/mL in distilled water at 25° C.

"Solution" is understood to mean a liquid solution which is free of visible particles, using the method according to the European pharmacopoeia 8.0, in point 2.9.20, and the American pharmacopoeia.

"Physically stable composition" is understood to mean compositions which, after a certain storage time at a certain temperature satisfy the criteria of the visual inspection described in the European pharmacopoeia, the American pharmacopoeia and the international pharmacopoeia, that is to say compositions which are clear and which contain no visible particles, but also colorless.

"Chemically stable composition" is understood to mean compositions which, after storage for a certain time and at a certain temperature, have a minimum recovery of the active principles and which comply with the specifications applicable to the pharmaceutical products.

"Injectable aqueous solution" is understood to mean water-based solution which meet the conditions of the European and American pharmacopoeias and which are sufficiently liquid to be injected.

"Co-polyamino acid consisting of glutamic or aspartic units" is understood to mean non-cyclic linear chains of glutamic acid or aspartic acid units bound to one another by peptide bonds, said chains having a C-terminal portion corresponding to the carboxylic acid at one end, and an N-terminal portion corresponding to the amine at the other end of the chain.

"Alkyl radical" is understood to mean a linear or branched carbon chain which comprises no heteroatom.

The co-polyamino acid is a statistical or block co-polyamino acid.

The co-polyamino acid is a statistical co-polyamino acid in the chain of the glutamic and/or aspartic units.

In the formulas, the * indicate the sites of attachments of the different elements represented.

In an embodiment, the composition according to the invention is characterized in that the co-polyamino acid originates from a polyamino acid obtained by polymerization.

In an embodiment, the composition according to the invention is characterized in that the co-polyamino acid originates from a polyamino acid obtained by polymerization by ring opening of a derivative of glutamic acid N-carboxyanhydride or of a derivative of aspartic acid N-carboxyanhydride.

In an embodiment, the composition according to the invention is characterized in that the co-polyamino acid originates from a polyamino acid obtained by polymerization of a derivative of glutamic acid N-carboxyanhydride or of a derivative of aspartic acid N-carboxyanhydride as described in the article Deming, T. J., Adv. Polym. Sci. 2006, 202, 1-18.

In an embodiment, the composition according to the invention is characterized in that the co-polyamino acid originates from a polyamino acid obtained by polymerization of a derivative of glutamic acid N-carboxyanhydride.

In an embodiment, the composition according to the invention is characterized in that the co-polyamino acid originates from a polyamino acid obtained by polymerization of a derivative of glutamic acid N-carboxyanhydride selected from the group consisting of methyl poly-glutamate N-carboxyanhydride (GluOMe-NCA), benzyl poly-glutamate N-carboxyanhydride (GluOBzl-NCA) and t-butyl poly-glutamate N-carboxyanhydride (GluOtBu-NCA).

In an embodiment, the derivative of glutamic acid N-carboxyanhydride is methyl poly-L-glutamate methyl poly-glutamate N-carboxyanhydride (L-GluOMe-NCA).

In an embodiment, the derivative of glutamic acid N-carboxyanhydride is benzyl poly-L-glutamate N-carboxyanhydride (L-GluOBzl-NCA).

In an embodiment, the composition according to the invention is characterized in that the co-polyamino acid originates from a polyamino acid obtained by polymerization of a derivative of glutamic acid N-carboxyanhydride or of a derivative of aspartic acid N-carboxyanhydride using as initiator an organometallic complex of a transition metal as described in the publication Deming, T. J., Nature 1997, 390, 386-389.

In an embodiment, the composition according to the invention is characterized in that the co-polyamino acid originates from a polyamino acid obtained by polymerization of a glutamic acid N-carboxyanhydride or of a derivative of aspartic acid N-carboxyanhydride using as initiator ammonia or a primary amine as described in the patent FR 2,801,226 and the references cited by this patent.

In an embodiment, the composition according to the invention is characterized in that the co-polyamino acid originates from a polyamino acid obtained by polymerization of a derivative of glutamic acid N-carboxyanhydride or of a derivative of aspartic acid N-carboxyanhydride using as initiator hexamethyldisilazane as described in the publication Lu H.; et al., J. Am. Chem. Soc. 2007, 129, 14114-14115 or a silylated amine as described in the publication Lu H.; et al., J. Am. Chem. Soc. 2008, 130, 12562-12563.

In an embodiment, the composition according to the invention is characterized in that the synthesis method of the polyamino acid obtained by polymerization of a derivative of glutamic acid N-carboxyanhydride or of a derivative of aspartic acid N-carboxyanhydride from which the co-polyamino acid originates comprises a step of hydrolysis of ester functions.

In an embodiment, this step of hydrolysis of ester functions can consist of a hydrolysis in an acidic medium or of a hydrolysis in a basic medium or it can be carried out by hydrogenation.

In an embodiment, this step of hydrolysis of ester groups is a hydrolysis in an acidic medium.

In an embodiment, this step of hydrolysis of ester groups is carried out by hydrogenation.

In an embodiment, the composition according to the invention is characterized in that the co-polyamino acid originates from a polyamino acid obtained by depolymerization of a polyamino acid of higher molecular weight.

In an embodiment, the composition according to the invention is characterized in that the co-polyamino acid originates from a polyamino acid obtained by enzymatic depolymerization of a polyamino acid of higher molecular weight.

In an embodiment, the composition according to the invention is characterized in that the co-polyamino acid originates from a polyamino acid obtained by chemical depolymerization of a polyamino acid of higher molecular weight.

In an embodiment, the composition according to the invention is characterized in that the co-polyamino acid originates from a polyamino acid obtained by enzymatic and chemical depolymerization of a polyamino acid of higher molecular weight.

In an embodiment, the composition according to the invention is characterized in that the co-polyamino acid originates from a polyamino acid obtained by depolymerization of a polyamino acid of higher molecular weight selected from the group consisting of sodium polyglutamate and sodium polyaspartate.

In an embodiment, the composition according to the invention is characterized in that the co-polyamino acid originates from a polyamino acid obtained by depolymerization of a sodium polyglutamate of higher molecular weight.

In an embodiment, the composition according to the invention is characterized in that the co-polyamino acid originates from a polyamino acid obtained by depolymerization of a sodium polyaspartate of higher molecular weight.

In an embodiment, the composition according to the invention is characterized in that the co-polyamino acid is obtained by grafting a hydrophobic group onto a poly-L-glutamic acid or poly-L-aspartic acid using the methods of amide bond formation which are well known to the person skilled in the art.

In an embodiment, the composition according to the invention is characterized in that the co-polyamino acid is obtained by grafting a hydrophobic group onto a poly-L- glutamic acid or poly-L-aspartic acid using the methods of amide bond formation used for peptide synthesis.

In an embodiment, the composition according to the invention is characterized in that the co-polyamino acid is obtained by grafting a hydrophobic group onto a poly-L-glutamic acid or poly-L-aspartic acid as described in the patent FR 2,840,614.

Amylin, or "islet amyloid polypeptide" (IAPP), is a 37-residue peptide hormone. It is co-secreted with insulin from the pancreatic beta cells in the ratio of approximately 100/1. Amylin plays a role in glycemic regulation by stopping the secretion of endogenous glucagon and by slowing the gastric emptying and by promoting satiety, thus reducing the post-prandial glycemic excursions of the blood glucose levels.

The IAPP is treated starting with an 89-residue coding sequence. The amyloid polypeptide pro-islet (proIAPP, proamylin, proislet protein) is produced in the pancreatic beta cells (beta cells) in the form of a 67-amino acid pro-peptide, 7404 dalton and it undergoes post-translational modifications comprising the protease cleavage to produce the amylin.

In the present application, the amylin as mentioned refers to the compounds described in U.S. Pat. Nos. 5,124,314 and 5,234,906.

"Analog", when the term is used to refer to a peptide or a protein, is understood to mean a peptide or a protein in which one or more constitutive amino acid residues of the primary sequence have been replaced by other amino acid residues and/or in which one or more constitutive amino acid residues have been eliminated and/or in which one or more constitutive amino acid residues have been added. The percentage of homology allowed for the present definition of an analog is 50%. In the case of amylin, an analog can be derived, for example, from the primary amino acid sequence of amylin by replacing one or more natural or nonnatural or peptidomimetic amino acids.

"Derivative", when the term is used to refer to a peptide or a protein, is understood to mean a peptide or a protein or an analog chemically modified by a substituent which is not present in the reference peptide or protein or analog, that is to say a peptide or a protein which has been modified by the creation of covalent bonds, in order to introduce substituents of non-amino acid type.

An agonist of the amylin receptor refers to a compound which imitates one or more characteristics of the activity of amylin.

Amylin derivatives are described in the article Yan et al., PNAS, vol. 103, no. 7, p. 2046-2051, 2006.

In an embodiment, the substituent is selected from the group consisting of fatty chains.

Amylin analogs are described in U.S. Pat. No. 5,686,411, 6,114,304 or 6,410,511.

In an embodiment, the composition is characterized in that the amylin analog is pramlintide (Symlin) marketed by the company ASTRAZENECA AB.

In an embodiment, the molar ratios co-polyamino acid/amylin, amylin receptor agonist or amylin analog are from 1.5 to 75.

In an embodiment, the molar ratios co-polyamino acid/amylin, amylin receptor agonist or amylin analog are from 1.8 to 50.

In an embodiment, the molar ratios co-polyamino acid/amylin, amylin receptor agonist or amylin analog are from 2 to 35.

In an embodiment, the molar ratios co-polyamino acid/amylin, amylin receptor agonist or amylin analog are from 2.5 to 30.

In an embodiment, the molar ratios co-polyamino acid/amylin, amylin receptor agonist or amylin analog are from 3 to 30.

In an embodiment, the molar ratios co-polyamino acid/amylin, amylin receptor agonist or amylin analog are from 3.5 to 30.

In an embodiment, the molar ratios co-polyamino acid/amylin, amylin receptor agonist or amylin analog are from 4 to 30.

In an embodiment, the molar ratios co-polyamino acid/amylin, amylin receptor agonist or amylin analog are from 5 to 30.

In an embodiment, the molar ratios co-polyamino acid/amylin, amylin receptor agonist or amylin analog are from 7 to 30.

In an embodiment, the molar ratios co-polyamino acid/amylin, amylin receptor agonist or amylin analog are from 9 to 30.

In an embodiment, the molar ratios co-polyamino acid/amylin are from 3 to 75.

In an embodiment, the molar ratios co-polyamino acid/amylin are from 7 to 50.

In an embodiment, the molar ratios co-polyamino acid/amylin are from 10 to 30.

In an embodiment, the molar ratios co-polyamino acid/amylin are from 15 to 30.

In an embodiment, the molar ratios co-polyamino acid/amylin are from 1.5 to 75.

In an embodiment, the molar ratios co-polyamino acid/amylin are from 2 to 50.

In an embodiment, the molar ratios co-polyamino acid/amylin are from 3 to 30.

In an embodiment, the molar ratios co-polyamino acid/amylin are from 4 to 30.

In an embodiment, the molar ratios co-polyamino acid/amylin are from 5 to 30.

In an embodiment, the molar ratios co-polyamino acid/amylin are from 8 to 30.

In an embodiment, the molar ratios co-polyamino acid/amylin are from 10 to 30.

In an embodiment, the molar ratios hydrophobic radical Hy/amylin, amylin receptor agonist or amylin analog are from 1.5 to 150.

In an embodiment, the molar ratios hydrophobic radical Hy/amylin, amylin receptor agonist or amylin analog are from 1.8 to 100.

In an embodiment, the molar ratios hydrophobic radical Hy/amylin, amylin receptor agonist or amylin analog are from 2 to 70.

In an embodiment, the molar ratios hydrophobic radical Hy/amylin, amylin receptor agonist or amylin analog are from 2.5 to 60.

In an embodiment, the molar ratios hydrophobic radical Hy/amylin, amylin receptor agonist or amylin analog are from 3 to 60.

In an embodiment, the molar ratios hydrophobic radical Hy/amylin, amylin receptor agonist or amylin analog are from 3.5 to 60.

In an embodiment, the molar ratios hydrophobic radical Hy/amylin, amylin receptor agonist or amylin analog are from 4 to 60.

In an embodiment, the molar ratios hydrophobic radical Hy/amylin, amylin receptor agonist or amylin analog are from 5 to 60.

In an embodiment, the molar ratios hydrophobic radical Hy/amylin, amylin receptor agonist or amylin analog are from 7 to 60.

In an embodiment, the molar ratios hydrophobic radical Hy/amylin, amylin receptor agonist or amylin analog are from 9 to 60.

In an embodiment, the molar ratios hydrophobic radical Hy/amylin are from 5 to 60.

In an embodiment, the molar ratios hydrophobic radical Hy/amylin are from 10 to 60.

In an embodiment, the molar ratios hydrophobic radical Hy/amylin are from 15 to 60.

In an embodiment, the molar ratios hydrophobic radical Hy/amylin are from 1.5 to 60.

In an embodiment, the molar ratios hydrophobic radical Hy/amylin are from 2 to 60.

In an embodiment, the molar ratios hydrophobic radical Hy/amylin are from 3 to 60.

In an embodiment, the molar ratios hydrophobic radical Hy/amylin are from 4 to 60.

In an embodiment, the molar ratios hydrophobic radical Hy/amylin are from 5 to 60.

In an embodiment, the molar ratios hydrophobic radical Hy/amylin are from 8 to 60.

In an embodiment, the molar ratios hydrophobic radical Hy/amylin are from 10 to 60.

In an embodiment, the weight ratios co-polyamino acid/amylin, amylin receptor agonist or amylin analog are from 1.0 to 70.

In an embodiment, the weight ratios co-polyamino acid/amylin, amylin receptor agonist or amylin analog are from 1.2 to 45.

In an embodiment, the weight ratios co-polyamino acid/amylin, amylin receptor agonist or amylin analog are from 1.3 to 30.

In an embodiment, the weight ratios co-polyamino acid/amylin, amylin receptor agonist or amylin analog are from 1.7 to 27.

In an embodiment, the weight ratios co-polyamino acid/amylin, amylin receptor agonist or amylin analog are from 2.0 to 27.

In an embodiment, the weight ratios co-polyamino acid/amylin, amylin receptor agonist or amylin analog are from 2.3 to 27.

In an embodiment, the weight ratios co-polyamino acid/amylin, amylin receptor agonist or amylin analog are from 2.7 to 27.

In an embodiment, the weight ratios co-polyamino acid/amylin, amylin receptor agonist or amylin analog are from 3.3 to 27.

In an embodiment, the weight ratios co-polyamino acid/amylin, amylin receptor agonist or amylin analog are from 4.7 to 27.

In an embodiment, the weight ratios co-polyamino acid/amylin, amylin receptor agonist or amylin analog are from 6.0 to 27.

In an embodiment, the weight ratios co-polyamino acid/amylin are from 2.0 to 67.

In an embodiment, the weight ratios co-polyamino acid/amylin are from 4.7 to 27.

In an embodiment, the weight ratios co-polyamino acid/amylin are from 6.7 to 27.

In an embodiment, the weight ratios co-polyamino acid/amylin are from 10 to 27.

In an embodiment, the weight ratios co-polyamino acid/amylin are from 1.0 to 67.

In an embodiment, the weight ratios co-polyamino acid/amylin are from 1.3 to 45.

In an embodiment, the weight ratios co-polyamino acid/amylin are from 2.7 to 27.

In an embodiment, the weight ratios co-polyamino acid/amylin are from 3.3 to 27.

In an embodiment, the weight ratios co-polyamino acid/amylin are from 5.3 to 27.

In an embodiment, the weight ratios co-polyamino acid/amylin are from 6.7 to 27.

In an embodiment, the composition is characterized in that it moreover includes insulin.

In an embodiment, the composition is characterized in that the insulin is a prandial insulin. The prandial insulins are soluble at pH 7.

Prandial insulin is understood to mean a so-called rapid or "regular" insulin.

The so-called rapid prandial insulins are insulins which have to meet the needs caused by the ingestion of proteins and carbohydrates during a meal; they have to act within less than 30 minutes.

In an embodiment, the so-called "regular" prandial insulin is human insulin.

In an embodiment, the prandial insulin is a recombinant human insulin as described in the European pharmacopoeia and the American pharmacopoeia.

The human insulin is marketed, for example, under the trade names Humulin® (ELI LILLY) and Novolin® (NOVO NORDISK).

The so-called rapid (fast acting) prandial insulins are insulins which are obtained by recombination and whose primary sequence has been modified to decrease their action time.

In an embodiment, the so-called rapid (fast acting) prandial insulins are selected from the group comprising insulin lispro (Humalog®), insulin glulisine (Apidra®) and insulin aspart (NovoLog®).

In an embodiment, the prandial insulin is insulin lispro.

In an embodiment, the prandial insulin is insulin glulisine.

In an embodiment, the prandial insulin is insulin aspart.

The units recommended by the pharmacopoeias for the insulins are presented in table 51 below with their equivalents in mg:

TABLE 51

| | Units recommended by the pharmacopoeias for the insulins | |
|---|---|---|
| Insulin | EP Pharmacopoeia 8.0 (2014) | US Pharmacopoeia - USP38 (2015) |
| Aspart | 1 U = 0.0350 mg of insulin aspart | 1 USP = 0.0350 mg of insulin aspart |
| Lispro | 1 U = 0.0347 mg of insulin lispro | 1 USP = 0.0347 mg of insulin lispro |
| Human | 1 IU = 0.0347 mg of human insulin | 1 USP = 0.0347 mg of human insulin |

In the case of the insulin glulisine, 100 U=3.49 mg of insulin glulisine (according to "Annex 1—Summary of product characteristics" pertaining to Adipra®).

Nevertheless, in the remainder of the text, U is routinely used equally for the quantities and the concentrations of all the insulins. The corresponding respective values in mg are the values given above for values expressed in U, IU or USP.

In an embodiment, it relates to a pharmaceutical formulation characterized in that the concentration of insulin is from 240 to 3000 µM (40 to 500 U/mL).

In an embodiment, it relates to a pharmaceutical formulation characterized in that the concentration of insulin is from 600 to 3000 μM (100 to 500 U/mL).

In an embodiment, it relates to a pharmaceutical formulation characterized in that the concentration of insulin is from 600 to 2400 μM (100 to 400 U/mL).

In an embodiment, it relates to a pharmaceutical formulation characterized in that the concentration of insulin is from 600 to 1800 μM (100 to 300 U/mL).

In an embodiment, it relates to a pharmaceutical formulation characterized in that the concentration of insulin is from 600 to 1200 μM (100 to 200 U/mL).

In an embodiment, it relates to a pharmaceutical formulation characterized in that the concentration of insulin is 600 μM (100 U/mL).

In an embodiment, it relates to a pharmaceutical formulation characterized in that the concentration of insulin is 1200 μM (200 U/mL).

In an embodiment, it relates to a pharmaceutical formulation characterized in that the concentration of insulin is 1800 μM (300 U/mL).

In an embodiment, it relates to a pharmaceutical formulation characterized in that the concentration of insulin is 2400 μM (400 U/mL).

In an embodiment, it relates to a pharmaceutical formulation characterized in that the concentration of insulin is 3000 μM (500 U/mL).

In an embodiment comprising prandial insulin, the molar ratios co-polyamino acid/amylin, amylin receptor agonist or amylin analog are from 1.5 to 75.

In an embodiment comprising prandial insulin, the molar ratios co-polyamino acid/amylin, amylin receptor agonist or amylin analog are from 1.8 to 50.

In an embodiment comprising prandial insulin, the molar ratios co-polyamino acid/amylin, amylin receptor agonist or amylin analog are from 2 to 35.

In an embodiment comprising prandial insulin, the molar ratios co-polyamino acid/amylin, amylin receptor agonist or amylin analog are from 2.5 to 30.

In an embodiment comprising prandial insulin, the molar ratios co-polyamino acid/amylin, amylin receptor agonist or amylin analog are from 3 to 30.

In an embodiment comprising prandial insulin, the molar ratios co-polyamino acid/amylin, amylin receptor agonist or amylin analog are from 3.5 to 30.

In an embodiment comprising prandial insulin, the molar ratios co-polyamino acid/amylin, amylin receptor agonist or amylin analog are from 4 to 30.

In an embodiment comprising prandial insulin, the molar ratios co-polyamino acid/amylin, amylin receptor agonist or amylin analog are from 5 to 30.

In an embodiment comprising prandial insulin, the molar ratios co-polyamino acid/amylin, amylin receptor agonist or amylin analog are from 7 to 30.

In an embodiment comprising prandial insulin, the molar ratios co-polyamino acid/amylin, amylin receptor agonist or amylin analog are from 9 to 30.

In an embodiment comprising prandial insulin, the molar ratios co-polyamino acid/amylin are from 5 to 75.

In an embodiment comprising prandial insulin, the molar ratios co-polyamino acid/amylin are from 10 to 50.

In an embodiment comprising prandial insulin, the molar ratios co-polyamino acid/amylin are from 15 to 30.

In an embodiment comprising prandial insulin, the molar ratios co-polyamino acid/pramlintide are from 1.5 to 75.

In an embodiment comprising prandial insulin, the molar ratios co-polyamino acid/pramlintide are from 2 to 50.

In an embodiment comprising prandial insulin, the molar ratios co-polyamino acid/pramlintide are from 3 to 30.

In an embodiment comprising prandial insulin, the molar ratios co-polyamino acid/pramlintide are from 4 to 30.

In an embodiment comprising prandial insulin, the molar ratios co-polyamino acid/pramlintide are from 5 to 30.

In an embodiment comprising prandial insulin, the molar ratios co-polyamino acid/pramlintide are from 8 to 30.

In an embodiment comprising prandial insulin, the molar ratios co-polyamino acid/pramlintide are from 10 to 30.

In an embodiment comprising prandial insulin, the molar ratios hydrophobic radical Hy/amylin, amylin receptor agonist or amylin analog are from 1.5 to 150.

In an embodiment comprising prandial insulin, the molar ratios hydrophobic radical Hy/amylin, amylin receptor agonist or amylin analog are from 1.8 to 100.

In an embodiment comprising prandial insulin, the molar ratios hydrophobic radical Hy/amylin, amylin receptor agonist or amylin analog are from 2 to 70.

In an embodiment comprising prandial insulin, the molar ratios hydrophobic radical Hy/amylin, amylin receptor agonist or amylin analog are from 2.5 to 60.

In an embodiment comprising prandial insulin, the molar ratios hydrophobic radical Hy/amylin, amylin receptor agonist or amylin analog are from 3 to 60.

In an embodiment comprising prandial insulin, the molar ratios hydrophobic radical Hy/amylin, amylin receptor agonist or amylin analog are from 3.5 to 60.

In an embodiment comprising prandial insulin, the molar ratios hydrophobic radical Hy/amylin, amylin receptor agonist or amylin analog are from 4 to 60.

In an embodiment comprising prandial insulin, the molar ratios hydrophobic radical Hy/amylin, amylin receptor agonist or amylin analog are from 5 to 60.

In an embodiment comprising prandial insulin, the molar ratios hydrophobic radical Hy/amylin, amylin receptor agonist or amylin analog are from 7 to 60.

In an embodiment comprising prandial insulin, the molar ratios hydrophobic radical Hy/amylin, amylin receptor agonist or amylin analog are from 9 to 60.

In an embodiment comprising prandial insulin, the molar ratios hydrophobic radical Hy/amylin are from 5 to 60.

In an embodiment comprising prandial insulin, the molar ratios hydrophobic radical Hy/amylin are from 10 to 60.

In an embodiment comprising prandial insulin, the molar ratios hydrophobic radical Hy/amylin are from 15 to 60.

In an embodiment comprising prandial insulin, the molar ratios hydrophobic radical Hy/pramlintide are from 1.5 to 60.

In an embodiment comprising prandial insulin, the molar ratios hydrophobic radical Hy/pramlintide are from 2 to 60.

In an embodiment comprising prandial insulin, the molar ratios hydrophobic radical Hy/pramlintide are from 3 to 60.

In an embodiment comprising prandial insulin, the molar ratios hydrophobic radical Hy/pramlintide are from 4 to 60.

In an embodiment comprising prandial insulin, the molar ratios hydrophobic radical Hy/pramlintide are from 5 to 60.

In an embodiment comprising prandial insulin, the molar ratios hydrophobic radical Hy/pramlintide are from 8 to 60.

In an embodiment comprising prandial insulin, the molar ratios hydrophobic radical Hy/pramlintide are from 10 to 60.

In an embodiment comprising prandial insulin, the weight ratios co-polyamino acid/amylin, amylin receptor agonist or amylin analog are from 1.0 to 70.

In an embodiment comprising prandial insulin, the weight ratios co-polyamino acid/amylin, amylin receptor agonist or amylin analog are from 1.2 to 45.

In an embodiment comprising prandial insulin, the weight ratios co-polyamino acid/amylin, amylin receptor agonist or amylin analog are from 1.3 to 30.

In an embodiment comprising prandial insulin, the weight ratios co-polyamino acid/amylin, amylin receptor agonist or amylin analog are from 1.7 to 27.

In an embodiment comprising prandial insulin, the weight ratios co-polyamino acid/amylin, amylin receptor agonist or amylin analog are from 2.0 to 27.

In an embodiment comprising prandial insulin, the weight ratios co-polyamino acid/amylin, amylin receptor agonist or amylin analog are from 2.3 to 27.

In an embodiment comprising prandial insulin, the weight ratios co-polyamino acid/amylin, amylin receptor agonist or amylin analog are from 2.7 to 27.

In an embodiment comprising prandial insulin, the weight ratios co-polyamino acid/amylin, amylin receptor agonist or amylin analog are from 3.3 to 27.

In an embodiment comprising prandial insulin, the weight ratios co-polyamino acid/amylin, amylin receptor agonist or amylin analog are from 4.7 to 27.

In an embodiment comprising prandial insulin, the weight ratios co-polyamino acid/amylin, amylin receptor agonist or amylin analog are from 6.0 to 27.

In an embodiment comprising prandial insulin, the weight ratios co-polyamino acid/amylin are from 3.3 to 67.

In an embodiment comprising prandial insulin, the weight ratios co-polyamino acid/amylin are from 6.6 to 27.

In an embodiment comprising prandial insulin, the weight ratios co-polyamino acid/amylin are from 10 to 27.

In an embodiment comprising prandial insulin, the weight ratios co-polyamino acid/pramlintide are from 1.0 to 67.

In an embodiment comprising prandial insulin, the weight ratios co-polyamino acid/pramlintide are from 1.2 to 45.

In an embodiment comprising prandial insulin, the weight ratios co-polyamino acid/pramlintide are from 1.3 to 27.

In an embodiment comprising prandial insulin, the weight ratios co-polyamino acid/pramlintide are from 1.7 to 27.

In an embodiment comprising prandial insulin, the weight ratios co-polyamino acid/pramlintide are from 2.0 to 27.

In an embodiment comprising prandial insulin, the weight ratios co-polyamino acid/pramlintide are from 2.3 to 27.

In an embodiment comprising prandial insulin, the weight ratios co-polyamino acid/pramlintide are from 2.7 to 27.

In an embodiment comprising prandial insulin, the weight ratios co-polyamino acid/pramlintide are from 3.3 to 27.

In an embodiment comprising prandial insulin, the weight ratios co-polyamino acid/pramlintide are from 4.7 to 27.

In an embodiment comprising prandial insulin, the weight ratios co-polyamino acid/pramlintide are from 6.0 to 27.

Moreover, it is particularly advantageous to combine the amylin, an amylin receptor agonist or an amylin analog, in combination or not with a prandial insulin, with GLP-1, GLP-1 analogs, GLP-1 receptor agonists which are routinely referred to as GLP-1 RA. In particular, this makes it possible to potentiate the effect of the insulin and is recommended in certain diabetes treatment types.

In an embodiment, the GLP-1, GLP-1 analogs or GLP-1 RA are referred to as "rapid."

"Rapid" is understood to mean GLP-1, GLP-1 analogs or GLP-1 RA whose apparent half-life of elimination after subcutaneous injection in humans is less than 8 h, in particular less than 5 h, preferably less than 4 h or even less than 3 h, such as, for example, exenatide and lixisenatide.

In an embodiment, the GLP-1, GLP-1 analogs or GLP-1 RA are selected from the group consisting of exenatide or Byetta® (ASTRAZENECA), lixisenatide or Lyxumia® (SANOFI), their analogs or derivatives and their pharmaceutically acceptable salts.

In an embodiment, the GLP-1, GLP-1 analog or GLP-1 RA is exenatide or Byetta®, its analogs or derivatives and their pharmaceutically acceptable salts.

In an embodiment, GLP-1, GLP-1 analog or GLP-1 RA is lixisenatide or Lyxumia®, its analogs or derivatives and their pharmaceutically acceptable salts.

In an embodiment, the concentration of exenatide, its analogs or derivatives and their pharmaceutically acceptable salts is in a range from 0.01 to 1.0 per 100 U of insulin.

In an embodiment, the concentration of exenatide, its analogs or derivatives and their pharmaceutically acceptable salts is 0.01 to 0.5 mg per 100 U of insulin.

In an embodiment, the concentration of exenatide, its analogs or derivatives and their pharmaceutically acceptable salts is 0.02 to 0.4 mg per 100 U of insulin.

In an embodiment, the concentration of exenatide, its analogs or derivatives and their pharmaceutically acceptable salts is 0.03 to 0.3 mg per 100 U of insulin.

In an embodiment, the concentration of exenatide, its analogs or derivatives and their pharmaceutically acceptable salts is 0.04 to 0.2 mg per 100 U of insulin.

In an embodiment, the concentration of exenatide, its analogs or derivatives and their pharmaceutically acceptable salts is 0.04 to 0.15 mg per 100 U of insulin.

In an embodiment, the concentration of lixisenatide, its analogs or derivatives and their pharmaceutically acceptable salts is in a range from 0.01 to 1 mg per 100 U of insulin.

In an embodiment, the concentration of lixisenatide, its analogs or derivatives and their pharmaceutically acceptable salts is in a range from 0.01 to 0.5 mg per 100 U of insulin.

In an embodiment, the concentration of lixisenatide, its analogs or derivatives and their pharmaceutically acceptable salts is 0.02 to 0.4 mg per 100 U of insulin.

In an embodiment, the concentration of lixisenatide, its analogs or derivatives and their pharmaceutically acceptable salts is 0.03 to 0.3 mg per 100 U of insulin.

In an embodiment, the concentration of lixisenatide, its analogs or derivatives and their pharmaceutically acceptable salts is 0.04 to 0.2 mg per 100 U of insulin.

In an embodiment, the concentration of lixisenatide, its analogs or derivatives and their pharmaceutically acceptable salts is 0.04 to 0.15 mg per 100 U of insulin.

In an embodiment, the compositions according to the invention are produced by mixing solutions of amylin and commercial solutions of GLP-1, GLP-1 analog or GLP-1 receptor agonist RA in volume ratios in a range from 10/90 to 90/10 in the presence of a co-polyamino acid.

In an embodiment, the composition moreover comprises zinc salts.

In an embodiment, the concentration of zinc salts is from 0 to 5000 μM.

In an embodiment, the concentration of zinc salts is from 0 to 4000 μM.

In an embodiment, the concentration of zinc salts is from 0 to 3000 μM.

In an embodiment, the concentration of zinc salts is from 0 to 2000 μM.

In an embodiment, the concentration of zinc salts is from 0 to 1000 μM.

In an embodiment, the concentration of zinc salts is from 50 to 600 μM.

In an embodiment, the concentration of zinc salts is from 100 to 500 μM.

In an embodiment, the concentration of zinc salts is from 200 to 500 μM.

In an embodiment, the zinc salt is zinc chloride.

In an embodiment, the compositions according to the invention moreover comprise zinc salts at a concentration from 0 to 500 μM per 100 U of insulin.

In an embodiment, the compositions according to the invention moreover comprise zinc salts at a concentration from 0 to 400 μM per 100 U of insulin.

In an embodiment, the compositions according to the invention moreover comprise zinc salts at a concentration from 0 to 300 μM per 100 U of insulin.

In an embodiment, the compositions according to the invention moreover comprise zinc salts at a concentration from 0 to 200 μM per 100 U of insulin.

In an embodiment, the compositions according to the invention moreover comprise zinc salts at a concentration from 0 to 100 μM per 100 U of insulin.

In an embodiment, the compositions according to the invention moreover comprise buffers.

In an embodiment, the compositions according to the invention comprise buffers at concentrations from 0 to 100 mM.

In an embodiment, the compositions according to the invention comprise buffers at concentrations from 15 to 50 mM.

In an embodiment, the compositions according to the invention comprise a buffer selected from the group consisting of a phosphate buffer, Tris (trishydroxymethylaminomethane) and sodium citrate.

In an embodiment, the buffer is sodium phosphate.

In an embodiment, the buffer is Tris (trishydroxymethylaminomethane).

In an embodiment, the buffer is sodium citrate.

In an embodiment, the compositions according to the invention moreover comprise preservatives.

In an embodiment, the preservatives are selected from the group consisting of m-cresol and phenol, alone or in a mixture.

In an embodiment, the concentration of preservatives is from 10 to 50 mM.

In an embodiment, the concentration of preservatives is from 10 to 40 mM.

In an embodiment, the compositions according to the invention moreover comprise a surfactant.

In an embodiment, the surfactant is selected from the group consisting of propylene glycol and polysorbate.

The compositions according to the invention can moreover comprise additives such as tonicity agents.

In an embodiment, the tonicity agents are selected from the group consisting of glycerol, sodium chloride, mannitol and glycine.

The compositions according to the invention can moreover comprise all the excipients in compliance with the pharmacopoeias and compatible with the insulins used at the usual concentrations.

The invention also relates to a pharmaceutical formulation according to the invention, characterized in that it is obtained by drying and/or lyophilization.

In the case of local and systemic releases, the modes of administration considered are by intravenous, subcutaneous, intradermal or intramuscular route.

The transdermal, oral, nasal, vaginal, ocular, buccal, pulmonary routes of administration are also considered.

The invention also relates to an implantable or transportable pump comprising a competition according to the invention.

The invention also relates to the use of a composition according to the invention intended to be placed in an implantable or transportable pump.

In an embodiment, the pump delivers the composition according to the invention by means of a bolus, basal flow or a combination of bolus and basal flow.

In an embodiment, the pump delivers the composition according to the invention by means of a combination of bolus and basal flow.

In an embodiment, the pump delivering the composition according to the invention is selected from the group of the following group of pump references: AccuCheck® Combo, Accu-Check® Insight, Accu-Check® Spirit, Animas® 2020, Animas® Vibe, CellNovo, Omnipod®, Minimed® 670G, Minimed® 640G, Minimed® 630G, Minimed® 530G, Minimed® Paradigm® Revel, Medtronic Paradigm® Veo™, Tandem t:slim®, Tandem t:slim X2®, Tandem t:flex®, Mylife YpsoPump®, BetaBionics iLet®, Asante Snap, Valeritas V-Go®, OneTouch®, Cequr PaQ® and Unilife Imperium®.

In an embodiment, the injection system delivering the composition according to the invention is a so-called "close-loop" or semi "close-loop" injection system.

In an embodiment, the injection system delivering the composition according to the invention is a "close-loop" system, system which is equipped with a processor using an algorithm which takes into consideration the quantity of insulin present in the organism of the patient by estimating this quantity by itself.

In an embodiment, the "close loop" injection system comprises a sensor which directly or indirectly supplies the blood glucose level of the patient, an infusion pump which delivers the product, and a processor which receives the measurement of the sensor, calculates the dose of product to be delivered by the pump based on this measurement and on an internal algorithm which predicts the evolution of the blood glucose level and sends the command to the pump to deliver the dose calculated.

In an embodiment, the injection system delivering the composition according to the invention is a semi "close-loop" system, a system equipped with a processor using an algorithm which takes into consideration the quantity of insulin present in the organism of the patient based on external data.

In an embodiment, this external data is supplied by the patient.

In an embodiment, this external data supplied by the patient concerns the quantity of carbohydrate ingested by the patient, and the beginning and the end of physical activity.

In an embodiment, this external data supplied by the patient relates to the quantity of carbohydrate ingested by the patient.

In an embodiment, this external data supplied by the patient concerns the start and the end of physical activity.

In an embodiment, the algorithm can take into consideration other external data which can be given automatically by a sensor.

In an embodiment, the processor present in the system for injecting the composition according to the invention can include additional steps ensuring the safety of the dose administered to the patient.

In an embodiment, the system for injecting the composition according to the invention comprises a sensor which directly or indirectly supplies the blood glucose level of the patient.

In an embodiment, the sensor is selected from the group of the sensors or sensors equipping the injection systems Medtronic Paradigm® Veo™, MiniMed® 640G with Smart-Guard®, Roche Dexcom® G4 PLATINUM CGM, Roche Dexcom G5™ Mobile CGM, Abbott Diabetes Care Free-Style Libre Flash glucose monitoring system, Abbott Diabetes Care FreeStyle Navigator II CGM system.

In an embodiment, the system for injecting the composition according to the invention comprises a two-compartment pump with a compartment containing the composition according to the invention and a compartment containing another drug.

In an embodiment, the system for injecting the composition according to the invention comprises a two-compartment pump with a compartment containing the composition according to the invention and a compartment containing glucagon.

In an embodiment, the composition according to the invention can be used in an artificial pancreas system with several hormones.

In an embodiment, the artificial pancreas system with several hormones using the composition according to the invention is a "close-loop" or semi "close-loop" system.

In an embodiment, the artificial pancreas system comprises the composition according to the invention and glucagon as other hormone.

In an embodiment, the artificial pancreas system comprises a two-compartment pump, one compartment containing the composition according to the invention and one compartment containing glucagon.

In an embodiment, the artificial pancreas system comprising a two-compartment pump is equipped with a processor using an algorithm which calculates two doses, a dose of the composition according to the invention and a dose of glucagon, the doses calculated by the algorithm being sent to the pump and being delivered to the patient.

In an embodiment, the artificial pancreas system comprises two pumps, a pump which delivers the composition according to the invention and a pump which delivers glucagon.

In an embodiment, the artificial pancreas system comprising two pumps comprises a processor using an algorithm calculating two doses, a dose of the composition according to the invention and a dose of glucagon, the doses calculated being sent to the pump containing the composition according to the invention and to the second pump containing the glucagon, respectively, the doses calculated by the algorithm being delivered to the patient.

In an embodiment, the system for injecting the composition according to the invention is an intelligent pen.

In an embodiment, the system for injecting the composition according to the invention is an intelligent pen capable of determining the dose to be injected.

In an embodiment, the intelligent pen which is capable of determining the dose to be injected is equipped with a sensor which directly or indirectly supplies the blood glucose level of the patient.

In an embodiment, the intelligent pen which is capable of determining the dose to be injected is equipped with a sensor and with a processor which calculates the dose of product to be delivered using the measurement of the sensor and an algorithm which predicts the evolution of the blood glucose level and sends the command to the pen to register the dose calculated.

In an embodiment, the dose calculated by the processor of the intelligent pen is the dose administered by the patient.

In an embodiment, the intelligent pen is equipped with a processor using an algorithm taking into consideration the quantity of insulin in the organism of the patient by estimating itself this quantity or by receiving this data externally.

In an embodiment, the intelligent pen is equipped with a processor using an algorithm taking into consideration other external data which can be given automatically by a sensor or by the patient, such as the quantity of carbohydrate ingested by the patient, or the beginning and the end of physical activity.

In an embodiment, the system for injecting the composition according to the invention comprises a pump, two pumps or an intelligent pen equipped with a processor using an algorithm.

In an embodiment, the algorithm used by the processor is selected from the "PID" (Proportional Integral Derivative) algorithms, of which an example is described in the article (Ruiz, J. et al., *Journal of diabetes science and technology*, 1123-1130, 2012), the "fuzzy logic" algorithms, of which an example is described in the article (Atlas, E. et al, *Diabetes care*, 1072-1076, 2010), the "MPC" (Model Predictive Control) algorithms, of which an example is described in the article (Hovorka, R. et al., *Physiol. Meas.*, 905-920, 2004), and the "PD" (Proportional Derivative) algorithms, of which an example is described in the article (Jacobs, P. et al, *IEEE Trans Biomed Eng*, 2569-2581, 2014).

The invention also relates to single-dose formulations at a pH from 6.0 to 8.0 comprising amylin, an amylin receptor agonist or an amylin analog, and a co-polyamino acid according to the invention.

The invention also relates to single-dose formulations at a pH from 6.0 to 8.0 comprising amylin, an amylin receptor agonist or amylin analog, a co-polyamino acid according to the invention, and a GLP-1, a GLP-1 analog or a GLP-1 RA as defined above.

The invention also relates to single-dose formulations at a pH from 6.6 to 7.8 comprising amylin, an amylin receptor agonist or an amylin analog, and a co-polyamino acid according to the invention.

The invention also relates to single-dose formulations at a pH from 6.6 to 7.8 comprising amylin, an amylin receptor agonist or an amylin analog, a co-polyamino acid according to the invention, and a prandial insulin as defined above.

The invention also relates to single-dose formulations at a pH from 6.6 to 7.6 comprising amylin, an amylin receptor agonist or an amylin analog, and a co-polyamino acid according to the invention.

The invention also relates to single-dose formulations at a pH from 6.6 to 7.6 comprising amylin, an amylin receptor agonist or an amylin analog, a co-polyamino acid according to the invention, and a prandial insulin as defined above.

In an embodiment, the single-dose formulations moreover comprise a co-polyamino acid as defined above.

In an embodiment, the formulations are in the form of an injectable solution.

The preparation of a composition according to the invention has the advantage that it can be prepared by simply mixing an aqueous solution of amylin, an amylin receptor agonist or an amylin analog, and a co-polyamino acid bearing carboxylate charges and at least one hydrophobic radical according to the invention, in an aqueous solution or in lyophilized form. If necessary, the pH of the preparation is adjusted to a pH from 6 to 8.

The preparation of a composition according to invention has the advantage that it can be prepared by simply mixing an aqueous solution of amylin, an amylin receptor agonist or an amylin analog, prandial insulin, and a co-polyamino acid bearing carboxylate charges and at least one hydrophobic radical according to the invention, in an aqueous solution or in lyophilized form. If necessary, the pH of the preparation is adjusted to a pH from 6 to 8.

In an embodiment, the mixture of prandial insulin and co-polyamino acid is concentrated by ultrafiltration.

If necessary, the composition of the mixture is adjusted in terms of excipients such as glycerol, m-cresol, zinc chloride and polysorbate (Tween®) by adding concentrated solutions of these excipients within the mixture. If necessary, the pH of the preparation is adjusted to a pH from 6 to 8.

In an embodiment, the compositions are characterized in that said compositions have a stability measured by ThT greater than the stability of a reference composition comprising amylin, an amylin receptor agonist or an amylin analog, but comprising no co-polyamino acid bearing carboxylate charges and hydrophobic radicals Hy.

In an embodiment, the compositions are characterized in that said compositions have a stability measured by ThT greater than the stability of a reference composition comprising amylin, an amylin receptor agonist or an amylin analog in combination with an insulin, but comprising no co-polyamino acid bearing carboxylate charges and hydrophobic radicals Hy.

In an embodiment, the compositions are characterized in that said compositions have a stability measured by ThT greater than the stability of a reference composition comprising amylin, an amylin receptor agonist or an amylin analog in combination with a GLP-1, a GLP-1 analog or a GLP-1 receptor agonist, but comprising no co-polyamino acid bearing carboxylate charges and hydrophobic radicals Hy.

In an embodiment, the compositions are characterized in that said compositions have a stability measured by ThT greater than the stability of a reference composition comprising amylin, an amylin receptor agonist or an amylin analog in combination with an insulin or a GLP-1, a GLP-1 analog or a GLP-1 receptor agonist, but comprising no co-polyamino acid bearing carboxylate charges and hydrophobic radicals Hy.

The invention also relates to a use of a co-polyamino acid bearing carboxylate charges and hydrophobic radicals Hy in order to stabilize a composition comprising amylin, an amylin receptor agonist or an amylin analog.

The invention also relates to a use of a co-polyamino acid bearing carboxylate charges and hydrophobic radicals Hy for stabilizing a composition comprising amylin, an amylin receptor agonist or an amylin analog and a prandial insulin, and optionally a GLP-1, a GLP-1 analog or a GLP-1 receptor agonist.

The invention relates to a method for stabilizing a composition comprising amylin, an amylin receptor agonist or an amylin analog, or to a method for stabilizing a composition comprising amylin, an amylin receptor agonist or an amylin analog and a prandial analog, and optionally a GLP-1, a GLP-1 analog or a GLP-1 receptor agonist.

DESCRIPTION OF THE FIGURES

FIG. 2 is a representation of the results of the pharmacokinetics of pramlintide obtained with the compositions described in examples CA1/CA2 and CA3. The analysis of these profiles indicates that the composition of example CA3 comprising the co-polyamino acid BB15, 100 IU/mL of insulin and 0.6 mg/mL of pramlintide (curve traced with the squares corresponding to example CA3) makes it possible to obtain a slower absorption of pramlintide than the absorption of the composition of the example with double injection comprising only pramlintide and insulin (curve traced with the triangles corresponding to the double-injection example CA1/CA2).

FIG. 3 is a representation of the results of the pharmacokinetics of pramlintide obtained with the compositions described in examples CA1/CA2 and CA4. The analysis of these profiles indicates that the composition of example CA4 comprising the co-polyamino acid AB24, 100 IU/mL of insulin and 0.6 μg/mL of pramlintide (curve traced with the squares corresponding to example CA4) makes it possible to obtain a slower absorption of pramlintide than the absorption of the composition of the example with double injection comprising only pramlintide and insulin (curve traced with the triangles corresponding to the double-injection example CA1/CA2).

Figure 1:
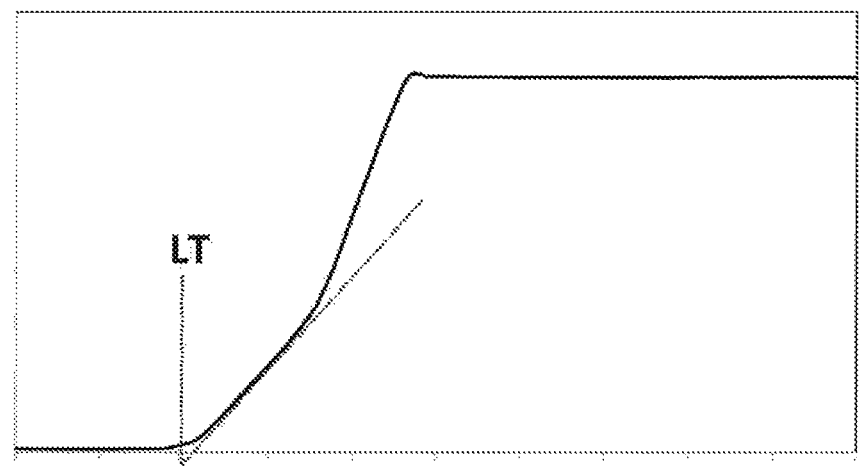
FIG. 1: This figure is a graphic representation of the determination of the latency time (LT) by monitoring the fluorescence of Thioflavin T, on a curve with the value of the fluorescence (in a.u. arbitrary units) on the ordinate and with the time in minutes on the abscissa.

The following examples illustrate the invention in a nonlimiting manner.

Part A

AA: Synthesis of the Hydrophobic Molecules in which p=1

The hydrophobic radicals are represented in the following table by the corresponding hydrophobic molecule before grafting onto the co-polyamino acid.

TABLE 1A list and structures of the hydrophobic molecules synthesized according to the invention.

| N° | STRUCTURE OF THE HYDROPHOBIC MOLECULE BEFORE GRAFTING ONTO THE CO-POLYAMINO ACID |
|---|---|
| AA1 | 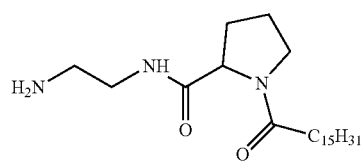 |

TABLE 1A-continued
list and structures of the hydrophobic molecules synthesized according to the invention.
| N° | STRUCTURE OF THE HYDROPHOBIC MOLECULE BEFORE GRAFTING ONTO THE CO-POLYAMINO ACID |
|---|---|
| AA2 | 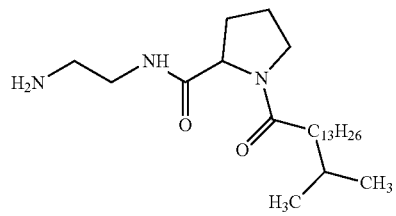 |
| AA3 | 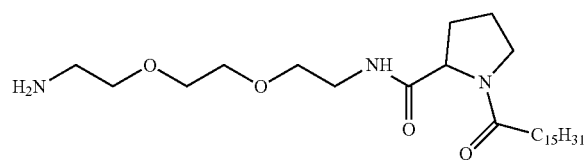 |
| AA4 | 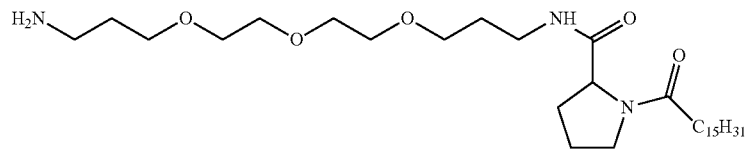 |
| AA5 | 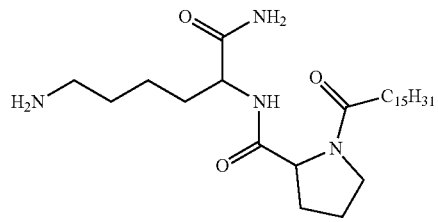 |
| AA6 | 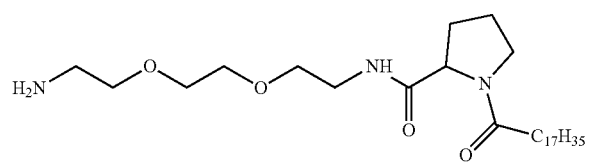 |
| AA7 | 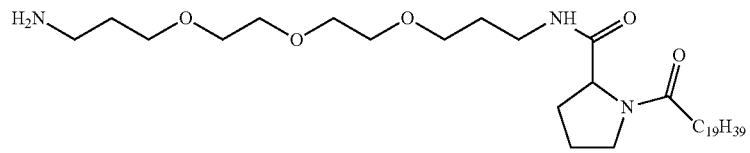 |
| AA8 | 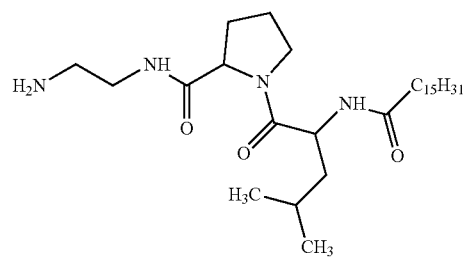 |

TABLE 1A-continued list and structures of the hydrophobic molecules synthesized according to the invention.

| N° | STRUCTURE OF THE HYDROPHOBIC MOLECULE BEFORE GRAFTING ONTO THE CO-POLYAMINO ACID |
|---|---|
| AA9 | 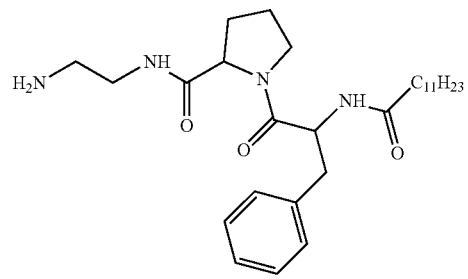 |
| AA10 | 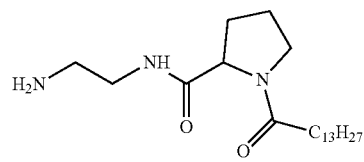 |
| AA11 | 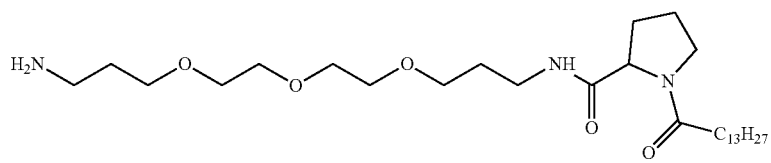 |
| AA12 | 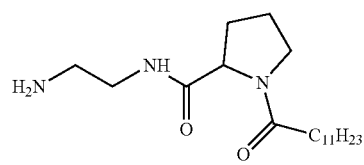 |
| AA13 | 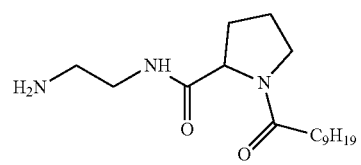 |
| AA14 | 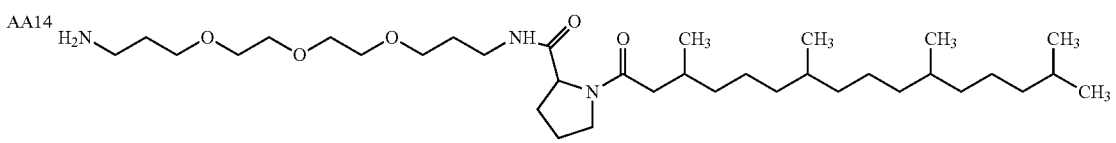 |

EXAMPLE AA1

MOLECULE AA1

Molecule A1: Product Obtained by the Reaction Between Palmitoyl Chloride and L-proline A solution of palmitoyl chloride (23.0 g, 83.7 mmol) in acetone (167 mL) is added dropwise in 90 min to a solution of L-proline (10.6 g, 92.1 mmol) in aqueous sodium hydroxide 1 N (230 mL, 230 mmol). After 14 h of stirring at ambient temperature, the heterogeneous mixture is cooled to 0° C., then filtered through a sinter filter to yield a white solid which is washed with water (2×100 mL), then with diisopropyl ether (100 mL). The sodium hydroxide is dried at reduced pressure. The solid is then dissolved at reflux in 200 mL of water, then 8 mL of a hydrochloric acid solution at 37% are added to obtain pH=1. The opalescent reaction medium is then cooled to 0° C. The precipitate obtained is filtered through a sinter filter, then washed with water (5×50 mL) until filtrates at physiological pH from 6.0 to 8.0 are obtained, followed by drying in an oven at 50° C. under a vacuum overnight. The product is purified by recrystallization in diisopropyl ether. A white solid is obtained.

Yield: 22.7 g (77%).

$^1$H NMR (CDCl$_3$, ppm): 0.88 (3H); 1.19-1.45 (24H); 1.58-1.74 (2H); 1.88-2.14 (3H); 2.15-2.54 (3H); 3.47 (1H); 3.58 (1H); 4.41 (0.1H); 4.61 (0.9H); 6.60-8.60 (1H).

Molecule A2: Product Obtained by Reaction Between Molecule A1 and Boc-ethylenediamine To a solution of molecule A1 (75.1 g, 212.4 mmol) in 1500 mL of chloroform, the following are slowly added successively and at ambient temperature: N,N-diisopropylethylamine (DIPEA) (68.8 g, 532.3 mmol), 1-hydroxybenzotriazole (HOBt) (37.1 g, 274.6 mmol), then N-(3-dimethylaminopropyl)-N'-ethylcarbodiimide (EDC) (53.1 g, 277.0 mmol). After 15 min of stirring at ambient temperature, a solution of Boc-ethylenediamine (BocEDA) (37.6 g, 234.7 mmol) in 35 mL of chloroform is added. After 18 h of stirring at ambient temperature, an HCl solution 0.1 N (2.1 L), then a saturated NaCl solution (1 L) are added. The phases are separated, then the organic phase is washed successively with an HCl solution 0.1 N/saturated NaCl (2.1 L/1 L), a saturated NaCl solution (2 L), a saturated NaHCO$_3$ solution (2 L), then a saturated NaCl solution (2 L). The organic phase is dried over anhydrous sodium sulfate, filtered, then concentrated at reduced pressure. The solid obtained is purified by trituration in diisopropyl ether (3×400 mL), to yield a solid after drying under a vacuum at 40° C.

Yield: 90.4 g (86%).

$^1$H NMR (CDCl$_3$, ppm): 0.88 (3H); 1.20-1.37 (24H); 1.44 (9H); 1.54-1.70 (2H); 1.79-1.92 (1H); 1.92-2.04 (1H); 2.03-2.17 (1H); 2.17-2.44 (3H); 3.14-3.36 (4H); 3.43 (1H); 3.56 (1H); 4.29 (0.1H); 4.51 (0.9H); 4.82 (0.1H); 5.02 (0.9H); 6.84 (0.1H); 7.22 (0.9H).

Molecule AA1

A hydrochloric acid solution 4 N in dioxane (100 mL, 400 mmol) is added dropwise and at 0° C. to a solution of molecule A2 (20.1 g, 40.5 mmol) in 330 mL of dichloromethane. After 3 h 30 of stirring at ambient temperature, the solution is concentrated at reduced pressure. The residue is purified by flash chromatography (methanol, dichloromethane) to yield a white solid of molecule AA1 in the form of a hydrochloride salt.

Yield: 16.3 g (93%).

$^1$H NMR (CDCl$_3$, ppm): 0.88 (3H); 1.07-1.40 (24H); 1.49-1.63 (2H); 1.77-2.18 (4H); 2.18-2.45 (2H); 3.14-3.32 (2H); 3.42-3.63 (2H); 3.63-3.84 (2H); 4.37 (0.1H); 4.48 (0.9H); 6.81-8.81 (4H). LC/MS (ESI): 396.5; (calculated ([M+H]$^+$): 396.4).

EXAMPLE AA2

MOLECULE AA2

Molecule A3: 15-methylhexadecan-1-ol

Magnesium (9.46 g, 389 mmol) in the form of chips is introduced into a three-neck flask under argon. The magnesium is covered with anhydrous THF (40 mL), and a few drops of 1-bromo-3-methylbutane are added at ambient temperature to initiate the reaction. After the observation of an exotherm and slight turbidity of the medium, the rest of the 1-bromo-3-methylbutane (53.87 g, 357 mmol) is added dropwise in 90 min, while the temperature of the medium remains stable between 50 and 60° C. The reaction mixture is then heated at 70° C. for 2 h.

In a three-neck flask under argon, a solution of 12-bromo-1-dodecanol (43 g, 162.1 mmol) in THF (60 mL) is added dropwise to a solution of CuCl (482 mg, 4.86 mmol) dissolved in NMP (62 mL) at 0° C. To this solution, the hot solution of organomanganese prepared extemporaneously while maintaining the temperature of the medium below 20° C. is then added dropwise. The mixture is then stirred at ambient temperature for 16 h. The medium is cooled to 0° C., and the reaction is stopped by addition of an aqueous HCl solution 1 N until the pH is 1 and the mixture is extracted with ethyl acetate. After washing of the organic phase with a saturated NaCl solution and drying over Na$_2$SO$_4$, the solution is filtered and concentrated under a vacuum to yield an oil. After purification by DCVC on silica gel (cyclohexane, ethyl acetate), an oil which crystallizes at ambient temperature is obtained.

Yield: 32.8 g (74%).

$^1$H NMR (CDCl$_3$, ppm): 0.87 (6H); 1.14 (2H); 1.20-1.35 (22H); 1.50-1.55 (3H); 3.64 (2H).

Molecule A4: 15-Methylhexadecanoic Acid

Small portions of potassium permanganate (38.2 g, 241.5 mmol) are added to a solution of molecule A3 (20.65 g, 80.5 mmol) and tetrabutylammonium bromide (14.02 g, 42.5 mmol) in a mixture of acetic acid/dichloroethane/water (124/400/320 mL) at ambient temperature. After stirring at reflux for 5 h and return to ambient temperature, the medium is acidified to pH 1 by gradual addition of HCl 5 N. Na$_2$SO$_3$ (44.6 g, 354.3 mmol) is then added gradually until discoloration of the medium. The aqueous phase is extracted with dichloromethane, and the combined organic phases are tried over Na$_2$SO$_4$, filtered and concentrated under a vacuum. After purification by chromatography on silica gel (cyclohexane, ethyl acetate, acetic acid), a white solid is obtained.

Yield: 19.1 g (quantitative)

$^1$H NMR (CDCl$_3$, ppm): 0.87 (6H); 1.14 (2H); 1.22-1.38 (20H); 1.51 (1H); 1.63 (2H); 2.35 (2H).

Molecule A5: Product Obtained by Reaction Between Molecule A4 and L-Proline

Dicyclohexyl carbodiimide (DCC) (8.01 g, 38.8 mmol) and N-hydroxysuccinimide (NETS) (4.47 g, 38.8 mmol) are added successively to a solution of molecule A4 (10 g, 37 mmol) in THF (360 mL) at 0° C. After 17 h of stirring at ambient temperature, the mixture is cooled to 0° C. for 20 min, filtered through a sinter filter. L-Proline (4 g, 37.7 mmol), triethylamine (34 mL) and water (30 mL) are added to the filtrate. After 20 h of stirring at ambient temperature, the medium is treated with an HCl solution −1 N until the pH is 1. The aqueous phase is extracted with dichloromethane (2×125 mL). The combined organic phases are washed with an aqueous HCl solution 1 N (2×100 mL), water (100 mL), then a saturated aqueous NaCl solution (100 mL). After drying over Na$_2$SO$_4$, the organic phase is filtered, concentrated under a vacuum, and the residue is purified by chromatography on silica gel (cyclohexane, ethyl acetate, acetic acid).

Yield: 9.2 g (72%).

$^1$H NMR (CDCl$_3$, ppm): 0.86 (6H); 1.14 (2H); 1.22-1.38 (20H); 1.50 (1H); 1.67 (2H); 1.95-2.10 (3H); 2.34 (2H); 2.49 (1H); 3.47 (1H); 3.56 (1H); 4.61 (1H).

LC/MS (ESI): 368.3; (calculated ([M+H]$^+$): 368.6).

Molecule A6: Product Obtained by Reaction Between Molecule A5 and Boc-Ethylenediamine Triethylamine (TEA) (5.23 mL) and 2-(1H-benzotriazol-1-yl)-1,1,3,3-tetramethyluronium tetrafluoroborate (TBTU) at ambient temperature are added to a solution of molecule A5 (9.22 g, 25.08 mmol) in a THF/DMF mixture (200/50 mL). After 10 min of stirring, Boc-ethylenediamine (4.42 g, 27.6 mmol) is added. After stirring at ambient temperature for 17 h, the mixture is diluted with water (300 mL) at 0° C. and stirred at cold temperature for 20 min. The precipitate formed is filtered through a sinter filter, and the filtrate is extracted with ethyl acetate. The combined organic phases are washed with a saturated NaHCO$_3$ solution, dried over Na$_2$SO$_4$, filtered, concentrated under a vacuum, and the residue is purified by flash chromatography (ethyl acetate, methanol).

Yield: 6.9 g (54%).

$^1$H NMR (CDCl$_3$, ppm): 0.86 (6H); 1.15 (2H); 1.22-1.38 (20H); 1.43 (9H); 1.50 (1H); 1.64 (4H); 1.85 (1H); 1.95 (1H); 2.10 (1H); 2.31 (2H); 3.20-3.35 (3H); 3.45 (1H); 3.56 (1H); 4.51 (1H); 5.05 (1H); 7.24 (1H).

LC/MS (ESI): 510.6; (calculated ([M+H]$^+$): 510.8).

Molecule AA2

An HCl solution 4 N in dioxane (13 mL) is added to a solution of molecule A6 (5.3 g, 10.40 mmol) in dichloromethane (50 mL) at 0° C. After 5 h of stirring at 0° C., the mixture is concentrated under a vacuum, dissolved in water, and lyophilized to yield a white solid of molecule AA2 in the form of a hydrochloride salt.

Yield: 4.6 g (99%).

$^1$H NMR (D$_2$O, ppm): 0.91 (6H); 1.22 (2H); 1.22-1.50 (20H); 1.63 (3H); 1.98 (1H); 2.10 (2H); 2.26 (1H); 2.39 (1H); 2.43 (1H); 3.22 (2H); 3.45-3.60 (3H); 3.78 (1H); 4.42 (1H).

LC/MS (ESI): 410.4; (calculated ([M+H]$^+$): 410.7).

EXAMPLE AA3

MOLECULE AA3

Molecule A7: Product Obtained by the Reaction Between Molecule A1 and Boc-tri(ethylene glycol)diamine By a method similar to the one used for preparing molecule A2 applied to molecule A1 (4.0 g, 11.3 mmol) and to Boc-tri(ethyleneglycol)diamine (3.1 g, 12.4 mmol), a colorless oil is obtained after purification by flash chromatography (methanol, toluene).

Yield: 5.5 g (84%).

$^1$H NMR (CDCl$_3$, ppm): 0.88 (3H); 1.09-1.39 (24H); 1.44 (9H); 1.64 (2H); 1.79-2.01 (2H); 2.06-2.43 (4H); 3.23-3.68 (14H); 4.33 (0.2H); 4.56 (0.8H); 5.25 (1H); 6.49 (0.2H); 7.13-7.50 (0.8H).

Molecule AA3

By a method similar to the one used for the preparation of molecule AA1 applied to molecule A7 (5.5 g, 9.4 mmol), a white solid of molecule AA3 in the form of a hydrochloride salt is obtained after purification by flash chromatography (methanol, dichloromethane).

Yield: 4.3 g (92%).

$^1$H NMR (DMSO-d$_6$, ppm): 0.85 (3H); 1.08-1.40 (24H); 1.40-1.52 (2H); 1.71-2.02 (4H); 2.02-2.31 (2H); 2.90-2.98 (2H); 3.15-3.47 (5H); 3.50-3.66 (7H); 4.24 (0.6H); 4.32 (0.4H); 7.83 (0.6H); 7.95 (3H); 8.17 (0.4H).

LC/MS (ESI): 484.6; (calculated ([M+H]$^+$): 484.4).

EXAMPLE AA4

MOLECULE AA4

Molecule A8: Product Obtained by the Reaction Between Molecule A1 and Boc-1-amino-4,7,10-trioxa-13-tridecane amine By a method similar to the one used for the preparation of molecule A2 applied to molecule A1 (4.5 g, 12.7 mmol) and to Boc-1-amino-4,7,10-trioxa-13-tridecane amine (4.5 g, 14.0 mmol), a yellow oil is obtained after purification by flash chromatography (methanol, dichloromethane).

Yield: 7.7 g (92%)

$^1$H NMR (CDCl$_3$, ppm): 0.88 (3H); 1.22-1.37 (24H); 1.44 (9H); 1.59-1.67 (2H); 1.67-2.00 (6H); 2.06-2.45 (4H); 3.18-3.76 (18H); 4.28 (0.2H); 4.52 (0.8H); 4.69-5.04 (1H); 6.77 (0.2H); 7.20 (0.8H).

Molecule AA4

By a method similar to the one used for the preparation of molecule AA1 applied to molecule A8 (7.7 g, 11.8 mmol), a yellow oil is obtained after purification by flash chromatography (methanol, dichloromethane). A co-evaporation with diisopropyl ether makes it possible to obtain molecule AA4 in the form of a hydrochloride salt in the form of a white solid which is dried under a vacuum at 50° C.

Yield: 5.4 g (76%).

$^1$H NMR (CDCl$_3$, ppm): 0.88 (3H); 1.08-1.40 (24H); 1.49-1.65 (2H); 1.76-2.39 (10H); 3.07-3.28 (3H); 3.34-3.80 (15H); 4.34 (0.05H); 4.64 (0.95H); 7.35 (0.05H); 7.66-8.58 (3.95H).

LC/MS (ESI): 556.7; (calculated ([M+H]$^+$): 556.5).

EXAMPLE AA5

MOLECULE AA5

Molecule A9: Product Obtained by Reaction Between Molecule A1 and the Methyl Ester of N-Boc-L-lysine By a method similar to the one used for the preparation of molecule A2 applied to molecule A1 (4 g, 11.3 mmol) and to the methyl ester of N-Boc-L-lysine (3.2 g, 12.4 mmol), a colorless oil is obtained after purification by flash chromatography (methanol, dichloromethane).

Yield: 4.9 g (73%).

$^1$H NMR (CDCl$_3$, ppm): 0.88 (3H); 0.99-1.54 (37H); 1.54-1.75 (3H); 1.75-2.04 (3H); 2.04-2.41 (4H); 2.94-3.19 (2H); 3.19-3.81 (5H); 4.28-4.64 (2H); 4.94 (1H); 6.45 (0.1H); 7.36 (0.9H).

LC/MS (ESI): 596.7; (calculated ([M+H]$^+$): 596.5)

Molecule A10: Product Obtained by Treatment of Molecule A9 with Ammonia 320 mL of an ammonia solution 7 N in methanol are added to a suspension of molecule A9 (4.9 g, 8.2 mmol) in 10 mL of methanol. After 19 h of stirring at ambient temperature in a closed atmosphere, 100 mL of additional ammonia solution are added. After 24 h of stirring at ambient temperature in a closed atmosphere, the reaction medium is concentrated at reduced pressure. The residue is purified by trituration in diisopropyl ether at reflux (100 mL), to yield a white solid which is dried under a vacuum at 50° C.

Yield: 4.1 g (85%).

$^1$H NMR (CDCl$_3$, ppm): 0.88 (3H); 1.06-1.57 (37H); 1.57-1.79 (3H); 1.88-2.41 (7H); 3.09 (2H); 3.49 (1H); 3.62 (1H); 4.34 (1H); 4.51 (1H); 4.69-4.81 (1H); 5.43 (0.95H); 5.57 (0.05H); 6.25 (0.05H); 6.52 (0.95H); 6.83 (0.05H); 7.11 (0.95H).

Molecule AA5

By a method similar to the one used for the preparation of molecule AA1 applied to molecule A10 (388 mg, 0.67 mmol), a white solid of molecule AA5 in the form of a hydrochloride salt is obtained after purification by trituration in diisopropyl ether.

Yield: 292 mg (85%):

$^1$H NMR (DMSO-d6, ppm): 0.85 (3H); 1.06-2.34 (38H); 2.61-2.81 (2H); 3.29-3.68 (2H); 4.05-4.17 (1.7H); 4.42 (0.3H); 7.00 (1H); 7.16 (0.7H); 7.43 (0.3H); 7.73-8.04 (3.7H); 8.16 (0.3H).

LC/MS (ESI): 481.6; (calculated ([M+H]$^+$): 481.4).

EXAMPLE AA6

MOLECULE AA6

Molecule A11: Product Obtained by the Reaction Between Stearoyl Chloride and L-proline By a method similar to the one used for the preparation of molecule A1 applied to L-proline (5.0 g, 43.4 mmol) and to stearoyl chloride (12.0 g, 39.6 mmol), a white solid is obtained after purification by flash chromatography (methanol, dichloromethane).

Yield: 5.37 g (36%).

$^1$H NMR (CDCl$_3$, ppm): 0.88 (3H); 1.26-1.37 (28H); 1.64-1.70 (2H); 1.88-2.10 (3H); 2.36 (2H); 2.54-2.58 (1H); 3.46 (1H); 3.56 (1H); 4.62 (1H).

LC/MS (ESI): 382.6; (calculated ([M+H]$^+$): 382.3).

Molecule A12: Product Obtained by Reaction Between Molecule A11 and Boc-tri(ethylene glycol)diamine By a method similar to the one used for the preparation of molecule A6 applied to molecule A11 (33.81 g, 88.6 mmol) and to Boc-tri(ethylene glycol)diamine (26.4 g, 106.3 mmol) in THF using DIPEA instead of TEA, a white solid is obtained after purification by flash chromatography (ethyl acetate, methanol).

Yield: 43.3 g (80%).

$^1$H NMR (CDCl$_3$, ppm): 0.87 (3H); 1.24 (30H); 1.43 (9H); 1.61 (2H); 1.82 (1H); 1.96 (1H); 2.25-2.45 (2H); 3.25-3.65 (14H); 4.30 (0.15H); 4.53 (0.85H); 5.25 (1H); 6.43 (0.15H); 7.25 (0.85H).

LC/MS (ESI): 612.6; (calculated ([M+H]$^+$): 612.9).

Molecule AA6

By a method similar to the one used for the preparation of molecule AA2 applied to molecule A12 (43 g, 70.3 mmol), the residue obtained after concentration under a vacuum is triturated in acetonitrile. The suspension is filtered, and the solid is washed with acetonitrile then with acetone. After drying under a vacuum, a white solid of molecule AA6 in the form of a hydrochloride salt is obtained.

Yield: 31.2 g (81%).

$^1$H NMR (DMSO-d$_6$, ppm): 0.85 (3H); 1.23 (28H); 1.45 (2H); 1.70-2.05 (4H); 2.13 (1H); 2.24 (1H); 2.95 (2H); 3.10-3.25 (2H); 3.30-3.65 (10H); 4.20-4.45 (1H); 7.85-8.25 (4H).

LC/MS (ESI): 512.4; (calculated ([M+H]$^+$): 512.8).

EXAMPLE AA7

MOLECULE AA7

Molecule A13: Product Obtained by Reaction Between Arachidonic Acid and L-proline By a method similar to the one used for the preparation of molecule A5 applied to arachidonic acid (15.51 g, 49.63 mmol) and to L-proline (6 g, 52.11 mmol), using DIPEA instead of TEA, a white solid is obtained after purification by chromatography column on silica gel (cyclohexane, ethyl acetate, acetic acid).

Yield: 12.9 g (63%).

$^1$H NMR (CDCl$_3$, ppm): 0.88 (3H); 1.28 (34H); 1.66 (2H); 1.95-2.15 (2H); 2.34 (2H); 2.45 (1H); 3.47 (1H); 3.56 (1H); 4.60 (1H).

LC/MS (ESI): 410.4; (calculated ([M+H]$^+$): 410.6).

Molecule A14: Product Obtained by the Reaction Between Molecule A13 and Boc-1-amino-4,7,10-trioxa-13-tridecane By a method similar to the one used for the preparation of molecule A12 applied to molecule A13 (10.96 g, 26.75 mmol) and to Boc-1-amino-4,7,10-trioxa-13-tridecane (10.29 g, 32.11 mmol), a solid is obtained after purification by chromatography column on silica gel (cyclohexane, ethyl acetate, methanol).

Yield: 14.2 g (75%).

$^1$H NMR (CDCl$_3$, ppm): 0.88 (3H); 1.24 (32H); 1.43 (9H); 1.61 (2H); 1.80 (1H); 1.96 (1H); 2.10-2.45 (4H); 3.20-3.75 (18H); 4.30 (0.20H); 4.55 (0.80H); 5.03 (1H); 6.75 (0.20H); 7.20 (0.80H).

LC/MS (ESI): 712.8; (calculated ([M+H]$^+$): 713.1).

Molecule AA7

After a method similar to the one used for the preparation of molecule AA2 applied to molecule A14 (14.25 g, 20.01 mmol), the residue obtained after concentration under a vacuum of the reaction medium is dissolved in methanol and evaporated at reduced pressure, the operation being repeated 4 times to yield a white solid of molecule AA7 in the form of a hydrochloride salt.

Yield: 12.7 g (98%).

$^1$H NMR (DMSO-d$_6$, ppm): 0.85 (3H); 1.23 (32H); 1.45 (2H); 1.64 (2H); 1.70-2.05 (6H); 2.10-2.30 (2H); 2.82 (2H); 3.08 (2H); 3.30-3.60 (15H); 4.15-4.30 (1H); 7.73-8.13 (4H).

LC/MS (ESI): 612.7; (calculated ([M+H]$^+$): 612.9).

EXAMPLE AA8

MOLECULE AA8

Molecule A15: Product Obtained by the Reaction Between L-leucine and Palmitoyl Chloride By a method similar to the one used for the preparation of molecule A1 applied to L-leucine (15.0 g, 114.4 mmol) and to palmitoyl chloride (34.5 g, 125 mmol), a white solid is obtained by trituration in diisopropyl ether.

Yield: 13.0 g (31%).

$^1$H NMR (CDCl$_3$, ppm): 0.88 (3H); 0.96 (6H); 1.16-1.35 (24H); 1.55-1.77 (5H); 2.23 (2H); 4.55-4.60 (1H); 5.88 (1H).

Molecule A16: Product Obtained by the Reaction Between Molecule A15 and the Methyl Ester of L-proline By a method similar to the one used for the preparation of molecule A2 applied to molecule A15 (6.00 g, 16.2 mmol) and to the methyl ester of L-proline (3.23 g, 19.5 mmol), a slightly yellow oil is obtained after purification by flash chromatography (methanol, dichloromethane).

Yield: 5.8 g (74%).

$^1$H NMR (CDCl$_3$, ppm): 0.83-1.00 (9H); 1.18-1.32 (24H); 1.40-1.73 (5H); 1.84-2.33 (6H); 3.47-3.89 (2H); 3.70 (1.14H); 3.71 (1.21H); 3.74 (0.53H); 3.76 (0.12H); 4.40-4.56 (1H); 4.63-4.67 (0.04H); 4.84 (0.38); 4.90 (0.40); 5.06 (0.18); 5.99 (0.18H); 6.08-6.21 (0.82).

LC/MS (ESI): 481.6; (calculated ([M+H]$^+$): 481.4).

Molecule A17: Product Obtained by the Saponification of the Methyl Ester of Molecule A16

Sodium hydroxide 1 N (13.5 mL, 13.5 mmol) is added to a solution of molecule A16 (5.8 g, 12.06 mmol) in 30 mL of methanol. After 20 h of stirring at ambient temperature, the solution is diluted with water, then acidified with 20 mL of hydrochloric acid 1 N at 0° C. The precipitate is filtered, then rinsed with water (50 mL), before being solubilized in 50 mL of dichloromethane. The organic phase is dried over Na$_2$SO$_4$, filtered, then concentrated at reduced pressure to yield a colorless oil.

Yield: 4.5 g (80%).

$^1$H NMR (CDCl$_3$, ppm): 0.85-0.99 (9H); 1.14-1.41 (24H); 1.43-1.72 (5H); 1.87-2.47 (7H); 3.48-3.55 (0.6H); 3.56-3.62 (0.4H); 3.83-3.90 (0.4H); 3.90-3.96 (0.6H); 4.52-4.56 (0.6H); 4.56-4.59 (0.4H); 4.80-4.86 (0.4H); 4.86-4.91 (0.6H); 6.05 (0.4H); 6.11 (0.6H).

LC/MS (ESI): 467.6; (calculated ([M+H]$^+$): 467.4).

Molecule A18: Product Obtained by Reacting Boc-ethylenediamine and Molecule A17

By a method similar to the one used for the preparation of molecule A2 applied to molecule A17 (4.5 g, 9.64 mmol) and to Boc-ethylenediamine (1.70 g, 10.61 mmol), a colorless oil is obtained after purification by flash chromatography (methanol, dichloromethane).

Yield: 2.0 g (34%)

$^1$H NMR (CDCl$_3$, ppm): 0.83-0.99 (9H); 1.19-1.32 (24H); 1.44 (9H); 1.48-2.37 (14H); 3.09-3.99 (4H); 4.28-5.01 (2H); 5.64-6.04 (1H); 6.87-7.06 (1H).

LC/MS (ESI): 609.7; (calculated ([M+H]$^+$): 609.5).

Molecule AA8

By a method similar to the one used for the preparation of molecule AA1 applied to molecule A18 (2 g, 3.28 mmol), a solid of molecule AA8 in the form of a hydrochloride salt is obtained after purification by flash chromatography (methanol, dichloromethane).

Yield: 1.5 g (90%).

$^1$H NMR (CDCl$_3$, ppm): 0.83-1.00 (9H); 1.18-1.32 (24H); 1.37-1.77 (5H); 1.93-2.41 (6H); 3.07-3.97 (6H); 4.44-4.77 (2H); 7.66-8.21 (2H)

LC/MS (ESI): 509.6; (calculated ([M+H]$^+$): 509.4).

EXAMPLE AA9

MOLECULE AA9

Molecule A19: Product Obtained by the Reaction Between Lauric Acid and L-phenylalanine By a method similar to the one used for the preparation of molecule A5 applied to lauric acid (8.10 g, 40.45 mmol) and to L-phenylalanine (7 g, 42.38 mmol), a white solid is obtained.

Yield: 12.7 g (98%).

$^1$H NMR (DMSO-d$_6$, ppm): 0.86 (3H); 1.10-1.30 (16H); 1.36 (2H); 2.02 (2H); 2.82 (1H); 3.05 (1H); 4.42 (1H); 7.15-7.30 (5H); 8.05 (1H); 12.61 (1H).

LC/MS (ESI): 348.2; (calculated ([M+H]$^+$): 348.5).

Molecule A20: Product Obtained by the Reaction Between Molecule A19 and the Hydrochloride Salt of the Methyl Ester of L-proline By a method similar to the one used for the preparation of molecule A6 applied to molecule A19 (9.98 g, 28.72 mmol) and to the hydrochloride salt of the methyl ester of L-proline (5.23 g, 31.59 mmol), a colorless oil is obtained after purification by chromatography column on silica gel (cyclohexane, ethyl acetate).

Yield: 5.75 g (44%).

$^1$H NMR (CDCl$_3$, ppm): 0.88 (3H); 1.10-1.30 (16H); 1.50-1.75 (3H); 1.80-2.02 (3H); 2.17 (2H); 2.65 (0.5H); 2.95 (1H); 3.05-3.20 (1.5H); 3.50-3.65 (1H); 3.75 (3H); 4.29 (0.5H); 4.46 (0.5H); 4.70 (0.1H); 4.95 (0.9H); 6.20-6.30 (1H); 7.15-7.30 (5H).

LC/MS (ESI): 459.2; (calculated ([M+H]$^+$): 459.6).

Molecule A21: Product Obtained by Saponification of Molecule A20

Lithium hydroxide (LiOH) (600.49 mg, 25.07 mmol) is added to a solution of molecule A20 (5.75 g, 12.54 mmol) in a THF/methanol/water mixture (40/40/40 mL) at 0° C., then the mixture is stirred at ambient temperature for 20 h. After evaporation of the organic solvents under a vacuum, the aqueous solution is diluted in water, acidified with an aqueous HCl solution 1 N until the pH is 1. The product is then extracted with ethyl acetate. The combined organic phases are washed with a saturated aqueous NaCl solution, dried over Na$_2$SO$_4$, filtered and concentrated at reduced pressure to yield a colorless oil.

Yield: 5.7 g (quantitative).

$^1$H NMR (CDCl$_3$, ppm): 0.88 (3H); 1.10-1.30 (16H); 1.50-1.80 (3H); 1.67-2.02 (2H); 2.20 (2H); 2.25 (0.4H); 2.60 (0.6H); 2.85-3.10 (2.6H); 3.55-3.65 (1.4H); 4.35 (0.6H); 4.55 (0.4H); 4.94 (1H); 6.28 (0.4H); 6.38 (0.6H); 7.20-7.30 (5H).

LC/MS (ESI): 445.2; (calculated ([M+H]$^+$): 445.6).

Molecule A22: Product Obtained by Reaction Between Boc-ethylenediamine and Molecule A21

By a method similar to the one used for the preparation of molecule A6 applied to molecule A21 (5.67 g, 12.75 mmol)

and to Boc-ethylenediamine (2.25 g, 14.03 mmol), a colorless oil is obtained after purification by chromatography column on silica gel (dichloromethane, methanol).

Yield: 5.7 g (76%).

$^1$H NMR (CDCl$_3$, ppm): 0.88 (3H); 1.25 (16H); 1.43 (9H); 1.58 (2.6H); 1.75-1.95 (1.4H); 2.15-2.30 (3H); 2.64 (0.5H); 2.95-3.10 (2.5H); 3.20-3.40 (4H); 3.45 (0.5H); 3.55 (0.2H); 3.66 (1H); 4.44 (1H); 4.50 (0.2H); 4.60 (0.6H); 4.99 (0.7H); 5.54 (0.5H); 5.95 (0.2H); 6.17 (1H); 6.60 (0.5H); 7.07 (0.5H); 7.20-7.40 (5H).

LC/MS (ESI): 587.4; (calculated ([M+H]$^+$): 587.8).

Molecule AA9

After a method similar to the one used for the preparation of molecule AA2 applied to molecule A22 (5.66 g, 9.65 mmol), the residue obtained after concentration under a vacuum of the reaction medium is dissolved in methanol and evaporated at reduced pressure, the operation being repeated 4 times to yield a white foam of molecule AA9 in the form of a hydrochloride salt.

Yield: 4.9 g (97%).

$^1$H NMR (DMSO-d$_6$, 120° C., ppm): 0.89 (3H); 1.26 (16H); 1.43 (2H); 1.68 (0.6H); 1.75-2.00 (3H); 2.05-2.25 (2.4H); 2.82-3.05 (5H); 3.38 (2H); 3.50-3.70 (1.4H); 4.25 (0.6H); 4.63 (0.4H); 4.77 (0.6H); 7.25-7.50 (5H); 7.55-8.20 (4H).

LC/MS (ESI): 487.4; (calculated ([M+H]$^+$): 487.7).

EXAMPLE AA10

MOLECULE AA10

Molecule A23: Product Obtained by the Reaction Between Molecule B7 and Boc-ethylenediamine HOBt (8.94 g, 58.37 mmol) and then Boc-ethylenediamine (112.20 g, 700.00 mmol) in solution in DCM (150 mL) are added successively to a solution of molecule B7 (190.00 g, 583.73 mmol) at 0° C. in DCM (2.9 L). EDC (123.10 g, 642.00 mmol) is then added, then the mixture is stirred for 17 h between 0° C. and ambient temperature. The reaction mixture is then washed with a saturated aqueous NaHCO$_3$ (2×1.5 L), an aqueous HCl solution 1 N (2×1.5 L), then a saturated aqueous NaCl solution (1.5 L), dried over Na$_2$SO$_4$, filtered and concentrated at reduced pressure. A white solid is obtained after recrystallization in acetonitrile.

Yield: 256.50 g (93%).

$^1$H NMR (CDCl$_3$, ppm): 0.88 (3H); 1.16-1.38 (20H); 1.44 (9H); 1.56-1.71 (2H); 1.78-2.45 (6H); 3.11-3.72 (6H); 4.30 (0.1H); 4.51 (0.9H); 4.87 (0.1H); 5.04 (0.9H); 6.87 (0.1H); 7.23 (0.9H).

LC/MS (ESI): 468.0; (calculated ([M+H]$^+$): 468.4).

Molecule AA10

According to a method similar to the method used for the preparation of molecule AA1 applied to molecule A23 (256.50 g, 548.43 mmol), a white solid of molecule AA10 in the form of a hydrochloride salt is obtained by trituration in pentane (1.6 L) and drying at reduced pressure at 40° C.

Yield: 220.00 g (99%).

$^1$H NMR (MeOD-d4, ppm): 0.90 (3H); 1.21-1.43 (20H); 1.54-1.66 (2H); 1.85-2.28 (4H); 2.39 (2H); 3.00-3.17 (2H); 3.30-3.40 (1H); 3.43-3.71 (3H); 4.29 (0.94H); 4.48 (0.06H).

LC/MS (ESI): 368.2; (calculated ([M+H]$^+$): 368.3).

EXAMPLE AA11

MOLECULE AA11

Molecule A24: Product Obtained by the Reaction Between Molecule B7 and Boc-1-amino-4,7,10-trioxa-13-tridecane amine By a method similar to the one used for the preparation of molecule A23 applied to molecule B7 (24.00 g, 73.73 mmol) and to Boc-1-amino-4,7,10-trioxa-13-tridecane amine (28.35 g, 88.48 mmol), an orange oil of molecule A24 is obtained.

Yield: 44.50 g (96%).

$^1$H NMR (CDCl$_3$, ppm): 0.87 (3H); 1.08-1.56 (20H); 1.43 (9H); 1.58-1.67 (2H); 1.70-2.00 (6H); 2.04-2.41 (4H); 3.16-3.77 (18H); 4.26-4.29 (0.2H); 4.50-4.54 (0.8H); 4.68-5.10 (1H); 6.74 (0.2H); 7.19 (0.8H).

LC/MS (ESI): 628.4; (calculated ([M+H]$^+$): 628.5).

Molecule AA11

After a method similar to the one used for the preparation for molecule AA1 applied to molecule A24 (43.40 g, 69.12 mmol), a white solid of molecule AA11 in the form of a hydrochloride salt is obtained after trituration 3 times in diethyl ether, solubilization of the residue in water, and lyophilization.

Yield: 38.70 g (98%).

$^1$H NMR (DMSO, ppm): 0.85 (3H); 1.07-1.38 (20H); 1.41-1.52 (2H); 1.55-1.66 (2H); 1.70-2.02 (6H); 2.08-2.30 (2H); 2.78-2.87 (2H); 3.00-3.16 (2H); 3.29-3.66 (14H); 4.16-4.22 (0.65H); 4.25-4.30 (0.35H); 7.74 (0.65H); 7.86 (3H); 8.10 (0.35H).

LC/MS (ESI): 528.4; (calculated ([M+H]$^+$): 528.4).

EXAMPLE AA12

MOLECULE AA12

Molecule A25: Product Obtained by the Reaction Between Molecule B4 and Boc-ethylenediamine By a method similar to the one used for the preparation of molecule A23 applied to molecule B4 (12.00 g, 40.35 mmol) and to Boc-ethylenediamine (7.76 g, 48.42 mmol), a colorless oil is obtained and used without other purification.

Yield: 17.40 g (94%).

$^1$H NMR (CDCl$_3$, ppm): 0.86 (3H); 1.11-1.68 (18H); 1.41 (9H); 1.80-2.38 (6H); 3.06-3.35 (4H); 3.37-3.49 (1H); 3.51-3.73 (1H); 4.26-4.31 (0.1H); 4.45-4.52 (0.9H); 4.91-5.19 (1H); 6.97 (0.1H); 7.23 (0.9H).

LC/MS (ESI): 440.4 (calculated ([M+H]$^+$): 440.3).

Molecule AA12

After a method similar to the one used for the preparation of molecule AA1 applied to molecule A25 (8.85 g, 20.13 mmol), a white solid of molecule AA12 is obtained after alkaline washing, concentration at reduced pressure, then recrystallization in acetonitrile.

Yield: 6.53 g (96%).

$^1$H NMR (DMSO, ppm): 0.85 (3H); 1.07-1.56 (20H); 1.68-2.03 (4H); 2.09-2.29 (2H); 2.50-2.58 (2H); 2.96-3.11 (2H); 3.21-3.59 (2H); 4.17-4.21 (0.65H); 4.25-4.29 (0.35H); 7.68 (0.65H); 8.00 (0.35H).

LC/MS (ESI): 340.3; (calculated ([M+H]$^+$): 340.3).

EXAMPLE AA13

MOLECULE AA13

Molecule A26: Product Obtained by Coupling Between Molecule B1 and Boc-ethylenediamine By a method similar to the one used for the preparation of molecule A23 applied to molecule B1 (30.00 g, 111.36 mmol) and to Boc-ethylenediamine (21.41 g, 133.64 mmol), a white solid is obtained after recrystallization in acetonitrile.

Yield: 34.90 g (76%).

$^1$H NMR (CDCl$_3$, ppm): 0.88 (3H); 1.10-1.70 (14H); 1.43 (9H); 1.80-1.91 (1H); 1.92-2.01 (1H); 2.04-2.42 (4H); 3.13-3.70 (6H); 4.27-4.31 (0.15H); 4.47-4.53 (0.85H); 4.83 (0.15H); 5.02 (0.85H); 6.85 (0.15H); 7.21 (0.85H).

LC/MS (ESI): 412.2; (calculated ([M+H]$^+$): 412.3).

Molecule AA13

After a method similar to the one used for the preparation of molecule AA1 applied to molecule A26 (34.90 g, 84.79 mmol), a white solid of molecule AA13 in the form of a hydrochloride salt is obtained after solubilization in a mixture of DCM/acetonitrile and concentration at reduced pressure.

Yield: 29.50 g (99%).

$^1$H NMR (DMSO, ppm): 0.85 (3H); 1.07-1.61 (14H); 1.70-2.06 (4H); 2.10-2.35 (2H); 2.76-2.87 (2H); 3.24-3.47 (3.25H); 3.56-3.64 (0.75H); 4.13-4.19 (0.75H); 4.31-4.36 (0.25H); 8.05-8.36 (3.75H); 8.50 (0.25H).

LC/MS (ESI): 312.2; (calculated ([M+H]$^+$): 312.3).

EXAMPLE AA14

MOLECULE AA14

Molecule A27: Product Obtained by Hydrogenation of Phytol

Platinum oxide (PtO$_2$, 1.15 g, 6.61 mmol) is added to a solution of phytol (30.00 g, 101.20 mmol) in THF (450 mL) under argon, and the mixture is placed under 1 bar of dihydrogen, then stirred for 4 h at ambient temperature. After filtration through celite rinsing with THF, a black oil of molecule A27 is obtained by concentration at reduced pressure.

Yield: 29.00 g (96%).

$^1$H NMR (CDCl$_3$, ppm): 0.84 (6H); 0.86 (6H); 0.89 (3H); 1.00-1.46 (22H); 1.46-1.68 (3H); 3.61-3.73 (2H).

Molecule A28: Product Obtained by Oxidation of Molecule A27

Tetrabutylammonium bromide (16.90 g, 52.45 mmol), acetic acid (150 mL, 2.62 mol), then KMnO$_4$ (46.05 g, 291.40 mmol) are added successively in small fractions, while maintaining the temperature between 16 and 19° C., to a solution of molecule A27 (29.0 g, 97.13 mmol) in a mixture of dichloroethane/water (485 mL/388 mL). The reaction mixture is then stirred for 4 h 30 at reflux, cooled to 10° C., then acidified until the pH is 1 with an HCl solution 6 N (20 mL). Na$_2$SO$_3$ (53.90 g) is then added gradually while maintaining the temperature at 10° C., and the mixture is stirred until the discoloration is complete. Water (200 mL) is added, the phases are separated, and the aqueous phase is extracted with DCM (2×400 mL). The combined organic phases are washed with an aqueous solution of HCl at 10% (20 mL), water (2×200 mL), a saturated aqueous NaCl solution (200 mL), dried over Na$_2$SO$_4$, filtered and concentrated at reduced pressure. A yellow oil of molecule A28 is obtained after purification by flash chromatography (eluent: cyclohexane, AcOEt).

Yield: 28.70 g (94%).

$^1$H NMR (CDCl$_3$, ppm): 0.84 (6H); 0.86 (6H); 0.97 (3H); 1.00-1.41 (20H); 1.52 (1H); 1.96 (1H); 2.14 (1H); 2.35 (1H); 11.31 (1H).

LC/MS (ESI): 311.1 (calculated ([M−H]$^-$): 311.3).

Molecule A29: Product Obtained by Coupling Between Molecule A28 and methyl L-prolinate By a method similar to the one used for the preparation of molecule A2 applied to molecule A28 (18.00 g, 57.59 mmol) and to the hydrochloride of methyl L-prolinate (14.31 g, 86.39 mmol), a yellow oil of molecule A29 is obtained after washing of the organic phase with a saturated aqueous NaHCO$_3$ solution (2×150 mL), an aqueous solution of HCl at 10% (2×150 mL), a saturated aqueous NaCl solution (2×150 mL), then drying over Na$_2$SO$_4$, filtration and concentration at reduced pressure.

Yield: 23.20 g (95%).

$^1$H NMR (DMSO-d$_6$, ppm): 0.78-0.89 (15H); 0.97-1.43 (20H); 1.43-1.56 (1H); 1.70-1.96 (4H); 1.96-2.32 (3H); 3.33-3.56 (2H); 3.59 (0.6H); 3.67 (2.4H); 4.27 (0.8H); 4.57 (0.2H).

LC/MS (ESI): 424.4 (calculated ([M+H]$^+$): 424.4).

Molecule A30: Product Obtained by the Saponification of Molecule A29

By a method similar to the one used for the preparation of molecule A21 applied to molecule A29 (21.05 g, 49.68 mmol), a yellow oil of molecule A30 is obtained.

Yield: 20.40 g (99%).

$^1$H NMR (DMSO-d$_6$, ppm): 0.77-0.91 (15H); 0.97-1.43 (20H); 1.43-1.56 (1H); 1.67-1.96 (4H); 1.96-2.29 (3H); 3.26-3.56 (2H); 4.20 (0.8H); 4.41 (0.2H).

LC/MS (ESI): 410.3 (calculated ([M+H]$^+$): 410.4).

Molecule A31: Product Obtained by the Coupling Between Molecule A30 and Boc-1-amino-4,7,10-trioxa-13-tridecane amine By a method similar to the one used for the preparation of molecule A23 applied to molecule A30 (8.95 g, 21.85 mmol) and to Boc-1-amino-4,7,10-trioxa-13-tridecane amine (8.40 g, 26.21 mmol), a colorless oil of molecule A31 is obtained after purification by flash chromatography (eluent: DCM, AcOEt, methanol).

Yield: 10.08 g (65%).

$^1$H NMR (DMSO-d$_6$, ppm): 0.78-0.89 (15H); 0.97-1.43 (29H); 1.43-1.55 (1H); 1.55-1.66 (4H); 1.71-2.30 (7H); 2.95 (2H); 3.00-3.19 (2H); 3.34-3.58 (14H); 4.17-4.29 (1H); 6.30-6.79 (1H); 7.67 (0.65H); 8.00 (0.35H).

LC/MS (ESI): 712.6 (calculated ([M+H]$^+$): 712.6).

Molecule AA14

After a method similar to the one used for the preparation of molecule AA1 applied to molecule A31 (10.08 g, 14.16 mmol), the residue obtained after concentration at reduced pressure is solubilized in DCM (200 mL), the organic phase is washed with an aqueous NaOH solution 2 N (2×100 mL), dried over $Na_2SO_4$, filtered and concentrated at reduced pressure. A colorless oil of molecule AA14 in the form of a neutral amine is obtained.

Yield: 8.23 g (95%).

$^1$H NMR (DMSO-$d_6$, ppm): 0.78-0.89 (15H); 0.97-1.43 (20H); 1.43-1.69 (6H); 1.69-2.30 (8H); 2.56 (2H); 2.99-3.19 (2H); 3.31-3.58 (14H); 4.15-4.29 (1H); 7.70 (0.65H); 8.04 (0.35H).

LC/MS (ESI): 612.5 (calculated ([M+H]$^+$): 612.5).

AB: Synthesis of the Co-Polyamino Acids Modified by Hydrophobic Molecules in which p=1

Statistical Co-Polyamino Acids of Formula VII or VIIa.

TABLE 1B

List of the co-polyamino acids of formula VII or VIIa synthesized according to the invention

| n° | co-polyamino acids bearing carboxylate charges and hydrophobic radicals |
|---|---|

AB1

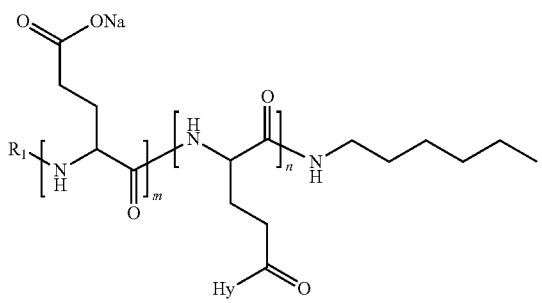

i = 0.05, DP (m + n) = 23

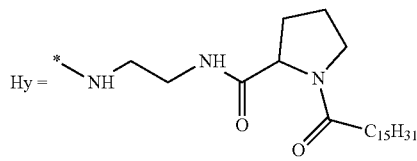

R1 = H or pyroglutamate

AB2

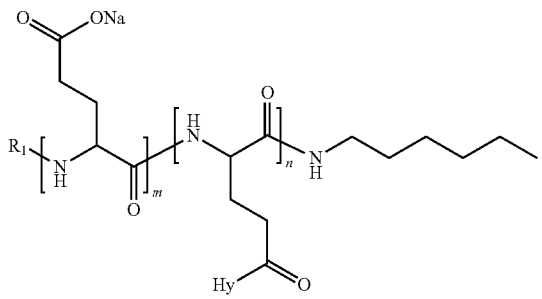

i = 0.05, DP (m + n) = 35

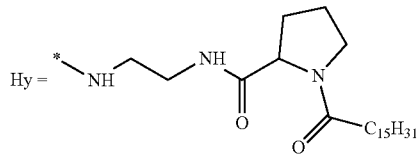

R1 = H or pyroglutamate

TABLE 1B-continued
List of the co-polyamino acids of formula VII or VIIa synthesized according to the invention
| n° | co-polyamino acids bearing carboxylate charges and hydrophobic radicals |
|---|---|
| AB3 | 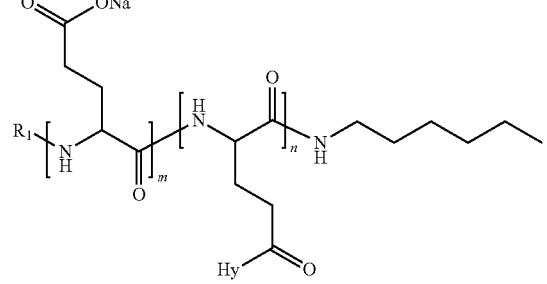 |
| | i = 0.10, DP (m + n) = 35 |
| | 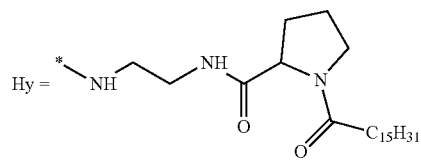 |
| | R1 = H or pyroglutamate |
| AB4 | 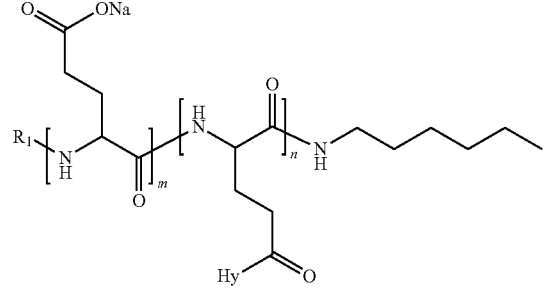 |
| | i = 0.052, DP (m + n) = 35 |
| | 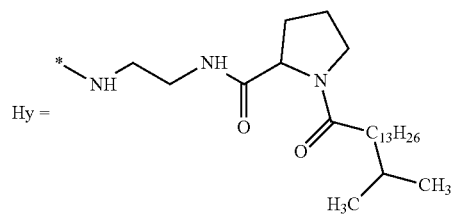 |
| | R1 = H or pyroglutamate |
| AB5 | 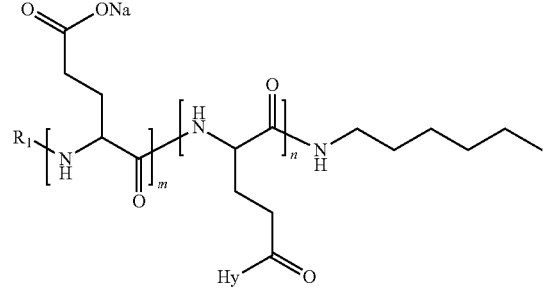 |
| | i = 0.05, DP (m + n) = 23 |

TABLE 1B-continued
List of the co-polyamino acids of formula VII or VIIa synthesized according to the invention
| n° | co-polyamino acids bearing carboxylate charges and hydrophobic radicals |
|---|---|
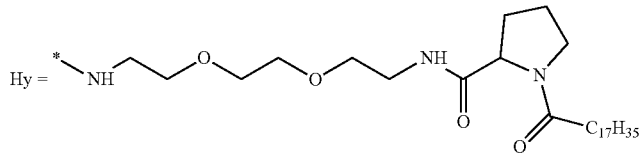
R1 = H ou pyroglutamate
AB6
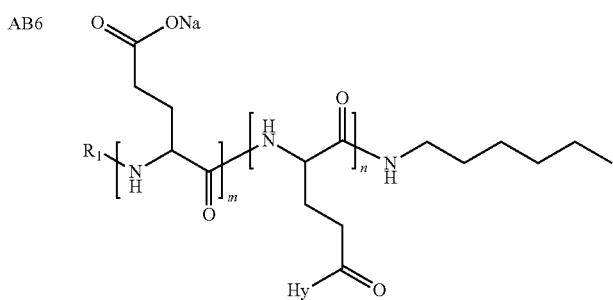
i = 0.025, DP (m + n) = 20
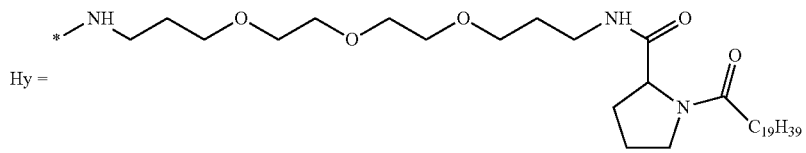
R1 = H or pyroglutamate
AB7
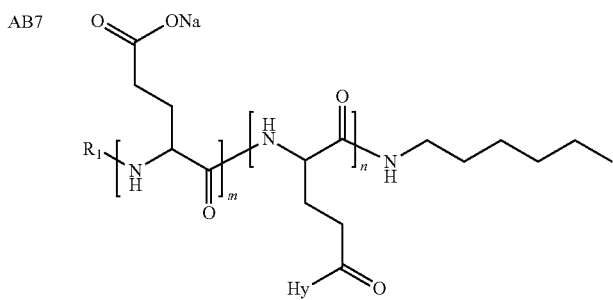
i = 0.03, DP (m + n) = 21
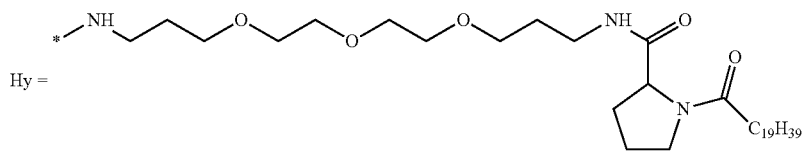
R1 = CH3—CO—, H or pyroglutamate TABLE 1B-continued
List of the co-polyamino acids of formula VII or VIIa synthesized according to the invention
| n° | co-polyamino acids bearing carboxylate charges and hydrophobic radicals |
|---|---|
| AB8 | 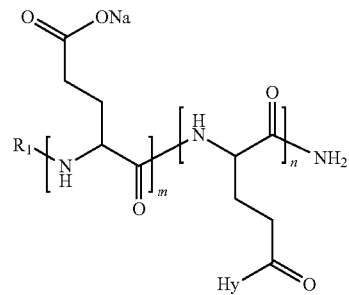 |
i = 0.03, DP (m + n) = 24
Hy = 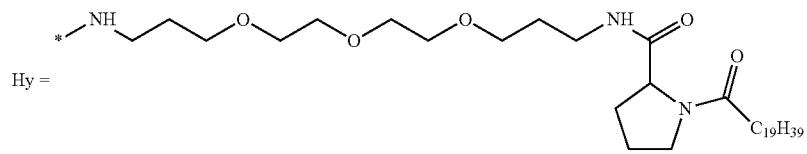
R1 = H or pyroglutamate
AB9 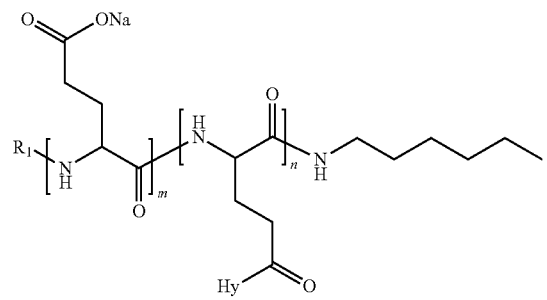
i = 0.12, DP (m + n) = 30
Hy = 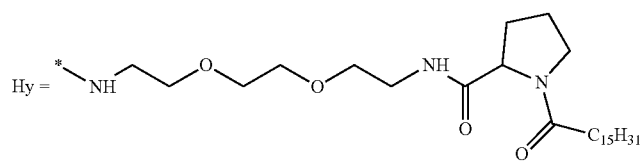
R1 = H or pyroglutamate
AB10 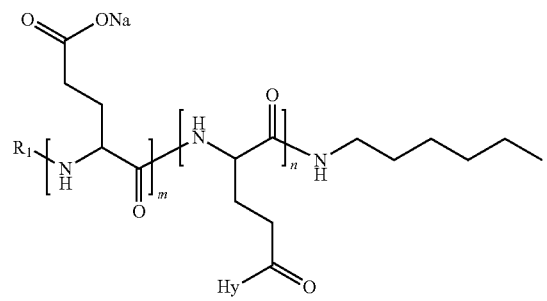
i = 0.8, DP (m + n) = 25

TABLE 1B-continued
List of the co-polyamino acids of formula VII or VIIa synthesized according to the invention
| n° | co-polyamino acids bearing carboxylate charges and hydrophobic radicals |
|---|---|
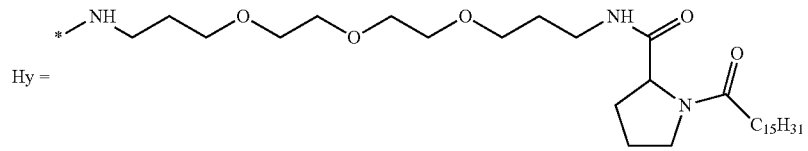
Hy =
R1 = CH3—CO— or H ou pyroglutamate
AB11
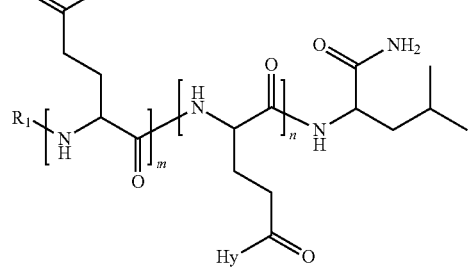
i = 0.05, DP (m + n) = 23
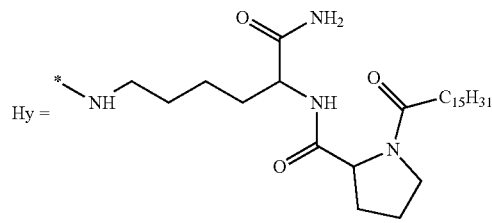
Hy =
R1 = H or pyroglutamate
AB12
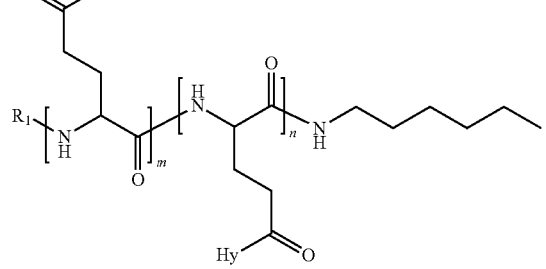
i = 0.04, DP (m + n) = 26
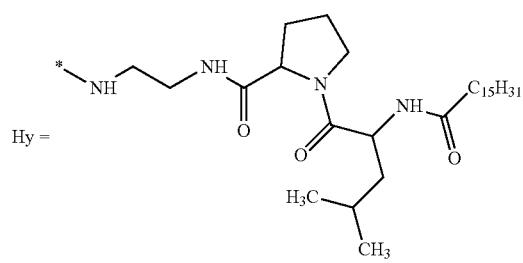
Hy =
R1 = H or pyroglutamate TABLE 1B-continued
List of the co-polyamino acids of formula VII or VIIa synthesized according to the invention
| n° | co-polyamino acids bearing carboxylate charges and hydrophobic radicals |
|---|---|
| AB13 | 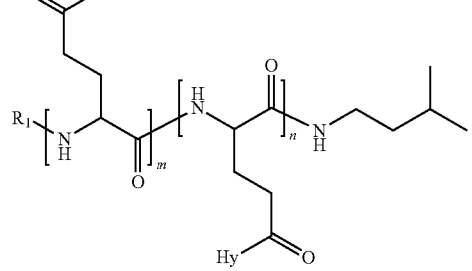 |
| | i = 0.12, DP (m + n) = 35 |
| | Hy = 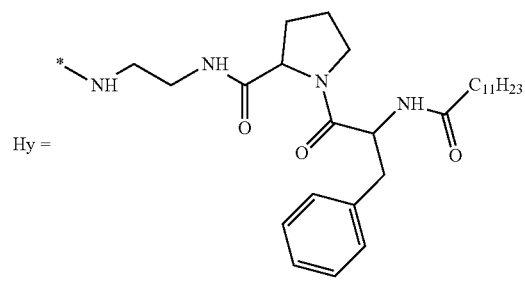 |
| | R1 = H or pyroglutamate |
| AB21 | 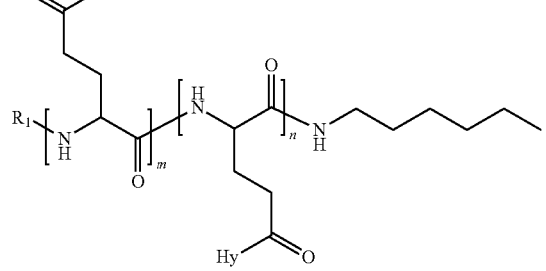 |
| | i = 0.056, DP (m + n) = 22 |
| | Hy = 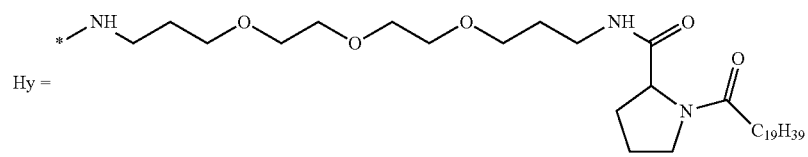 |
| | R1 = H or pyroglutamate |
| AB22 | 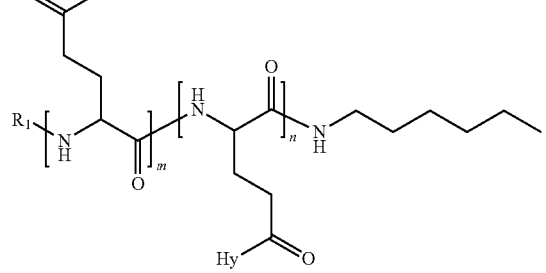 |
| | i = 0.16, DP (m + n) = 38 |

TABLE 1B-continued
List of the co-polyamino acids of formula VII or VIIa synthesized according to the invention
| n° | co-polyamino acids bearing carboxylate charges and hydrophobic radicals |
|---|---|
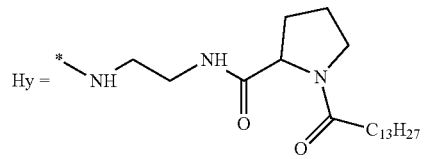
R1 = CH3CO or pyroglutamate
AB23
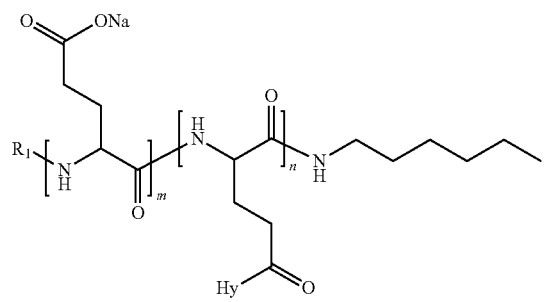
i = 0.10, DP (m + n) = 60
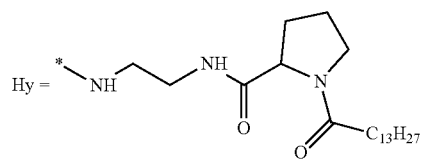
R1 = H or pyroglutamate
AB24
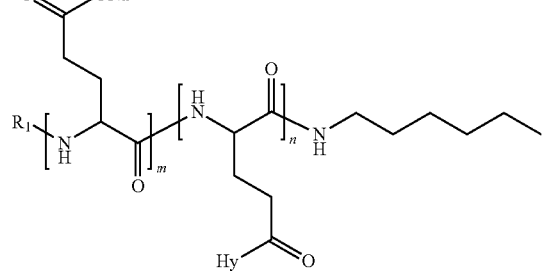
i = 0.15, DP (m + n) = 39
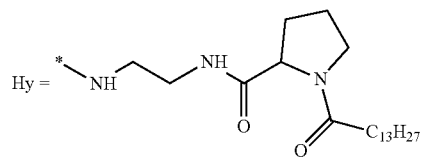
R1 = H or pyroglutamate TABLE 1B-continued
List of the co-polyamino acids of formula VII or VIIa synthesized according to the invention
| n° | co-polyamino acids bearing carboxylate charges and hydrophobic radicals |
|---|---|
| AB25 | 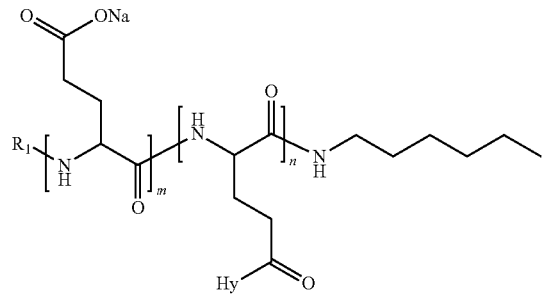<br>i = 0.20, DP (m + n) = 39<br>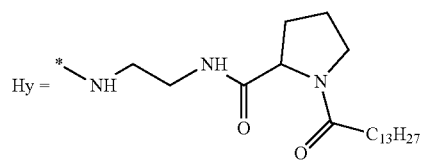<br>R1 = H or pyroglutamate |
| AB26 | 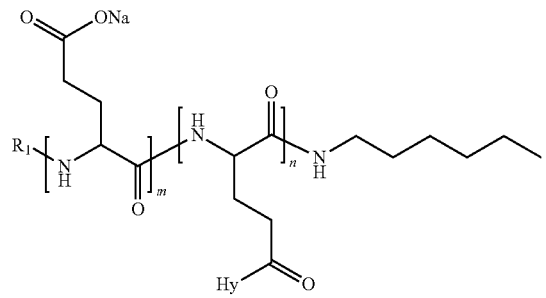<br>i = 0.20, DP (m + n) = 22<br>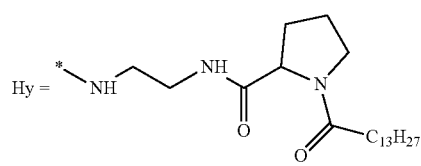<br>R1 = H or pyroglutamate |
| AB27 | 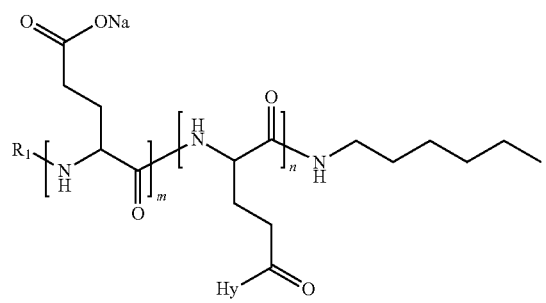<br>i = 0.15, DP (m + n) = 39 |

TABLE 1B-continued
List of the co-polyamino acids of formula VII or VIIa synthesized according to the invention
| n° | co-polyamino acids bearing carboxylate charges and hydrophobic radicals |
|---|---|
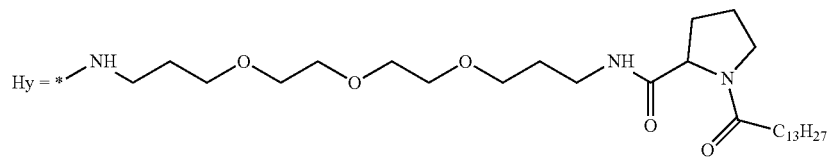
R1 = H or pyroglutamate
AB28
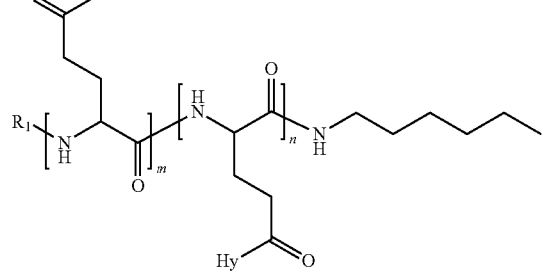
i = 0.15, DP (m + n) = 39
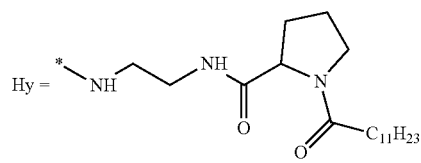
R1 = H or pyroglutamate
AB29
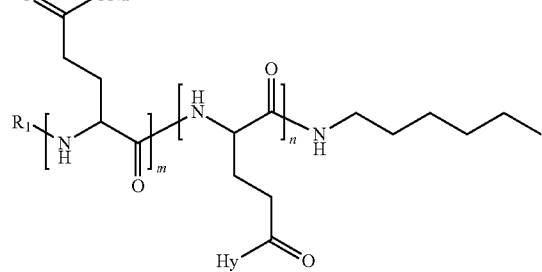
i = 0.15, DP (m + n) = 40
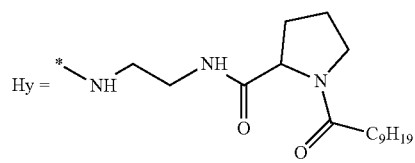
R1 = pyroglutamate TABLE 1B-continued
List of the co-polyamino acids of formula VII or VIIa synthesized according to the invention
| n° | co-polyamino acids bearing carboxylate charges and hydrophobic radicals |
|---|---|
| AB30 | 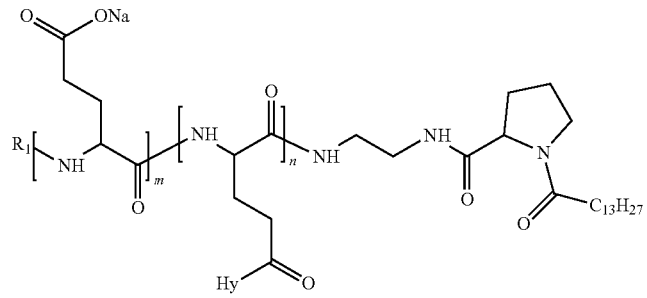
i = 0.125, DP (m + n) = 40
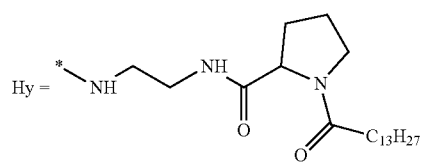
R1 = pyroglutamate |
| AB31 | 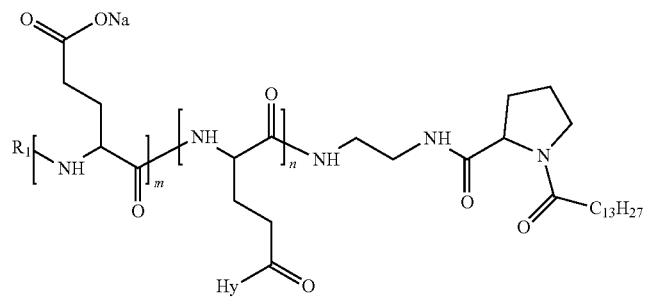
i = 0.175, DP (m + n) = 40
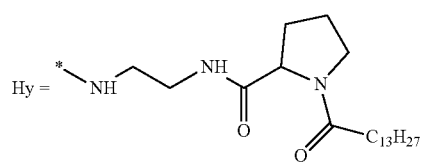
R1 = pyroglutamate |
| AB32 | 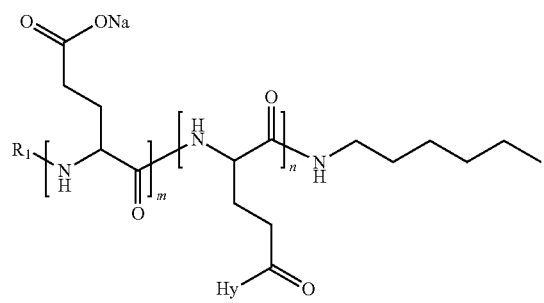
i = 0.109 DP (m + n) = 40 |

TABLE 1B-continued

List of the co-polyamino acids of formula VII or VIIa synthesized according to the invention

| n° | co-polyamino acids bearing carboxylate charges and hydrophobic radicals |
|---|---|
| | 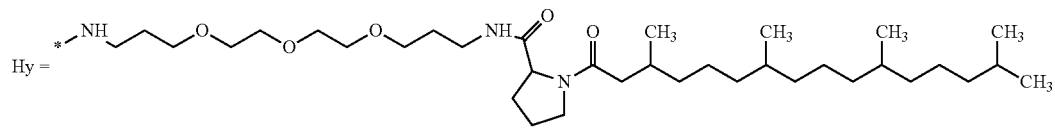 [SMILES: *NCCCOCCOCCOCCCNC(=O)C1CCCN1C(=O)CC(C)CCCC(C)CCCC(C)CCCC(C)C]<br>Hy =<br><br>R1 = pyroglutamate |

Defined Co-Polyamino Acids of Formula VII or VIIb

TABLE 1C list of the co-polyamino acids of formula VII or VIIb synthesized according to the invention.

| Example N° | co-polyamino acids bearing carboxylate charges and hydrophobic radicals |
|---|---|
| AB14 | 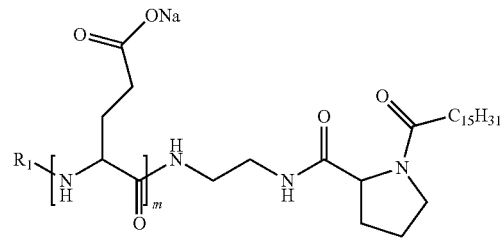<br>i = 0.04, DP (m) = 25<br>$R_1$ = H or pyroglutamate |
| AB15 | 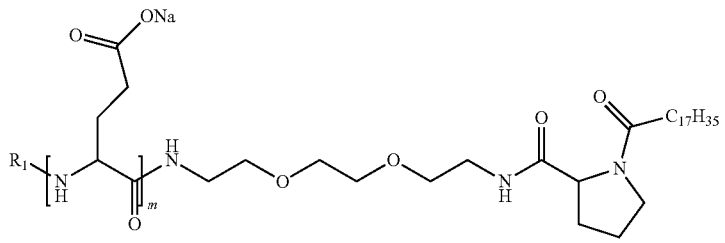<br>i = 0.033, DP (m) = 30<br>$R_1$ = H or pyroglutamate |
| AB16 | 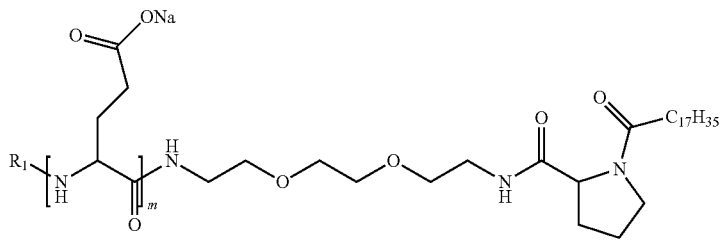<br>i = 0.021, DP (m) = 48<br>$R_1$ = H or pyroglutamate |

TABLE 1C-continued list of the co-polyamino acids of formula VII or VIIb synthesized according to the invention.

| Example N° | co-polyamino acids bearing carboxylate charges and hydrophobic radicals |
|---|---|
| AB17 | 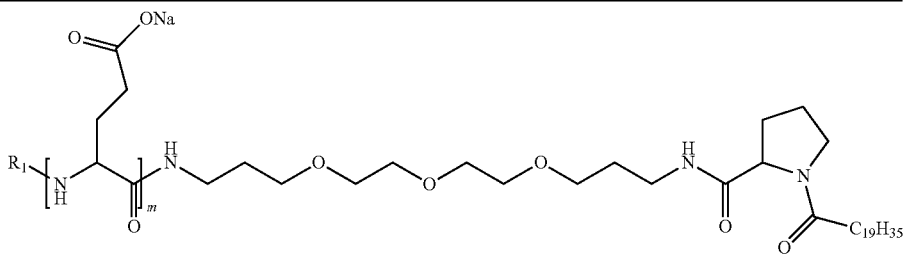<br>i = 0.038, DP (m) = 26<br>R1 = H or pyroglutamate |
| AB18 | 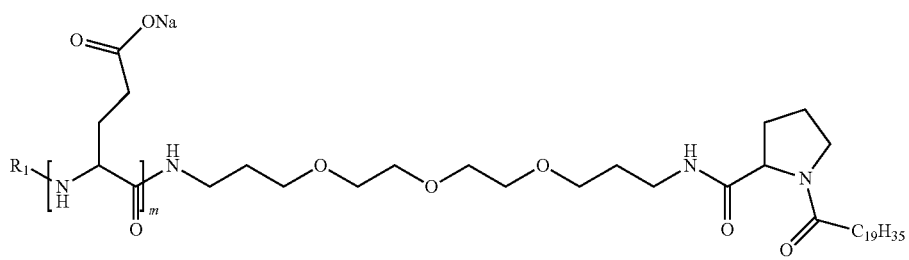<br>i = 0.045, DP (m) = 22<br>$R_1$ = H or pyroglutamate |
| AB19 | 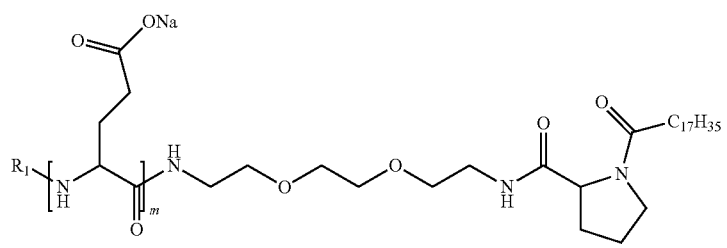<br>i = 0.015, DP (m) = 65<br>$R_1$ = H or pyroglutamate |
| AB20 | 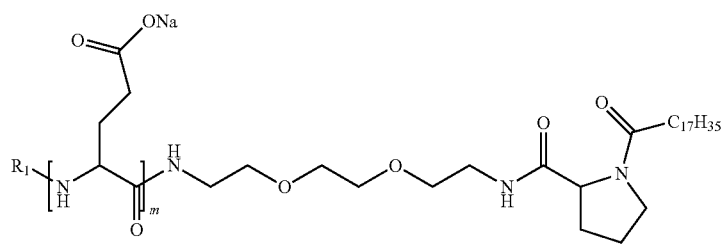<br>i = 0.017, DP (m) = 60<br>R1 = CH$_3$—CO—, H or pyroglutamate |

Co-Polyamino Acids of Formula VII or VIIa

EXAMPLE AB1: CO-POLYAMINO ACID AB1-SODIUM POLY-L-GLUTAMATE MODIFIED BY MOLECULE AA1 AND HAVING A NUMBER AVERAGE MOLECULAR WEIGHT (MN) OF 2900 G/MOL

Co-polyamino acid AB1-1: poly-L-glutamic acid of relative number average molecular weight (Mn) 3861 g/mol origi- nating from the polymerization of γ-benzyl-L-glutamate N-carboxyanhydride initiated by hexylamine.

In a round-bottom flask dried in the oven, γ-benzyl-L-glutamate N-carboxyanhydride (89.9 g, 341 mmol) is placed under a vacuum for 30 min, then anhydrous DMF (200 mL) is introduced. The mixture is then stirred under argon until the dissolution is complete, cooled to 4° C., then hexylamine (2.05 mL, 15.5 mmol) is introduced rapidly. The mixture is stirred between 4° C. and ambient temperature for 2 days. The reaction medium is then heated at 65° C. for 2 h, cooled to ambient temperature, then poured dropwise into diisopropyl ether (3 L) under stirring. The white precipitate is recovered by a filtration, washed with diisopropyl ether (2×20 mL), then dried under a vacuum at 30° C. to yield a poly(gamma-benzyl-L-glutamic acid) (PBLG).

A solution of hydrobromic acid (HBr) at 33% in acetic acid (240 mL, 1.37 mol) is added dropwise to a solution of PBLG (74.8 g) in trifluoroacetic acid (TFA, 340 mL) at 4° C. The mixture is stirred at ambient temperature for 2 h, then poured dropwise into a 1:1 (v/v) mixture of diisopropyl ether and water under stirring (4 L). After 2 h of stirring, the heterogeneous mixture is allowed to stand overnight. The white precipitate is recovered by filtration, washed with a 1:1 (v/v) mixture of diisopropyl ether and water (340 mL), then with water (340 mL).

The solid obtained is then solubilized in water (1.5 L) by adjusting the pH to 7 by adding an aqueous sodium hydroxide solution 10 N, then an aqueous sodium hydroxide solution 1 N. After solubilization, the theoretical concentration is adjusted to 20 g/L theoretical by addition of water to obtain a final volume of 2.1 L.

The solution is filtered through a 0.45 µm filter, then purified by ultrafiltration against a NaCl solution 0.9%, then water until the conductimetry of the permeate is less than 50 µS/cm. The solution of co-polyamino acid is then concentrated until a final volume of 1.8 L is obtained.

The aqueous solution is then acidified by adding a hydrochloric acid solution 37% until a pH of 2 is reached. After 4 h of stirring, the precipitate obtained is filtered, washed with water (2×340 mL), then dried under a vacuum at 30° C. to yield a poly-L-glutamic acid of number average molecular weight (Mn) 3861 g/mol with respect to a polyoxyethylene standard (PEG).

Co-polyamino Acid AB1

The co-polyamino acid AB1-1 (10.0 g) is solubilized in DMF (700 mL) at 30° C., then cooled to 0° C. Molecule AA1 in the form of a hydrochloride salt (1.64 g, 3.8 mmol) is suspended in DMF (23 mL), and triethylamine (0.39 g, 3.8 mmol) is then added, and the mixture is heated slightly under stirring until the dissolution is complete. N-methylmorpholine (NMM, 7.6 g, 75 mmol) in DMF (14 mL) and ethyl chloroformate (ECF, 8.2 g, 75 mmol) are added to the solution of co-polyamino acid at 0° C. After 10 min at 0° C., the solution containing molecule AA1 is added and the mixture is maintained at 30° C. for 2 h. The reaction mixture is poured dropwise into 5.5 L of water containing NaCl at 15 wt % and HCl (pH 2), and then allowed to stand overnight. The precipitate is collected by filtration and dried under a vacuum for approximately 30 min. The white solid obtained is dissolved in water (500 mL), and the pH is adjusted to 7 by slow addition of an aqueous NaOH solution 1 N. After filtration through a 0.45 µm filter, the clear solution obtained is purified by ultrafiltration against a solution of NaCl 0.9%, then water, until the conductimetry of the permeate is less than 50 µS/cm. After removal, the solution is filtered through a 0.2 µm filter and stored at 2-8° C.

Dry extract: 24.9 mg/g.

An average degree of polymerization (DP) of 23 is estimated by $^1$H NMR in $D_2O$ by comparing the integration of the signals from the grafted hydrophobe with the integration of the signals from the main chain.

Based on $^1$H NMR: i=0.05.

The calculated average molecular weight of co-polyamino acid AB1 is calculated based on the molecular weights of the radicals $R_1$ and $R_2$, the aspartate and/or glutamate residues (including an amide bond), the hydrophobic radical, DS and DP.

The calculated average molecular weight of co-polyamino acid AB1 is 3945 g/mol.

HPLC-aqueous SEC (calibrant PEG): Mn=2900 g/mol.

EXAMPLE AB2: CO-POLYAMINO ACID AB2-SODIUM POLY-L-GLUTAMATE MODIFIED BY MOLECULE AA1 AND HAVING A NUMBER AVERAGE MOLECULAR WEIGHT (MN) OF 3700 G/MOL

By a method similar to the one used for the preparation of co-polyamino acid AB1 applied to the hydrochloride salt of molecule AA1 (1.64 g, 3.8 mmol) and to a poly-L-glutamic acid of relative Mn 5200 g/mol (10.0 g) obtained by a method similar to the one used for the preparation of co-polyamino acid AB1-1, a sodium poly-L-glutamate modified by molecule AA1 is obtained.

Dry extract: 14.1 mg/g.

DP (estimated based on $^1$H NMR): 35.

Based on $^1$H NMR: i=0.05.

The calculated average molecular weight of co-polyamino acid AB2 is 5972 g/mol.

HPLC-aqueous SEC (calibrant PEG): Mn=3700 g/mol.

EXAMPLE AB3: CO-POLYAMINO ACID AB3-SODIUM POLY-L-GLUTAMATE MODIFIED BY MOLECULE AA1 AND HAVING A NUMBER AVERAGE MOLECULAR WEIGHT (MN) OF 4900 G/MOL

By a method similar to the one used for the preparation of co-polyamino acid AB1 applied to the hydrochloride salt of molecule AA1 (3.30 g, 7.6 mmol) and to a poly-L-glutamic acid of relative number average weight (Mn) 5200 g/mol (10.0 g) obtained by a method similar to the one used for the preparation of co-polyamino acid AB1-1, a sodium poly-L-glutamate modified by molecule AA1 is obtained.

Dry extract: 23.4 mg/g.

DP (estimated based on $^1$H NMR): 35.

The calculated average molecular weight of co-polyamino acid AB3 is 6594 g/mol.

Based on $^1$H NMR: i=0.10.

HPLC-aqueous SEC (calibrant PEG): Mn=4900 g/mol.

EXAMPLE AB4: CO-POLYAMINO ACID AB4-SODIUM POLY-L-GLUTAMATE MODIFIED BY MOLECULE AA2 AND HAVING A NUMBER AVERAGE MOLECULAR WEIGHT (MN) OF 1800 G/MOL

By a method similar to the one used for the preparation of co-polyamino acid AB1 applied to the hydrochloride salt of molecule AA2 (1.09 g, 2.4 mmol) and to a poly-L-glutamic acid of average weight Mn=5600 g/mol (6.3 g) obtained by a method similar to the one used for the preparation of co-polyamino acid AB1-1, but with a step of deprotection of the benzyl esters using trimethylsilane iodide according to the protocol described in the publication Subramanian G. et al., J. Am. Chem. Soc. 2000, 122, 26-34, a sodium poly-L-glutamate modified by molecule AA2 is obtained.

Dry extract: 21.5 mg/g.

DP (estimated based on $^1$H NMR): 35.

Based on $^1$H NMR: i=0.052.

The calculated average molecular weight of co-polyamino acid AB4 is 6022 g/mol.

HPLC-aqueous SEC (calibrant PEG): Mn=1800 g/mol.

EXAMPLE AB5: CO-POLYAMINO ACID AB5-SODIUM POLY-L-GLUTAMATE MODIFIED BY MOLECULE AA6 AND HAVING A NUMBER AVERAGE MOLECULAR WEIGHT (MN) OF 2600 G/MOL

By a method similar to the one used for the preparation of co-polyamino acid AB1 applied to the hydrochloride salt of molecule AA6 (2.06 g, 3.8 mmol) and to a poly-L-glutamic acid (9.8 g) obtained by a method similar to the one used for the preparation of co-polyamino acid AB1-1, a sodium poly-L-glutamate modified by molecule AA6 is obtained.

Dry extract: 20.9 mg/g.

DP (estimated based on 1H NMR): 23.

Based on 1H NMR: i=0.05.

The calculated average molecular weight of co-polyamino acid AB5 is 4079 g/mol.

HPLC-aqueous SEC (calibrant PEG): Mn=2600 g/mol.

EXAMPLE AB6: CO-POLYAMINO ACID AB6-SODIUM POLY-L-GLUTAMATE MODIFIED BY MOLECULE AA7 AND HAVING A NUMBER AVERAGE MOLECULAR WEIGHT (MN) OF 4000 G/MOL

A poly-L-glutamic acid of average weight Mn=3500 g/mol and degree of polymerization 22 (10.0 g) obtained by a method similar to the one used for the preparation of co-polyamino acid AB1-1 is solubilized in DMF (420 mL) at 30-40° C., then maintained at this temperature. In parallel, the hydrochloride salt of molecule AA7 (1.47 g, 2.3 mmol) is suspended in DMF (12 mL), and triethylamine (0.23 g, 2.3 mmol) is added, then the mixture is heated slightly under stirring until the dissolution is complete. NMM (7.6 g, 75 mmol), the solution of AA7 and then the N-oxide of 2-hydroxypyridine (HOPO, 0.84 g, 7.5 mmol) are added successively to the solution of co-polyamino acid in DMF. The reaction medium is then cooled to 0° C., then EDC (1.44 g, 7.5 mmol) is added, and the medium is brought again to ambient temperature in 2 h. The reaction medium is filtered through a 0.2 mm woven filter and poured dropwise into 3.5 L of water containing NaCl at 15 wt % and HCl (pH 2) under stirring. At the end of the addition, the pH is readjusted to 2 with an HCl solution 37%, and the suspension is allowed to stand overnight. The precipitate is collected by filtration, then rinsed with 100 mL of water. The white solid obtained is solubilized in 500 mL of water by slow addition of an aqueous solution of NaOH 1 N until the pH is 7 under stirring, then the solution is filtered through a 0.45 µm filter. The clear solution obtained is purified by ultrafiltration against a solution of NaCl 0.9%, then water, until the conductimetry of the permeate is less than 50 µS/cm. The solution is filtered through a 0.2 µm filter and stored at 2-8° C.

Dry extract: 21.6 mg/g.

DP (estimated based on 1H NMR): 20.

Based on 1H NMR: i=0.025.

The calculated average molecular weight of co-polyamino acid AB6 is 3369 g/mol.

HPLC-aqueous SEC (calibrant PEG): Mn=4000 g/mol.

EXAMPLE AB7: CO-POLYAMINO ACID AB7-SODIUM POLY-L-GLUTAMATE CAPPED AT ONE OF ITS ENDS BY AN ACETYL GROUP AND MODIFIED BY MOLECULE AA7 AND HAVING A NUMBER AVERAGE MOLECULAR Weight (Mn) of 3300 g/mol Co-polyamino acid AB7-1: poly-L-glutamic acid of relative number average molecular weight (Mn) 3600 g/mol and DP 21 originating from the polymerization of γ-benzyl-L-glutamate N-carboxyanhydride, initiated by hexylamine and capped at one of its ends by an acetyl group.

γ-Benzyl-L-glutamate N-carboxyanhydride (Glu(OBn)-NCA, 100.0 g, 380 mmol) is placed for 30 min under a vacuum in a round-bottom flask dried in the oven, then anhydrous DMS (225 mL) is introduced. The mixture is then stirred under argon until the dissolution is complete, cooled to 4° C., then hexylamine (1.78 g, 17 mmol) is introduced rapidly. The mixture is stirred between 4° C. and ambient temperature for 2 days, then precipitated in diisopropyl ether (3.4 L). The precipitate is recovered by filtration, washed two times with diisopropyl ether (225 mL), then dried to yield a white solid which is dissolved in 450 mL of THF. DIPEA (31 mL, 176 mmol) and then acetic anhydride (17 mL, 176 mmol) are added successively to this solution. After stirring overnight at ambient temperature, the solution is poured slowly into diisopropyl ether (3 L) under stirring. After 1 h of stirring, the precipitate is filtered, washed two times with diisopropyl ether (250 mL), then dried under a vacuum at 30° C. to yield a poly(gamma-benzyl-L-glutamic acid) capped at one of its ends by an acetyl group.

A solution of hydrobromic acid (HBr) at 33% in acetic acid (235 mL) is added dropwise to a solution of the above co-polyamino acid (72 g) in trifluoroacetic acid (TFA, 335 mL) at 4° C. The mixture is stirred at ambient temperature for 3 h 30, then poured dropwise into a 1:1 (v/v) mixture of diisopropyl ether and water under stirring (4 L). After 2 h of stirring, the heterogeneous mixture is allowed to stand overnight. The white precipitate is recovered by filtration, washed with a 1:1 (v/v) mixture of diisopropyl ether and water (340 mL), then with water (340 mL).

The solid obtained is then solubilized in water (1.5 L) by adjusting the pH to 7 by addition of an aqueous solution of sodium hydroxide 10 N, then an aqueous solution of sodium hydroxide 1 N. After solubilization, the solution is diluted by addition of water to obtain a final volume of 2.1 L. The solution is filtered through a 0.45 µm filter, then purified by ultrafiltration against a solution of NaCl 0.9%, then water until the conductimetry of the permeate is less than 50 µS/cm. The solution of co-polyamino acid is then concentrated until a final volume of 1.8 L is obtained.

The aqueous solution is then acidified by addition of a hydrochloric acid solution 37% until a pH of 2 is reached. After 4 h of stirring, the precipitate obtained is filtered, washed with water (330 mL), then dried under a vacuum at 30° C. to yield a poly-L-glutamic acid of number average molecular weight (Mn) 3600 g/mol with respect to a polyoxyethylene standard (PEG) and of average degree of polymerization 21.

Co-Polyamino Acid AB7:

By a method similar to the one used for the preparation of co-polyamino acid AB6 applied to the hydrochloride salt of molecule AA7 (1.43 g, 2.2 mmol) and to co-polyamino acid AB7-1 (10.0 g), a sodium poly-L-glutamate acid modified by molecule AA7 is obtained.

Dry extract: 24.3 mg/g.
DP (estimated based on 1H NMR): 21.
Based on 1H NMR: i=0.03.
The calculated average molecular weight of co-polyamino acid AB7 is 3677 g/mol.
HPLC-aqueous SEC (calibrant PEG): Mn=3300 g/mol.

EXAMPLE AB8: CO-POLYAMINO ACID AB8-SODIUM POLY-L-GLUTAMATE MODIFIED BY MOLECULE AA7 AND HAVING A NUMBER AVERAGE MOLECULAR WEIGHT (MN) OF 3600 G/MOL

Co-polyamino acid AB8-1: poly-L-glutamic acid of number average molecular weight (Mn) 3800 g/mol and degree of polymerization 24 originating from the polymerization of γ-methyl-L-glutamate N-carboxyanhydride initiated by ammonia.

By a method similar to the one described in the patent application FR-A-2 801 226 applied to γ-methyl-L-glutamic acid N-carboxyanhydride (25.0 g, 133.6 mmol) and to an ammonia solution 0.5 N in dioxane (12.1 mL, 6.05 mmol), a poly-L-glutamic acid is obtained.

Co-Polyamino Acid AB8:

By a method similar to the one used for the preparation of co-polyamino acid AB6 applied to the hydrochloride salt of molecule AA7 (2.1 g, 3.24 mmol) and to co-polyamino acid AB8-1 (14.3 g), a sodium poly-L-glutamate modified by molecule AA7 is obtained.

Dry extract: 25.2 mg/g.
DP (estimated based on 1H NMR): 24.
Based on $^1$H NMR: i=0.03.
The calculated average molecular weight of co-polyamino acid AB8 is 4099 g/mol.
HPLC-aqueous SEC (calibrant PEG): Mn=3600 g/mol.

EXAMPLE AB9: CO-POLYAMINO ACID AB9-SODIUM POLY-L-GLUTAMATE MODIFIED BY MOLECULE AA3 AND HAVING A NUMBER AVERAGE MOLECULAR WEIGHT (MN) OF 3200 G/MOL

By a method similar to the one used for the preparation of co-polyamino acid AB1 applied to the hydrochloride salt of molecule AA3 and to a poly-L-glutamic acid obtained by a method similar to the one used for the preparation of co-polyamino acid AB1-1, a sodium poly-L-glutamate modified by molecule AA3 is obtained.

Dry extract: 14.7 mg/g.
DP (estimated based on $^1$H NMR): 30.
Based on $^1$H NMR: i=0.12.
The calculated average molecular weight of co-polyamino acid AB9 is 6192 g/mol.
HPLC-aqueous SEC (calibrant PEG): Mn=3200 g/mol.

EXAMPLE AB10: CO-POLYAMINO ACID AB10-SODIUM POLY-L-GLUTAMATE MODIFIED BY MOLECULE AA4 AND HAVING A NUMBER AVERAGE MOLECULAR WEIGHT (MN) OF 2600 G/MOL

By a method similar to the one used for the preparation of co-polyamino acid AB7 applied to the hydrochloride salt of molecule AA4 and to a poly-L-glutamic acid obtained by a method similar to the one used for the preparation of co-polyamino acid AB1-1, a sodium poly-L-glutamate modified by molecule AA4 is obtained.

Dry extract: 18.3 mg/g.
DP (estimated based on $^1$H NMR): 25.
Based on $^1$H NMR: i=0.08.
The calculated average molecular weight of co-polyamino acid AB10 is 4870 g/mol.
HPLC-aqueous SEC (calibrant PEG): Mn=2600 g/mol.

EXAMPLE AB11: CO-POLYAMINO ACID AB11-SODIUM POLY-L-GLUTAMATE MODIFIED BY MOLECULE AA5 AND HAVING A NUMBER AVERAGE MOLECULAR WEIGHT (MN) OF 2700 G/MOL

By a method similar to the one used for the preparation of co-polyamino acid AB6 applied to the hydrochloride salt of molecule AA5 and to a poly-L-glutamic acid obtained by a method similar to the one used for the preparation of co-polyamino acid AB1-1, a sodium poly-L-glutamate modified by molecule AA5 is obtained.

Dry extract: 20.2 mg/g.
DP (estimated based on $^1$H NMR): 23.
Based on $^1$H NMR: i=0.05.
The calculated average molecular weight of co-polyamino acid AB11 is 4072 g/mol.
HPLC-aqueous SEC (calibrant PEG): Mn=2700 g/mol.

EXAMPLE AB12: CO-POLYAMINO ACID AB12-SODIUM POLY-L-GLUTAMATE MODIFIED BY MOLECULE AA8 AND HAVING A NUMBER AVERAGE MOLECULAR WEIGHT (MN) OF 3000 G/MOL

By a method similar to the one used for the preparation of co-polyamino acid AB1 applied to the hydrochloride salt of molecule AA8 and to a poly-L-glutamic acid obtained by a method similar to the one used for the preparation of co-polyamino acid AB1-1, a sodium poly-L-glutamate modified by molecule AA8 is obtained.

Dry extract: 19.5 mg/g.
DP (estimated based on $^1$H NMR): 26.
Based on $^1$H NMR: i=0.04.
The calculated average molecular weight of co-polyamino acid AB12 is 4477 g/mol.
HPLC-aqueous SEC (calibrant PEG): Mn=3000 g/mol.

EXAMPLE AB13: CO-POLYAMINO ACID AB13-SODIUM POLY-L-GLUTAMATE MODIFIED BY MOLECULE AA9 AND HAVING A NUMBER AVERAGE MOLECULAR WEIGHT (NM) OF 3300 G/MOL

By a method similar to the one used for the preparation of co-polyamino acid AB6 applied to the hydrochloride salt of molecule AA9 and to a poly-L-glutamic acid obtained by a method similar to the one used for the preparation of co-polyamino acid AB1-1 using isoamylamine as initiator instead of hexylamine, a sodium poly-L-glutamate modified by molecule AA9 is obtained.

Dry extract: 22.3 mg/g.
DP (estimated based on $^1$H NMR): 35.
Based on $^1$H NMR: i=0.12.
The calculated average molecular weight of co-polyamino acid AB13 is 7226 g/mol.
HPLC-aqueous SEC (calibrant PEG): Mn=3300 g/mol.

EXAMPLE AB21: CO-POLYAMINO ACID AB21-SODIUM POLY-L-GLUTAMATE MODIFIED BY MOLECULE AA7 AND HAVING A NUMBER AVERAGE MOLECULAR WEIGHT (MN) OF 3400 G/MOL

By a method similar to the one used for the preparation of co-polyamino acid AB6 applied to the hydrochloride salt of molecule AA7 (2.44 g, 2.4 mmol) and to a poly-L-glutamic acid (10 g) obtained by a method similar to the one used for the preparation of co-polyamino acid AB1-1, a sodium poly-L-glutamate modified by molecule AA7 is obtained.
Dry extract: 22.7 mg/g.
DP (estimated based on $^1$H NMR): 22.
Based on $^1$H NMR: i=0.056.
The calculated average molecular weight of co-polyamino acid AB21 is 4090 g/mol.
HPLC-aqueous SEC (calibrant PEG): Mn=3400 g/mol.

EXAMPLE AB22: CO-POLYAMINO ACID AB22-SODIUM POLY-L-GLUTAMATE CAPPED AT ONE OF ITS ENDS BY AN ACETYL GROUP AND MODIFIED BY MOLECULE AA10 AND HAVING A NUMBER AVERAGE MOLECULAR WEIGHT (MN) OF 4000 G/MOL

The hydrochloride salt of molecule AA10 (4.56 g, 11.29 mmol) is dissolved in chloroform (60 mL) and triethylamine (1.14 g, 11.29 mmol) is added. To a solution of co-polyamino acid (10.0 g, 75.3 mmol) obtained by a method similar to the one used for the preparation of co-polyamino acid B7-1 in DMF (420 mL), NMM (7.6 g, 75.26 mmol), then HOPO (2.51 g, 22.58 mmol) are added successively. The reaction medium is then cooled to 0° C., then EDC (4.33 g, 22.58 mmol) is added, the medium is stirred for 1 h at 0° C., then the solution of molecule AA10 is added. The reaction mixture is stirred for 2 h between 0° C. and ambient temperature. The reaction medium is filtered through a 0.2 mm woven filter and poured dropwise into 3.95 L of water containing NaCl at 15 wt % and HCl (pH 2) under stirring. At the end of the addition, the pH is readjusted to 2 with a solution of HCl 37% and the suspension is allowed to stand overnight. The precipitate is collected by a filtration, then solubilized in 780 mL of water by slow addition of an aqueous NaOH solution 1 N until the pH is 7 under stirring. After filtration through a 0.45 μm filter, the solution is diluted by addition of water, then acetone is added to obtain a solution containing 30 wt % of acetone. This solution is filtered through an activated charcoal filter, then the acetone is distilled (40° C., 100 mbar). After filtration through a 0.45 μm filter, the product is purified by ultrafiltration against an aqueous solution of NaCl at 0.9%, a carbonate buffer solution (150 mM), an aqueous solution of NaCl at 0.9%, a phosphate buffer solution (150 mM), an aqueous solution of NaCl at 0.9%, then water until the conductimetry of the permeate is less than 50 μS/cm. The solution is then concentrated, filtered through a 0.2 μm filter and stored at 2-8° C.
Dry extract: 19.7 mg/g.
DP (estimated based on $^1$H NMR): 38.
Based on $^1$H NMR: i=0.16.
The calculated average molecular weight of co-polyamino acid AB22 is 7877 g/mol.
HPLC-organic SEC (calibrant PEG): Mn=4000 g/mol.

EXAMPLE AB23: CO-POLYAMINO ACID AB23-SODIUM POLY-L-GLUTAMATE AND MODIFIED BY MOLECULE AA10 AND HAVING A NUMBER AVERAGE MOLECULAR WEIGHT (MN) OF 7600 G/MOL

Co-polyamino acid AB23-1: poly-L-glutamic acid originating from the polymerization of γ-benzyl-L-glutamate N-carboxyanhydride initiated by hexylamine and capped at one of its ends by a pyroglutamate group.

A poly-L-glutamic acid (20.0 g) obtained by a method similar to the one used for the preparation of co-polyamino acid AB1-1 is solubilized in DMF at 80° C., then maintained at this temperature. After 24 h, the reaction medium is poured into a solution of NaCl at 15% and at pH 2. After 4 h, the white solid is collected by filtration, rinsed with water, then dried under a vacuum at 30° C.
Co-Polyamino Amide AB23
By a method similar to the one used for the preparation of co-polyamino acid AB22 applied to the hydrochloride salt of molecule AA10 (2.742 g, 6.79 mmol) and to co-polyamino acid AB23-1 (9.0 g), a sodium poly-L-glutamic acid modified by molecule AA10 is obtained.
Dry extract: 21.9 mg/g.
DP (estimated based on $^1$H NMR): 60.
Based on $^1$H NMR: i=0.1.
The calculated average molecular weight of co-polyamino acid AB23 is 11,034 g/mol.
HPLC-organic SEC (calibrant PEG): Mn=7600 g/mol.

EXAMPLE AB24: CO-POLYAMINO ACID AB24-SODIUM POLY-L-GLUTAMATE AND MODIFIED BY MOLECULE AA10 AND HAVING A NUMBER AVERAGE MOLECULAR WEIGHT (MN) OF 4300 G/MOL

By a method similar to the one used for the preparation of co-polyamino acid AB23 applied to the hydrochloride salt of molecule AA10 and to a poly-L-glutamic acid obtained by a method similar to the one used for the preparation of co-polyamino acid AB23-1, a sodium poly-L-glutamate modified by molecule AA10 is obtained.
Dry extract: 22.9 mg/g.
DP (estimated based on $^1$H NMR): 39.
Based on $^1$H NMR: i=0.15.
The calculated average molecular weight of co-polyamino acid AB24 is 7870 g/mol.
HPLC-organic SEC (calibrant PEG): Mn=4300 g/mol.

EXAMPLE AB25: CO-POLYAMINO ACID AB25-SODIUM POLY-L-GLUTAMATE AND MODIFIED BY MOLECULE AA10 AND HAVING A NUMBER AVERAGE MOLECULAR WEIGHT (MN) OF 4200 G/MOL

By a method similar to the one used for the preparation of co-polyamino acid AB23 applied to the hydrochloride salt of molecule AA10 and to a poly-L-glutamic acid obtained by a method similar to the one used for the preparation of co-polyamino acid AB23-1, a sodium poly-L-glutamate modified by molecule AA10 is obtained.
Dry extract: 25.9 mg/g.
DP (estimated based on $^1$H NMR): 39.

Based on ¹H NMR: i=0.2.
The calculated average molecular weight of co-polyamino acid AB25 is 8509 g/mol.
HPLC-organic SEC (calibrant PEG): Mn=4200 g/mol.

EXAMPLE AB26: CO-POLYAMINO ACID AB26-SODIUM POLY-L-GLUTAMATE AND MODIFIED BY MOLECULE AA10 AND HAVING A NUMBER AVERAGE MOLECULAR WEIGHT (MN) OF 2700 G/MOL

By a method similar to the one used for the preparation of co-polyamino acid AB23 applied to the hydrochloride salt of molecule AA10 and to a poly-L-glutamic acid obtained by a method similar to the one used for the preparation of co-polyamino acid AB23-1, a sodium poly-L-glutamate modified by molecule AA10 is obtained.
Dry extract: 23.9 mg/g.
DP (estimated based on ¹H NMR): 22.
Based on ¹H NMR: i=0.21.
The calculated average molecular weight of co-polyamino acid AB26 is 4899 g/mol.
HPLC-organic SEC (calibrant PEG): Mn=2700 g/mol.

EXAMPLE AB27: CO-POLYAMINO ACID AB27-SODIUM POLY-L-GLUTAMATE AND MODIFIED BY MOLECULE AA11 AND HAVING A NUMBER AVERAGE MOLECULAR WEIGHT (MN) OF 4500 G/MOL

By a method similar to the one used for the preparation of co-polyamino acid AB23 applied to the hydrochloride salt of molecule AA11 and to a poly-L-glutamic acid obtained by a method similar to the one used for the preparation of co-polyamino acid AB23-1, a sodium poly-L-glutamate modified by molecule AA11 is obtained.
Dry extract: 26.8 mg/g.
DP (estimated based on ¹H NMR): 39.
Based on ¹H NMR: i=0.15.
The calculated average molecular weight of co-polyamino acid AB27 is 8808 g/mol.
HPLC-organic SEC (calibrant PEG): Mn=4500 g/mol.

EXAMPLE AB28: CO-POLYAMINO ACID AB28-SODIUM POLY-L-GLUTAMATE AND MODIFIED BY MOLECULE AA12 AND HAVING A NUMBER AVERAGE MOLECULAR WEIGHT (MN) OF 4000 G/MOL

By a method similar to the one used for the preparation of co-polyamino acid AB23 applied to the hydrochloride salt of molecule AA12 and to a poly-L-glutamic acid obtained by a method similar to the one used for the preparation of co-polyamino acid AB23-1, a sodium poly-L-glutamate modified by molecule AA12 is obtained.
Dry extract: 22.9 mg/g.
DP (estimated based on ¹H NMR): 39.
Based on ¹H NMR: i=0.15.
The calculated average molecular weight of co-polyamino acid AB28 is 7706 g/mol.
HPLC-organic SEC (calibrant PEG): Mn=4000 g/mol.

EXAMPLE AB29: CO-POLYAMINO ACID AB29-SODIUM POLY-L-GLUTAMATE AND MODIFIED BY MOLECULE AA13 AND HAVING A NUMBER AVERAGE MOLECULAR WEIGHT (MN) OF 4000 G/MOL

Co-polyamino acid B29-1: poly-L-glutamic acid originating from the polymerization of γ-benzyl-L-glutamate N-carboxyanhydride initiated by hexylamine. In a double jacket reactor, γ-benzyl-L-glutamate N-carboxyanhydride (500 g, 1.90 mol) is solubilized in anhydrous DMF (1100 mL). The mixture is then stirred until the dissolution is complete, cooled to 0° C., then hexylamine (6.27 mL, 47.5 mmol) is introduced rapidly. The mixture is stirred at 0° C. for 5 h, between 0° C. and 20° C. for 7 h, then at 20° C. for 7 h. The reaction mixture is then heated at 65° C. for 2 h, cooled to 55° C., and methanol (3300 mL) is introduced in 1 h 30. The reaction mixture is then cooled to 0° C. and left under stirring for 18 h. The white precipitate is recovered by filtration, washed with diisopropyl ether (2×800 mL), then dried at reduced pressure at 30° C. to yield a poly(gamma-benzyl-L-glutamic acid) (PBLG).
To a solution of PBLG (180 g) in N,N-dimethylacetamide (DMAc, 450 mL), Pd/Al$_2$O$_3$ (36 g) is added under an argon atmosphere. The mixture is placed under a hydrogen atmosphere (10 bar) and stirred at 60° C. for 24 h. After cooling at ambient temperature and filtration of the catalyst through a sintered filter P4, then through a 0.2 μm Omnipore membrane hydrophilic PTFE, a solution of water at pH 2 (2700 mL) is added dropwise to the solution of DMAc, over a period of 45 min and under stirring. After 18 h under stirring, the white precipitate is recovered by filtration, washed with water, then dried at reduced pressure at 30° C.
Co-Polyamino Acid AB29
By a method similar to the one used for the preparation of co-polyamino acid AB23 applied to the hydrochloride salt of molecule AA13 and to co-polyamino acid AB29-1, a sodium poly-L-glutamate modified by molecule AA13 is obtained.
Dry extract: 16.1 mg/g.
DP (estimated based on ¹H NMR): 40.
Based on ¹H NMR: i=0.15.
The calculated average molecular weight of co-polyamino acid AB29 is 7734 g/mol.
HPLC-organic SEC (calibrant PEG): Mn=4000 g/mol.

EXAMPLE AB30: CO-POLYAMINO ACID AB30-SODIUM POLY-L-GLUTAMATE AND MODIFIED BY MOLECULE AA10 AND HAVING A NUMBER AVERAGE MOLECULAR WEIGHT (MN) OF 4300 G/MOL

By a method similar to the one used for the preparation of co-polyamino acid AB29 applied to the hydrochloride salt of molecule AA10 and to a poly-L-glutamic acid obtained by a method similar to the one used for the preparation of co-polyamino acid AB29-1 using a molecule AA10 as initiator instead of hexylamine, a sodium poly-L-glutamate modified by molecule AA10 is obtained.
Dry extract: 29.2 mg/g.
DP (estimated based on ¹H NMR): 40.
Based on ¹H NMR: i=0.125.
The calculated average molecular weight of co-polyamino acid AB30 is 7682 g/mol.
HPLC-organic SEC (calibrant PEG): Mn=4300 g/mol.

EXAMPLE AB31: CO-POLYAMINO ACID AB30-SODIUM POLY-L-GLUTAMATE AND MODIFIED BY MOLECULE AA10 AND HAVING A NUMBER AVERAGE MOLECULAR WEIGHT (MN) OF 6300 G/MOL

By a method similar to the one used for the preparation of co-polyamino acid AB29 applied to the hydrochloride salt of molecule AA10 and to a poly-L-glutamic acid obtained by a method similar to the one used for the preparation of co-polyamino acid AB29-1 using molecule AA10 as initiator instead of hexylamine, a sodium poly-L-glutamate modified by molecule AA10 is obtained.
Dry extract: 23.1 mg/g.
DP (estimated based on $^1$H NMR): 40.
Based on $^1$H NMR: i=0.175.
The calculated average molecular weight of co-polyamino acid AB31 is 8337 g/mol.
HPLC-organic SEC (calibrant PEG): Mn=6300 g/mol.

EXAMPLE AB32: CO-POLYAMINO ACID AB32-SODIUM POLY-L-GLUTAMATE AND MODIFIED BY MOLECULE AA14 AND HAVING A NUMBER AVERAGE MOLECULAR WEIGHT (MN) OF 4700 G/MOL

By a method similar to the one used for the preparation of co-polyamino acid AB29 applied to molecule AA14 and to poly-L-glutamic acid AB29-1, a sodium poly-L-glutamate modified by molecule AA14 is obtained.
Dry extract: 13.5 mg/g.
DP (estimated based on $^1$H NMR): 40.
Based on $^1$H NMR: i=0.109.
The calculated average molecular weight of co-polyamino acid AB32 is 8599 g/mol.
HPLC-organic SEC (calibrant PEG): Mn=4700 g/mol.
Co-Polyamino Acids Defined by Formula VII or VIIb EXAMPLE AB14: CO-POLYAMINO ACID AB14-SODIUM POLY-L-GLUTAMATE MODIFIED AT ONE OF ITS ENDS BY MOLECULE AA1 AND HAVING A NUMBER AVERAGE MOLECULAR WEIGHT (MN) OF 3400 G/MOL The hydrochloride salt of molecule AA1 (2.03 g, 4.70 mmol), chloroform (5 mL), molecular mesh 4 Å (1.3 g) as well as the ion exchange resin Amberlite IRN 150 (1.3 g) are introduced successively into a suitable container. After 1 h of stirring on rollers, the medium is filtered and the resin is rinsed with chloroform. The mixture is evaporated, then co-evaporated with toluene. The residue is solubilized in anhydrous DMF (30 mL) to be used directly in the polymerization reaction.

γ-Benzyl-L-glutamate N-carboxyanhydride (25.59 g, 97.2 mmol) is placed under a vacuum for 30 min in a round-bottom flask dried in the oven, then anhydrous DMF (140 mL) is introduced. The mixture is stirred under argon until the solubilization is complete, cooled at 4° C., then the solution of molecule AA1 prepared as described above is introduced rapidly. The mixture is stirred between 4° C. and ambient temperature for 2 days, then heated at 65° C. for 2 h. The reaction mixture is then cooled to ambient temperature, then poured dropwise into diisopropyl ether (1.7 L) under stirring. The white precipitate is recovered by filtration, washed two times with diisopropyl ether (140 mL), then dried under a vacuum at 30° C. to obtain a white solid. The solid is diluted in TFA (160 mL), and a solution of hydrobromic acid (HBr) at 33% in acetic acid (62 mL, 354 mmol) is then added dropwise and at 0° C. The solution is stirred for 2 h at ambient temperature, then poured dropwise into a 1:1 (v/v) mixture of diisopropyl ether/water and under stirring (1.9 L). After 2 h of stirring, the heterogeneous mixture is allowed to stand overnight. The white precipitate is recovered by filtration, washed successively with a 1:1 (v/v) mixture of diisopropyl ether and water (280 mL), then with water (140 mL). The solid obtained is solubilized in water (530 mL) by adjusting the pH to 7 by addition of an aqueous sodium hydroxide solution 10 N, then an aqueous sodium hydroxide solution 1 N. After solubilization, the theoretical concentration is adjusted to 20 g/L theoretical by addition of water to obtain a final volume of 800 mL. The mixture is filtered through a 0.45 µm filter, then purified by ultrafiltration against a solution of NaCl 0.9%, then water until the conductimetry of the permeate is less than 50 µS/cm. The solution of co-polyamino acid is then concentrated to approximately 30 g/L theoretical and the pH is adjusted to 7.0. The aqueous solution is filtered through a 0.2 µm filter and stored at 4° C.
Dry extract: 24.1 mg/g.
DP (estimated by $^1$H NMR)=25, thus i=0.04.
The calculated average molecular weight of co-polyamino acid AB14 is 3378 g/mol.
HPLC-aqueous SEC (calibrant PEG): Mn=3400 g/mol.

EXAMPLE AB15: CO-POLYAMINO ACID AB15-SODIUM POLY-L-GLUTAMATE MODIFIED AT ONE OF ITS ENDS BY MOLECULE AA6 AND HAVING A NUMBER AVERAGE MOLECULAR WEIGHT (MN) 4100 G/MOL

By a method similar to the one used for the preparation of co-polyamino acid AB14 applied to the hydrochloride salt of molecule AA6 (2.16 g, 3.94 mmol) and to 25.58 g (97.2 mmol) of γ-benzyl-L-glutamate N-carboxyanhydride, a sodium poly-L-glutamate modified at one of its ends by molecule AA6 is obtained.
Dry extract: 45.5 mg/g.
DP (estimated by $^1$H NMR)=30, thus i=0.033.
The calculated average molecular weight of co-polyamino acid AB15 is 5005 g/mol.
HPLC-aqueous SEC (calibrant PEG): Mn=4100 g/mol.

EXAMPLE AB16: CO-POLYAMINO ACID AB16-SODIUM POLY-L-GLUTAMATE MODIFIED AT ONE OF ITS ENDS BY MOLECULE AA6 AND HAVING A NUMBER AVERAGE MOLECULAR WEIGHT (MN) OF 6500 G/MOL

By a method similar to the one used for the preparation of co-polyamino acid AB14 applied to the hydrochloride salt of molecule AA6 (2.39 g, 4.36 mmol) and to 50.0 g (189.9 mmol) of γ-benzyl-L-glutamate N-carboxyanhydride, a sodium poly-L-glutamate modified at one of its ends by molecule AA6 is obtained.
Dry extract: 28.5 mg/g.
DP (estimated by $^1$H NMR)=48, thus i=0.021.
The calculated average molecular weight of co-polyamino acid AB16 is 7725 g/mol.
HPLC-aqueous SEC (calibrant PEG): Mn=6500 g/mol.

EXAMPLE AB17: CO-POLYAMINO ACID AB17-SODIUM POLY-L-GLUTAMATE MODIFIED AT ONE OF ITS ENDS BY MOLECULE AA7 AND HAVING A NUMBER AVERAGE MOLECULAR WEIGHT (MN) OF 3500 G/MOL

By a method similar to the one used for the preparation of co-polyamino acid AB14 applied to the hydrochloride salt of molecule AA7 (2.80 g, 4.32 mmol) and to 25.0 g (94.9 mmol) of γ-benzyl-L-glutamate N-carboxyanhydride, a sodium poly-L-glutamate modified at one of its ends by molecule AA7 is obtained
Dry extract: 25.2 mg/g.
DP (estimated by $^1$H NMR)=26, thus i=0.038.
The calculated average molecular weight of co-polyamino acid AB17 is 4500 g/mol.
HPLC-aqueous SEC (calibrant PEG): Mn=3500 g/mol.

EXAMPLE AB18: CO-POLYAMINO ACID AB18-SODIUM POLY-L-GLUTAMATE MODIFIED AT ONE OF ITS ENDS BY MOLECULE AA7 AND HAVING A NUMBER AVERAGE MOLECULAR WEIGHT (MN) OF 3700 G/MOL

A sodium poly-L-glutamate modified at one of its ends by molecule AA7 is obtained by polymerization of the γ-methyl N-carboxyanhydride of glutamic acid (25.0 g, 133.6 mmol) using the hydrochloride salt of molecule AA7 (2.80 g, 4.32 mmol) as initiator and by carrying out a deprotection of the methyl esters by using a solution of hydrochloric acid at 37% according to the method described in the patent application FR-A-2 801 226.
Dry extract: 44.3 mg/g.
DP (estimated by $^1$H NMR)=22, thus i=0.045.
The calculated average molecular weight of co-polyamino acid AB18 is 3896 g/mol.
HPLC-aqueous SEC (calibrant PEG): Mn=3700 g/mol.

EXAMPLE AB19: CO-POLYAMINO ACID AB19-SODIUM POLY-L-GLUTAMATE MODIFIED AT ONE OF ITS ENDS BY MOLECULE AA6 AND HAVING A NUMBER AVERAGE MOLECULAR WEIGHT (MN) OF 10,500 G/MOL

By a method similar to the one used for the preparation of co-polyamino acid AB14 applied to the hydrochloride salt of molecule AA6 (1.64 g, 2.99 mmol) and to γ-benzyl-L-glutamate N-carboxyanhydride (49.3 g, 187 mmol), a sodium poly-L-glutamate modified at one of its ends by molecule AA6 is obtained.
Dry extract: 23.4 mg/g.
DP (estimated by $^1$H NMR)=65, thus i=0.015.
The calculated average molecular weight of co-polyamino acid AB19 is 10,293 g/mol.
HPLC-aqueous SEC (calibrant PEG): Mn=10,500 g/mol.

EXAMPLE AB20: CO-POLYAMINO ACID AB20-SODIUM POLY-L-GLUTAMATE CAPPED AT ONE OF ITS ENDS BY AN ACETYL GROUP AND MODIFIED AT ONE OF ITS ENDS BY MOLECULE AA6 AND HAVING A NUMBER AVERAGE MOLECULAR WEIGHT (MN) OF 10,400 G/MOL

The hydrochloride salt of molecule AA6 (0.545 g, 1.00 mmol), chloroform (10 mL), molecular mesh 4 Å (3 g) as well as the ion exchange resin Amberlite IRN 150 (3 g) are introduced successively into a suitable container. After 1 h of stirring on rollers, the medium is filtered and the resin is rinsed with chloroform. The mixture is evaporated, then co-evaporated with toluene. The residue is solubilized in anhydrous DMF (10 mL) to be used directly in the polymerization reaction.

γ-Benzyl-L-glutamate N-carboxyanhydride (17.0 g, 64.6 mmol) is placed under vacuum for 30 min in a round-bottom flask dried in the oven, then anhydrous DMF (30 mL) is introduced. The mixture is stirred under argon until the solubilization is complete, cooled at 4° C., then the solution of molecule AA6 prepared as described above is introduced rapidly. The mixture is stirred between 4° C. and ambient temperature for 2 days, then precipitated in diisopropyl ether (0.6 L). The precipitate is recovered by filtration, washed two times with diisopropyl ether (40 mL), then dried to yield a white solid which is dissolved in 80 mL of THF. DIPEA (1.7 mL, 9.8 mmol) then acetic anhydride (0.9 mL, 9.5 mmol) are added successively to this solution. After stirring overnight at ambient temperature, the solution is poured slowly into diisopropyl ether (480 mL) in 30 min and under stirring. After 1 h of stirring, the precipitate is filtered, washed two times with diisopropyl ether (80 mL), then dried under a vacuum at 30° C. to yield a poly(gamma-benzyl-L-glutamic acid) capped at one end by an acetyl group and modified at the other end by molecule AA6 in the form of a white solid.

The solid is diluted in TFA (65 mL), and then a solution of hydrobromic acid (HBr) at 33% in acetic acid (45 mL, 257.0 mmol) is added dropwise and at 4° C. The solution is stirred for 2 h at ambient temperature, then poured dropwise into a 1:1 (v/v) mixture of diisopropyl ether/water and under stirring (780 mL). After 2 h of stirring, the heterogeneous mixture is allowed to stand overnight. The white precipitate is recovered by filtration, washed successively with a 1:1 (v/v) mixture of diisopropyl ether and water (70 mL), then with water (70 mL). The solid obtained is solubilized in water (300 mL) by adjusting the pH to 7 by addition of an aqueous sodium hydroxide solution 10 N, then an aqueous sodium hydroxide solution 1 N. After solubilization, the theoretical concentration is adjusted to 20 g/L theoretical by addition of water to obtain a final volume of 440 mL. The mixture is filtered through a 0.45 μm filter, then purified by ultrafiltration against a solution of NaCl 0.9%, then water until the conductimetry of the permeate is less than 50 μS/cm. The solution of co-polyamino acid is then concentrated to approximately 30 g/L theoretical and the pH is adjusted to 7.0. The aqueous solution is filtered through a 0.2 μm filter and stored at 4° C.
Dry extract: 21.5 mg/g.
DP (estimated by $^1$H NMR)=60, thus i=0.017.
The calculated average molecular weight of co-polyamino acid AB20 is 9619 g/mol.
HPLC-aqueous SEC (calibrant PEG): Mn=10,400 g/mol.
BA: Synthesis of the Hydrophobic Molecules in which p=2

The radicals are represented in the following table by the corresponding hydrophobic molecule after grafting onto the co-polyamino acid.

TABLE 1D
list of the hydrophobic molecules synthesized according to the invention in which p = 2.
| N° | Structure of the hydrophobic molecule before grafting onto the co-polyamino acid |
|---|---|
| BA1 | 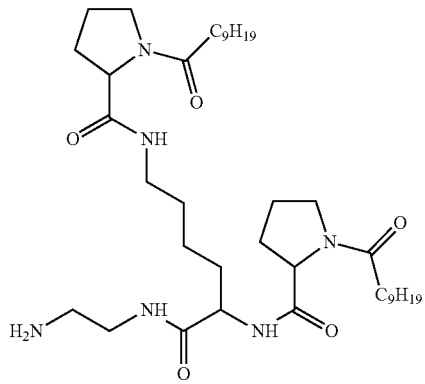 |
| BA2 | 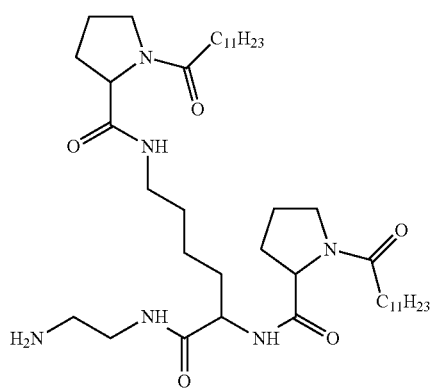 |
| BA3 | 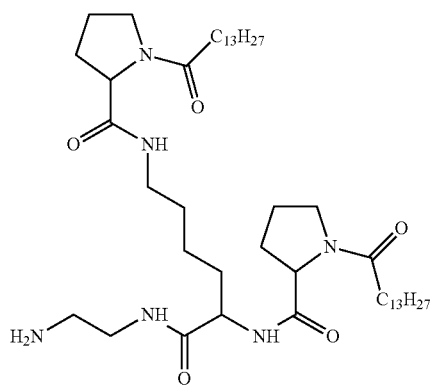 |
| BA4 | 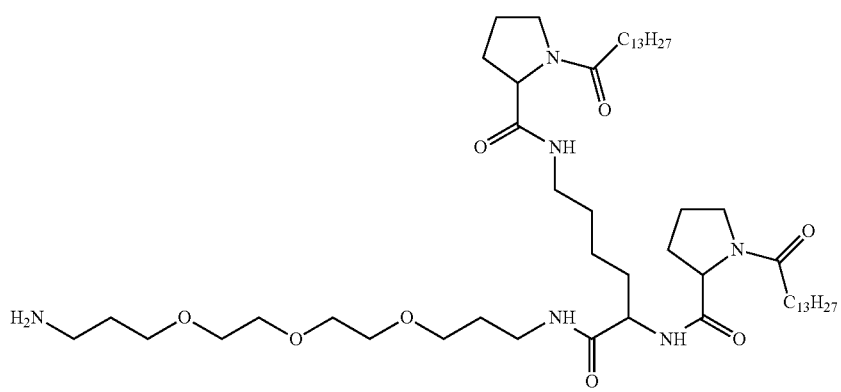 |

TABLE 1D-continued list of the hydrophobic molecules synthesized according to the invention in which p = 2.

| N° | Structure of the hydrophobic molecule before grafting onto the co-polyamino acid |
|---|---|
| BA5 | 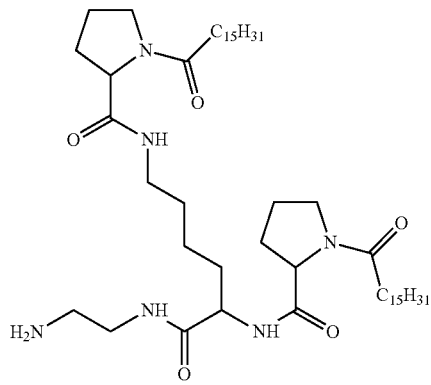 |
| BA6 | 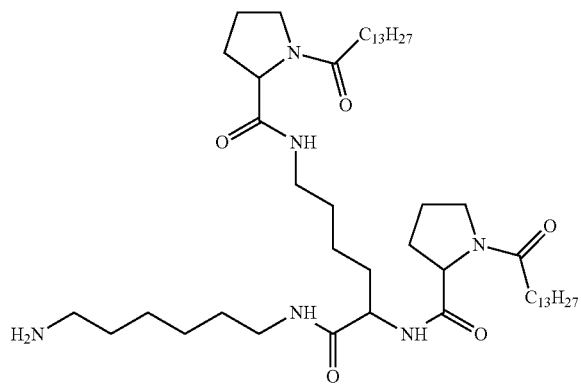 |
| BA7 | 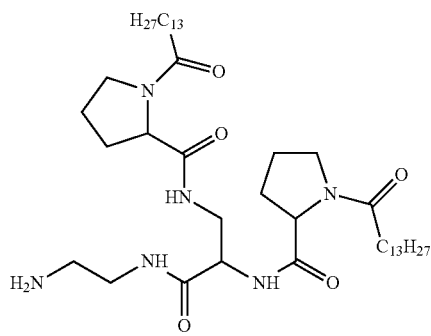 |

EXAMPLE BA1: MOLECULE BA1

Molecule B1: Product Obtained by the Reaction Between Decanoic Acid and L-proline Dicyclohexyl carbodiimide (DCC) (16.29 g, 78.96 mmol) and N-hydroxysuccinimide (NHS) (9.09 g, 78.96 mmol) are added successively to a solution of decanoic acid (14.28 g, 82.91 mmol) in THF (520 mL) at 0° C. After 60 h of stirring at ambient temperature, the medium is cooled at 0° C. for 20 min, filtered through a sintered filter. L-Proline (10 g, 86.86 mmol), diisopropylethylamine (DIPEA) (68.8 mL) and water (60 mL) are added to the filtrate. After 24 h of stirring at ambient temperature, the mixture is diluted with water (300 mL). The aqueous phase is washed with ethyl acetate (2×250 mL), acidified to pH ~1 with an aqueous HCl solution 1 N, then extracted with dichloromethane (3×150 mL). The combined organic phases are dried over $Na_2SO_4$, filtered, concentrated under a vacuum, and the residue is purified by chromatography on silica gel (cyclohexane, ethyl acetate).

Yield: 14.6 g (69%).

$^1$H NMR ($CDCl_3$, ppm): 0.87 (3H); 1.26 (12H); 1.65 (2H); 2.02 (3H); 2.34 (2H); 2.41 (1H); 3.48 (1H); 3.56 (1H); 4.58 (1H).

LC/MS (ESI): 270.2; (calculated ([M+H]$^+$): 270.4).

Molecule B2: Product Obtained by the Reaction Between Molecule B1 and L-lysine

By a method similar to the one used for the preparation of molecule B1 applied to molecule B1 (14.57 g, 54.07 mmol) and to L-lysine (4.15 g, 28.39 mmol), a yellow oil is obtained.

Yield: 16.4 g (93%).
$^1$H NMR $^1$H (CDCl$_3$, ppm): 0.88 (6H); 1.26 (24H); 1.35-1.65 (8H); 1.85-2.35 (12H); 2.53 (0.2H); 2.90 (0.8H); 3.45-3.75 (5H); 4.50-4.70 (3H); 7.82 (1H).
LC/MS (ESI): 649.6; (calculated ([M+H]$^+$): 649.9).

Molecule B3: Product Obtained by Reaction Between Molecule B2 and Boc-ethylenediamine DIPEA (8.80 mL) and 2-(1H-benzotriazol-1-yl)-1,1,3,3-tetramethyluronium tetrafluoroborate (TBTU, 8.52 g, 26.54 mmol) at ambient temperature are added to a solution of molecule B2 (16.4 g, 25.27 mmol) in THF (170 mL). After 30 min of stirring, Boc-ethylenediamine (4.45 g, 27.8 mmol) is added. After stirring at ambient temperature for 2 h, the solvent is evaporated at reduced pressure and the residue is diluted with ethyl acetate (400 mL). The organic phase is washed with water (250 mL), a saturated aqueous solution of NaHCO$_3$ (250 mL), a 1 N aqueous HCl solution (250 mL), a saturated aqueous solution of NaCl (250 mL) and dried over Na$_2$SO$_4$. After filtration and concentration under a vacuum, the residue obtained is purified by chromatography on silica gel (ethyl acetate, methanol) to yield a colorless oil.
Yield: 12.8 g (64%).
$^1$H NMR (CDCl$_3$, ppm): 0.87 (6H); 1.25-1.60 (42H); 1.80-2.05 (4H); 2.15-2.45 (9H); 3.10-3.75 (10H); 4.30 (1H); 4.50 (2H); 5.50 (0.6H); 5.89 (0.2H); 6.15 (0.2H); 7.03 (1H); 7.47 (1H).
LC/MS (ESI): 791.8; (calculated ([M+H]$^+$): 792.1).

Molecule BA1

To a solution of molecule B3 (12.78 g, 16.15 mmol) in dichloromethane (110 mL) at 5° C., an HCl solution 4 N in dioxane (20.2 mL) is added. After 20 h of stirring at 5° C., the medium is concentrated under a vacuum. The residue obtained is dissolved in methanol and evaporated under a vacuum, this operation being repeated 4 times to yield a white solid of molecule BA1 in the form of a hydrochloride salt.
Yield: 11.4 g (97%).
$^1$H NMR (DMSO-d$_6$, ppm): 0.85 (6H); 1.25-1.50 (33H); 1.57 (1H); 1.70-2.40 (12H); 2.82 (2H); 3.00 (2H); 3.25-3.70 (6H); 4.05-4.50 (3H); 7.75-8.45 (6H).
LC/MS (ESI): 691.6; (calculated ([M+H]$^+$): 692.0).

EXAMPLE BA2: MOLECULE BA2

Molecule B4: Product Obtained by the Reaction Between Lauric Acid and L-proline

By a method similar to the one used for the preparation of molecule B1, applied to lauric acid (31.83 g, 157.9 mmol) and to L-proline (20 g, 173.7 mmol), a yellow oil is obtained.
Yield: 34.3 g (73%).
$^1$H NMR (CDCl3, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).
LC/MS (ESI): 298.2; (calculated ([M+H]$^+$): 298.4).

Molecule B5: Product Obtained by the Reaction Between Molecule B4 and L-lysine

By a method similar to the one used for the preparation of molecule B1 applied to molecule B4 (33.72 g, 113.36 mmol) and to L-lysine (8.70 g, 59.51 mmol), a white solid is obtained.

Yield: 26.2 g (66%).
$^1$H NMR (CDCl$_3$, ppm): 0.88 (6H); 1.26 (32H); 1.35-1.65 (8H); 1.85-2.35 (15H); 2.87 (1H); 3.40-3.75 (5H); 4.50-4.75 (3H); 7.87 (1H).
LC/MS (ESI): 705.6; (calculated ([M+H]$^+$): 706.0).

Molecule B6: Product Obtained by Reaction Between Boc-ethylenediamine and Molecule B5

By a method similar to the one used for the preparation of molecule B3 applied to molecule B5 (25.74 g, 36.51 mmol) and to Boc-ethylenediamine (6.43 g, 40.16 mmol), a colorless oil is obtained.
Yield: 30.9 g (quantitative).
$^1$H NMR (CDCl$_3$, ppm): 0.88 (6H); 1.35-1.65 (50H); 1.85-2.35 (13H); 3.05-3.75 (10H); 4.25-4.65 (3H); 5.50 (0.4H); 5.88 (0.2H); 6.16 (0.2H); 7.08 (1H); 7.26 (1H); 7.49 (0.2H).
LC/MS (ESI): 847.8; (calculated ([M+H]$^+$): 848.2).

Molecule BA2

After a method similar to the one used for the preparation of molecule BA1 applied to molecule B6 (30.9 g, 36.47 mmol), the residue obtained after concentration under a vacuum is dissolved in methanol and evaporated under a vacuum, this operation being repeated 4 times to yield a white solid of molecule BA2 in the form of a hydrochloride salt after drying at reduced pressure.
Yield: 27.65 g (97%).
$^1$H NMR (DMSO-d$_6$, ppm): 0.85 (6H); 1.10-2.40 (54H); 2.75-3.15 (4H); 3.25-3.60 (6H); 4.05-4.50 (3H); 7.50-8.50 (6H).
LC/MS (ESI): 747.6; (calculated ([M+H]$^+$): 748.1).

EXAMPLE BA3: MOLECULE BA3

Molecule B7: Product Obtained by the Reaction Between Myristic Acid and L-proline By a method similar to the one used for the preparation of molecule B1, applied to myristic acid (18.93 g, 82.91 mmol) and to L-proline (10 g, 86.86 mmol), a yellowish oil is obtained.
Yield: 20 g (78%).
$^1$H NMR (CDCl$_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).
LC/MS (ESI): 326.2; (calculated ([M+H]$^+$): 326.6).

Molecule B8: Product Obtained by the Reaction Between Molecule B7 and L-lysine

By a method similar to the one used for the preparation of molecule B1 applied to molecule B7 (20.02 g, 61.5 mmol) and to L-lysine (4.72 g, 32.29 mmol), a white solid is obtained.
Yield: 12.3 g (53%).
$^1$H NMR (DMSO-d$_6$, ppm): 0.85 (6H); 1.26 (40H); 1.35-1.50 (6H); 1.50-2.10 (10H); 2.10-2.25 (4H); 3.01 (2H); 3.31-3.55 (4H); 4.10-4.40 (3H); 7.68 (0.6H); 7.97 (1H); 8.27 (0.4H); 12.50 (1H).
LC/MS (ESI): 761.8; (calculated ([M+H]$^+$): 762.1).

Molecule B9: Product Obtained by the Reaction Between Boc-ethylenediamine and Molecule B8

By a method similar to the one used for the preparation of molecule B3 applied to molecule B8 (12 g, 15.77 mmol) and to Boc-ethylenediamine (3.03 g, 18.92 mmol), a colorless oil is obtained after purification by chromatography column on silica gel (ethyl acetate, methanol).

Yield: 12.5 g (88%).

$^1$H NMR (DMSO-$d_6$, ppm): 0.85 (6H); 1.20-1.55 (55H); 1.50-2.25 (14H); 2.95-3.10 (6H); 3.31-3.55 (4H); 4.10-4.40 (3H); 6.74 (1H); 7.60-8.25 (3H).

LC/MS (ESI): 904.1; (calculated ([M+H]$^+$): 904.3).

Molecule BA3

After a method similar to the one used for the preparation of molecule BA1 applied to molecule B9 (12.5 g, 13.84 mmol), the residue obtained after concentration under a vacuum is dissolved in methanol and evaporated under a vacuum, this operation being repeated 4 times to yield a white solid of molecule BA3 in the form of a hydrochloride salt after drying at reduced pressure.

Yield: 9.2 g (79%).

$^1$H NMR (DMSO-$d_6$, ppm): 0.85 (6H); 1.10-1.65 (48H); 1.70-2.35 (12H); 2.85 (2H); 3.01 (2H); 3.25-3.65 (6H); 4.10-4.50 (3H); 7.70-8.40 (6H).

LC/MS (ESI): 803.9; (calculated ([M+H]$^+$): 804.2).

EXAMPLE BA4: MOLECULE BA4

Molecule B10: Product Obtained by the Reaction Between Molecule B8 and Boc-1-amino-4,7,10-trioxa-13-tridecane amine By a method similar to the one used for the preparation of molecule B3 applied to molecule B8 (29.80 g, 39.15 mmol) and to Boc-1-amino-4,7,10-trioxa-13-tridecane amine (15.05 g, 46.96 mmol), a thick colorless oil is obtained.

Yield: 25.3 g (61%).

$^1$H NMR (DMSO-$d_6$, ppm): 0.85 (6H); 1.25-2.35 (75H); 2.85-3.20 (6H); 3.25-3.65 (16H); 4.10-4.45 (3H); 6.38 (0.1H); 6.72 (0.9H); 7.50-8.25 (3H).

LC/MS (ESI): 1064.2; (calculated ([M+H]$^+$): 1064.5).

Molecule BA4

After a method similar to the one used for the preparation of molecule BA1 applied to molecule B10 (25.3 g, 23.8 mmol), the residue obtained after concentration under a vacuum is dissolved in methanol and evaporated under a vacuum, this operation being repeated 4 times to yield a white solid of molecule BA4 in the form of a hydrochloride salt after drying at reduced pressure.

Yield: 20.02 g (84%).

$^1$H NMR (DMSO-$d_6$, ppm): 0.85 (6H); 1.15-2.35 (66H); 2.80-3.20 (6H); 3.30-3.65 (16H); 4.10-4.45 (3H); 7.55-8.60 (6H).

LC/MS (ESI): 964.9; (calculated ([M+H]$^+$): 964.6).

EXAMPLE BA5: MOLECULE BA5

Molecule B11: Product Obtained by Reaction Between Molecule A1 and L-lysine

By a method similar to the one used for the preparation of molecule B1 applied to molecule A1 (19.10 g, 54.02 mmol) and to L-lysine (4.15 g, 28.36 mmol), an oily residue is obtained after concentration of the reaction medium at reduced pressure. This residue is diluted in water (150 mL), washed with ethyl acetate (2×75 mL), then the aqueous phase is acidified until the pH is 1 by slow addition of HCl 6 N. The product is extracted 3 times with dichloromethane, the organic phase is dried over $Na_2SO_4$, then filtered and concentrated at reduced pressure to yield 11.2 g of yellow oily residue. In parallel, the previous preceding organic phase of ethyl acetate is washed with an aqueous HCl solution 2 N (2×75 mL), a saturated aqueous solution of NaCl (75 mL), dried over $Na_2SO_4$, filtered and concentrated to yield 10.2 g of yellow oily residue. A white solid is obtained after recrystallization of each one of these residues in acetone.

Yield: 11.83 g (54%).

$^1$H NMR (CDCl$_3$, ppm): 0.87 (6H); 1.06-2.44 (70H); 2.78-2.96 (1H); 3.35-3.75 (5H); 4.28-4.43 (0.1H); 4.43-4.52 (0.2H); 4.52-4.61 (1.8H); 4.61-4.75 (0.9H); 7.74-8.02 (2H).

LC/MS (ESI): 818.0; (calculated ([M+H]$^+$): 818.7).

Molecule B12: Product Obtained by Coupling Between Molecule B11 and Boc-ethylenediamine By a method similar to the one used for the preparation of molecule B3 applied to molecule B11 (18.00 g, 22.02 mmol) in solution in THF and to Boc-ethylenediamine (4.23 g, 26.43 mmol), a white solid is obtained after recrystallization two times in acetonitrile.

Yield: 17.5 g (83%).

$^1$H NMR (DMSO-$d_6$, ppm): 0.85 (6H); 1.15-2.29 (79H); 2.92-3.12 (6H); 3.30-3.59 (4H); 4.06-4.13 (0.65H); 4.16-4.29 (2H); 4.38-4.42 (0.35H); 6.71-6.76 (1H); 7.60-7.69 (1.3H); 7.76-7.81 (0.65H); 7.93-7.97 (0.35H); 8.00-8.04 (0.35H); 8.10-8.17 (0.35H).

LC/MS (ESI): 960.4; (calculated ([M+H]$^+$): 960.8).

Molecule BA5

By a method similar to the one used for the preparation of molecule BA1 applied to molecule B12 (24.4 g, 25.43 mmol), the residue obtained after concentration under a vacuum is solubilized in dichloromethane (150 mL), the organic phase is washed 2 times with an aqueous sodium hydroxide solution 2 N (90 mL). Acetonitrile (120 mL) is added, and the dichloromethane is eliminated by concentration at reduced pressure. The medium is then left to stand for 72 h and a white solid is obtained after filtration and rinsing with acetonitrile, followed by drying at reduced pressure. This operation is repeated 4 times.

Yield: 14.28 g (65%).

$^1$H NMR (DMSO-$d_6$, ppm): 0.85 (6H); 1.06-2.32 (70H); 2.53-2.63 (2H); 2.89-3.61 (10H); 4.04-4.43 (3H); 7.55-7.62 (0.65H); 7.65-7.72 (0.65H); 7.80 (0.65H); 7.91 (0.35H); 8.03 (0.35H); 8.14-8.23 (0.35H).

LC/MS (ESI): 860.0; (calculated ([M+H]$^+$): 860.8).

EXAMPLE BA6: MOLECULE BA6

Molecule B13: Product Obtained by the Reaction Between N-(tert-butoxycarbonyl)-1,6-diaminohexane and Molecule B8

By a method similar to the one used for the preparation of molecule B3 applied to molecule B8 (10 g, 13.14 mmol) and to N-(tert-butoxycarbonyl)-1,6-diaminohexane (3.41 g, 15.77 mmol) in dichloromethane, a white solid is obtained after recrystallization in acetonitrile.

Yield: 10.7 g (85%).

$^1$H NMR (CDCl$_3$, ppm): 0.88 (6H); 1.17-2.40 (79H); 3.00-3.71 (10H); 4.26-4.58 (3H); 4.67 (1H); 6.74 (1H); 7.34-7.49 (2H).

LC/MS (ESI): 959.9; (calculated ([M+H]$^+$): 959.8).

Molecule BA6

After a method similar to the one used for the preparation of molecule BA1 applied to molecule B13 (10.5 g, 10.94 mmol), an aqueous NaOH solution 2 N is added dropwise to the reaction medium cooled to 0° C. The aqueous phase is extracted with dichloromethane, then the organic phase is washed 3 times with an aqueous solution of NaCl 5%. After drying over Na$_2$SO$_4$, the organic phase is filtered, concentrated under a vacuum, and the residue is recrystallized in acetonitrile.

Yield: 5.4 g (58%).

$^1$H NMR (CDCl$_3$, ppm): 0.88 (6H); 1.19-2.40 (72H); 2.67 (2H); 3.03-3.70 (8H); 4.26-4.57 (3H); 6.71 (1H); 7.39-7.49 (2H).

LC/MS (ESI): 859.8; (calculated ([M+H]$^+$): 859.7).

EXAMPLE BA7: MOLECULE BA7

Molecule B14: Product Obtained by Coupling Between Molecule B7 and 2,3-diaminopropionic Acid By a method similar to the one used for the preparation of molecule B1 applied to molecule B7 (80.00 g, 245.78 mmol) and to the dihydrochloride of 2,3-diaminopropionic acid (22.84 g, 129.04 mmol), a white solid is obtained after recrystallization in acetonitrile.

Yield: 69 g (78%).

$^1$H NMR (DMSO-d$_6$, ppm): 0.86 (6H); 1.08-1.38 (40H); 1.40-1.55 (4H); 1.68-2.30 (12H); 3.16-3.66 (6H); 4.20-4.39 (3H); 7.67-8.31 (2H); 12.70 (1H).

LC/MS (ESI): 719.4; 741.5; (calculated ([M+H]$^+$): 719.6; ([M+Na]$^+$): 741.6).

Molecule B15: Product Obtained by Coupling Between Molecule B14 and Boc-ethylenediamine By a method similar to the one used for the preparation of molecule B3 applied to molecule B14 (32.00 g, 44.50 mmol) in solution in dichloromethane and to Boc-ethylenediamine (8.56 g, 53.40 mmol), a colorless oil is obtained after purification by chromatography on silica gel (ethyl acetate, methanol).

Yield: 24.5 g (64%).

$^1$H NMR (DMSO-d$_6$, ppm): 0.85 (6H); 1.16-2.42 (65H); 2.89-3.14 (4H); 3.17-3.66 (6H); 4.11-4.43 (3H); 6.77 (1H); 7.38-8.23 (3H).

LC/MS (ESI): 861.7; (calculated ([M+H]$^+$): 861.7).

Molecule BA7

After a method similar to the one used for the preparation of molecule BA1 applied to molecule B15 (24.50 g, 28.45 mmol), the reaction medium is concentrated at reduced pressure, the residue is solubilized in dichloromethane, the organic phase is washed with an aqueous NaOH solution 2 N, dried over Na$_2$SO$_4$, filtered and concentrated at reduced pressure. A white solid is obtained after recrystallization in acetonitrile.

Yield: 19.7 g (91%).

$^1$H NMR (DMSO-d$_6$, ppm): 0.85 (6H); 1.10-2.40 (58H); 2.51-2.62 (2H); 2.90-3.16 (2H); 3.16-3.67 (6H); 4.04-4.47 (3H); 7.33-8.27 (3H).

LC/MS (ESI): 761.5; (calculated ([M+H]$^+$): 761.6).

BB: Synthesis of the Co-Polyamino Acids Modified by Hydrophobic Molecules in which p=2 Co-Polyamino Acids of formula VII or VIIa TABLE 1e list of the co-polyamino acids of formula VII or VIIa according to the invention.

| n° | co-polyamino acids bearing carboxylate charges and hydrophobic radicals |
|---|---|
| BB1 | 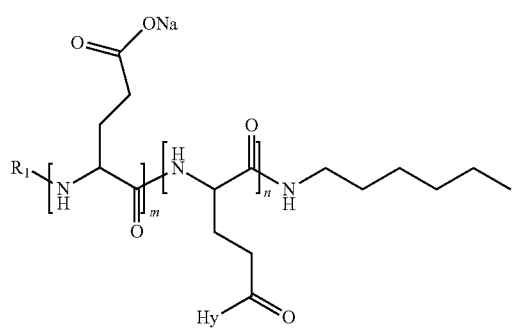 $i = 0.05$, DP $(m + n) = 23$ |

TABLE 1e-continued
list of the co-polyamino acids of formula VII or VIIa according to the invention.
| n° | co-polyamino acids bearing carboxylate charges and hydrophobic radicals |
|---|---|
| | Hy = 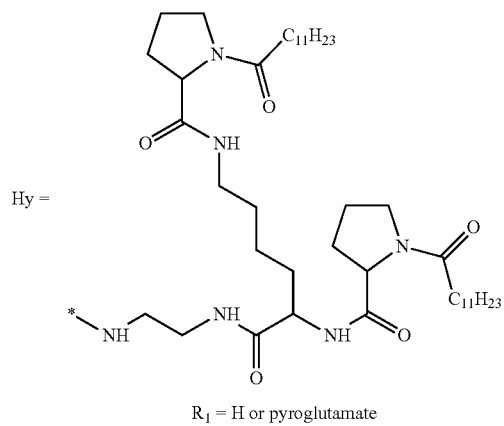<br>$R_1$ = H or pyroglutamate |
| BB2 | 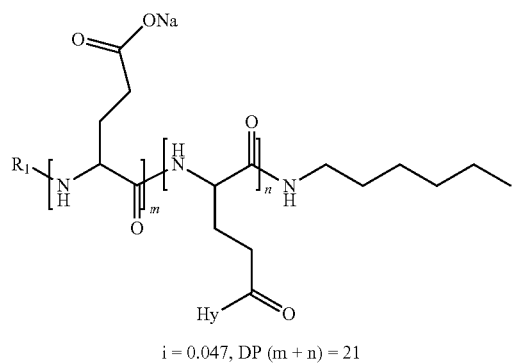<br>i = 0.047, DP (m + n) = 21 |
| | Hy = 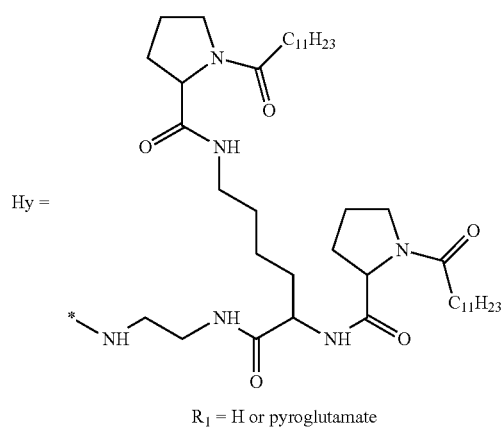<br>$R_1$ = H or pyroglutamate |

TABLE 1e-continued
list of the co-polyamino acids of formula VII or VIIa according to the invention.
| n° | co-polyamino acids bearing carboxylate charges and hydrophobic radicals |
|---|---|
| BB3 | 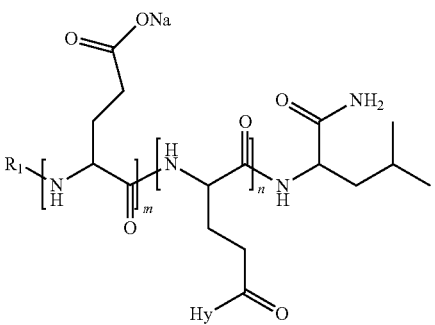 i = 0.049, DP (m + n) = 34 |
| | Hy = 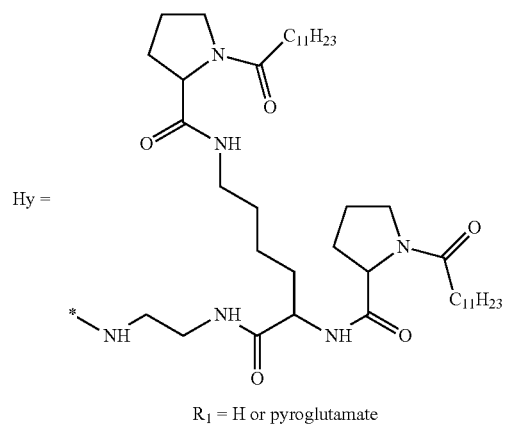 $R_1$ = H or pyroglutamate |
| BB4 | 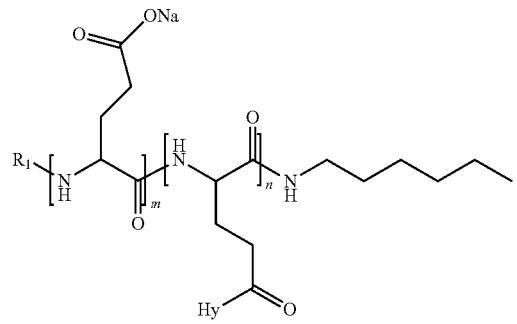 i = 0.04, DP (m + n) = 65 |

TABLE 1e-continued
list of the co-polyamino acids of formula VII or VIIa according to the invention.
| n° | co-polyamino acids bearing carboxylate charges and hydrophobic radicals |
|---|---|
| | Hy = 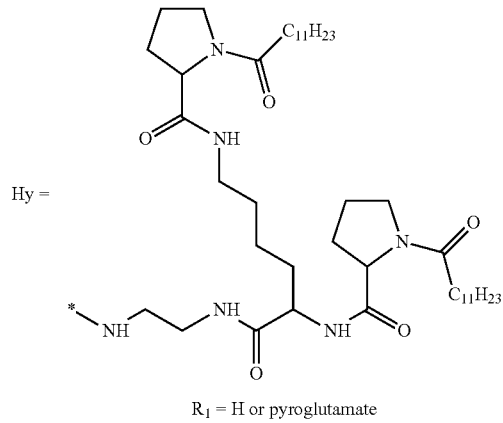<br>R1 = H or pyroglutamate |
| BB5 | 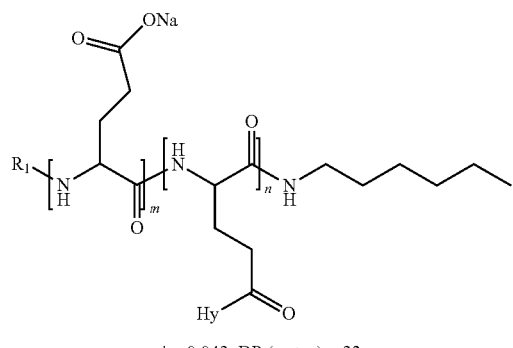<br>i = 0.042, DP (m + n) = 23 |
| | Hy = 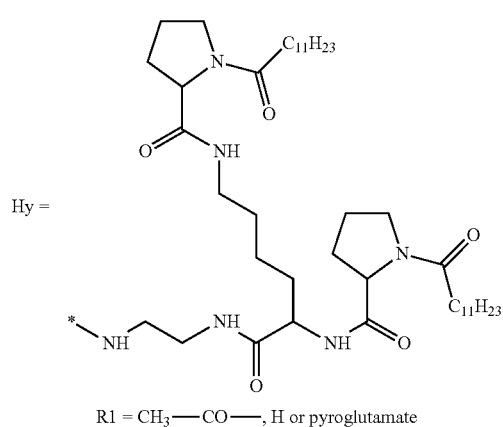<br>R1 = CH₃—CO—, H or pyroglutamate |
| BB6 | 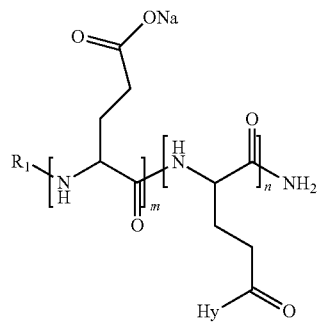<br>i = 0.04, DP (m + n) = 24 |

TABLE 1e-continued
list of the co-polyamino acids of formula VII or VIIa according to the invention.
| n° | co-polyamino acids bearing carboxylate charges and hydrophobic radicals |
|---|---|
| | Hy = 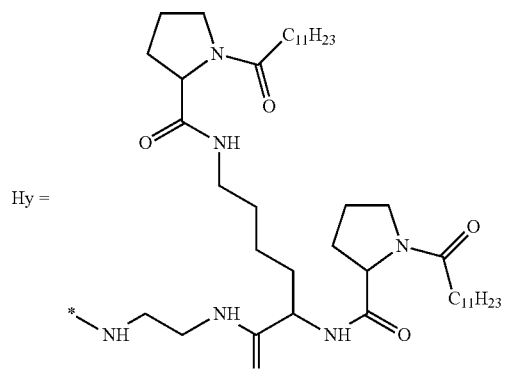<br>R1 = CH$_3$—CO—, H or pyroglutamate |
| BB7 | 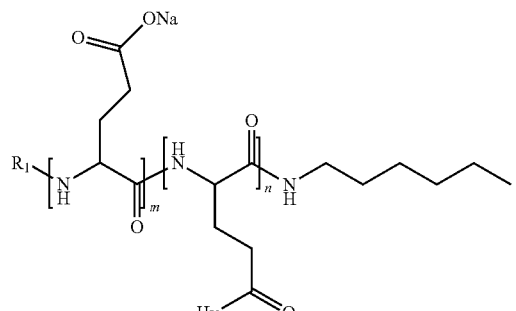<br>i = 0.042, DP (m + n) = 22<br><br>Hy = 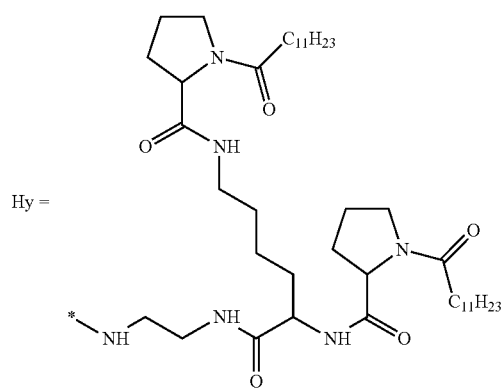<br>R$_1$ = H or pyroglutamate |

TABLE 1e-continued
list of the co-polyamino acids of formula VII or VIIa according to the invention.
| n° | co-polyamino acids bearing carboxylate charges and hydrophobic radicals |
|---|---|
| BB8 | 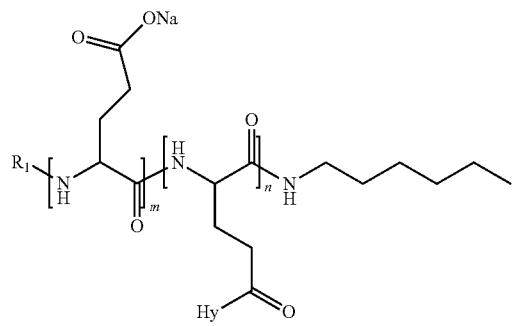
i = 0.026, DP (m + n) = 21
Hy = (structure shown)
$R_1$ = H or pyroglutamate |
| BB9 | 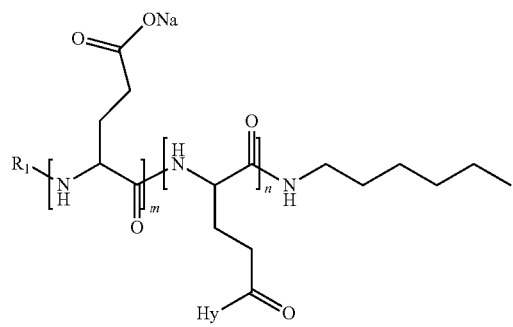
i = 0.05, DP (m + n) = 26 |

TABLE 1e-continued
list of the co-polyamino acids of formula VII or VIIa according to the invention.
| n° | co-polyamino acids bearing carboxylate charges and hydrophobic radicals |
|---|---|
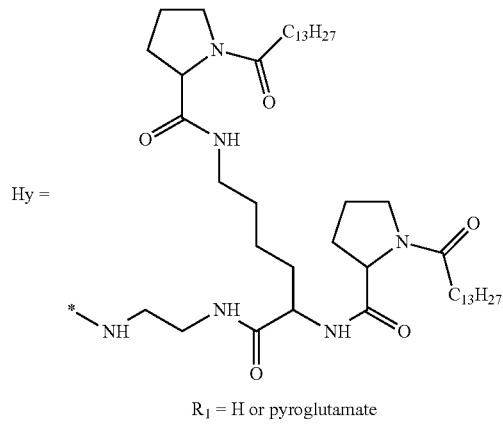
$R_1$ = H or pyroglutamate
BB10
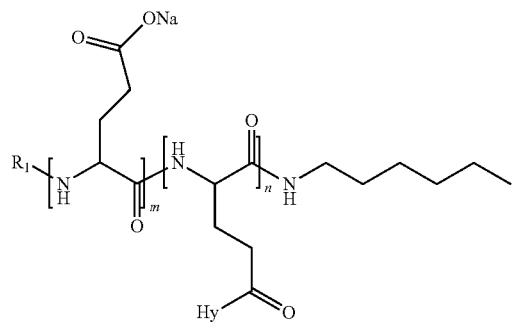
i = 0.029, DP (m + n) = 22
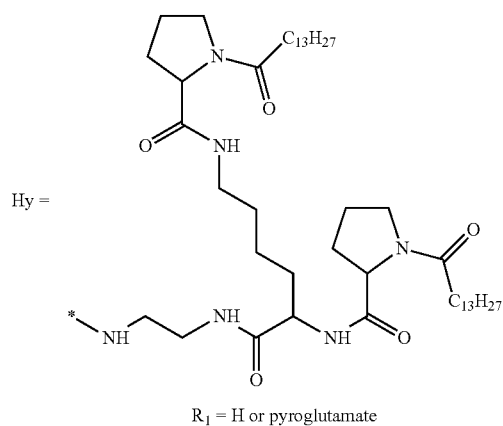
$R_1$ = H or pyroglutamate TABLE 1e-continued
list of the co-polyamino acids of formula VII or VIIa according to the invention.
| n° | co-polyamino acids bearing carboxylate charges and hydrophobic radicals |
|---|---|
| BB11 | 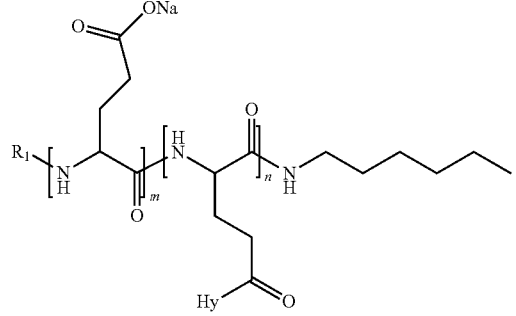
i = 0.032, DP (m + n) = 22
Hy = 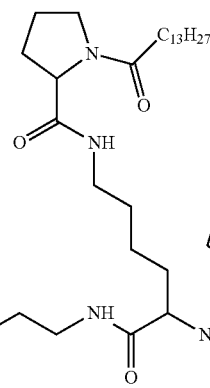
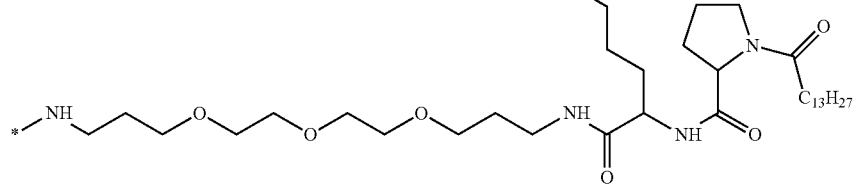
R1 = CH₃—CO—, H or pyroglutamate |
| BB12 | 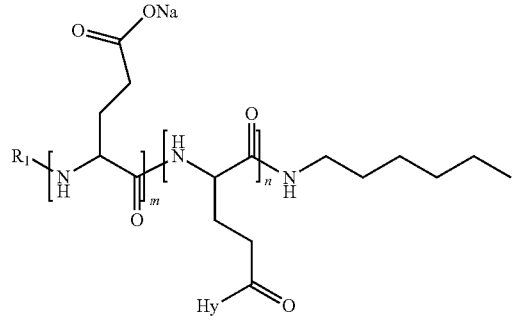
i = 0.03, DP (m + n) = 23
Hy = 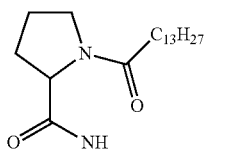
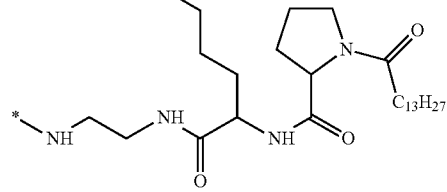
R1 = CH₃—CO—, H or pyroglutamate |

115 116

TABLE 1e-continued list of the co-polyamino acids of formula VII or VIIa according to the invention.

| n° | co-polyamino acids bearing carboxylate charges and hydrophobic radicals |
|---|---|
| BB13 | 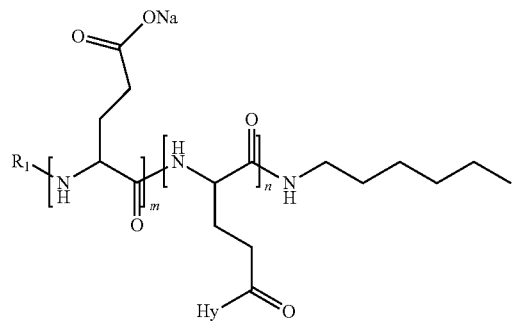<br>i = 0.08, DP = 25<br><br>Hy = 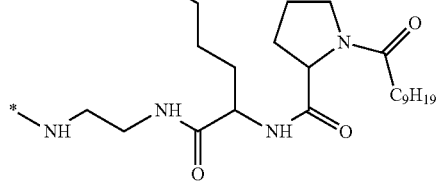<br><br>$R_1$ = H or pyroglutamate |

Co-Polyamino Acids of Formula VII or VIIb

TABLE 1F list of the co-polyamino acids of formula VII or VIIb synthesized according to the invention.

| n° | co-polyamino acids bearing carboxylate charges and hydrophobic radicals |
|---|---|
| BB14 | 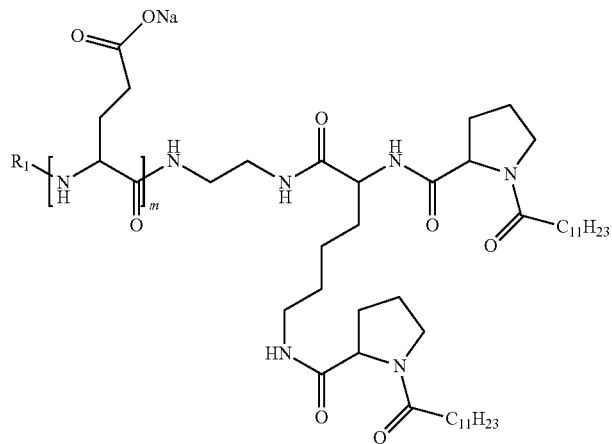<br>i = 0.034, DP (m) = 29<br>$R_1$ = H or pyroglutamate |

TABLE 1F-continued
list of the co-polyamino acids of formula VII or VIIb synthesized according to the invention.
| n° | co-polyamino acids bearing carboxylate charges and hydrophobic radicals |
|---|---|
| BB15 | 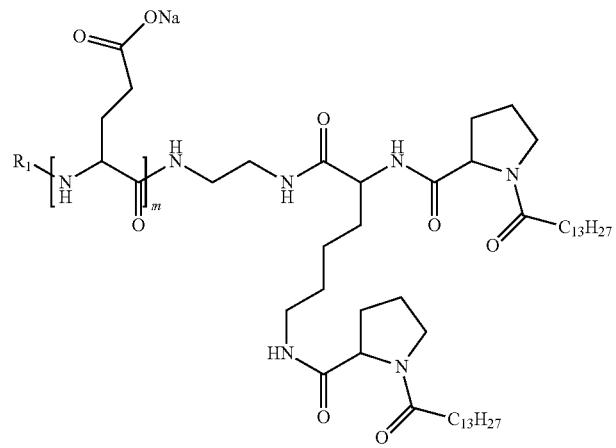 i = 0.045, DP (m) = 22<br>$R_1$ = H or pyroglutamate |
| BB16 | 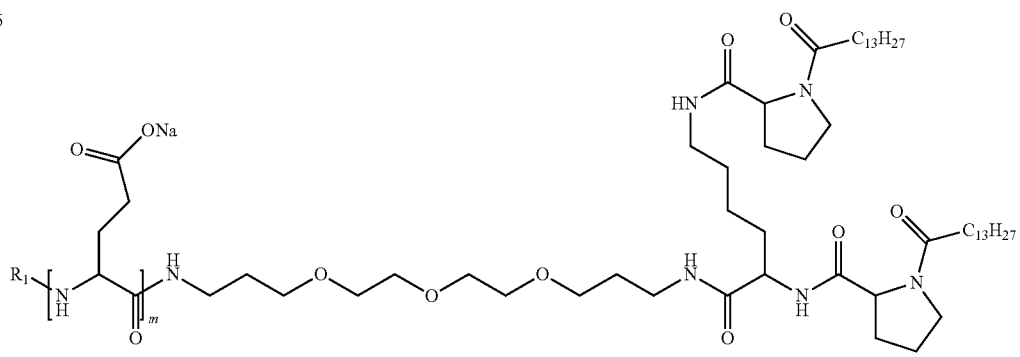 i = 0.043, DP (m) = 23<br>$R_1$ = H or pyroglutamate |
| BB17 | 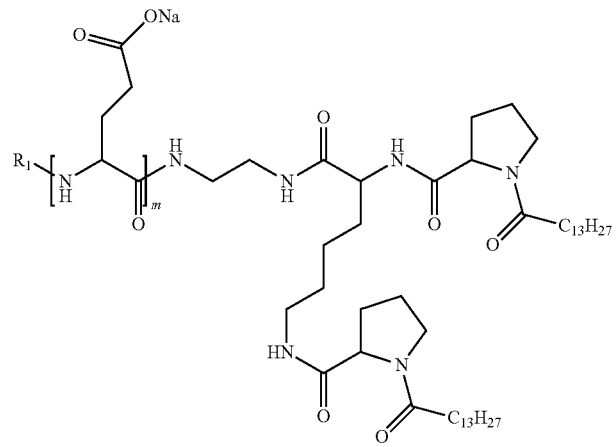 i = 0.015, DP (m) = 65<br>$R_1$ = H or pyroglutamate |

TABLE 1F-continued
list of the co-polyamino acids of formula VII or VIIb synthesized according to the invention.
| n° | co-polyamino acids bearing carboxylate charges and hydrophobic radicals |
|---|---|
| BB18 | 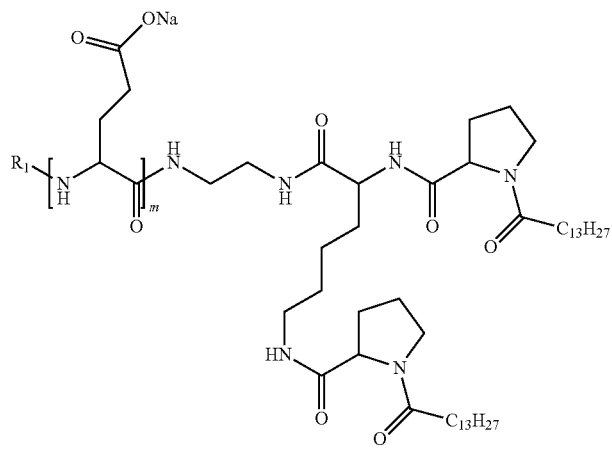<br>i = 0.025, DP (m) = 40<br>R1 = H or pyroglutamate |
| BB19 | 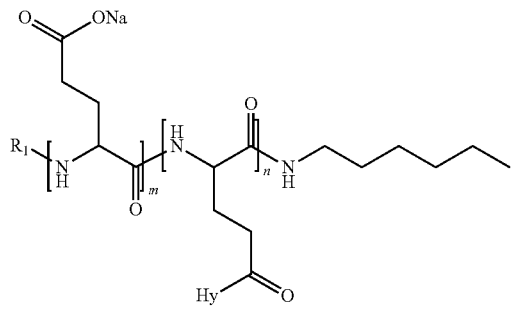<br>i = 0.045, DP (m + n) = 60<br>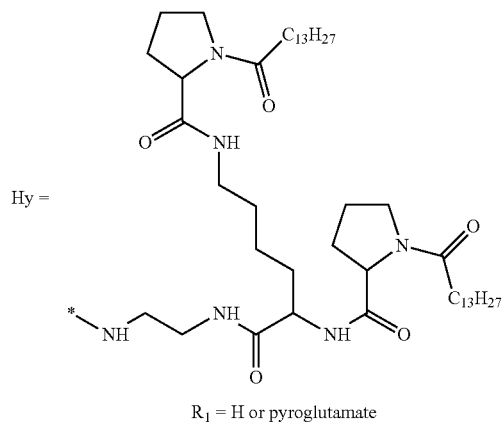<br>R₁ = H or pyroglutamate |

TABLE 1F-continued
list of the co-polyamino acids of formula VII or VIIb synthesized according to the invention.
| n° | co-polyamino acids bearing carboxylate charges and hydrophobic radicals |
|---|---|
| BB20 | 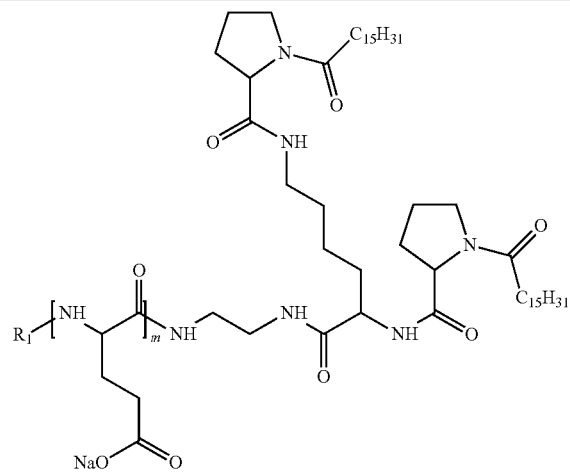<br>i = 0.043, DP (m) = 23<br>R1 = H ou pyroglutamate |
| BB21 | 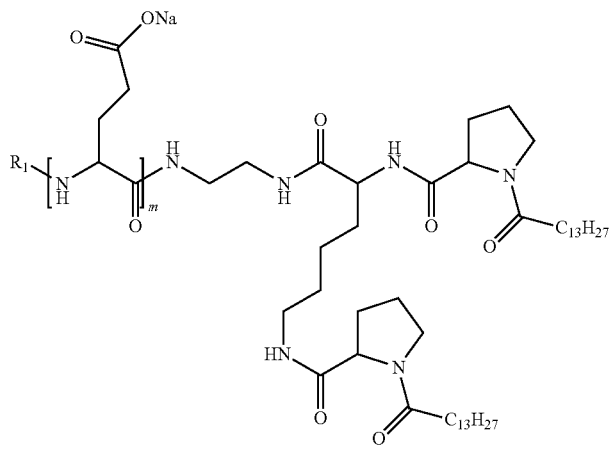<br>i = 0.11, DP (m) = 9<br>R1 = H or pyroglutamate |
| BB22 | 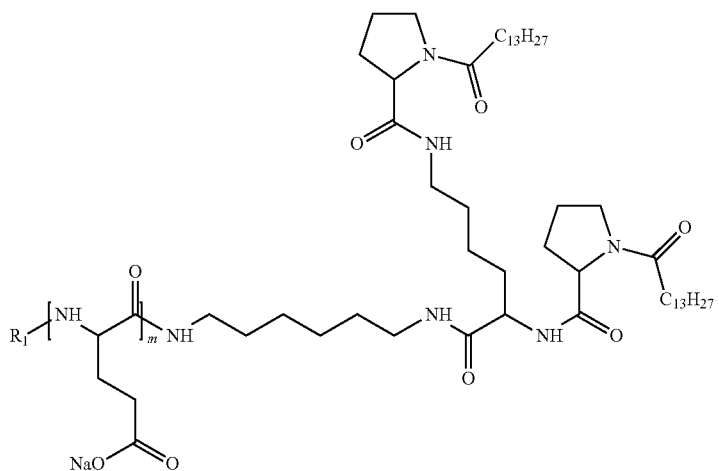<br>i = 0.04, DP (m) = 25<br>R1 = H or pyroglutamate |

TABLE 1F-continued
list of the co-polyamino acids of formula VII or VIIb synthesized according to the invention.
| n° | co-polyamino acids bearing carboxylate charges and hydrophobic radicals |
|---|---|
| BB23 | 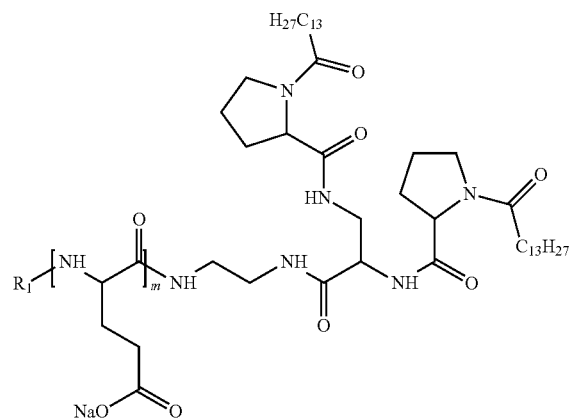<br>i = 0.048, DP (m) = 21<br>R1 = H or pyroglutamate |
| BB24 | 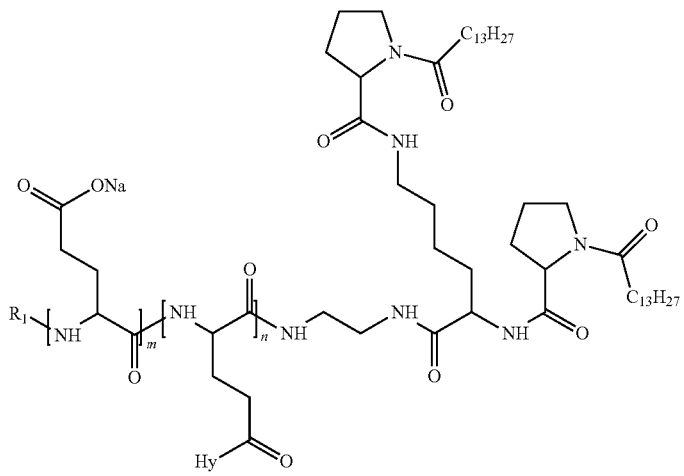<br>i = 0.089, DP (m) = 22<br><br>Hy = 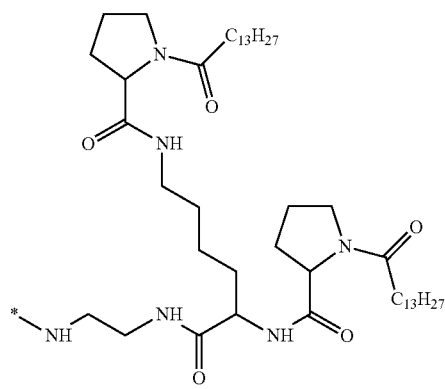<br>R1 = H or pyroglutamate |

TABLE 1F-continued list of the co-polyamino acids of formula VII or VIIb synthesized according to the invention.

| n° | co-polyamino acids bearing carboxylate charges and hydrophobic radicals |
|---|---|
| BB25 | 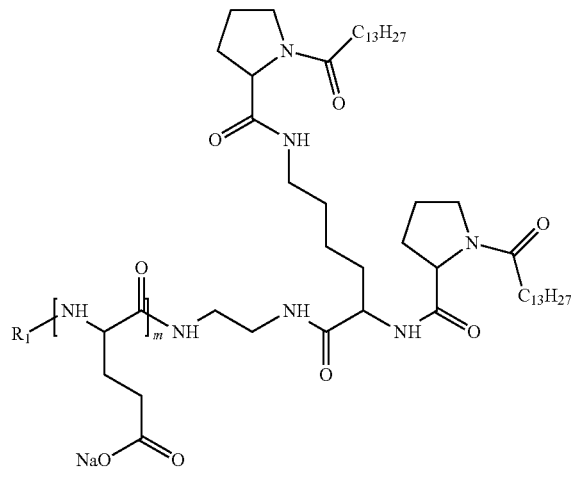<br>i = 0.09, DP (m) = 22<br><br>$R_1 = $ 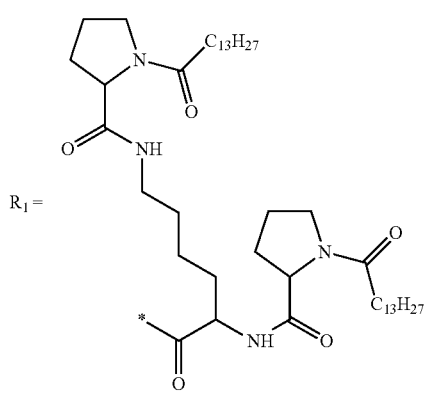 |

EXAMPLE BB1: CO-POLYAMINO ACID BB1-SODIUM POLY-L-GLUTAMATE MODIFIED BY MOLECULE BA2 AND HAVING A NUMBER AVERAGE MOLECULAR WEIGHT (MN) OF 2400 G/MOL

Co-polyamino acid BB1-1: poly-L-glutamic acid having a relative number average molecular weight (Mn) 3860 g/mol originating from the polymerization of γ-benzyl-L-glutamate N-carboxyanhydride initiated by hexylamine.

In a previously oven-heated round-bottom flask, γ-benzyl-L-glutamate N-carboxyanhydride (90.0 g, 342 mmol) is placed under vacuum for 30 min, then anhydrous DMF (465 mL) is introduced. The mixture is then stirred under argon until the dissolution is complete, cooled to 4° C., then hexylamine (1.8 mL, 14 mmol) is introduced rapidly. The mixture is stirred between 4° C. and ambient temperature for 2 days. The reaction mixture is then heated at 65° C. for 4 h, cooled to ambient temperature, then poured dropwise into cold diisopropyl ether (6 L) under stirring. The white precipitate is recovered by filtration, washed with diisopropyl ether (500 mL, then 250 mL), then dried under a vacuum at 30° C. to yield poly(γ-benzyl-L-glutamic acid) (PBLG).

A hydrobromic acid solution (HBr) at 33% in acetic acid (135 mL, 0.77 mol) is added dropwise to a solution of PBLG (42.1 g) in trifluoroacetic acid (TFA, 325 mL). The mixture is stirred at ambient temperature for 2 h, then poured dropwise into a 1:1 (v/v) mixture of diisopropyl ether and water under stirring (1.6 L). After 1 h 30 of stirring, the heterogeneous mixture is allowed to stand overnight. The white precipitate is recovered by filtration, washed with a 1:1 (v/v) mixture of diisopropyl ether and water (200 mL).

The solution obtained is then solubilized in water (1 L) by adjusting the pH to 7 by addition of an aqueous sodium hydroxide solution 10 N, then an aqueous sodium hydroxide solution 1 N. After solubilization, the theoretical concentration is adjusted to 25 g/L theoretical by addition of water to obtain a final volume of 1.5 L.

The solution is filtered through a 0.45 μm filter, then purified by ultrafiltration against a solution of NaCl 0.9%, then water until the conductimetry of the permeate is less than 50 μS/cm.

The aqueous solution is then acidified by addition of a solution of hydrochloric acid 37% until a pH of 2 is reached. After 4 h of stirring, the precipitate obtained is filtered, then dried under a vacuum at 30° C. to yield a poly-L-glutamic acid having a number average molecular weight (Mn) 3860 g/mol with respect to a polyoxyethylene standard (PEG).

Co-Polyamino Acid BB1

The co-polyamino acid BB1-1 (10.0 g) is solubilized in DMF (700 mL) at 30-40° C., then cooled to 0° C. The hydrochloride salt of molecule BA2 (2.95 g, 3.8 mmol) is suspended in DMF (45 mL) and triethylamine (0.39 g, 3.8 mmol) is then added to this suspension, then the mixture is heated slightly under stirring until the dissolution is complete. N-Methylmorpholine 7.6 g, 75 mmol) in DMF (14 mL) and ethyl chloroformate (ECF, 8.1 g, 75 mmol) are added to the solution of co-polyamino acid at 0° C. After 10 min at 0° C., the solution of molecule BA2 is added, and the mixture is maintained at 30° C. for 1 h. The reaction mixture is poured dropwise into 6 L of water containing NaCl at 15 wt % and HCl (pH 2), then allowed to stand overnight. The precipitate is collected by filtration, washed with the solution of sodium chloride at pH 2 (1 L) and dried under a vacuum for approximately 1 h. The white solid obtained is taken up in water (600 mL), and the pH is adjusted to 7 by slow addition of an aqueous NaOH solution 1 N. The volume is adjusted to 700 mL by addition of water. After filtration through a 0.45 µm filter, the clear solution obtained is purified by ultrafiltration against a solution of NaCl 0.9%, then water until the conductimetry of the permeate is less than 50 µS/cm. After removal, the solution is filtered through a 0.2 µm filter and stored at 2-8° C.

Dry extract: 19.7 mg/g.
DP (estimated based on $^1$H NMR): 23.
Based on $^1$H NMR: i=0.05.
The calculated average molecular weight of co-polyamino acid BB1 is 4350 g/mol.
HPLC-aqueous SEC (calibrant PEG): Mn=2400 g/mol.

EXAMPLE BB2: CO-POLYAMINO ACID BB2-SODIUM POLY-L-GLUTAMATE MODIFIED BY MOLECULE BA2 AND HAVING A NUMBER AVERAGE MOLECULAR WEIGHT (MN) OF 4900 G/MOL

A poly-L-glutamic acid having a number average molecular (Mn) 4100 g/mol (5.0 g) obtained by a method similar to the one used for the preparation of co-polyamino acid BB1-1 is solubilized in DMF (205 mL) at 30-40° C., then maintained at this temperature. In parallel, the hydrochloride salt of molecule BA2 (1.44 g, 1.84 mmol) is suspended in DMF (10 mL), and triethylamine (0.19 g, 1.84 mmol) is added, then the mixture is heated slightly under stirring until the dissolution is complete. To the solution of co-polyamino acid in DMF, NMM (3.7 g, 36.7 mmol), the solution of molecule BA2, then the N-oxide of 2-hydroxypyridine (HOPO, 0.31 g, 2.76 mmol) are added successively. The reaction medium is then cooled to 0° C., then EDC (0.53 g, 2.76 mmol) is added, and the mixture is brought to ambient temperature in 3 h. The reaction medium is poured dropwise into 1.55 L of water containing NaCl at 15 wt % and HCl (pH 2) under stirring. At the end of the addition, the pH is readjusted to 2 with an HCl solution 1 N, and the suspension is allowed to stand overnight. The precipitate is collected by filtration, then rinsed with 100 mL of water. The white solid obtained is solubilized in 200 mL of water by slow addition of an aqueous NaOH solution 1 N until the pH is 7 under stirring, then the solution is filtered through a 0.45 µm filter. The clear solution obtained is purified by ultrafiltration against a solution of NaCl 0.9%, then water until the conductimetry of the permeate is less than 50 µS/cm. The solution obtained is filtered through a 0.2 µm filter and stored at 2-8° C.

Dry extract: 16.3 mg/g.
DP (estimated based on $^1$H NMR): 21.
Based on $^1$H NMR: i=0.047.
The calculated average molecular weight of co-polyamino acid BB2 is 3932 g/mol.
HPLC-aqueous SEC (calibrant PEG): Mn=4900 g/mol.

EXAMPLE BB3: CO-POLYAMINO ACID BB3-SODIUM POLY-L-GLUTAMATE MODIFIED BY MOLECULE BA2 AND HAVING A NUMBER AVERAGE MOLECULAR WEIGHT (MN) OF 6400 G/MOL

Co-Polyamino Acid BB3-1: poly-L-glutamic Acid Having a Number Average Molecular Weight (Mn) 17,500 g/mol Originating from the Polymerization of γ-methyl-L-glutamate N-carboxyanhydride initiated by L-leucinamide.

A poly-L-glutamic acid having a number average molecular weight (Mn) 17,500 g/mol with respect to a methyl polymethacrylate (PMMA) standard is obtained by polymerization of the γ-methyl N-carboxyanhydride of glutamic acid using L-leucinamide as initiator and by carrying out a deprotection of the methyl esters by using a solution of hydrochloric acid at 37% according to the method described in the patent application FR-A-2 801 226.

By a method similar to the one used for the preparation of co-polyamino acid BB2 applied to the hydrochloride salt of molecule BA2 (3.23 g, 4.1 mmol) and to co-polyamino acid BB3-1 (11 g), a sodium poly-L-glutamate modified by molecule BA2 is obtained.

Dry extract: 27.5 mg/g.
DP (estimated based on $^1$H NMR): 34.
Based on $^1$H NMR: i=0.049.
The calculated average molecular weight of co-polyamino acid BB3 is 6405 g/mol.
HPLC-aqueous SEC (calibrant PEG): Mn=6400 g/mol.

EXAMPLE BB4: CO-POLYAMINO ACID BB4-SODIUM POLY-L-GLUTAMATE MODIFIED BY MOLECULE BA2 AND HAVING A NUMBER AVERAGE MOLECULAR WEIGHT (MN) OF 10,500 G/MOL

By a method similar to the one used for the preparation of co-polyamino acid BB2 applied to the hydrochloride salt of molecule BA2 (5 g, 6.35 mmol) and to a poly-L-glutamic acid having a number average molecular weight Mn=10,800 g/mol (21.7 g) obtained by a method similar to the one used for the preparation of copolyamino acid BB1-1, a sodium poly-L-glutamate modified by molecule BA2 is obtained.

Dry extract: 28.2 mg/g.
DP (estimated based on $^1$H NMR): 65.
Based on $^1$H NMR: i=0.04.
The calculated average molecular weight of co-polyamino acid BB4 is 11,721 g/mol.
HPLC-aqueous SEC (calibrant PEG): Mn=10,500 g/mol.

EXAMPLE BB5: CO-POLYAMINO ACID BB5-SODIUM POLY-L-GLUTAMATE CAPPED AT ONE OF ITS ENDS BY AN ACETYL GROUP AND MODIFIED BY MOLECULE BA2 AND HAVING A NUMBER AVERAGE MOLECULAR WEIGHT (MN) OF 3600 G/MOL

Co-Polyamino Acid BB5-1: poly-L-glutamic Acid of Mn 3700 g/mol Originating from the Polymerization of γ-benzyl-L-glutamate N-carboxyanhydride Initiated by Hexylamine and Capped at One of its Ends by an Acetyl Group.

In a round-bottom flask dried in the oven, γ-benzyl-L-glutamate N-carboxyanhydride (100.0 g, 380 mmol) is placed under a vacuum for 30 min, then anhydrous DMF (250 mL) is introduced. The mixture is then stirred under argon until the dissolution is complete, cooled to 4° C., then hexylamine (2.3 mL, 17 mmol) is introduced rapidly. The mixture is stirred between 4° C. and ambient temperature for 2 days, then precipitated in diisopropylene (3.4 L). The precipitate is recovered by filtration, washed 2 times with diisopropyl ether (225 mL), then dried to yield a white solid which is dissolved in 450 mL of THF. To this solution, N,N-diisopropylethylamine (DIPEA, 31 mL, 176 mmol), then acetic anhydride (17 mL, 176 mmol) are added successively. After stirring overnight at ambient temperature, the solution is poured slowly into diisopropyl ether (3 L) for a duration of 30 min and under stirring. After 1 h of stirring, the precipitate is filtered, washed two times with diisopropyl ether (200 mL), then dried under a vacuum at 30° C. to yield a poly(γ-benzyl-L-glutamic acid) capped at one of its ends by an acetyl group.

A solution of hydrobromic acid (HBr) at 33% in acetic acid (235 mL, 1.34 mol) is added dropwise to a solution of the capped co-polyamino acid (72 g) in trifluoroacetic acid (TFA, 335 mL) at 4° C. The mixture is stirred at ambient temperature for 3 h 30, then poured dropwise onto a 1:1 (v/v) mixture of diisopropyl ether and water under stirring (4 L). After 2 h of stirring, the heterogeneous mixture is allowed to stand overnight. The white precipitate is recovered by filtration, washed with a 1:1 (v/v) mixture of diisopropyl ether and water (340 mL), then with water (340 mL). The solid obtained is then solubilized in water (1.5 L) by adjusting the pH to 7 by addition of an aqueous sodium hydroxide solution 10 N, then an aqueous sodium hydroxide solution 1 N. After solubilization, the theoretical concentration is adjusted to 20 g/L theoretical by addition of water to obtain a final volume of 2.1 L. The solution is filtered through a 0.45 μm filter, then purified by ultrafiltration against a solution of NaCl 0.9%, then water until the conductimetry of the permeate is less than 50 μS/cm. The solution of co-polyamino acid is then concentrated until a final volume of 1.8 L is obtained. The aqueous solution is then acidified by addition of solution of hydrochloric acid 37% until a pH of 2 is obtained. After 4 h of stirring, the precipitate obtained is filtered, washed with water (330 mL), then dried under a vacuum at 30° C. to yield a poly-L-glutamic acid having a number average molecular weight (Mn) 3700 g/mol with respect to a polyoxyethylene standard (PEG).

Co-Polyamino Acid BB5

By a method similar to the one used for the preparation of co-polyamino acid BB2 applied to the hydrochloride salt of molecule BA2 (6.92 g, 8.8 mmol) and to co-polyamino acid BB5-1 (30.0 g), a sodium poly-L-glutamate capped at one of its ends by an acetyl group and modified by molecule BA2 is obtained.

Dry extract: 29.4 mg/g.
DP (estimated based on $^1$H NMR): 23.
Based on $^1$H NMR: i=0.042.
The calculated average molecular weight of co-polyamino acid BB5 is 4302 g/mol.
HPLC-aqueous SEC (calibrant PEG): Mn=3600 g/mol.

EXAMPLE BB6: CO-POLYAMINO ACID BB6-SODIUM POLY-L-GLUTAMATE CAPPED AT ONE OF ITS ENDS BY AN ACETYL GROUP AND MODIFIED BY MOLECULE BA2 AND HAVING A NUMBER AVERAGE MOLECULAR WEIGHT (MN) OF 4100 G/MOL

By a method similar to the one used for the preparation of co-polyamino acid BB2 applied to the hydrochloride salt of molecule BA2 (5.8 g, 7.4 mmol) and to a poly-L-glutamic acid having a number average molecular weight Mn=3800 g/mol (25 g) obtained by a method similar to the one used for the preparation of co-polyamino acid BB5-1 using ammonia instead of hexylamine, a sodium poly-L-glutamate capped at one of its ends by an acetyl group and modified by molecule BA2 is obtained.

Dry extract: 27.6 mg/g.
DP (estimated based on $^1$H NMR): 24.
Based on $^1$H NMR: i=0.04.
The calculated average molecular weight of co-polyamino acid BB6 is 4387 g/mol.
HPLC-aqueous SEC (calibrant PEG): Mn=4100 g/mol.

EXAMPLE BB7: CO-POLYAMINO ACID BB7-SODIUM POLY-L-GLUTAMATE MODIFIED BY MOLECULE BA2 AND HAVING A NUMBER AVERAGE MOLECULAR WEIGHT (MN) OF 4200 G/MOL

By a method similar to the one used for the preparation of co-polyamino acid BB2 applied to the hydrochloride acid of molecule BA2 (7.07 g, 9.0 mmol) and to a poly-L-glutamic acid having a number average molecular weight Mn=3600 g/mol (30.0 g) obtained by a method similar to the one used for the preparation of co-polyamino acid BB1-1, a sodium poly-L-glutamate modified by molecule BA2 is obtained.

Dry extract: 28.3 mg/g.
DP (estimated based on $^1$H NMR): 22.
Based on $^1$H NMR: i=0.042.
The calculated average molecular weight of co-polyamino acid BB7 is 4039 g/mol.
HPLC-aqueous SEC (calibrant PEG): Mn=4200 g/mol.

EXAMPLE BB8: CO-POLYAMINO ACID BB8-SODIUM POLY-L-GLUTAMATE MODIFIED BY MOLECULE BA2 AND HAVING A NUMBER AVERAGE MOLECULAR WEIGHT (MN) OF 5200 G/MOL

By a method similar to the one used for the preparation of co-polyamino acid BB2 applied to the hydrochloride salt of molecule BA2 (0.85 g, 1.1 mmol) and to a poly-L-glutamic acid having a number average molecular weight Mn=4100 g/mol (5.0 g) obtained by a method similar to the one used for the preparation of co-polyamino acid BB1-1, a sodium poly-L-glutamate modified by molecule BA2 is obtained.

Dry extract: 28.6 mg/g.
DP (estimated based on $^1$H NMR): 21.
Based on $^1$H NMR: i=0.026.
The calculated average molecular weight of co-polyamino acid BB8 is 3620 g/mol.
HPLC-aqueous SEC (calibrant PEG): Mn=5200 g/mol.

EXAMPLE BB9: CO-POLYAMINO ACID BB9-SODIUM POLY-L-GLUTAMATE MODIFIED BY MOLECULE BA3 AND HAVING A NUMBER AVERAGE MOLECULAR WEIGHT (MN) OF 4700 G/MOL

By a method similar to the one used for the preparation of co-polyamino acid BB2 applied to the hydrochloride salt of molecule BA3 (3.05 g, 3.6 mmol) and to a poly-L-glutamic acid having a number average molecular weight Mn=4100 g/mol (10.0 g) obtained by a method similar to the one used for the preparation of co-polyamino acid BB1-1, a sodium poly-L-glutamate modified by molecule BA3 is obtained.

Dry extract: 28.6 mg/g.
DP (estimated based on $^1$H NMR): 26.
Based on $^1$H NMR: i=0.05.
The calculated average molecular weight of co-polyamino acid BB9 is 4982 g/mol.
HPLC-aqueous SEC (calibrant PEG): Mn=4700 g/mol.

EXAMPLE BB10: CO-POLYAMINO ACID BB10-SODIUM POLY-L-GLUTAMATE MODIFIED BY MOLECULE BA3 AND HAVING A NUMBER AVERAGE MOLECULAR WEIGHT (MN) OF 4200 G/MOL

By a method similar to the one used for the preparation of co-polyamino acid BB2 applied to the hydrochloride salt of molecule BA3 (1.90 g, 2.3 mmol) and a poly-L-glutamic acid having a number average molecular weight Mn=3500 g/mol (10.0 g) by a method similar to the one used for the preparation of co-polyamino acid BB1-1, a sodium poly-L-glutamate modified by molecule BA3 is obtained.
Dry extract: 25.9 mg/g.
DP (estimated based on $^1$H NMR): 22.
Based on $^1$H NMR: i=0.029.
The calculated average molecular weight of co-polyamino acid BB10 is 3872 g/mol.
HPLC-aqueous SEC (calibrant PEG): Mn=4200 g/mol.

EXAMPLE BB11: CO-POLYAMINO ACID BB11-SODIUM POLY-L-GLUTAMATE CAPPED AT ONE OF ITS ENDS BY AN ACETYL GROUP AND MODIFIED BY MOLECULE BA4 AND HAVING A NUMBER AVERAGE MOLECULAR WEIGHT (MN) OF 3900 G/MOL

By a method similar to the one used for the preparation of co-polyamino acid BB2 applied to the hydrochloride salt of molecule BA4 (2.21 g, 2.2 mmol) and to a poly-L-glutamic acid having a number average molecular weight Mn=3700 g/mol (10 g) obtained by a method similar to the one used for the preparation of co-polyamino acid BB5-1, a sodium poly-L-glutamate capped at one of its ends by an acetyl group and modified by molecule BA4 is obtained.
Dry extract: 28.1 mg/g.
DP (estimated based on $^1$H NMR): 22.
Based on $^1$H NMR: i=0.032.
The calculated average molecular weight of co-polyamino acid BB11 is 4118 g/mol.
HPLC-aqueous SEC (calibrant PEG): Mn=3900 g/mol.

EXAMPLE BB12: CO-POLYAMINO ACID BB12-SODIUM POLY-L-GLUTAMATE CAPPED AT ONE OF ITS ENDS BY AN ACETYL GROUP AND MODIFIED BY MOLECULE BA3 AND HAVING A NUMBER AVERAGE MOLECULAR WEIGHT (MN) OF 3900 G/MOL

By a method similar to the one used for the preparation of co-polyamino acid BB2 applied to the hydrochloride salt of molecule BA3 (1.9 g, 2.3 mmol) and a poly-L-glutamic acid having a number average molecular weight Mn=3600 g/mol (10 g) obtained by a method similar to the one used for the preparation of co-polyamino acid BB5-1, a sodium poly-L-glutamate capped at one of its ends by an acetyl group and modified by molecule BA3 is obtained.
Dry extract: 26.7 mg/g.
DP (estimated based on $^1$H NMR): 23.
Based on $^1$H NMR: i=0.03.
The calculated average molecular weight of co-polyamino acid BB12 is 4145 g/mol.
HPLC-aqueous SEC (calibrant PEG): Mn=3900 g/mol.

EXAMPLE BB13: CO-POLYAMINO ACID BB13-SODIUM POLY-L-GLUTAMATE MODIFIED BY MOLECULE BA1 AND HAVING A NUMBER AVERAGE MOLECULAR WEIGHT (MN) OF 2800 G/MOL

By a method similar to the one used for the preparation of co-polyamino acid BB1 applied to the hydrochloride salt of molecule BA1 (3.65 g, 5 mmol) and to a poly-L-glutamic acid having a number average molecular weight Mn=3600 g/mol (10 g) also by a method similar to the one used for the preparation of co-polyamino acid BB1-1, a sodium poly-L-glutamate modified by molecule BA1 is obtained.
Dry extract: 25.6 mg/g.
DP (estimated based on $^1$H NMR): 25.
Based on $^1$H NMR: i=0.08.
The calculated average molecular weight of co-polyamino acid BB13 is 5253 g/mol.
HPLC-aqueous SEC (calibrant PEG): Mn=2800 g/mol.

EXAMPLE BB14: CO-POLYAMINO ACID BB14-SODIUM POLY-L-GLUTAMATE MODIFIED AT ONE OF ITS ENDS BY MOLECULE BA2 AND HAVING A NUMBER AVERAGE MOLECULAR WEIGHT (MN) OF 4020 G/MOL

The hydrochloride salt of molecule BA2 (2.12 g, 2.70 mmol), chloroform (40 mL), molecular mesh 4 Å (1.5 g) as well as the ion exchange resin Amberlite IRN 150 (1.5 g) are introduced successively into a suitable container. After 1 h of stirring on rollers, the medium is filtered and the resin is rinsed with chloroform. The mixture is evaporated, then co-evaporated with toluene. The residue is solubilized in anhydrous DMF (20 mL) to be used directly in the polymerization reaction.

In a round-bottom flask dried in the oven, γ-benzyl-L-glutamate N-carboxyanhydride (18 g, 68.42 mmol) is placed under a vacuum for 30 min, then anhydrous DMF (100 mL) is introduced. The mixture is stirred under argon until the solubilization is complete, cooled to 4° C., then the solution of molecule BA2 prepared as described above is introduced rapidly. The mixture is stirred between 4° C. and ambient temperature for 2 days, then heated at 65° C. for 2 h. The reaction mixture is then cooled to ambient temperature, then poured dropwise into diisopropyl ether (1.2 L) under stirring. The white precipitate is recovered by filtration, washed two times with diisopropyl ether (100 mL), then dried under a vacuum at 30° C. to obtain a white solid. The solid is diluted in TFA (105 mL), and a solution of hydrobromic acid (HBr) at 33% in acetic acid (38 mL, 220 mmol) is then added dropwise and at 0° C. The solution is stirred for 2 h at ambient temperature, then poured dropwise into a 1:1 (v/v) mixture of diisopropyl ether/water and under stirring (600 mL). After 2 h of stirring, the heterogeneous mixture is allowed to stand overnight. The white precipitate is recovered by filtration, washed successively with a 1:1 (v/v) mixture of diisopropyl ether and water (200 mL), then with water (100 mL). The solid obtained is solubilized in water (450 mL) by adjusting the pH to 7 by addition of an aqueous sodium hydroxide solution 10 N, then an aqueous sodium hydroxide solution 1 N. The mixture is filtered through a 0.45 μm filter, then purified by ultrafiltration against a solution of NaCl 0.9%, then water until the conductimetry of the permeate is less than 50 µS/cm. The solution of co-polyamino acid is then concentrated to approximately 30 g/L theoretical and the pH is adjusted to 7.0. The aqueous solution is filtered through a 0.2 µm filter and stored at 4° C.
Dry extract: 22.3 mg/g.
DP (estimated by $^1$H NMR)=29, thus i=0.034.
The calculated average molecular weight of co-polyamino acid BB14 is 5089 g/mol.
HPLC-aqueous SEC (calibrant PEG): Mn=4020 g/mol.

EXAMPLE BB15: CO-POLYAMINO ACID BB15-SODIUM POLY-L-GLUTAMATE MODIFIED AT ONE OF ITS ENDS BY MOLECULE BA3 AND HAVING A NUMBER AVERAGE MOLECULAR WEIGHT (MN) OF 3389 G/MOL

By a method similar to the one used for the preparation of co-polyamino acid BB14 applied to the hydrochloride salt of molecule BA3 (3.62 g, 4.32 mmol) and to 25.0 g (94.97 mmol) of γ-benzyl-L-glutamate N-carboxyanhydride, a sodium poly-L-glutamate modified at one of its ends by molecule BA3 is obtained.
Dry extract: 30.4 mg/g.
DP (estimated by $^1$H NMR)=24, thus i=0.042.
The calculated average molecular weight of co-polyamino acid BB15 is 4390 g/mol.
HPLC-aqueous SEC (calibrant PEG): Mn=3389 g/mol.

EXAMPLE BB16: CO-POLYAMINO ACID BB16-SODIUM POLY-L-GLUTAMATE MODIFIED AT ONE OF ITS ENDS BY MOLECULE BA4 AND HAVING A NUMBER AVERAGE MOLECULAR WEIGHT (MN) OF 3300 G/MOL

By a method similar to the one used for the preparation of co-polyamino acid BB14 applied to the hydrochloride salt of molecule BA4 (5.70 g, 5.70 mmol) and to 29.99 g (113.9 mmol) of γ-benzyl-L-glutamate N-carboxyanhydride, a sodium poly-L-glutamate modified at one of its ends by molecule BA4 is obtained.
Dry extract: 32.3 mg/g.
DP (estimated by $^1$H NMR)=23, thus i=0.043.
The calculated average molecular weight of co-polyamino acid BB16 is 4399 g/mol.
HPLC-aqueous SEC (calibrant PEG): Mn=3300 g/mol.

EXAMPLE BB17: CO-POLYAMINO ACID BB17-SODIUM POLY-L-GLUTAMATE MODIFIED AT ONE OF ITS ENDS BY MOLECULE BA3 AND HAVING A NUMBER AVERAGE MOLECULAR WEIGHT OF 10,700 G/MOL

By a method similar to the one used for the preparation of co-polyamino acid BB14 applied to the hydrochloride salt of molecule BA3 (2.51 g, 3 mmol) and to 52.7 g (200 mmol) of γ-benzyl-L-glutamate N-carboxyanhydride, a sodium poly-L-glutamate modified at one of its ends by molecule BA3 is obtained.
Dry extract: 24.5 mg/g.
DP (estimated by $^1$H NMR)=65, thus i=0.015.
The calculated average molecular weight of co-polyamino acid BB17 is 10,585 g/mol.
HPLC-aqueous SEC (calibrant PEG): Mn=10,700 g/mol.

EXAMPLE BB18: CO-POLYAMINO ACID BB18-SODIUM POLY-L-GLUTAMATE MODIFIED AT ONE OF ITS ENDS BY MOLECULE BA3 AND HAVING A NUMBER AVERAGE MOLECULAR WEIGHT OF 6600 G/MOL

By a method similar to the one used for the preparation of co-polyamino acid BB14 applied to the hydrochloride salt of molecule BA3 (2.51 g, 3 mmol) and to 31.6 g (120 mmol) of γ-benzyl-L-glutamate N-carboxyanhydride, a sodium poly-L-glutamate modified at one of its ends by molecule BA3 is obtained.
Dry extract: 27.3 mg/g.
DP (estimated by $^1$H NMR)=40, thus i=0.025.
The calculated average molecular weight of co-polyamino acid BB18 is 6889 g/g/mol.
HPLC-aqueous SEC (calibrant PEG): Mn=6600 g/g/mol.

EXAMPLE BB19: CO-POLYAMINO ACID BB19-SODIUM POLY-L-GLUTAMATE AND MODIFIED BY MOLECULE BA3 AND HAVING A NUMBER AVERAGE MOLECULAR WEIGHT (MN) OF 7700 G/MOL

By a method similar to the one used for the preparation of co-polyamino acid AB23 applied to the hydrochloride salt of molecule BA3 and to co-polyamino acid AB23-1, a sodium poly-L-glutamate modified by molecule BA3 is obtained.
Dry extract: 25.3 mg/g.
DP (estimated based on $^1$H NMR): 60.
Based on $^1$H NMR: i=0.045.
The calculated average molecular weight of co-polyamino acid BB19 is 11,188 g/g/mol.
HPLC-organic SEC (calibrant PEG): Mn=7700 g/mol.

EXAMPLE BB20: CO-POLYAMINO ACID BB20-SODIUM POLY-L-GLUTAMATE MODIFIED AT ONE OF ITS ENDS BY MOLECULE BA5 AND HAVING A NUMBER AVERAGE MOLECULAR WEIGHT (MN) OF 2800 G/MOL

By a method similar to the one used for the preparation of co-polyamino acid BB14 applied to molecule BA5 in the form of a free amine (1.70 g, 1.98 mmol) and to γ-benzyl-L-glutamate N-carboxyanhydride (11.46 g, 43.5 mmol), a sodium poly-L-glutamate modified at one of its ends by molecule BA5 is obtained.
Dry extract: 20.7 mg/g.
DP (estimated by $^1$H NMR)=23, thus i=0.043.
The calculated average molecular weight of co-polyamino acid BB20 is 4295 g/g/mol.
HPLC-aqueous SEC (calibrant PEG): Mn=2800 g/g/mol.

EXAMPLE BB21: CO-POLYAMINO ACID BB21-SODIUM POLY-L-GLUTAMATE MODIFIED AT ONE OF ITS ENDS BY MOLECULE BA3 AND HAVING A NUMBER AVERAGE MOLECULAR WEIGHT (MN) OF 1100 G/MOL

By a method similar to the one used for the preparation of co-polyamino acid BB14 applied to molecule BA3 in the form of a free amine (3.814 g, 4.75 mmol) and to γ-benzyl- L-glutamate N-carboxyanhydride (10.0 g, 38.0 mmol), a sodium poly-L-glutamate modified at one of its ends by molecule BA3 is obtained.
Dry extract: 16.1 mg/g.
DP (estimated by $^1$H NMR)=9, thus i=0.11.
The calculated average molecular weight of co-polyamino acid BB21 is 2123 g/g/mol.
HPLC-aqueous SEC (calibrant PEG): Mn=1100 g/g/mol.

EXAMPLE BB22: CO-POLYAMINO ACID BB22-SODIUM POLY-L-GLUTAMATE MODIFIED AT ONE OF ITS ENDS BY MOLECULE BA6 AND HAVING A NUMBER AVERAGE MOLECULAR WEIGHT (MN) OF 3300 G/MOL

By a method similar to the one used for the preparation of co-polyamino acid BB14 applied to molecule BA6 in the form of a free amine (4.45 g, 5.18 mmol) and to 30.0 g (113.96 mmol) of γ-benzyl-L-glutamate N-carboxyanhydride, a sodium poly-L-glutamate modified at one of its ends by molecule BA6 is obtained.
Dry extract: 29.0 mg/g.
DP (estimated by $^1$H NMR)=25, thus i=0.04.
The calculated average molecular weight of co-polyamino acid BB22 is 4597 g/mol.
HPLC-aqueous SEC (calibrant PEG): Mn=3300 g/mol.

EXAMPLE BB23: CO-POLYAMINO ACID BB23-SODIUM POLY-L-GLUTAMATE MODIFIED AT ONE OF ITS ENDS BY MOLECULE BA7 AND HAVING A NUMBER AVERAGE MOLECULAR WEIGHT (MN) OF 2900 G/MOL

By a method similar to the one used for the preparation of co-polyamino acid BB14 applied to molecule BA7 in the form of a free amine (3.05 g, 4.01 mmol) and to γ-benzyl-L-glutamate N-carboxyanhydride (22.78 g, 86.5 mmol), a sodium poly-L-glutamate modified at one of its ends by molecule BA7 is obtained.
Dry extract: 16.9 mg/g.
DP (estimated by $^1$H NMR)=21, thus i=0.048.
The calculated average molecular weight of co-polyamino acid BB23 is 3894 g/mol.
HPLC-aqueous SEC (calibrant PEG): Mn=2900 g/mol.

EXAMPLE BB24: CO-POLYAMINO ACID BB27-SODIUM POLY-L-GLUTAMATE MODIFIED AT ONE OF ITS ENDS BY MOLECULE BA3 AND MODIFIED BY MOLECULE BA3 AND HAVING A NUMBER AVERAGE MOLECULAR WEIGHT (MN) OF 2300 G/MOL

Co-polyamino acid BB24-1: poly-L-glutamic acid modified at one of its ends by molecule BA3 and capped at the other end by pidolic acid.
In a round-bottom flask dried in the oven, γ-benzyl-L-glutamate N-carboxyanhydride (122.58 g, 466 mmol) is placed under a vacuum for 30 min, then anhydrous DMF (220 mL) is introduced. The mixture is stirred under argon until the solubilization is complete, cooled to −10° C., then a solution of molecule BA3 in the form of a free amine (17.08 g, 21.3 mmol) in chloroform (40 mL) is introduced rapidly. The mixture is stirred between 0° C. and ambient temperature for 2 days, then heated at 65° C. for 4 h. The reaction mixture is then cooled to 25° C., then pidolic acid (13.66 g, 105.8 mmol) is added, HOBt (2.35 g, 15.3 mmol) and EDC (20.28 g, 105.8 mmol) are added. After 24 h of stirring at 25° C., the solution is concentrated under a vacuum to eliminate the chloroform and 50% of the DMF. The reaction mixture is then heated to 55° C. and 1150 mL of methanol are introduced in 1 h. The reaction mixture is then cooled to 0° C. After 18 h, the white precipitate is recovered by filtration, washed three times with 270 mL of diisopropyl ether, then dried under a vacuum at 30° C. to obtain a white solid. The solid is diluted in TFA (390 mL), and a solution of hydrobromic acid (HBr) at 33% in acetic acid (271 mL, 1547 mmol) is then added dropwise and at 0° C. The solution is stirred for 2 h at ambient temperature, then poured dropwise into a 1:1 (v/v) mixture of diisopropyl ether/water and under stirring (970 mL). After 2 h of stirring, the heterogeneous mixture is allowed to stand overnight. The white precipitate is recovered by filtration, washed successively with diisopropyl ether (380 mL), then two times with water (380 mL mL). The solid obtained is solubilized in water (3.6 L) by adjusting the pH to 7 by addition of an aqueous sodium hydroxide solution 10 N, then an aqueous sodium hydroxide solution 1 N. The mixture is filtered through a 0.45 µm filter, then purified by ultrafiltration against a solution of NaCl 0.9%, a solution of NaOH 0.1 N, a solution of NaCl 0.9%, a phosphate buffer solution (150 mM), a solution of NaCl 0.9%, then water until the conductimetry of the permeate is less than 50 µS/cm. The solution of co-polyamino acid is then concentrated to approximately 30 g/L theoretical, filtered through a 0.2 µm filter, then acidified to pH 2 under stirring by addition of a solution of HCl at 37%. The precipitate is then recovered by filtration, washed two times with water, then dried under a vacuum at 30° C. to obtain a white solid.

Co-Polyamino Acid BB24

By a method similar to the one used for the preparation of co-polyamino acid BB2 applied to molecule BA3 in the form of a free amine (1.206 g, 1.50 mmol) and to co-polyamino acid BB24-1 (5.5 g, 33.4 mmol), a sodium poly-L-glutamate modified at one of its ends by molecule BA3 and modified by molecule BA3 is obtained.
Dry extract: 19.0 mg/g.
DP (estimated based on $^1$H NMR): 22.
Based on $^1$H NMR: i=0.089.
The calculated average molecular weight of co-polyamino acid BB24 is 4826 g/mol.
HPLC-aqueous SEC (calibrant PEG): Mn=2300 g/mol

EXAMPLE BB25: CO-POLYAMINO ACID BB25-SODIUM POLY-L-GLUTAMATE MODIFIED AT ONE OF ITS ENDS BY MOLECULE BA3 AND AT THE OTHER END BY MOLECULE B8 AND HAVING A NUMBER AVERAGE MOLECULAR WEIGHT (MN) OF 2000 G/MOL

DCC (0.257 g, 1.24 mmol) and NHS (0.143 g, 1.24 mmol) are introduced into a solution of molecule B8 (0.946 g, 1.24 mmol) in DMF (8 mL). After 16 h of stirring at ambient temperature, the solution is filtered to be used directly in the next reaction.

In a round-bottom flask dried in the oven, γ-benzyl-L-glutamate N-carboxyanhydride (6.0 g, 22.8 mmol) is placed under a vacuum for 30 min, then anhydrous DMF (14 mL) is introduced. The mixture is then stirred under argon until the dissolution is complete, cooled to 0° C., then a solution of molecule BA3 in the form of a free amine (0.832 g, 1.04 mmol) in chloroform (2.0 mL) is introduced rapidly. After 18 h of stirring at 0° C., the previously prepared solution of molecule B8 is added. The solution is stirred between 0° C. and ambient temperature for 22 h, then poured dropwise into diisopropyl ether (0.34 L) under stirring. The precipitate is recovered by filtration, washed with diisopropyl ether (7 times 15 mL), then dried under a vacuum at 0° C. to yield a white solid. The solid is diluted in TFA (23 mL), then the solution is cooled to 4° C. A solution of HBr at 33% in acetic acid (15 mL, 85.7 mmol) is then added dropwise. The mixture is stirred at ambient temperature for 2 h, then poured dropwise into a 1:1 (v/v) mixture of diisopropyl ether and water under stirring (0.28 L). After 2 h of stirring, the heterogeneous mixture is allowed to stand overnight. The white precipitate is recovered by filtration, washed two times with a 1:1 (v/v) mixture of diisopropyl ether and water (24 mL), then two times with water (24 mL). The solid obtained is then solubilized in water (0.16 L) by adjusting the pH to 12 by addition of an aqueous sodium hydroxide solution 10 N, then an aqueous sodium hydroxide solution 1 N. After 30 min, the pH is adjusted to 7 by slow addition of an aqueous HCl solution 1 N. The solution is filtered through a 0.45 μm filter, then purified by ultrafiltration against a solution of NaCl 0.9% %, then water until the conductimetry of the permeate is less than 50 μS/cm. The solution obtained is filtered through a 0.2 μm filter and stored at 2-8° C.

Dry extract: 18.9 mg/g.

DP (estimated based on $^1$H NMR): 22.

Based on $^1$H NMR: i=0.09.

The calculated average molecular weight of co-polyamino acid BB25 is 4871 g/mol.

HPLC-aqueous SEC (calibrant PEG): Mn=2000 g/mol

C. Compositions

EXAMPLE CV1: PREPARATION OF A SOLUTION OF HUMAN AMYLIN AT 0.6 MG/ML CONTAINING M-CRESOL (29 MM), GLYCEROL (174 MM) AT PH 7.4

A concentrated solution of human amylin at 3 mg/mL is prepared by dissolution of human amylin in the form of a powder purchased from AmbioPharm. This solution is added to a concentrated solution of excipients (m-cresol, glycerol) in such a manner as to obtain the intended final composition. The final pH is adjusted to 7.4 by addition of NaOH/HCl.

EXAMPLE CV2: PREPARATION OF A SOLUTION OF HUMAN AMYLIN AT 0.6 MG/ML CONTAINING CO-POLYAMINO ACID BB15, M-CRESOL (29 MM) AND GLYCEROL (174 MM) AT PH 7.4

A concentrated solution of co-polyamino acid BB15 and excipients is prepared by adding concentrated solutions of excipients (m-cresol, glycerol) to a concentrated solution of co-polyamino acid BB15.

The concentrated solution of human amylin at 3 mg/mL C1 is added to this concentrated solution of co-polyamino acid BB15 and excipients in such a manner as to obtain the final compositions CV5 to CV11 (table 1g). The final pH is adjusted to 7.4 by addition of NaOH/HCl.

TABLE 1g

Compositions and visual appearance of solutions of human amylin at pH 7.4 at different concentrations of co-polyamino acid BB15.

| Solution | Ratio BB15/ human amylin mol/mol | Concentration of co-polyamino acid BB15 mg/mL | mM | Visual appearance of the solution |
|---|---|---|---|---|
| CV1 | — | — | — | Clear |
| CV5 | 5 | 3 | 0.73 | Clear |
| CV6 | 6 | 3.6 | 0.88 | Clear |
| CV7 | 7 | 4.2 | 1.03 | Clear |
| CV8 | 8 | 4.8 | 1.17 | Clear |
| CV9 | 9 | 5.4 | 1.32 | Clear |
| CV10 | 10 | 6 | 1.47 | Clear |
| CV11 | 17 | 10.5 | 2.57 | Clear |

EXAMPLE CY1: PREPARATION OF A SOLUTION OF PRAMLINTIDE AT 0.9 MG/ML CONTAINING M-CRESOL (29 MM) AND GLYCEROL (174 MM) AT PH 7.4

A concentrated solution of pramlintide at 5 mg/mL is prepared by dissolution of pramlintide in the form of a powder purchased from Hybio. This solution is added to a concentrated solution of excipients (m-cresol, glycerol) in such a manner as to obtain the intended final composition. The final pH is adjusted to 7.4 by addition of NaOH/HCl.

EXAMPLE CW1: PREPARATION OF A SOLUTION OF PRAMLINTIDE AT 0.4 MG/ML CONTAINING PHENOL (30 MM), GLYCEROL (174 MM) AND GLYCYLGLYCINE (8 MM) AT PH 7.4

By a method similar to the one used in Example CY1, a solution of pramlintide at 0.4 mg/mL containing phenol (30 mM), glycerol (174 mM) and glycylglycine (8 mM) at pH 7.4 is obtained.

EXAMPLE CY0: PREPARATION OF A SOLUTION OF PRAMLINTIDE AT 0.9 MG/ML CONTAINING CO-POLYAMINO ACID BB15, M-CRESOL (29 MM) AND GLYCEROL (174 MM) AT PH 7.4

A concentrated solution of co-polyamino acid BB15 and excipients is prepared by adding concentrated solutions of excipients (m-cresol, glycerol) to a concentrated solution of co-polyamino acid BB15.

A concentrated solution of pramlintide at 5 mg/mL is added to this concentrated solution of co-polyamino acid BB15 and excipients in such a manner as to obtain the final compositions CY2 to CY7 (table 3). The final pH is adjusted to 7.4 by addition of NaOH/HCl.

TABLE 3

Compositions and visual appearance of solutions of pramlintide at pH 7.4 at different concentrations of co-polyamino acids BB15.

| Solution | Ratio BB15/ pramlintide mol/mol | Concentration of co-polyamino acid BB15 mg/mL | mM | Visual appearance of the solution |
|---|---|---|---|---|
| CY1 | — | — | — | Clear |
| CY2 | 2 | 1.8 | 0.44 | Clear |

TABLE 3-continued

Compositions and visual appearance of solutions of pramlintide at pH 7.4 at different concentrations of co-polyamino acids BB15.

| Solution | Ratio BB15/ pramlintide mol/mol | Concentration of co-polyamino acid BB15 | | Visual appearance of the solution |
|---|---|---|---|---|
| | | mg/mL | mM | |
| CY3 | 3 | 2.7 | 0.66 | Clear |
| CY4 | 4 | 3.6 | 0.88 | Clear |
| CY5 | 5 | 4.5 | 1.10 | Clear |
| CY6 | 6 | 5.4 | 1.32 | Clear |
| CY7 | 10 | 9 | 2.20 | Clear |

EXAMPLE CW0: PREPARATION A SOLUTION OF PRAMLINTIDE AT 0.4 MG/ML CONTAINING CO-POLYAMINO ACID BB15, PHENOL (30 MM), GLYCEROL (174 MM) AND GLYCYLGLYCINE (8 MM) AT PH 7.4

By a method similar to the one used in Example CY0, starting with a solution of pramlintide at 0.4 mg/mL CW1, solutions of pramlintide at 0.4 mg/mL containing co-polyamino acid BB15, phenol (30 mM), glycerol (174 mM) and glycylglycine (8 mM) at pH 7.4, CW2 and CW3 are obtained.

TABLE 4

Compositions and visual appearance of solutions of pramlintide at 0.4 mg/mL at pH 7.4 at different concentrations of co-polyamino acid BB15.

| Solution | Concentration of co-polyamino acid BB15 | | Ratio BB15/ pramlintide mol/mol | Visual appearance of the solution |
|---|---|---|---|---|
| | mg/mL | mM | | |
| CW2 | 2.4 | 0.59 | 6 | Clear |
| CW3 | 4 | 0.98 | 10 | Clear |

EXAMPLE CP0: PREPARATION OF A SOLUTION OF PRAMLINTIDE AT 0.9 MG/ML CONTAINING DIFFERENT CO-POLYAMINO ACIDS OF THE INVENTION, M-CRESOL (29 MM) AND GLYCEROL (174 MM) AT PH 7.4

By a method similar to the one described in Example CY0, solutions of pramlintide at 0.9 mg/mL containing different co-polyamino acids of the invention, m-cresol (29 mM) and glycerol (174 mM) at pH 7.4, CP2 to CP12 are obtained.

TABLE 8

Compositions and visual appearance of solutions of pramlintide at 0.9 mg/mL at pH 7.4 in the presence of different co-polyamino acids.

| Solution | Co-polyamino acid | Concentration of co-polyamino acid | | Ratio co-polyamino acid/ pramlintide mol/mol | Visual appearance of the solution |
|---|---|---|---|---|---|
| | | mg/mL | mM | | |
| CP2 | BB15 | 5 | 1.22 | 5.4 | Clear |
| | | 10 | 2.45 | 10.8 | Clear |
| CP3 | BB14 | 5 | 0.98 | 4.3 | Clear |
| | | 10 | 1.96 | 8.6 | Clear |
| CP4 | AB17 | 5 | 1.11 | 4.9 | Clear |
| | | 10 | 1.22 | 9.8 | Clear |
| CP5 | AB15 | 5 | 0.99 | 4.4 | Clear |
| | | 10 | 1.99 | 8.8 | Clear |
| CP6 | AB14 | 5 | 1.48 | 6.5 | Clear |
| | | 10 | 2.96 | 13 | Clear |
| CP10 | BB18 | 5 | 0.72 | 3.2 | Clear |
| | | 10 | 1.44 | 6.3 | Clear |
| CP11 | BB9 | 5 | 1 | 4.4 | Clear |
| | | 10 | 2.01 | 8.8 | Clear |
| CP12 | BB2 | 5 | 1.27 | 5.6 | Clear |
| | | 10 | 2.54 | 11.2 | Clear |

EXAMPLE CH1: PREPARATION OF A SOLUTION OF PRAMLINTIDE AT 0.6 MG/ML CONTAINING M-CRESOL (29 MM) AND GLYCEROL (174 MM) AT PH 6.6

A concentrated solution of pramlintide at 5 mg/mL is prepared by dissolution of pramlintide in the form of a powder purchased from Ambiopharm. This solution is added to a concentrated solution of excipients (m-cresol, glycerol) in such a manner as to obtain the intended final composition. The final pH is adjusted to 6.6 by addition of NaOH/HCl.

EXAMPLE CH0: PREPARATION OF A SOLUTION OF PRAMLINTIDE AT 0.6 MG/ML CONTAINING CO-POLYAMINO ACID BB15, M-CRESOL (29 MM) AND GLYCEROL (174 MM) AT PH 6.6

A concentrated solution of copolyamino acid BB15 and excipients is prepared by adding concentrated solutions of excipients (m-cresol, glycerol) to a concentrated solution of co-polyamino acid BB15.

A concentrated solution of pramlintide at 5 mg/mL at pH 4 is added to this concentrated solution of co-polyamino acid BB15 and excipients in such a manner as to obtain the final compositions CH2 to CH8 (table 9). The final pH is adjusted to 6.6 by addition of NaOH/HCl.

TABLE 9

Compositions and visual appearance of solutions of pramlintide at pH 6.6 at different concentrations of co-polyamino acid BB15.

| Solution | Ratio BB15/ pramlintide mol/mol | Concentration of co-polyamino acid BB15 | | Visual appearance of the solution |
|---|---|---|---|---|
| | | mg/mL | mM | |
| CH1 | — | — | — | Clear |
| CH2 | 2 | 1.3 | 0.29 | Clear |
| CH3 | 3 | 2 | 0.45 | Clear |
| CH4 | 4 | 2.7 | 0.61 | Clear |
| CH5 | 6 | 4 | 0.90 | Clear |
| CH6 | 8 | 5.3 | 1.19 | Clear |
| CH7 | 10 | 6.7 | 1.50 | Clear |
| CH8 | 15 | 10 | 2.24 | Clear |

EXAMPLE CI0: PREPARATION OF A SOLUTION OF PRAMLINTIDE AT 0.6 MG/ML CONTAINING DIFFERENT CO-POLYAMINO ACIDS OF THE INVENTION, M-CRESOL (29 MM) AND GLYCEROL (174 MM) AT PH 6.6

By a method similar to the one described in example CH0, solutions of pramlintide at 0.6 mg/mL containing different co-polyamino acids of the invention, m-cresol (29 mM) and glycerol (174 mM) at pH 6.6, CI1 to CI14 are obtained.

TABLE 10

Compositions and visual appearance of solutions of pramlintide at pH 6.6 in the presence of different co-polyamino acids.

| Solution | Co-polyamino acid | Concentration of co-polyamino acid mg/mL | mM | Ratio co-polyamino acid/pramlintide mol/mol | Visual appearance of the solution |
|---|---|---|---|---|---|
| CI1 | BB20 | 1.3 | 0.3 | 2 | Clear |
|  |  | 2.6 | 0.6 | 4 | Clear |
| CI2 | BB21 | 1.3 | 0.6 | 4 | Clear |
| CI3 | AB22 | 2.4 | 0.3 | 2 | Clear |
| CI4 | BB24 | 2.9 | 0.6 | 4 | Clear |
| CI5 | BB25 | 1.5 | 0.3 | 2 | Clear |
|  |  | 3 | 0.6 | 4 | Clear |
| CI6 | AB23 | 3.4 | 0.23 | 2 | Clear |
| CI7 | AB28 | 2.3 | 0.3 | 2 | Clear |
|  |  | 4.7 | 0.6 | 4 | Clear |
| CI8 | AB24 | 1.2 | 0.15 | 1 | Clear |
|  |  | 2.4 | 0.3 | 2 | Clear |
| CI9 | AB25 | 1.3 | 0.15 | 1 | Clear |
|  |  | 2.6 | 0.3 | 2 | Clear |
| CI10 | AB26 | 0.7 | 0.15 | 1 | Clear |
|  |  | 1.5 | 0.3 | 2 | Clear |
| CI11 | AB27 | 1.3 | 0.15 | 1 | Clear |
|  |  | 2.7 | 0.3 | 2 | Clear |
| CI12 | AB31 | 1.3 | 0.15 | 1 | Clear |
|  |  | 2.5 | 0.3 | 2 | Clear |
| CI13 | AB29 | 8.9 | 1.15 | 7.6 | Clear |
| CI14 | AB32 | 1.3 | 0.15 | 1 | Clear |
|  |  | 2.5 | 0.3 | 2 | Clear |

EXAMPLE CT0: PREPARATION OF A SOLUTION OF PRAMLINTIDE AT 0.6 MG/ML CONTAINING CO-POLYAMINO ACID AB14, M-CRESOL (29 MM), GLYCEROL (174 MM), NACL AND ZINC CHLORIDE AT PH 6.6

A concentrated solution of co-polyamino acid AB14 and excipients is prepared by adding concentrated solutions of excipients (m-cresol, glycerol, NaCl, zinc chloride) to a concentrated solution of co-polyamino acid AB14.

A concentrated solution of pramlintide at 5 mg/mL at pH 4 is added to this concentrated solution of co-polyamino acid AB14 and excipients in such a manner as to obtain the final composition CT1 to CT5 (table 11). The final pH is adjusted to 6.6 by addition of NaOH/HCl.

TABLE 11

Compositions and visual appearance of the solutions of pramlintide at pH 6.6 in the presence of co-polyamino acid AB14 and of different contents of sodium chloride and zinc chloride.

| Solution | Co-polyamino acid | Concentration of co-polyamino acid mg/mL | mM | [NaCl] (mM) | [ZnCl$_2$] (mM) | Visual appearance of the solution |
|---|---|---|---|---|---|---|
| CT1 | AB14 | 6.3 | 1.87 | — | 0.75 | Clear |
| CT2 | AB14 | 6.3 | 1.87 | 50 | — | Clear |
| CT3 | AB14 | 6.3 | 1.87 | 100 | — | Clear |
| CT4 | AB14 | 6.3 | 1.87 | 50 | 0.75 | Clear |
| CT5 | AB14 | 6.3 | 1.87 | 100 | 0.75 | Clear |

EXAMPLE CS0: PREPARATION OF A SOLUTION OF PRAMLINTIDE AT 0.6 MG/ML CONTAINING DIFFERENT CO-POLYAMINO ACIDS OF THE INVENTION, M-CRESOL (29 MM), GLYCEROL (174 MM), NACL AND ZINC CHLORIDE AT PH 6.6

By a method similar to the one described in example CA4, solutions of pramlintide at 0.6 mg/mL containing different co-polyamino acids of the invention, m-cresol (29 mM) and glycerol (174 mM), sodium chloride and zinc chloride at pH 6.6, BS1 to BS11 are obtained.

TABLE 12

Compositions and visual appearance of the solutions of pramlintide at pH 6.6 in the presence of different co-polyamino acids and of different contents of sodium chloride and zinc chloride

| Solution | Co-polyamino acid | Concentration of co-polyamino acid mg/mL | mM | [NaCl] (mM) | [ZnCl$_2$] (mM) | Visual appearance of the solution |
|---|---|---|---|---|---|---|
| CS1 | AB15 | 7.8 | 1.6 | — | — | Clear |
| CS2 | AB15 | 11.7 | 2.3 | — | — | Clear |
| CS3 | AB15 | 3.9 | 0.8 | 50 | — | Clear |
| CS4 | AB15 | 6.3 | 1.3 | 50 | — | Clear |
| CS5 | AB15 | 7.8 | 1.6 | 50 | — | Clear |
| CS6 | AB15 | 3.9 | 0.8 | 100 | — | Clear |
| CS7 | AB16 | 12.4 | 1.5 | — | — | Clear |
| CS8 | AB16 | 16.7 | 2.1 | — | — | Clear |
| CS9 | AB16 | 7.4 | 0.9 | 50 | | Clear |
| CS10 | AB16 | 12.4 | 1.5 | 50 | | Clear |
| CS11 | AB16 | 7.4 | 0.9 | 50 | 1 | Clear |

EXAMPLE CX1: PREPARATION OF A SOLUTION OF HUMAN AMYLIN AT 0.6 MG/ML AND HUMAN INSULIN AT 100 IU/ML CONTAINING M-CRESOL (29 MM), GLYCEROL (174 MM) AND ZINC CHLORIDE (229 µM) AT PH 7.4

The concentrated solution of human amylin at 3 mg/mL CV1 is added to a concentrated solution of excipients (m-cresol, glycerol). A solution of human insulin at 500 IU/mL is prepared by dissolution of human insulin in the form of a powder purchased from Amphastar. This solution is added to the concentrated solution of human amylin and excipients in such a manner as to obtain the intended final composition. The final pH is adjusted to 7.4 by addition of NaOH/HCl.

EXAMPLE CX2: PREPARATION OF A SOLUTION OF HUMAN AMYLIN AT 0.6 MG/ML AND OF HUMAN INSULIN AT 100 IU/ML CONTAINING CO-POLYAMINO ACID BB15, M-CRESOL (29 MM), GLYCEROL (174 MM) AND ZINC CHLORIDE (229 µM) AT PH 7.4

A concentrated solution of co-polyamino acid BB15 and excipients is prepared by adding concentrated solutions of excipients (m-cresol, glycerol, zinc chloride) to a concentrated solution of co-polyamino acid BB15.

A concentrated solution of human amylin at 3 mg/mL, then a solution of human insulin at 500 IU/mL are added to the concentrated solution of co-polyamino acid BB15 and excipients in such a manner as to obtain the intended final composition (table 13). The final pH is adjusted to 7.4 by addition of NaOH/HCl.

The solutions CX1, CX6, CX10 and CX11 are prepared according to the above protocol.

TABLE 11

Composition and visual appearance of solutions of human amylin and of human insulin at pH 7.4 at different concentrations of co-polyamino acid BB15.

| Solution | Ratio BB15/ human amylin mol/mol | Concentration of co-polyamino acid BB15 mg/mL | mM | Visual appearance of the solution |
|---|---|---|---|---|
| CX1 | — | — | — | Turbid |
| CX6 | 6 | 3.6 | 0.88 | Clear |
| CX10 | 10 | 6 | 1.47 | Clear |
| CX11 | 17 | 10.5 | 2.57 | Clear |

In the presence of co-polyamino acid BB15, a clear solution of human amylin (0.6 mg/mL) and of human insulin (100 IU/mL) is obtained at pH 7.4.

EXAMPLE CN1: PREPARATION OF A SOLUTION OF PRAMLINTIDE AT 0.4 MG/ML AND OF HUMAN INSULIN AT 100 IU/ML CONTAINING PHENOL (30 MM), GLYCEROL (174 MM), GLYCYLGLYCINE (8 MM) AND ZINC CHLORIDE (229 µM) AT PH 7.4

A concentrated solution of pramlintide at 5 mg/mL is added to a concentrated solution of excipients (m-cresol, glycerol, glycylglycine, zinc chloride). A solution of human insulin at 500 IU/mL is added to this concentrated solution of pramlintide and excipients in such a manner as to obtain the intended final composition. The final pH is adjusted to 7.4 by addition of NaOH/HCl.

EXAMPLE CR1: PREPARATION OF A SOLUTION OF PRAMLINTIDE AT 0.9 MG/ML AND OF HUMAN INSULIN AT 100 IU/ML CONTAINING M-CRESOL (29 MM), GLYCEROL (174 MM) AND ZINC CHLORIDE (229 µM) AT PH 7.4

By a method similar to the one used in example CN1, a solution of pramlintide at 0.9 mg/mL and of human insulin at 100 IU/mL containing m-cresol (29 mM), glycerol (174 mM) and zinc chloride (229 µM) at pH 7.4 is obtained.

EXAMPLE CN0: PREPARATION OF A SOLUTION OF PRAMLINTIDE AT 0.4 MG/ML AND OF HUMAN INSULIN AT 100 IU/ML CONTAINING CO-POLYAMINO ACID BB15, PHENOL (30 MM), GLYCEROL (174 MM), GLYCYLGLYCINE (8 MM) AND ZINC CHLORIDE (229 µM) AT PH 7.4

A concentrated solution of co-polyamino acid BB15 and excipients is prepared by adding concentrated solutions of excipients (m-cresol, glycerol, glycylglycine, zinc chloride) to a concentrated solution of co-polyamino acid BB15.

A concentrated solution of pramlintide at 5 mg/mL, then a solution of human insulin at 500 IU/mL are added to this concentrated solution of co-polyamino acid BB15 and excipients in such a manner as to obtain the intended final composition (table 14). The final pH is adjusted to 7.4 by addition of NaOH/HCl.

The solutions CN2 and CN3 are prepared according to the above protocol.

TABLE 14

Compositions and visual appearance of the solutions of pramlintide at 0.4 mg/mL and of human insulin at 100 IU/mL at pH 7.4 at different concentrations of co-polyamino acid BB15.

| Solution | Concentration of co-polyamino acid BB15 mg/mL | mM | Ratio BB15/ pramlintide mol/mol | Visual appearance of the mixture |
|---|---|---|---|---|
| CN1 | — | — | — | Turbid |
| CN2 | 2.4 | 0.59 | 6 | Clear |
| CN3 | 4 | 0.98 | 10 | Clear |

In the presence of co-polyamino acid BB15, a clear solution of pramlintide (0.4 mg/mL) and of human insulin (100 IU/mL) is obtained at pH 7.4.

EXAMPLE CR0: PREPARATION OF A SOLUTION OF PRAMLINTIDE AT 0.9 MG/ML AND OF HUMAN INSULIN AT 100 IU/ML CONTAINING CO-POLYAMINO ACID BB15, M-CRESOL (29 MM), GLYCEROL (174 MM) AND ZINC CHLORIDE (229 µM) AT PH 7.4

By a method similar to the one used in example CN0, a solution of pramlintide at 0.9 mg/mL and of human insulin at 100 IU/mL containing co-polyamino acid BB15, m-cresol (29 mM), glycerol (174 mM) and zinc chloride (229 µM) at pH 7.4 is obtained.

The solutions CR2 to CR4 and CU2 to CU8 are prepared according to the above protocol.

TABLE 15

Compositions and appearance of the solutions of pramlintide at 0.9 mg/mL and of human insulin at 100 IU/mL at pH 7.4 at different concentrations of co-polyamino acid BB15.

| Solution | Concentration of co-polyamino acid BB15 mg/mL | mM | Ratio BB15/ pramlintide mol/mol | Visual appearance of the solution |
|---|---|---|---|---|
| CR1 | — | — | — | Turbid |
| CR2 | 2.7 | 0.66 | 3 | Clear |
| CR3 | 3.6 | 0.88 | 4 | Clear |

TABLE 15-continued

Compositions and appearance of the solutions of pramlintide at 0.9 mg/mL and of human insulin at 100 IU/mL at pH 7.4 at different concentrations of co-polyamino acid BB15.

| Solution | Concentration of co-polyamino acid BB15 | | Ratio BB15/ pramlintide | Visual appearance of the solution |
|---|---|---|---|---|
| | mg/mL | mM | mol/mol | |
| CR4 | 4.5 | 1.10 | 5 | Clear |
| CU2 | 0.9 | 0.22 | 1 | Clear |
| CU3 | 1.8 | 0.44 | 2 | Clear |
| CU7 | 5.4 | 1.32 | 6 | Clear |
| CU8 | 9 | 2.20 | 10 | Clear |

In the presence of co-polyamino acid BB15, a clear solution of pramlintide (0.9 mg/mL) and of human insulin (100 IU/mL) at pH 7.4 is obtained.

EXAMPLE CG0: PREPARATION OF A SOLUTION OF PRAMLINTIDE AT 0.9 MG/ML AND OF HUMAN INSULIN AT 100 IU/ML CONTAINING DIFFERENT CO-POLYAMINO ACIDS OF THE INVENTION, M-CRESOL (29 MM), GLYCEROL (174 MM) AND ZINC CHLORIDE (229 µM) AT PH 7.4

By a method similar to example CN0, a solution of pramlintide at 0.9 mg/mL and of human insulin at 100 IU/mL containing a co-polyamino acid of the invention, m-cresol (29 mM), glycerol (174 mM) and zinc chloride (229 µM) at pH 7.4 is obtained.

The solutions CG2 to CG12 are prepared according to the above-described protocol.

TABLE 16

Compositions and visual appearance of solutions of pramlintide at 0.9 mg/mL and of human insulin at 100 IU/mL at pH 7.4 at different concentrations of co-polyamino acids.

| Solution | Co-polyamino acid | Concentration of co-polyamino acid | | Ratio Co-polyamino acid/pramlintide | Visual appearance of the solution |
|---|---|---|---|---|---|
| | | mg/mL | mM | mol/mol | |
| CG2 | BB15 | 5 | 1.22 | 5.4 | Clear |
| | | 10 | 2.45 | 10.8 | Clear |
| CG3 | BB14 | 5 | 0.98 | 4.3 | — |
| | | 10 | 1.96 | 8.6 | Clear |
| CG4 | AB17 | 5 | 1.11 | 4.9 | Clear |
| | | 10 | 1.22 | 9.8 | Clear |
| CG5 | AB15 | 5 | 0.99 | 4.4 | — |
| | | 10 | 1.99 | 8.8 | Clear |
| CG6 | AB14 | 5 | 1.48 | 6.5 | — |
| | | 10 | 2.96 | 13 | Clear |
| CG10 | BB18 | 5 | 0.72 | 3.2 | Clear |
| | | 10 | 1.44 | 6.3 | Clear |
| CG11 | BB9 | 5 | 1 | 4.4 | Clear |
| | | 10 | 2.01 | 8.8 | Clear |
| CG12 | BB2 | 5 | 1.27 | 5.6 | Clear |
| | | 10 | 2.54 | 11.2 | Clear |

EXAMPLE CD1: PREPARATION OF A SOLUTION OF PRAMLINTIDE AT 0.9 MG/ML AND OF INSULIN LISPRO AT 100 IU/ML CONTAINING M-CRESOL (29 MM), GLYCEROL (174 MM) AND ZINC CHLORIDE (300 µM) AT PH 7.4

A concentrated solution of pramlintide at 5 mg/mL is added to a concentrated solution of excipients (m-cresol, glycerol, zinc chloride). A solution of insulin lispro at 500 IU/mL is added to this concentrated solution of pramlintide and excipients in such a manner as to obtain the intended final composition. The final pH is adjusted to 7.4 by addition of NaOH/HCl.

EXAMPLE CD0: PREPARATION OF A SOLUTION OF PRAMLINTIDE AT 0.9 MG/ML AND OF INSULIN LISPRO AT 100 IU/ML CONTAINING CO-POLYAMINO ACID BB15, M-CRESOL (29 MM), GLYCEROL (174 MM) AND ZINC CHLORIDE (300 µM) AT PH 7.4

A concentrated solution of co-polyamino acid BB15 and excipients is prepared by adding concentrated solutions of excipients (m-cresol, glycerol, zinc chloride) to a concentrated solution of co-polyamino acid BB15.

A concentrated solution of pramlintide at 5 mg/mL, then a solution of insulin lispro at 500 IU/mL are added to the concentrated solution of co-polyamino acid BB15 and excipients in such a manner as to obtain the intended final composition. The final pH is adjusted to pH 7.4 by addition of NaOH/HCl.

The solutions CD3 to CD9 are prepared according to the above-described protocol.

TABLE 17

Compositions and visual appearance of the solutions of pramlintide at 0.9 mg/mL and of insulin lispro at 100 IU/mL at pH 7.4 at different concentrations of co-polyamino acid BB15.

| Solution | Ratio BB15/ pramlintide | Concentration of co-polyamino acid BB15 | | Visual appearance of the solution |
|---|---|---|---|---|
| | mol/mol | mg/ml | mM | |
| CD1 | — | — | — | Turbid |
| CD3 | 2 | 1.8 | 0.44 | Clear |
| CD4 | 3 | 2.7 | 0.66 | Clear |
| CD5 | 4 | 3.6 | 0.88 | Clear |
| CD6 | 5 | 4.5 | 1.10 | Clear |
| CD7 | 6 | 5.4 | 1.32 | Clear |
| CD8 | 10 | 9 | 2.20 | Clear |
| CD9 | 15 | 13.5 | 3.30 | Clear |

In the presence of co-polyamino acid BB15, a clear solution of pramlintide (0.9 mg/mL) and of insulin lispro (100 IU/mL) at pH 7.4 is obtained.

EXAMPLE CK1: PREPARATION OF A SOLUTION OF PRAMLINTIDE AT 0.6 MG/ML AND OF HUMAN INSULIN AT 100 IU/ML CONTAINING M-CRESOL (29 MM), GLYCEROL (174 MM) AND ZINC CHLORIDE (229 µM) AT PH 6.6

By a method similar to the one used in example BR1, a solution of pramlintide at 0.6 mg/mL and of human insulin at 100 IU/mL containing m-cresol (29 mM), glycerol (174 mM) and zinc chloride (229 µM) at pH 6.6 is obtained.

EXAMPLE CK0: PREPARATION OF A SOLUTION OF PRAMLINTIDE AT 0.6 MG/ML AND OF HUMAN INSULIN AT 100 IU/ML CONTAINING CO-POLYAMINO ACID BB15, M-CRESOL (29 MM), GLYCEROL (174 MM) AND ZINC CHLORIDE (229 µM) AT PH 6.6

By a method similar to the one used in example BR0, a solution of pramlintide at 0.6 mg/mL and of human insulin at 100 IU/mL containing co-polyamino acid BB15, m-cresol (29 mM), glycerol (174 mM) and zinc chloride (229 µM) at pH 6.6 is obtained.

The solutions CK2 to CK8 are prepared according to the above protocol.

TABLE 18

Compositions and visual appearance of the solutions of pramlintide at 0.6 mg/mL and of human insulin at 100 IU/mL at pH 6.6 at different concentrations of co-polyamino acid BB15.

| Solution | Ratio BB15/pramlintide mol/mol | Concentration of co-polyamino acid BB15 mg/mL | mM | Visual appearance of the solution |
|---|---|---|---|---|
| CK1 | — | — | — | Turbid |
| CK2 | 2 | 1.3 | 0.29 | Clear |
| CK3 | 3 | 2 | 0.45 | Clear |
| CK4 | 4 | 2.7 | 0.61 | Clear |
| CK5 | 6 | 4 | 0.90 | Clear |
| CK6 | 8 | 5.3 | 1.19 | Clear |
| CK7 | 10 | 6.7 | 1.50 | Clear |
| CK8 | 15 | 10 | 2.24 | Clear |

In the presence of co-polyamino acid BB15, a clear solution of pramlintide (0.6 mg/mL) and of human insulin (100 IU/mL) at pH 6.6 is obtained.

EXAMPLE CF1: PREPARATION OF COMPOSITIONS CONTAINING VARIABLE CONCENTRATIONS OF PRAMLINTIDE, OF HUMAN INSULIN AT 100 IU/ML, M-CRESOL (29 MM), GLYCEROL (174 MM) AND ZINC CHLORIDE (229 µM) AT PH 6.6

By a method similar to the one used in example CR1, solutions containing different concentrations of pramlintide, of human insulin at 100 IU/mL, m-cresol (29 mM), glycerol (174 mM) and zinc chloride (229 µM) at pH 6.6 are obtained.

TABLE 18a

Compositions and visual appearance of the solutions of pramlintide at different concentrations and of human insulin at 100 IU/mL at pH 6.6.

| Solution | Concentration of pramlintide (mg/mL) | Visual appearance of the solution |
|---|---|---|
| CF1A | 0.9 | turbid |
| CF1B | 0.8 | turbid |
| CF1C | 0.6 | turbid |
| CF1D | 0.3 | turbid |
| CF1E | 0.2 | turbid |

EXAMPLE CF0: PREPARATION OF COMPOSITIONS CONTAINING VARIABLE CONCENTRATIONS OF PRAMLINTIDE AND OF HUMAN INSULIN AT 100 IU/ML IN THE PRESENCE OF CO-POLYAMINO ACID AB24, M-CRESOL (29 MM), GLYCEROL (174 MM) AND ZINC CHLORIDE (229 µM) AT PH 6.6

By a method similar to the one used in example CR0, solutions containing different concentrations of pramlintide, of human insulin at 100 IU/mL, co-polyamino acid AB24, m-cresol (29 mM), glycerol (174 mM) and zinc chloride (229 µM) at pH 6.6 are obtained.

TABLE 18b

Compositions and visual appearance of the solutions of pramlintide at different concentrations and of human insulin at 100 IU/mL in the presence of co-polyamino acid AB24 at pH 6.6.

| Solution | Concentration of pramlintide (mg/mL) | Concentration of co-polyamino acid AB24 mg/mL | mM | Ratio co-polyamino acid/pramlintide mol/mol | Visual appearance of the solution |
|---|---|---|---|---|---|
| CF2 | 0.9 | 5.4 | 0.67 | 3 | clear |
| CF3 | 0.8 | 4.8 | 0.6 | 3 | clear |
| CF4 | 0.6 | 3.6 | 0.45 | 3 | clear |
| CF5 | 0.3 | 1.8 | 0.22 | 3 | clear |
| CF6 | 0.2 | 1 | 0.125 | 2.5 | clear |

EXAMPLE CM0: PREPARATION OF A SOLUTION OF PRAMLINTIDE AT 0.6 MG/ML AND OF HUMAN INSULIN AT 100 IU/ML CONTAINING DIFFERENT CO-POLYAMINO ACIDS OF THE INVENTION, M-CRESOL (29 MM), GLYCEROL (174 MM) AND ZINC CHLORIDE (229 µM) AT PH 6.6

By a method similar to example CG0, solutions of pramlintide at 0.6 mg/mL and of human insulin at 100 IU/mL containing different co-polyamino acids of the invention, m-cresol (29 mM), glycerol (174 mM) and zinc chloride (229 µM) at pH 6.6 are obtained.

The solutions CM1 to CM18 are prepared according to the above-described protocol.

TABLE 19

Compositions and visual appearance of the solutions of pramlintide at 0.6 mg/mL and of human insulin at 100 IU/mL at pH 6.6 in the presence of different co-polyamino acids.

| Solution | Co-polyamino acid | Concentration of co-polyamino acid mg/mL | mM | Ratio co-polyamino acid/pramlintide mol/mol | Visual appearance of the solution |
|---|---|---|---|---|---|
| CM1 | BB20 | 2.6 | 0.61 | 4 | Clear |
|  |  | 5.3 | 1.22 | 8 | Clear |

TABLE 19-continued

Compositions and visual appearance of the solutions of pramlintide at 0.6 mg/mL and of human insulin at 100 IU/mL at pH 6.6 in the presence of different co-polyamino acids.

| Solution | Co-polyamino acid | Concentration of co-polyamino acid mg/mL | mM | Ratio co-polyamino acid/pramlintide mol/mol | Visual appearance of the solution |
|---|---|---|---|---|---|
| CM2 | BB21 | 1.3 | 0.6 | 4 | Clear |
| CM3 | AB22 | 2.4 | 0.3 | 2 | Clear |
| CM4 | BB24 | 2.9 | 0.6 | 4 | Clear |
| CM5 | BB23 | 3 | 0.76 | 5 | Clear |
| CM6 | BB25 | 1.5 | 0.3 | 2 | Clear |
| CM7 | BB22 | 2.7 | 0.6 | 4 | Clear |
| CM8 | AB23 | 7.7 | 0.69 | 4.6 | Clear |
| CM9 | BB19 | 4.7 | 0.4 | 2.8 | Clear |
| CM10 | AB28 | 2.3 | 0.3 | 2 | Clear |
| CM11 | AB24 | 1.2 | 0.15 | 1 | Clear |
|  |  | 2.4 | 0.3 | 2 | Clear |
|  |  | 3.6 | 0.45 | 3 |  |
| CM12 | AB25 | 2.6 | 0.3 | 2 | Clear |
| CM13 | AB26 | 1.5 | 0.3 | 2 | Clear |
|  |  | 2.3 | 0.5 | 3 | Clear |
| CM14 | AB27 | 1.3 | 0.15 | 1 | Clear |
|  |  | 2.7 | 0.3 | 2 | Clear |
| CM15 | AB30 | 1.2 | 0.15 | 1 | Clear |
|  |  | 2.3 | 0.3 | 2 | Clear |
| CM16 | AB31 | 1.3 | 0.15 | 1 | Clear |
|  |  | 2.5 | 0.3 | 2 | Clear |
| CM17 | AB29 | 5.9 | 0.8 | 5 | Clear |
|  |  | 8.9 | 1.15 | 7.6 | Clear |
| CM18 | AB32 | 2.5 | 0.3 | 2 | Clear |

EXAMPLE CQ1: PREPARATION OF A SOLUTION OF PRAMLINTIDE AT 0.6 MG/ML AND OF HUMAN INSULIN AT 100 IU/ML AT PH 6.6 CONTAINING CO-POLYAMINO ACID AB14, M-CRESOL (29 MM), GLYCEROL (174 MM), SODIUM CHLORIDE (100 MM) AND ZINC CHLORIDE (1 MM)

A concentrated solution of co-polyamino acid AB14 and excipients is prepared by adding concentrated solutions of excipients (m-cresol, glycerol, sodium chloride, zinc chloride) to a concentrated solution of co-polyamino acid AB14.

A concentrated solution of pramlintide at 5 mg/mL at pH 4, then a solution of human insulin at 500 IU/mL are added to this concentrated solution of co-polyamino acid AB14 and excipients in such a manner as to obtain the intended final composition. The final pH is adjusted to 6.6 by addition of NaOH/HCl.

The solution CQ1 is prepared according to the above protocol.

EXAMPLE CQ0: PREPARATION OF A SOLUTION OF PRAMLINTIDE AT 0.6 MG/ML AND OF HUMAN INSULIN AT 100 IU/ML CONTAINING DIFFERENT CO-POLYAMINO ACIDS OF THE INVENTION, M-CRESOL (29 MM), GLYCEROL (174 MM) AND DIFFERENT CONTENTS OF SODIUM CHLORIDE AND OF ZINC CHLORIDE

By a method similar to example CQ0, solutions of pramlintide at 0.6 mg/mL and of human insulin at 100 IU/mL containing different co-polyamino acids of the invention, m-cresol (29 mM), glycerol (174 mM), sodium chloride and zinc chloride at pH 6.6 are obtained.

The solutions CQ2 to CQ12 are prepared according to the above protocol.

TABLE 20

Compositions and visual appearance of the solutions of pramlintide at 0.6 mg/mL and of human insulin at 100 IU/mL pH 6.6 in the presence of different co-polyamino acids and of different contents of sodium chloride and of zinc chloride.

| Solution | Co-polyamino acid | Concentration of co-polyamino acid mg/mL | mM | [NaCl] (mM) | [ZnCl$_2$] (mM) | Visual appearance of the solution |
|---|---|---|---|---|---|---|
| CQ1 | AB14 | 6.3 | 1.87 | 100 | 1 | Clear |
| CQ2 | AB15 | 7.8 | 1.6 | — | 0.23 | Clear |
| CQ3 | AB15 | 11.7 | 2.3 | — | 0.23 | Clear |
| CQ4 | AB15 | 3.9 | 0.8 | 50 | 0.23 | Clear |
| CQ5 | AB15 | 6.3 | 1.3 | 50 | 0.23 | Clear |
| CQ6 | AB15 | 7.8 | 1.6 | 50 | 0.23 | Clear |
| CQ7 | AB15 | 3.9 | 0.8 | 100 | 0.23 | Clear |
| CQ8 | AB15 | 6.3 | 1.3 | 100 | 0.23 | Clear |
| CQ9 | AB15 | 7.8 | 1.6 | 100 | 0.23 | Clear |
| CQ10 | AB16 | 7.4 | 0.9 | 50 | 0.23 | Clear |
| CQ11 | AB16 | 12.4 | 1.5 | 50 | 0.23 | Clear |
| CQ12 | AB16 | 7.4 | 0.9 | 50 | 1 | Clear |

EXAMPLE CZ0: PREPARATION OF A SOLUTION OF PRAMLINTIDE AT 0.6 MG/ML CONTAINING DMPG, M-CRESOL (29 MM), GLYCEROL (174 MM) AT P-H 6.6

A concentrated solution of DMPG and excipients is prepared by adding concentrated solutions of excipients (m-cresol, glycerol) to a concentrated solution of DMPG.

A concentrated solution of pramlintide at 10 mg/mL is added to this concentrated solution of DMPG and excipients in such a manner as to obtain the intended final composition. The final pH is adjusted to 6.6 by addition of NaOH/HCl.

EXAMPLE CZ1: PREPARATION OF A SOLUTION OF PRAMLINTIDE AT 0.6 MG/ML CONTAINING DMPG (4.5 MM), PHENOL (30 MM), GLYCEROL (174 MM) AND GLYCYLGLYCINE (8 MM) AT PH 7.4

TABLE 21

Compositions and visual appearance of the solutions of pramlintide at 0.6 mg/mL in the presence of DMPG.

| Solution | DMPG (mM) | Concentration pramlintide (mg/mL) | pH | Excipients | Visual appearance of the solution |
|---|---|---|---|---|---|
| CZ0 | 4.5 | 0.6 | 6.6 | m-cresol 29 mM Glycerol 174 mM | Clear |
| CZ1 | 4.5 | 0.6 | 7.4 | phenol 30 mM Glycylglycine 8 mM Glycerol 174 mM | Clear |

EXAMPLE CA1: PREPARATION OF A SOLUTION OF PRAMLINTIDE AT 1 MG/ML CONTAINING M-CRESOL (20 MM), MANNITOL (43 MG/ML) AND A SODIUM ACETATE BUFFER, AT PH 4

A concentrated solution of pramlintide at 10 mg/mL is added to a concentrated solution of excipients (m-cresol, mannitol, sodium acetate) in such a manner as to obtain the intended final composition. The final pH is adjusted to 4 by addition of NaOH/HCl. The clear solution is filtered (0.22 µm) and introduced into 3 mL glass cartridges for injector pen.

EXAMPLE CA2: INTRODUCTION INTO CARTRIDGES OF A COMMERCIAL SOLUTION OF HUMAN INSULIN AT 100 IU/ML (HUMULIN®) CONTAINING M-CRESOL (23 MM), GLYCEROL (174 MM) AND ZINC CHLORIDE (230 µM)

A commercial solution of Humulin® in a 10 mL vial is collected and introduced into 3 mL glass cartridges for injector pen.

EXAMPLE CA3: PREPARATION OF A SOLUTION OF PRAMLINTIDE AT 0.6 MG/ML AND OF HUMAN INSULIN AT 100 IU/ML CONTAINING CO-POLYAMINO ACID BB15 (3.1 MG/ML), M-CRESOL (29 MM), GLYCEROL (35 MM), MANNITOL (2.6% % W/V), TRIS (18.75 MM), SODIUM ACETATE (18 MM), AND ZINC CHLORIDE (260 µM) AT PH 6.2

3 mL glass vials are filled with 0.5 mL of a solution containing 10 mg/mL of co-polyamino acid BB15 and 60 mM of Tris at pH 8.3. The solution is lyophilized in such a manner as to obtain 3 mL vials containing 5 mg of co-polyamino acid BB15 and 30 µmol of Tris.

A solution of human insulin at 500 IU/mL containing 23 mM of m-cresol, 174 mM of glycerol and 260 µM of zinc chloride at pH 7.4 is prepared by adding concentrated solutions of excipients (m-cresol, glycerol, zinc chloride) to a concentrated solution of human insulin concentrated at 760 IU/mL.

In the vial containing 5 mg of co-polyamino acid BB15 and 30 µmol of Tris, the following are introduced successively:

0.96 mL of the solution of Pramlintide at 1 mg/mL at pH 4 described in example CA1;

0.32 mL of sterile water for injection;

0.32 mL of concentrated human insulin at 500 IU/mL containing 23 mM of m-cresol, 174 mM of glycerol and 260 µM of zinc chloride at pH 7.4.

The clear solution is filtered (0.22 µm) and introduced into 3 mL glass cartridges for injector pen.

EXAMPLE CA4: INTRODUCTION INTO CARTRIDGES OF A SOLUTION OF PRAMLINTIDE AT 0.6 MG/ML AND OF HUMAN INSULIN AT 100 IU/ML IN THE PRESENCE OF CO-POLYAMINO ACID AB24 AT 2.4 MG/ML, M-CRESOL (29 MM), GLYCEROL (174 MM) AND ZINC CHLORIDE (229 µM) AT PH 6.6

The solution of pramlintide at 0.6 mg/mL and of human insulin at 100 IU/mL in the presence of co-polyamino acid AB24 at 2.4 mg/mL, m-cresol (29 mM), glycerol (174 mM) and zinc chloride (229 µM) at pH 6.6 described in example CF4 is filtered (0.22 µM) is introduced into 3 mL glass cartridges for injector pen.

EXAMPLE CA5 (PUMP STABILITY): PREPARATION OF A SOLUTION OF PRAMLINTIDE AT 0.6 MG/ML AND OF INSULIN LISPRO AT 100 IU/ML AT PH 6.6 CONTAINING CO-POLYAMINO ACID AB24, M-CRESOL (29 MM), GLYCEROL (174 MM) AND ZINC CHLORIDE (300 µM)

A concentrated solution of co-polyamino acid AB24 and excipients is prepared by adding concentrated solutions of excipients (m-cresol, glycerol, zinc chloride) to a concentrated solution of co-polyamino acid AB24.

A concentrated solution of pramlintide at 10 mg/mL, then a solution of insulin lispro at 200 IU/mL are added to this concentrated solution of co-polyamino acid AB24 and excipients in such a manner as to obtain the intended final composition. The final pH is adjusted to 6.6 by addition of NaOH/HCl.

EXAMPLE CA6: PREPARATION OF A SOLUTION OF HUMAN INSULIN AT 100 IU/ML CONTAINING CO-POLYAMINO ACID BB15 (10 MG/ML), M-CRESOL (29 MM), GLYCEROL (174 MM) AND ZINC CHLORIDE (229 µM) AT PH 6.6

A concentrated solution of co-polyamino acid BB15 and excipients is prepared by adding concentrated solutions of excipients (m-cresol, glycerol, zinc chloride) to a concentrated solution of co-polyamino acid BB15.

A solution of human insulin at 800 IU/mL is added to this concentrated solution of co-polyamino acid BB15 and excipients in such a manner as to obtain the intended final composition. The final pH is adjusted to 6.6 by addition of NaOH/HCl. The clear solution is filtered (0.22 µM) and introduced into 3 mL glass cartridges for injector pen.

EXAMPLE CA7: PREPARATION OF A SOLUTION OF PRAMLINTIDE AT 0.6 MG/ML AND OF HUMAN INSULIN AT 100 IU/ML CONTAINING CO-POLYAMINO ACID BB15 (10 MG/ML), M-CRESOL (29 MM), GLYCEROL (174 MM) AND ZINC CHLORIDE (229 µM) AT PH 6.6

A concentrated solution of co-polyamino acid BB15 and excipients is prepared by adding concentrated solutions of excipients (m-cresol, glycerol, zinc chloride) to a concentrated solution of co-polyamino acid BB15.

A concentrated solution of pramlintide at 10 mg/mL, then a concentrated solution of human insulin at 500 IU/mL are added to this concentrated solution of co-polyamino acid BB15 and excipients in such a manner as to obtain the intended final composition. The final pH is adjusted to 6.6 by addition of NaOH/HCl. The clear solution is filtered (0.22 µM) and introduced into 3 mL glass cartridges.

D. Physicochemistry

D I: Results of Visual Observations Made During the Mixing and of Measurements of Fibrillation by ThT Principle The poor stability of a peptide can lead to the formation of amyloid fibrils, which are defined as ordered macromolecular structures. These structures may result in the formation of a gel within the sample.

The test of monitoring the fluorescence of Thioflavin T (ThT) is used to analyze the physical stability of the solutions. Thioflavin is a small probe molecule having a characteristic fluorescence signature when it binds to amyloid type fibrils (Naiki et al. (1989) Anal. BioChem. 177, 244-249; LeVine (1999) Methods. Enzymol. 309, 274-284).

This method makes it possible to monitor the formation of fibrils for low concentrations of ThT within undiluted solutions. This monitoring is carried out under accelerated stability conditions: under stirring and at 37° C.

Experimental Conditions

The samples were prepared immediately before the start of the measurement. The preparation of each composition is described in the associated example. Thioflavin T is added to the composition from a concentrated stock solution in such a manner as to induce a negligible dilution of the composition. The concentration of Thioflavin T in the composition is 1, 2 or 40 µM depending on the composition type: 40 µM in the case of compositions of human amylin at 0.6 mg/mL, 2 µM in the case of compositions of pramlintide at 0.9 mg/mL and 1 µM in the compositions of pramlintide at 0.4 mg/mL. This concentration is indicated in the legend pertaining to the table of results of the latency times for each type of composition.

A volume of 150 µL of the composition was introduced into a well of a 96-well plate. Each composition was analyzed in three tests (triplicate) on the same plate. The plate was sealed with a transparent film in order to prevent evaporation of the composition.

This plate was then placed into the enclosure of a plate reader (EnVision 2104 Multilabel, Perkin Elmer). The temperature is adjusted to 37° C., and lateral agitation at 960 rpm with an amplitude of 1 mm is applied.

A reading of the fluorescence intensity in each well is carried out at an excitation wavelength of 442 nm and an emission wavelength of 482 nm over time.

The fibrillation process manifests itself in a strong increase in fluorescence after a delay referred to as latency time.

For each well, this delay was determined graphically from the intersection between the baseline of the fluorescence signal and the slope of the fluorescence curve as a function of time determined during the strong initial increase in fluorescence. The value of the latency time plotted corresponds to the average of the latency time measurements performed on three wells.

An example of a graphic determination is represented in FIG. 1.

This figure is a graphic representation of the determination of the latency time (LT) by monitoring the fluorescence of Thioflavin T, on a curve having the fluorescence value (in u.a., arbitrary units) on the ordinate and the time in minutes on the abscissa.

EXAMPLE D1: STABILITY OF SOLUTIONS OF HUMAN AMYLIN AT 0.6 MG/ML AT PH 7.4 IN THE PRESENCE OF CO-POLYAMINO ACID BB15 AT DIFFERENT CONCENTRATIONS

TABLE 22

Measurement of the latency time by ThT (40 µM) of the solutions CV1 to CV10.

| Solution | Ratio BB15/human amylin mol/mol | Concentration of co-polyamino acid BB15 mg/mL | mM | Latency time (h) |
| --- | --- | --- | --- | --- |
| CV1 | — | — | — | <0.02 |
| CV5 | 5 | 3 | 0.73 | >1 |
| CV6 | 6 | 3.6 | 0.88 | >5 |
| CV7 | 7 | 4.2 | 1.03 | >30 |
| CV8 | 8 | 4.8 | 1.17 | >54 |
| CV9 | 9 | 5.4 | 1.32 | >54 |
| CV10 | 10 | 6 | 1.47 | >72 |

The latency times of a solution of human amylin at pH 7.4 (CV1), without co-polyamino acid, is less than 0.02 h; the solutions CV5 to CV10 according to the invention, containing molar ratios BB15/human amylin greater than 5 make it possible to obtain latency times of more than one hour, a molar ratio of 10 making it possible to obtain latency times of more than 72 h.

EXAMPLE D2: STABILITY OF SOLUTIONS OF HUMAN AMYLIN AT 0.6 MG/ML AND OF HUMAN INSULIN AT 100 IU AT PH 7.4 IN THE PRESENCE OF CO-POLYAMINO ACID BB15 AT DIFFERENT CONCENTRATIONS

TABLE 23

Measurement of the latency time by ThT (40 µM) of the solutions, CX6, CX10 and CX11.

| Solution | Ratio BB15/human amylin mol/mol | Concentration of co-polyamino acid BB15 mg/mL | mM | Latency time (h) |
| --- | --- | --- | --- | --- |
| CX1 | — | — | — | * |
| CX6 | 6 | 3.6 | 0.88 | >0.1 |

TABLE 23-continued

Measurement of the latency time by ThT (40 μM) of the solutions, CX6, CX10 and CX11.

| Solution | Ratio BB15/human amylin mol/mol | Concentration of co-polyamino acid BB15 | | Latency time (h) |
|---|---|---|---|---|
| | | mg/mL | mM | |
| CX10 | 10 | 6 | 1.47 | >0.5 |
| CX11 | 17.5 | 10.5 | 2.57 | >5 |

\* Latency time not measured because of turbid solution.

The solution of human amylin and of human insulin at pH 7.4 (CX1) is turbid. The co-polyamino acid BB15 makes it possible to obtain a clear solution containing human amylin in the presence of human insulin at pH 7.4 with latency times of more than 0.1 hour starting with a molar ratio BB15/human amylin of 6, and latency times of more than 5 h for a molar ratio of BB15/human amylin of 17.5.

EXAMPLE D3: STABILITY OF SOLUTIONS OF PRAMLINTIDE AT 0.4 MG/ML AT PH 7.4 IN THE PRESENCE OF CO-POLYAMINO ACID BB15 AT DIFFERENT CONCENTRATIONS

TABLE 24

Measurement of the latency time by ThT (1 μM) of the solutions CW1 to CW3.

| Solution | Concentration of co-polyamino acid BB15 | | Ratio BB15/pramlintide mol/mol | Latency time (h) |
|---|---|---|---|---|
| | mg/mL | mM | | |
| CW1 | — | — | — | 0.7 |
| CW2 | 2.4 | 0.59 | 6 | >40 |
| CW3 | 4 | 0.98 | 10 | >63 |

The solution of pramlintide at pH 7.4 (CW1) without co-polyamino acid has a short latency time. The co-polyamino acid BB15 makes it possible to obtain a solution containing pramlintide at pH 7.4 with latency times of more than 40 h starting with a molar ratio of BB15/pramlintide of 6.

EXAMPLE D4: STABILITY OF SOLUTIONS OF PRAMLINTIDE AT 0.9 MG/ML AT PH 7.4 IN THE PRESENCE OF CO-POLYAMINO ACID BB15 AT DIFFERENT CONCENTRATIONS

TABLE 25

Measurement of the latency time by ThT (2 μM) of the solutions CY1 to CY7

| Solution | Ratio BB15/pramlintide mol/mol | Concentration of BB15 | | Latency time (h) |
|---|---|---|---|---|
| | | mg/mL | mM | |
| CY1 | — | — | — | 0.7 |
| CY2 | 2 | 1.8 | 0.44 | >0.8 |
| CY3 | 3 | 2.7 | 0.66 | >4 |
| CY4 | 4 | 3.6 | 0.88 | >30 |
| CY5 | 5 | 4.5 | 1.10 | >63 |
| CY6 | 6 | 5.4 | 1.22 | >63 |
| CY7 | 10 | 9 | 1.32 | >63 |

The solution of pramlintide at pH 7.4 (CY1) without co-polyamino acid has a short latency time; the latency times of solutions containing a co-polyamino acid are greater than or equal to the latency times of the composition without co-polyamino acid at a molar ratio of co-polyamino acid BB15/pramlintide of 2:1.

EXAMPLE D5: STABILITY OF SOLUTIONS OF PRAMLINTIDE AT 0.9 MG/ML AT PH 7.4 IN THE PRESENCE OF DIFFERENT CO-POLYAMINO ACIDS

TABLE 26

Measurement of the latency time by ThT (2 μM) of the compositions CY1, CP2 to CP12.

| Solution | Co-polyaminoacid | Concentration of co-polyamino acid | | Ratio co-polyamino acid/pramlintide mol/mol | Latency time (h) |
|---|---|---|---|---|---|
| | | mg/mL | mM | | |
| CY1 | — | — | — | — | <0.7 |
| CP2 | BB15 | 5 | 1.22 | 5.4 | >63 |
| | | 10 | 2.45 | 10.8 | >63 |
| CP3 | BB14 | 10 | 1.96 | 8.6 | >15 |
| CP4 | AB17 | 10 | 1.22 | 9.8 | >63 |
| CP10 | BB18 | 5 | 0.72 | 3.2 | >63 |
| | | 10 | 1.44 | 6.3 | >63 |
| CP11 | BB9 | 5 | 1 | 4.4 | >50 |
| | | 10 | 2.01 | 8.8 | >63 |
| CP12 | BB2 | 5 | 1.27 | 5.6 | >10 |
| | | 10 | 2.54 | 11.2 | >63 |

The solution of pramlintide at pH 7.4 (CY1) without co-polyamino acid has a short latency time. The co-polyamino acids of the invention make it possible to obtain latency times of more than 10 h under the conditions tested.

EXAMPLE D6: STABILITY OF SOLUTIONS OF PRAMLINTIDE AT 0.6 MG/ML AT PH 6.6 IN THE PRESENCE OF CO-POLYAMINO ACID BB15 AT DIFFERENT CONCENTRATIONS

TABLE 27

Measurement of the latency time by ThT (2 μM) of the solutions CH1 and CH2 to CH8.

| Solution | Ratio BB15/pramlintide mol/mol | Concentration of co-polyamino acid BB15 | | Latency time (h) |
|---|---|---|---|---|
| | | mg/mL | mM | |
| CH1 | — | — | — | 1 |
| CH2 | 2 | 1.3 | 0.29 | >4 |
| CH3 | 3 | 2 | 0.45 | >10 |
| CH4 | 4 | 2.7 | 0.61 | >50 |
| CH5 | 6 | 4 | 0.90 | >50 |

TABLE 27-continued

Measurement of the latency time by ThT (2 µM) of the solutions CH1 and CH2 to CH8.

| Solution | Ratio BB15/pramlintide mol/mol | Concentration of co-polyamino acid BB15 mg/mL | mM | Latency time (h) |
|---|---|---|---|---|
| CH6 | 8 | 5.3 | 1.19 | >50 |
| CH7 | 10 | 6.7 | 1.50 | >50 |
| CH8 | 15 | 10 | 2.24 | >50 |

The solution of pramlintide at pH 6.6 (CH1) without co-polyamino acid has a short latency time; the latency times of the solutions containing a co-polyamino acid are greater than the latency times of the composition without co-polyamino acid at a molar ratio of co-polyamino acid BB15/pramlintide of 2:1.

EXAMPLE D7: STABILITY OF SOLUTIONS OF PRAMLINTIDE AT 0.6 MG/ML AT PH 6.6 IN THE PRESENCE OF DIFFERENT CO-POLYAMINO ACIDS

TABLE 28

Measurement of the latency time by ThT (2 µM) of the compositions CI1 to CI14.

| Solution | Co-polyamino acid | Concentration of co-polyamino acid mg/mL | mM | Ratio co-polyamino acid/pramlintide mol/mol | Latency time (h) |
|---|---|---|---|---|---|
| CI1 | BB20 | 1.3 | 0.3 | 2 | >10 |
|  |  | 2.6 | 0.6 | 4 | >20 |
| CI2 | BB21 | 1.3 | 0.6 | 4 | >10 |
| CI3 | AB22 | 2.4 | 0.3 | 2 | >10 |
| CI4 | BB24 | 2.9 | 0.6 | 4 | >10 |
| CI5 | BB25 | 1.5 | 0.3 | 2 | >50 |
|  |  | 3 | 0.6 | 4 | >50 |
| CI6 | AB23 | 3.4 | 0.23 | 2 | >10 |
| CI7 | AB28 | 2.3 | 0.3 | 2 | >10 |
|  |  | 4.7 | 0.6 | 4 | >10 |
| CI8 | AB24 | 1.2 | 0.15 | 1 | >10 |
|  |  | 2.4 | 0.3 | 2 | >50 |
| CI9 | AB25 | 1.3 | 0.15 | 1 | >10 |
|  |  | 2.6 | 0.3 | 2 | >10 |
| CI10 | AB26 | 1.5 | 0.3 | 2 | >10 |
| CI11 | AB27 | 1.3 | 0.15 | 1 | >5 |
|  |  | 2.7 | 0.3 | 2 | >10 |
| CI12 | AB31 | 1.3 | 0.15 | 1 | >10 |
|  |  | 2.5 | 0.3 | 2 | >10 |
| CI13 | AB29 | 8.9 | 1.15 | 7.6 | >5 |
| CI14 | AB32 | 1.3 | 0.15 | 1 | >10 |
|  |  | 2.5 | 0.3 | 2 | >10 |

The solution of pramlintide at pH 6.6 (CH1) without co-polyamino acid has a short latency time. The co-polyamino acids of the invention make it possible to obtain a latency time of more than 5 h under the conditions tested.

EXAMPLE D7A: STABILITY OF SOLUTIONS OF PRAMLINTIDE AT 0.6 MG/ML AT PH 6.6 IN THE PRESENCE OF CO-POLYAMINO ACID AB14 AND OF DIFFERENT CONTENTS OF SODIUM CHLORIDE AND OF ZINC CHLORIDE

TABLE 29

Measurement of the latency time by ThT (2 µM) of the compositions BT1 to BT5

| Solution | Co-polyamino acid | Concentration of co-polyamino acid mg/mL | mM | [NaCl] (mM) | [ZnCl$_2$] (mM) | Latency time (h) |
|---|---|---|---|---|---|---|
| CT1 | AB14 | 6.3 | 1.87 | — | 0.75 | 0.6 |
| CT2 | AB14 | 6.3 | 1.87 | 50 | — | >2 |
| CT3 | AB14 | 6.3 | 1.87 | 100 | — | >5 |
| CT4 | AB14 | 6.3 | 1.87 | 50 | 0.75 | >5 |
| CT5 | AB14 | 6.3 | 1.87 | 100 | 0.75 | >20 |

The solution of pramlintide at pH 6.6 and of co-polyamino acid AB14 has a longer latency time in the presence of sodium chloride or of sodium and zinc chloride.

EXAMPLE D7B: STABILITY OF SOLUTIONS OF PRAMLINTIDE AT 0.6 MG/ML AT PH 6.6 IN THE PRESENCE OF DIFFERENT CO-POLYAMINO ACIDS AND OF DIFFERENT CONTENTS OF SODIUM CHLORIDE AND OF ZINC CHLORIDE

TABLE 30

Measurement of the latency time by ThT (2 µM) of the compositions BS1 to BS11

| Solution | Co-polyamino acid | Concentration of co-polyamino acid mg/mL | mM | [NaCl] (mM) | [ZnCl$_2$] (mM) | Latency time (h) |
|---|---|---|---|---|---|---|
| CS1 | AB15 | 7.8 | 1.6 | — | — | 3.5 |
| CS2 | AB15 | 11.7 | 2.3 | — | — | >30 |
| CS3 | AB15 | 3.9 | 0.8 | 50 | — | >10 |
| CS4 | AB15 | 6.3 | 1.3 | 50 | — | >50 |
| CS5 | AB15 | 7.8 | 1.6 | 50 | — | >30 |
| CS6 | AB15 | 3.9 | 0.8 | 100 | — | >50 |
| CS7 | AB16 | 12.4 | 1.5 | — | — | 8 |
| CS8 | AB16 | 16.7 | 2.1 | — | — | >50 |
| CS9 | AB16 | 7.4 | 0.9 | 50 | — | >20 |
| CS10 | AB16 | 12.4 | 1.5 | 50 | — | >50 |
| CS11 | AB16 | 7.4 | 0.9 | 50 | 1 | >30 |

The solutions of pramlintide at pH 6.6 and of co-polyamino acid AB15 and AB16 have a longer latency time in the presence of sodium chloride or of sodium and zinc chloride.

EXAMPLE D8: STABILITY OF SOLUTIONS OF PRAMLINTIDE AT 0.4 MG/ML AND OF HUMAN INSULIN 100 IU/ML AT PH 7.4 CONTAINING CO-POLYAMINO ACID BB15

TABLE 31

Measurement of the latency time by ThT (1 μM) of the compositions CN1 to CN3.

| Solution | Concentration of co-polyamino acid BB15 mg/mL | mM | Ratio BB15/pramlintide mol/mol | Latency time (h) |
|---|---|---|---|---|
| CN1 | — | — | — | * |
| CN2 | 2.4 | 0.59 | 6 | >19 |
| CN3 | 4 | 0.98 | 10 | >19 |

* Latency time not measured because of turbid solution.

The solution of pramlintide and of human insulin at pH 7.4 (CN1) without copolyamino acid is turbid.

Co-polyamino acid BB15 makes it possible to obtain a clear solution of pramlintide at 0.4 mg/mL and of human insulin at 100 IU/mL at pH 7.4 with latency times of more than 19 h for molar ratios BB15/pramlintide greater than 6.

EXAMPLE D9: STABILITY OF SOLUTIONS OF PRAMLINTIDE AT 0.9 MG/ML AND OF HUMAN INSULIN 100 IU/ML AT PH 7.4 IN THE PRESENCE OF CO-POLYAMINO ACID BB15 AT DIFFERENT CONCENTRATIONS

TABLE 32

Measurement of the latency time by ThT (2 μM) of the compositions CR1 to CR4 and CU3 to CU8.

| Solution | Ratio BB15/pramlintide mol/mol | Concentration of co-polyamino acid BB15 mg/mL | mM | Latency time (h) |
|---|---|---|---|---|
| CR1 | — | — | — | * |
| CU3 | 2 | 1.8 | 0.44 | >0.5 |
| CR2 | 3 | 2.7 | 0.66 | >2 |
| CR3 | 4 | 3.6 | 0.88 | >6 |
| CR4 | 5 | 4.5 | 1.10 | >9 |
| CU7 | 6 | 5.4 | 1.32 | >9 |
| CU8 | 10 | 9 | 2.20 | >9 |

* Latency time not measured because of turbid solution.

A solution of pramlintide at 0.9 mg/mL and of human insulin 100 IU/mL at pH 7.4 (BR1) without co-polyamino acid is turbid. The clear solutions of pramlintide at 0.9 mg/mL and of human insulin 100 IU/mL at pH 7.4 in the presence of co-polyamino acid BB15 have latency times of more than 0.5 hour at the molar ratio BB15/pramlintide of 2, which can be greater than 9 h for molar ratios BB15/pramlintide greater than 5.

EXAMPLE D10: STABILITY OF SOLUTIONS OF PRAMLINTIDE AT 0.9 MG/ML AND OF HUMAN INSULIN 100 IU/ML AT PH 7.4 IN THE PRESENCE OF DIFFERENT CO-POLYAMINO ACIDS

TABLE 33

Measurement of the latency time by ThT (2 μM) of the solutions CG2 to CG12.

| Solution | Co-polyamino acid | Concentration of co-polyamino acid mg/mL | mM | Ratio co-polyamino acid/pramlintide mol/mol | Latency time (h) |
|---|---|---|---|---|---|
| CR1 | — | — | — | — | * |
| CG2 | BB15 | 5 | 1.22 | 5.4 | >9 |
|  |  | 10 | 2.45 | 10.8 | >7 |
| CG3 | BB14 | 10 | 1.96 | 8.6 | >9 |
| CG4 | AB17 | 5 | 1.11 | 4.9 | >2 |
|  |  | 10 | 1.22 | 9.8 | >5 |
| CGS | AB15 | 10 | 1.99 | 8.8 | >2 |
| CG10 | BB18 | 5 | 0.72 | 3.2 | >1 |
|  |  | 10 | 1.44 | 6.3 | >4 |
| CG11 | BB9 | 5 | 1 | 4.4 | >4 |
|  |  | 10 | 2.01 | 8.8 | >3 |
| CG12 | BB2 | 5 | 1.27 | 5.6 | >5 |
|  |  | 10 | 2.54 | 11.2 | >6 |

* Latency time not measured because of turbid solution.

The solution of pramlintide and of human insulin at pH 7.4 (CR1) is turbid. The co-polyamino acids make it possible to obtain latency times of more than 1 hour under the conditions tested.

EXAMPLE D11: STABILITY OF SOLUTIONS OF PRAMLINTIDE AT 0.9 MG/ML AND OF INSULIN LISPRO 100 IU/ML AT PH 7.4 IN THE PRESENCE OF CO-POLYAMINO ACID BB15 AT DIFFERENT CONCENTRATIONS

TABLE 34

Measurement of the latency time by ThT (2 μM) of the solutions CD1 and CD3 to CD8.

| Solution | Ratio BB15/pramlintide mol/mol | Concentration of co-polyamino acid BB15 mg/mL | mM | Latency time (h) |
|---|---|---|---|---|
| CD1 | — | — | — | * |
| CD3 | 2 | 1.8 | 0.44 | 0.8 |
| CD4 | 3 | 2.7 | 0.66 | >2 |
| CD5 | 4 | 3.6 | 0.88 | >7 |
| CD6 | 5 | 4.5 | 1.10 | >9 |
| CD7 | 6 | 5.4 | 1.22 | >9 |
| CD8 | 10 | 9 | 1.32 | >9 |

* Latency time not measured because of turbid solution.

The solution of pramlintide and of insulin lispro at pH 7.4 (CD1) is turbid. The co-polyamino acids make it possible to obtain latency times of more than 0.8 hour under the conditions tested.

EXAMPLE D12: STABILITY OF SOLUTIONS OF PRAMLINTIDE AT 0.6 MG/ML AND OF HUMAN INSULIN 100 IU/ML AT PH 6.6 IN THE PRESENCE OF CO-POLYAMINO ACID BB15 AT DIFFERENT CONCENTRATIONS

TABLE 35

Measurement of the latency time by ThT (2 µM) of the solutions CK1 and CK3 to CK8.

| Solution | Ratio BB15/pramlintide mol/mol | Concentration of co-polyamino acid BB15 mg/mL | mM | Latency time (h) |
|---|---|---|---|---|
| CK1 | — | — | — | * |
| CK3 | 3 | 2 | 0.45 | >0.5 |
| CK4 | 4 | 2.7 | 0.61 | >5 |
| CK5 | 6 | 4 | 0.90 | >5 |
| CK6 | 8 | 5.3 | 1.19 | >5 |
| CK7 | 10 | 6.7 | 1.50 | >5 |
| CK8 | 15 | 10 | 2.24 | >5 |

* Latency time not measured because of turbid solution.

The solution of pramlintide and of human insulin at pH 6.6 (CK1) is turbid. The clear solutions of pramlintide at 0.6 mg/mL and of human insulin 100 IU/mL at pH 6.6 in the presence of co-polyamino acid BB15 have latency times of more than 0.5 h at a molar ratio BB15/pramlintide of 3, which can be greater than 5 h starting with a ratio BB15/pramlintide of 4.

EXAMPLE D13: STABILITY OF SOLUTIONS OF PRAMLINTIDE AT 0.6 MG/ML AND OF HUMAN INSULIN 100 IU/ML AT PH 6.6 IN THE PRESENCE OF DIFFERENT CO-POLYAMINO ACIDS

TABLE 36

Measurement of the latency time by ThT (2 µM) of the solutions CM1 to CM18.

| Solution | Co-polyamino acid | Concentration of co-polyamino acid mg/mL | mM | Ratio co-polyamino acid/pramlintide mol/mol | Latency time (h) |
|---|---|---|---|---|---|
| CM1 | BB20 | 2.6 | 0.61 | 4 | >1 |
|  |  | 5.3 | 1.22 | 8 | >1 |
| CM2 | BB21 | 1.3 | 0.6 | 4 | >10 |
| CM3 | AB22 | 2.4 | 0.3 | 2 | >5 |
| CM4 | BB24 | 2.9 | 0.6 | 4 | >10 |
| CM5 | BB23 | 3 | 0.76 | 5 | >10 |
| CM6 | BB25 | 1.5 | 0.3 | 2 | >10 |
| CM7 | BB22 | 2.7 | 0.6 | 4 | >5 |
| CM8 | AB23 | 7.7 | 0.69 | 4.6 | >15 |
| CM9 | BB19 | 4.7 | 0.4 | 2.8 | >1 |
| CM10 | AB28 | 2.3 | 0.3 | 2 | >10 |
| CM11 | AB24 | 2.4 | 0.3 | 2 | >5 |
| CM12 | AB25 | 2.6 | 0.3 | 2 | >5 |
| CM13 | AB26 | 1.5 | 0.3 | 2 | >1 |
|  |  | 2.3 | 0.5 | 3 | >10 |
| CM14 | AB27 | 1.3 | 0.15 | 1 | >1 |
|  |  | 2.7 | 0.3 | 2 | >5 |
| CM15 | AB30 | 1.2 | 0.15 | 1 | >1 |
|  |  | 2.3 | 0.3 | 2 | >10 |
| CM16 | AB31 | 1.3 | 0.15 | 1 | >1 |
|  |  | 2.5 | 0.3 | 2 | >10 |
| CM17 | AB29 | 5.9 | 0.8 | 5 | >1 |
|  |  | 8.9 | 1.15 | 7.6 | >5 |
| CM18 | AB32 | 2.5 | 0.3 | 2 | >1 |

The solution of pramlintide and of human insulin at pH 6.6 (CK1) is turbid. The co-polyamino acids make it possible to obtain latency times of more than 1 h under the conditions tested.

EXAMPLE D13A: STABILITY OF SOLUTIONS OF PRAMLINTIDE AT 0.6 MG/ML AND OF HUMAN INSULIN 100 IU/ML AT PH 6.6 IN THE PRESENCE OF DIFFERENT CO-POLYAMINO ACIDS AND OF DIFFERENT CONTENTS OF SODIUM CHLORIDE AND OF ZINC CHLORIDE

TABLE 37

Measurement of the latency time by ThT (2 µM) of the solutions BQ1 and BQ2 to BQ12

| Solution | Co-polyamino acid | Concentration of co-polyamino acid mg/mL | mM | [NaCl] (mM) | [ZnCl$_2$] (mM) | Latency time (h) |
|---|---|---|---|---|---|---|
| BQ1 | AB14 | 6.3 | 1.87 | 100 | 1 | >5 |
| BQ2 | AB15 | 7.8 | 1.6 | — | 0.23 | >2 |
| BQ3 | AB15 | 11.7 | 2.3 | — | 0.23 | >2 |
| BQ5 | AB15 | 6.3 | 1.3 | 50 | 0.23 | >2 |
| BQ6 | AB15 | 7.8 | 1.6 | 50 | 0.23 | >5 |
| BQ7 | AB15 | 3.9 | 0.8 | 100 | 0.23 | >2 |
| BQ8 | AB15 | 6.3 | 1.3 | 100 | 0.23 | >2 |
| BQ9 | AB15 | 7.8 | 1.6 | 100 | 0.23 | >5 |
| BQ10 | AB16 | 7.4 | 0.9 | 50 | 0.23 | >1 |
| BQ11 | AB16 | 12.4 | 1.5 | 50 | 0.23 | >2 |
| BQ12 | AB16 | 7.4 | 0.9 | 50 | 1 | >2 |

The solutions of pramlintide and of human insulin at pH 6.6 in the presence of the co-polyamino acids AB14, AB15 and AB16, of sodium and zinc chloride have latency times of more than 1 h under the conditioned tested. The addition of sodium chloride or sodium and zinc chloride makes it possible to increase the latency times.

EXAMPLE D14: STABILITY OF COMPOSITIONS HAVING VARIABLE PRAMLINTIDE CONCENTRATIONS AND HUMAN INSULIN AT 100 IU/ML IN THE PRESENCE OF CO-POLYAMINO ACID AB24, M-CRESOL (29 MM), GLYCEROL (174 MM) AND ZINC CHLORIDE (229 µM) AT PH 6.6

TABLE 38

Measurement of the latency time by ThT (2 µM) of solutions CF2 to CF6.

| Solution | Concentration of pramlintide (mg/mL) | Concentration of co-polyamino acid AB24 | | Ratio co-polyamino acid/ pramlintide mol/mol | Latency time (h) |
|---|---|---|---|---|---|
| | | mg/mL | mM | | |
| CF2 | 0.9 | 5.4 | 0.67 | 3 | >10 (12) |
| CF3 | 0.8 | 4.8 | 0.6 | 3 | >10 (14.1) |
| CF4 | 0.6 | 3.6 | 0.45 | 3 | >5 (5.5) |
| CF5 | 0.3 | 1.8 | 0.22 | 3 | >5 (5.6) |
| CF6 | 0.2 | 1 | 0.125 | 2.5 | >5 (5.4) |

The solutions of pramlintide at variable concentrations and of human insulin at 100 IU/mL at pH 6.6 are turbid (examples CF1A-E). The solutions of pramlintide at variable concentrations and of human insulin at 100 IU/mL at pH 6.6 in the presence of co-polyamino acid AB24 have latency times of more than 5 h under the conditions tested.

D II: Study of the Stability of the Compositions According to the Invention

D II A: Preparation of the Compositions

Composition D1: Preparation of a solution of pramlintide at 0.9 mg/mL containing m-cresol (29 mM) and glycerol (174 mM) at pH 6.6.

By a method similar to the one used in example CH1, a solution of pramlintide at 0.9 mg/mL containing m-cresol (29 mM) and glycerol (174 mM) at pH 6.6 is obtained. The solution is clear.

Composition D2: Preparation of a solution of pramlintide at 0.9 mg/mL containing co-polyamino acid BB15, m-cresol (29 mM) and glycerol (174 mM) at pH 6.6.

By a method similar to the one used in example BH0, a solution of pramlintide at 0.9 mg/mL and of co-polyamino acid BB15 at 10 mg/mL containing m-cresol (29 mM) and glycerol (174 mM) at pH 6.6 is obtained. The solution is clear.

D II B: Procedure for Visual Inspection:

The 3 mL vials or cartridges filled with 1 mL of formulation are inspected visually in order to detect the appearance of visible particles or of turbidity. This inspection is carried out according to the recommendations of the European pharmacopoeia (EP 2.9.20): the vials are subjected to elimination of at least 2000 lux and are observed on a white background and a black background. The number of weeks or months of stability corresponds to the duration after which the solutions contain visible particles or are turbid.

These results are in agreement with the US pharmacopoeia (USP <790>).

D II C: Procedure for Assaying the Formulations:

The quantification of the purity of pramlintide and of insulin and of the recovery of native peptide is carried out by reversed-phase HPLC, provided with a CA18 column having the dimensions 4.6×150 mm with a particle size of 3.5 µm. The pramlintide is detected at a wavelength of 214 nm, and the insulin is detected at a wavelength of 276 nm. The elution is carried out in an aqueous mobile phase with a linear acetonitrile gradient.

The recovery of pramlintide or of insulin (%) at time t represents the ratio between the area under the peak of pramlintide or the area under the peak of insulin at time t and the area of the initial pramlintide peak.

The purity of pramlintide and of insulin (%) represents the ratio between the area of the absorbance peak of pramlintide or of insulin and the total area of all the peaks including pramlintide and its impurities.

D II D: Physical Stability in Cartridges at 37° C. of Solutions of Pramlintide at 0.9 mg/mL in the Presence of Co-Polyamino Acid BB15, m-cresol (29 mM) and Glycerol (174 mM) at pH 6.6 or pH 7.4

The solutions D1, CY1, D2 and CY7 are filtered (0.22 µm). 1 mL of solution is introduced into a 3 mL glass cartridge for auto-injector pen. The cartridges are placed in an oven at 37° C. under static conditions. The cartridges are observed at a weekly frequency.

TABLE 39

Results of the physical stabilities at 37° C. in cartridges of the compositions of pramlintide at 0.9 mg/mL in the presence of co-polyamino acid BB15.

| Solution | Concentration of co-polyamino acid BB15 mg/mL | pH | Physical stability 37° C. in cartridges (weeks) |
|---|---|---|---|
| D1 | — | 6.6 | <1 |
| CY1 | — | 7.4 | <1 |
| D2 | 10 | 6.6 | >4 |
| CY7 | 10 | 7.4 | >4 |

The solutions of pramlintide at 0.9 mg/mL at pH 6.6 and pH 7.4 have a physical stability at 37° C. in a cartridge of less than one week.

The solutions of pramlintide at 0.9 mg/mL at pH 6.6 and pH 7.4 in the presence of co-polyamino acid BB15 have a physical stability at 37° C. in cartridges of at least 4 weeks.

EXAMPLE D II C: CHEMICAL STABILITY IN CARTRIDGES AT 37° C. OF SOLUTIONS OF PRAMLINTIDE AT 0.9 MG/ML IN THE PRESENCE OF CO-POLYAMINO ACID BB15, M-CRESOL (29 MM) AND GLYCEROL (174 MM) AT PH 6.6 AND 7.4

The solutions described in example D II D are analyzed by RP-HPLC chromatography.

TABLE 40

Results of the chemical stabilities of the compositions of pramlintide at 0.9 mg/mL in the presence of co-polyamino acid BB15.

| Solution | Concentration of co-polyamino acid BB15 mg/mL | pH | Recovery pramlintide (%) 32 days - 37° C. | Purity pramlintide (%) T0 | 32 days 37° C. |
|---|---|---|---|---|---|
| D1 | — | 6.6 | <60 | 97.2 | <50 |
| CY1 | — | 7.4 | <20 | 94.7 | <50 |
| D2 | 10 | 6.6 | >90 | 97.8 | >60 |
| CY7 | 10 | 7.4 | >60 | 98.6 | >60 |

The solutions of pramlintide at 0.9 mg/mL at pH 6.6 and pH 7.4 present have a recovery of pramlintide less than 60% % and the purity of pramlintide is less than 50% % after 32 days at 37° C. in a cartridge.

The solutions of pramlintide at 0.9 mg/mL at pH 6.6 and pH 7.4 in the presence of co-polyamino acid BB15 have a recovery of more than 65% % and can be greater than 90% % at pH 6.6 after 32 days at 37° C. in cartridges. In the presence of co-polyamino acid BB15, the purity of pramlintide is greater than 65% and can be greater than 85% at pH 6.6.

EXAMPLE D II E: PHYSICAL STABILITY IN A VIAL AND CARTRIDGE AT 30° C. OF SOLUTIONS OF PRAMLINTIDE AT 0.9 MG/ML AND AT 0.6 MG/ML IN THE PRESENCE OF CO-POLYAMINO ACID BB15, M-CRESOL (29 MM) AND GLYCEROL (174 MM) AT PH 6.6

The solutions D1, CH1, D2 and CH8 are filtered (0.22 µm). 1 mL of solution is introduced into 3 mL glass cartridges for auto-injector pen and in 3 mL glass vials. The cartridges and the vials are placed in an oven at 30° C. under static conditions, then observed every 2 weeks.

TABLE 41

Results of the physical stabilities in a vial and in a cartridge at 30° C. of the compositions of pramlintide at 0.9 and 0.6 mg/mL in the presence of co-polyamino acid BB15.

| Solution | Concentration co-polyamino acid BB15 mg/mL | Concentration Pramlintide (mg/mL) | pH | Physical stability 30° C. in vial (weeks) | Physical stability 30° C. in cartridge (weeks) |
|---|---|---|---|---|---|
| D1 | — | 0.9 | 6.6 | <7 | <2 |
| CH1 | — | 0.6 | 6.6 | <7 | — |
| D2 | 10 | 0.9 | 6.6 | >12 | >12 |
| CH8 | 10 | 0.6 | 6.6 | >12 | >12 |

The solutions of pramlintide at 0.9 mg/mL and 0.6 mg/mL at pH 6.6 have a physical stability in a vial of less than 7 weeks at 30° C. The physical stability in a cartridge of the solution of pramlintide at 0.9 mg/mL pH 6.6 is less than 2 weeks.

The solutions of pramlintide at 0.9 mg/mL and 0.6 mg/mL at pH 6.6 in the presence of co-polyamino acid BB15 have a physical stability at 30° C. of more than 12 weeks in a vial and in a cartridge.

EXAMPLE D II F: CHEMICAL STABILITY IN A VIAL AT 30° C. OF SOLUTIONS OF PRAMLINTIDE AT 0.9 MG/ML AND AT 0.6 MG/ML IN THE PRESENCE OF CO-POLYAMINO ACID BB15, M-CRESOL (29 MM) AND GLYCEROL (174 MM) AT PH 6.6

The solutions described in example D II E are analyzed by RP-HPLC chromatography.

TABLE 42

Results of the chemical stabilities in a vial at 30° C. of the compositions of pramlintide at 0.9 and 0.6 mg/mL in the presence of co-polyamino acid BB15 at pH 6.6.

| Solution | Concentration co-polyamino acid BB15 mg/mL | Concentration pramlintide (mg/mL) | Recovery pramlintide (%) 5 weeks 30° C. | Purity pramlintide (%) T0 | Purity pramlintide (%) 5 weeks 30° C. |
|---|---|---|---|---|---|
| D1 | — | 0.9 | <70 | 97.2 | <60 |
| D2 | 10 | 0.9 | >95 | 97.8 | >90 |
| CH8 | 10 | 0.6 | >95 | 94.6 | >90 |

The solution of pramlintide at 0.9 mg/mL at pH 6.6 has a recovery of pramlintide of less than 70% and the purity of pramlintide is less than 60% after 5 weeks at 30° C. in a vial.

The solutions of pramlintide at 0.9 mg/mL and 0.6 mg/mL at pH 6.6 in the presence of co-polyamino acid BB15 have a recovery of pramlintide greater than 95% and the purity of pramlintide is greater than 90% after 5 weeks at 30° C.

EXAMPLE D II F: PHYSICAL STABILITY IN A VIAL AND CARTRIDGES AT 30° C. OF SOLUTIONS OF PRAMLINTIDE AT 0.6 MG/ML AND OF INSULIN 100 IU/ML AT PH 6.6 IN THE PRESENCE OF CO-POLYAMINO ACID BB15, M-CRESOL (29 MM), GLYCEROL (174 MM) AND ZINC AT PH 6.6

The solution CK8 is filtered (0.22 µM). 1 mL of solution is introduced into 3 mL glass cartridges for auto-injector pen and in 3 mL glass vials. The cartridges and the vials are placed in an oven at 30° C. under static conditions, then observed every 2 weeks.

TABLE 43

Results of the physical stabilities in a vial and in a cartridge at 30° C. of the compositions of pramlintide at 0.6 mg/mL, of insulin 100 IU/mL, and in the presence of co-polyamino acid BB15 at pH 6.6.

| Solution | Concentration co-polyamino acid BB15 mg/mL | Concentration pramlintide (mg/mL) | Concentration Insulin (IU/mL) | Physical stability 30° C. in vial (weeks) | Physical stability 30° C. in cartridge (weeks) |
|---|---|---|---|---|---|
| CK1 | — | 0.6 | 100 | * | * |
| CK8 | 10 | 0.6 | 100 | >3 | >12 |

* solution turbid from its preparation on.

The solution of pramlintide at 0.6 mg/mL and of insulin at 100 IU/mL at pH 6.6 is turbid.

The solution of pramlintide at 0.6 mg/mL and of human insulin at 100 IU/mL at pH 6.6 in the presence of co-polyamino acid BB15 has a physical stability at 30° C. of more than 3 weeks in a vial and more than 12 weeks in a cartridge.

EXAMPLE D II G: CHEMICAL STABILITY IN A VIAL AT 30° C. OF A SOLUTION OF PRAMLINTIDE AT 0.6 MG/ML AND OF INSULIN 100 IU/ML AT PH 6.6 IN THE PRESENCE OF CO-POLYAMINO ACID BB15, M-CRESOL (29 MM), GLYCEROL (174 MM) AND ZINC

The solution described in example D II F is analyzed by RP-HPLC chromatography.

TABLE 44

Results of chemical stability in a vial at 30° C. of a composition of pramlintide at 0.6 mg/mL, of insulin 100 IU in the presence of co-polyamino acid BB15 at pH 6.6.

| Solution | Recovery pramlintide (%) 5 weeks 30° C. | Purity pramlintide (%) T0 | | Recovery Insulin (%) 5 weeks 30° C. | Purity Insulin (%) T0 | 5 weeks 30° C. |
|---|---|---|---|---|---|---|
| | | | 5 weeks 30° C. | | | |
| CK8 | >90 | 96.8 | >90 | >90 | 97.9 | >90 |

The solution of pramlintide at 0.6 mg/mL and of insulin at 100 IU/mL at pH 6.6 in the presence of co-polyamino acid BB15 has a recovery of pramlintide of more than 90% and the purity of pramlintide is greater than 90% after 5 weeks at 30° C. in a vial. The recovery of insulin is greater than 90% and the purity of the insulin is greater than 90% after 5 weeks at 30° C. in a vial.

EXAMPLE D II H: PHYSICAL STABILITY IN A VIAL AT 30° C. AND IN A CARTRIDGE AT 30° C./37° C. OF SOLUTIONS OF PRAMLINTIDE AT 0.6 MG/ML AND OF INSULIN 100 IU/ML AT PH 6.6 IN THE PRESENCE OF CO-POLYAMINO ACID AB24 AT 2.4 MG/ML, M-CRESOL (29 MM), GLYCEROL (174 MM) AND ZINC AT PH 6.6

Solution CM11 is filtered (0.22 μM). 1 mL of solution is introduced into 3 mL glass cartridges for auto-injector pen and into 3 mL glass vials. The cartridges and the vials are placed in an oven at 30° C. under static conditions, then observed every 2 weeks. Cartridges are also placed in an oven at 37° C. under static conditions, then observed every week.

TABLE 45

Results of the physical stabilities in a vial at 30° C. and in a cartridge at 30 and 37° C. of the compositions of pramlintide at 0.6 mg/mL, of insulin 100 IU/mL and in the presence of co-polyamino acid AB24 at pH 6.6.

| Solution | Concentration co-polyamino acid AB24 mg/mL | Concentration pramlintide (mg/mL) | Concentration Insulin (IU/mL) | Physical stability 30° C. in vial (weeks) | Physical stability 30° C. in cartridge (weeks) | Physical stability 37° C. in cartridge (weeks) |
|---|---|---|---|---|---|---|
| CK1 | — | 0.6 | 100 | * | * | * |
| CM11 | 2.4 | 0.6 | 100 | >9 | >12 | >9 |

* solution turbid from its preparation on.

The solution of pramlintide at 0.6 mg/mL and of insulin at 100 IU/mL at pH 6.6 is turbid.

The solution of pramlintide at 0.6 mg/mL and of human insulin at 100 IU/mL at pH 6.6 in the presence of co-polyamino acid AB24 has a physical stability at 37° C. of more than 9 weeks in a vial and of more than 12 weeks in a cartridge. The physical stability at 37° C. in a cartridge is greater than 9 weeks.

EXAMPLE D II I: CHEMICAL STABILITY IN A VIAL AND CARTRIDGE AT 30° C. OF SOLUTIONS OF PRAMLINTIDE AT 0.6 MG/ML AND OF INSULIN 100 IU/ML AT PH 6.6 IN THE PRESENCE OF CO-POLYAMINO ACID AB24 AT 2.4 MG/ML, M-CRESOL (29 MM), GLYCEROL (174 MM) AND ZINC AT PH 6.6

The solution described in example D II H is analyzed by RP-HPLC chromatography.

TABLE 46

Results of the chemical stabilities in a vial and cartridge at 30° C. of the compositions of pramlintide at 0.6 mg/mL, of insulin 100 IU in the presence of co-polyamino acid AB24 at pH 6.6.

| Solution | Recovery pramlintide (%) 9 weeks 30° C. | Purity pramlintide (%) T0 | 9 weeks 30° C. | Recovery Insulin (%) 9 weeks 30° C. | Purity Insulin (%) T0 | 9 weeks 30° C. |
|---|---|---|---|---|---|---|
| CM11 | | | | | | |
| Vial | >88 | 96.7 | >90 | >90 | 97.4 | >90 |
| Cartridge | >88 | 96.9 | >85 | >90 | 97.7 | >90 |

The solution of pramlintide at 0.6 mg/mL and of human insulin at 100 IU/mL at pH 6.6 in the presence of co-polyamino acid AB24 has a recovery of pramlintide greater than 88% and a purity greater than 90 and 85%, respectively, after 9 weeks of storage at 30° C. in a vial and in a cartridge. Under these conditions, the recovery of insulin is greater than 90% and the purity of the insulin is greater than 90% in a vial and in a cartridge.

EXAMPLE D II J: PHYSICAL STABILITY IN A CARTRIDGE AT 4° C. OF SOLUTIONS OF PRAMLINTIDE AT 0.6 MG/ML AT PH 6.6 IN THE PRESENCE OF CO-POLYAMINO ACID BB15, M-CRESOL (29 MM), GLYCEROL (174 MM) AT PH 6.6

Solution CH8 is filtered (0.22 μm). 1 mL of solution is introduced into 3 mL glass cartridges for auto-injector pen. The cartridges are placed in a refrigerator at 4° C.

TABLE 47

Results of the physical stability in a cartridge at 4° C. of a composition of pramlintide at 0.6 mg/mL in the presence of co-polyamino acid BB15 at pH 6.6.

| Solution | Concentration co-polyamino acid BB15 mg/mL | Concentration pramlintide (mg/mL) | pH | Physical stability 4° C. in cartridge (month) |
|---|---|---|---|---|
| CH8 | 10 | 0.6 | 6.6 | >6 |

The solution of pramlintide at 0.6 mg/mL and of human insulin at 100 IU/mL at pH 6.6 in the presence of co-polyamino acid BB15 has a physical stability in a cartridge of more than 6 months.

EXAMPLE D II K: PHYSICAL STABILITY IN A CARTRIDGE AT 4° C. OF SOLUTIONS OF PRAMLINTIDE AT 0.6 MG/ML AT PH 6.6 AND PH 7.4 IN THE PRESENCE OF DMPG AT 4.5 MM

The solutions of CZ0 and CZ1 are filtered (0.22 μM). 1 mL of solution is introduced into 3 mL glass cartridges for auto-injector pen. The cartridges are placed in a refrigerator at 4° C.

TABLE 48

Results of the physical stabilities in a cartridge at 4° C. of the compositions of pramlintide at 0.6 mg/mL and in the presence of DMPG at pH 6.6 and 7.4.

| Solution | DMPG (mM) | Concentration pramlintide (mg/mL) | pH | Excipients | Physical stability at 4° C. in cartridges (month) |
|---|---|---|---|---|---|
| CZ0 | 4.5 | 0.6 | 6.6 | m-cresol 29 mM Glycerol 174 mM | <1.5 |
| CZ1 | 4.5 | 0.6 | 7.4 | phenol 30 mM Glycylglycine 8 mM pH 7.4 Glycerol 174 mM | <1.5 |

The solutions of pramlintide at 0.6 mg/mL at pH 6.6 and at pH 7.4 have a physical stability at 4° C. and in cartridges of less than 1.5 month (turbid solutions).

EXAMPLE D II L: PUMP STABILITY OF SOLUTIONS OF PRAMLINTIDE AT 0.6 MG/ML AND OF HUMAN INSULIN AT 100 IU/ML AT PH 6.6 IN THE PRESENCE OF CO-POLYAMINO ACID AB24 AT 3.6 MG/ML

The solution CM11 consisting of 0.6 mg/mL of pramlintide and 100 IU/mL of human insulin at pH 6.6 in the presence of co-polyamino acid AB24 at 3.6 mg/mL is filtered (0.22 μm) and introduced into a 3 mL reservoir for insulin pump (Minimed 530G system manufactured by Medtronic). The pump is provided with an infusion set (Quick set Paradigm 9/100 manufactured by Medtronic).

The insulin pump is placed in an oven at 37° C. on an orbital stirrer adjusted at a speed of 100 rpm. The pump is adjusted to a basal flow rate of 0.8 IU/h. Bolus injections of 6 IU are performed 3 times per day for a total duration of 8 days.

Table 49 presents the results of the measurements of MFI (Micro-Flow Imaging) and the assays carried out by RP-HPLC on the fractions collected between the 7$^{th}$ day and the 8$^{th}$ day of stability testing.

TABLE 49

Results of the chemical pump stability at 37° C. of the compositions of pramlintide at 0.6 mg/mL, of insulin 100 IU/mL and in the presence of co-polyamino acid AB24 at pH 6.6.

| Solution | Subvisible particles (Micro Flow Imaging. MFI) 1 week 37° C. | Recovery pramlintide (%) 1 week 37° C. | Purity pramlintide (%) T0 | Purity pramlintide (%) 1 week 37° C. | Recovery Human insulin (%) 1 week 37° C. | Purity Insulin (%) T0 | Purity Insulin (%) 1 week 37° C. |
|---|---|---|---|---|---|---|---|
| CM11 | particles >10 μM <6000 particles per container* particles >25 μM <600 particles per container* | >95 | 97.3 | >95 | >95 | 97.4 | >95 |

*Standard USP <788> on the number of subvisible particles in the products for parenteral injection.

After one week of pump stability at 37° C., the solution of pramlintide at 0.6 mg/mL and of human insulin at 100 IU/mL at pH 6.6 in the presence of co-polyamino acid AB24 is clear and has a number of subvisible particles in compliance with the standard USP <788>. Under these conditions, the recovery and the purities of pramlintide and of insulin are greater than 95%.

EXAMPLE D II M: PUMP STABILITY OF SOLUTIONS OF PRAMLINTIDE AT 0.6 MG/ML AND OF INSULIN LISPRO AT 100 IU/ML AT PH 6.6 IN THE PRESENCE OF CO-POLYAMINO ACID AB24 AT 3.6 MG/ML

The solution CA5 consisting of 0.6 mg/mL of pramlintide and of 100 IU/mL of insulin lispro at pH 6.6 in the presence of co-polyamino acid AB24 at 3.6 mg/mL is filtered (0.22 µm) and subjected to a pump stability test using a protocol identical to the one described in example DC11.

TABLE 50

Results of the chemical pump stability at 37° C. of the compositions of pramlintide at 0.6 mg/mL., of insulin lispro at 100 IU/mL and in the presence of co-polyamino acid AB24 at pH 6.6.

| Solution | Subvisible particles (Micro Flow Imaging. MFI) 1 week 37° C. | Recovery pramlintide (%) 1 week 37° C. | Purity pramlintide (%) T0 | Purity pramlintide (%) 1 week 37° C. | Recovery lispro (%) 1 week 37° C. | Purity Insulin (%) T0 | Purity Insulin (%) 1 week 37° C. |
|---|---|---|---|---|---|---|---|
| CA5 | particles >10 µM <6000 particles per container* particles >25 µM <600 particles per container* | >95 | 97.2 | >95 | >95 | 99.3 | >95 |

*USP <788> criterion for the number of subvisible particles in the products for parenteral injections.

After one week of pump stability at 37° C., the solution of pramlintide at 0.6 mg/mL and of insulin lispro at 100 IU/mL at pH 6.6 in the presence of co-polyamino acid AB24 is clear and has a number of subvisible particles in compliance with the USP <788> standard. Under these conditions of recovery and the purities of pramlintide and insulin lispro are greater than 95%.

E. Pharmacodynamics and Pharmacokinetics

E1: Protocol of the Measurement of the Pharmacokinetics of Formulations of Pramlintide and of Insulin.

Domestic pigs weighing approximately 50 kg, which had been catheterized beforehand at the jugular, are fasted for 2.5 hours before the start of the experiment. In the hour preceding the injection of the formulations of pramlintide and of insulin, 3 blood samples were collected in order to determine the basal level of pramlintide.

The injection of formulations at the dose of 1.125 µg/kg for pramlintide and 0.1875 IU/kg for insulin is carried out subcutaneously in the flank of the animal using an insulin pen (Novo, Sanofi or Lilly) equipped with a 31 G needle.

Blood samples are then collected every 4 minutes for 20 minutes, then every 10 to 60 minutes up to 3 hours. After each sample collection, the catheter is rinsed with a diluted heparin solution.

The blood so drawn is collected in a K2EDTA tube and centrifuged to isolate the plasma. The pramlintide levels in the plasma samples are measured using the sandwich ELISA immune-enzymatic method for each animal.

The pharmacokinetics curves expressed in delta of the basal level are then traced.

The following pharmacokinetics parameters are then determined by non-compartmental analysis using the software Phoenix WinNonlin:

$t_{max}$ pramlintide corresponding to the time needed to reach the maximum concentration of pramlintide in the plasma;

$AUC_{Pram\ 0-30\ min}$ corresponding to the area under the curve of the pramlintide concentrations as a function of time between 0 and 30 minutes post-administration;

$AUC_{Pram\ 60-180\ min}$ corresponding to the area under the curve of the concentrations of pramlintide as a function of time between 60 and 180 minutes post-administration;

$C_{last}$ corresponding to the last quantifiable pramlintide concentration in the plasma;

$t_{last}$ corresponding to the time at which $C_{last}$ is observed.

$t_{max}$ is routinely used for evaluating the start of the absorption. $AUC_{Pram\ 0-30\ min}$ is routinely used for evaluating the early exposure to pramlintide in the plasma. As to $AUC_{Pram\ 60-180\ min}$, it makes it possible to evaluate the late exposure to pramlintide in the plasma. $C_{last}$ and $t_{last}$ make it possible to study the late concentration levels.

E2: Pharmacokinetic Results of Pramlintide of the Formulations of Pramlintide and of Insulin of Examples CA2 and CA3

| Example | Rh-Insulin | co-polyamino acid | Pramlintide (mg/mL) | Number of pigs |
|---|---|---|---|---|
| CA1/CA2 (double | 100 | — | 1 | 8 |
| CA3 | 100 | BB15 | 0.6 | 10 |

Figure 2:
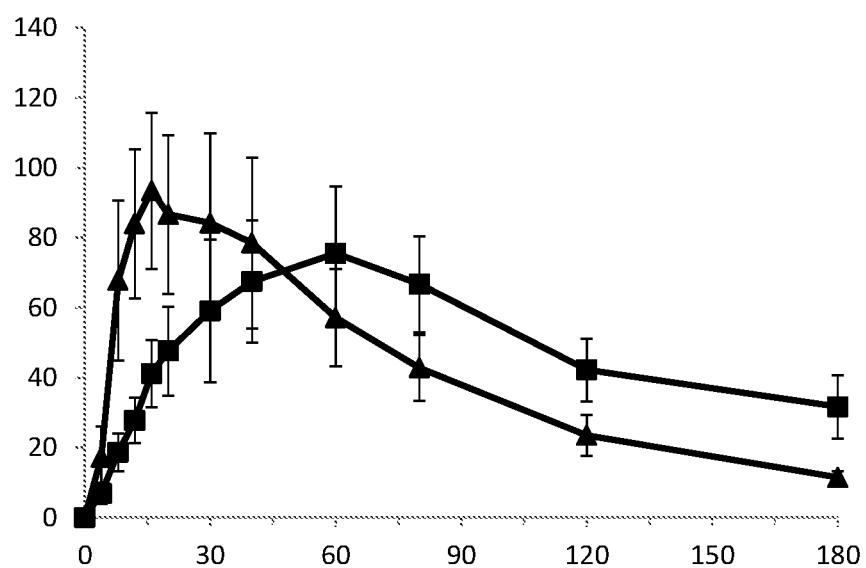
FIG. 2.

The pharmacokinetic results of pramlintide, which are obtained with the compositions described in examples CA1/CA2 and CA3, are presented in FIG. 2. The analysis of these profiles indicates that the composition of example CA3 comprising co-polyamino acid BB15, 100 IU/mL of insulin and 0.6 mg/mL of pramlintide (curve traced with the squares corresponding to example CA3) makes it possible to obtain an absorption of pramlintide which is slower than the absorption of the composition of the example with double injection comprising only pramlintide and insulin (curve traced with the triangles corresponding to the double-injection examples CA1/CA2). The pharmacokinetics parameters of pramlintide are given in the following table:

| Example | $t_{max}$ pramlintide (min) | $AUC_{Pram\ 0\text{-}30\ min}$ (min*pmol/L) | $AUC_{Pram\ 60\text{-}180\ min}$ (min*pmol/L) | $C_{last}$ pramlintide (min) | $t_{last}$ pramlintide (min) |
|---|---|---|---|---|---|
| CA1/CA2 | 20 ± 10 | 2076 ± 1596 | 3286 ± 1951 | 12 ± 5 | 153 ± 40 |
| CA3 | 77 ± 44 | 1006 ± 885 | 5989 ± 3146 | 28 ± 24 | 168 ± 25 |

E3: Pharmacokinetic Results of the Pramlintide of the Formulations of Pramlintide and of Insulin of Examples CA1/CA2 and CA4

| Example | Rh-Insulin (IU/mL) | co-polyamino acid | Pramlintide (µg/mL) | Number of pigs |
|---|---|---|---|---|
| CA1/CA2 | 100 | — | — | 8 |
| CA4 | 100 | AB24 | 0.6 | 12 |

Figure 3:
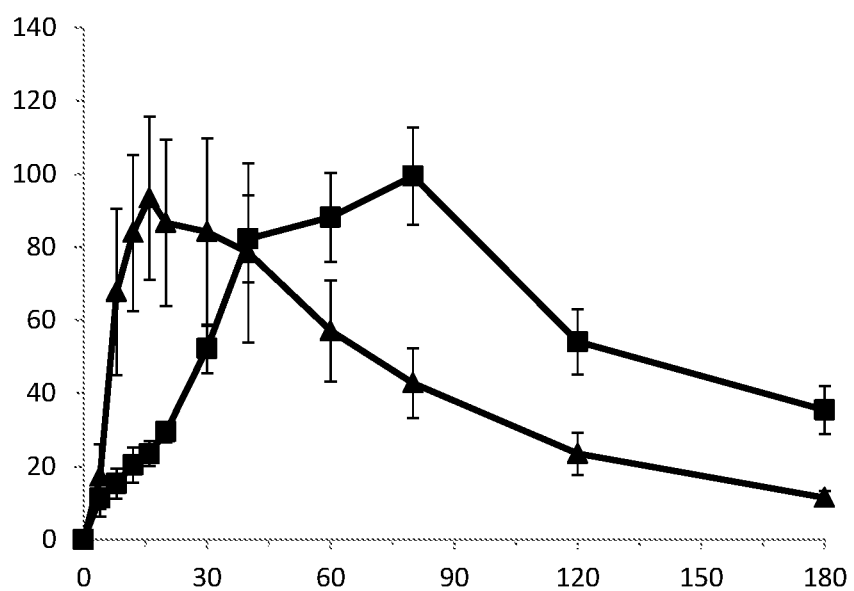
FIG. 3.

The pharmacokinetic results of pramlintide obtained with the compositions described in examples CA1/CA2 and CA4 are presented in FIG. 3. The analysis of these profiles indicates that the composition of example CA4 comprising co-polyamino acid AB24, 100 IU/mL of insulin and 0.6 µg/mL of pramlintide (curve traced with the squares corresponding to example CA4) makes it possible to obtain an absorption of pramlintide which is slower than the absorption of the composition of the example with double injection comprising only pramlintide and insulin (curve traced with the triangles corresponding to the double-injection examples CA1/CA2). The pharmacokinetic parameters of pramlintide are reported in the following table:

| Example | $t_{max}$ pramlintide (min) | $AUC_{Pram\ 0\text{-}30\ min}$ (min*pmol/L) | $AUC_{Pram\ 60\text{-}180\ min}$ (min*pmol/L) | $C_{last}$ pramlintide (min) | $t_{last}$ pramlintide (min) |
|---|---|---|---|---|---|
| CA1/CA2 | 20 ± 10 | 2076 ± 1596 | 3286 ± 1951 | 12 ± 5 | 153 ± 40 |
| CA4 | 68 ± 23 | 749 ± 316 | 8064 ± 2963 | 34 ± 22 | 175 ± 17 |

The invention claimed is:

1. A composition in the form of an injectable aqueous solution, of which the pH is from 6.0 to 8.0, comprising at least:
   a) amylin or pramlintide;
   b) a co-polyamino acid bearing carboxylate charges and hydrophobic radicals Hy, said co-polyamino acid consisting of glutamic or aspartic units and said hydrophobic radicals Hy having the following formula I:

*-(-GpR-)$_r$-(-GpA-)$_a$-(-GpC)$_p$   I in which
   GpR is a radical of formula II or II':

II

*—NH—R—NH—*   or

II'

*—C(O)—R—NH—*   or or

II''

*—C(O)—R—C(O)—*

GpA is a radical of formula III or III':

III

*—C(O)—CH(HN—*)—HN—*   or

III'

*—C(O)—A—NH—*

GpC is a radical of formula IV:

IV

[structure with piperidine ring, (CH$_2$)$_c$, N, B, NH, C$_x$, (CH$_2$)$_d$, b subscript]

the * indicate the sites of attachment of the different groups;
   a is a whole number equal to 0 or to 1;
   b is a whole number equal to 0 or to 1;
   p is a whole number equal to 1 or 2 and
      if p is equal to 1 then a is equal to 0 or to 1 and GpA is a radical of formula III', and
      if p is equal to 2 then a is equal to 1, and GpA is a radical of formula III;
   c is a whole number equal to 0 or to 1, and if c is equal to 0 then d is equal to 1 or to 2;
   d is a whole number equal to 0, to 1 or to 2;
   r is a whole number equal to 0 or to 1, and
      if r is equal to 0 then the hydrophobic radical of formula I is attached to the co-polyamino acid via a covalent bond between a carbonyl of the hydrophobic radical and a nitrogen atom in N-terminal position of the co-polyamino acid, thus forming an amide function originating from the reaction of an amine function in N-terminal position of the precursor of the co-polyamino acid and an acid function borne by the precursor of the hydrophobic radical, and
      if r is equal to 1 then the hydrophobic radical of formula I is attached to the co-polyamino acid:
         via a covalent bond between a nitrogen atom of the hydrophobic radial and a carbonyl of the copolyamino acid, thus forming an amide function originating from the reaction of an amine function of the precursor of the hydrophobic radical and an acid function borne by the precursor of the co-polyamino acid, or via a covalent bond between a carbonyl of the hydrophobic radical and a nitrogen atom in N-terminal position of the co-polyamino acid, thus forming an amide function originating from the reaction of an acid function of the precursor of the hydrophobic radical and an amine function in N-terminal position borne by the precursor of the co-polyamino acid;

R is a radical selected from the group consisting of:
a linear or branched divalent alkyl radical comprising 2 to 12 carbon atoms if GpR is a radical of formula II or 1 to 11 carbon atoms if GpR is a radical of formula II' or II'';
a linear or branched divalent alkyl radical comprising 2 to 11 carbon atoms if GpR is a radical of formula II or 1 to 11 carbon atoms if GpR is a radical of formula II' or II'', 1 to 11 carbon atoms, said alkyl radical bearing one or more —CONH$_2$ functions, and
an unsubstituted ether or polyether radical comprising 4 to 14 carbon atoms and 1 to 5 oxygen atoms;

A is a linear or branched alkyl radical comprising 1 to 6 carbon atoms;

B is a linear or branched alkyl radical, optionally comprising an aromatic ring, comprising 1 to 9 carbon atoms;

Cx is a linear or branched monovalent alkyl radical, in which x indicates the number of carbon atoms and:
if p is equal to 1, x is from 11 to 25 ($11 \leq x \leq 25$):
if p is equal to 2, x is from 9 to 15 ($9 \leq x \leq 15$), the ratio i between the number of hydrophobic radicals and the number of glutamic or aspartic units being from 0 to 0.5 ($0 < i \leq 0.5$);

when several hydrophobic radicals are borne by a co-polyamino acid, then they are identical or different, the degree of polymerization DP of glutamic or aspartic units is from 5 to 250;

the free acid functions being in the form of a salt of an alkali cation selected from the group consisting of Na+ and K+;

wherein the composition does not comprise a basal insulin of which the isoelectric point pI is from 5.8 to 8.5.

2. The composition according to claim 1, wherein said hydrophobic radicals are selected from the hydrophobic radicals of formula I in which p=1, represented by the following formula V:

   formula V wherein GpR, GpA, GpC, r and a have the definitions given above.

3. The composition according to claim 1, wherein said hydrophobic radicals are selected from the hydrophobic radicals of formula I in which a=1 and p=2, represented by the following formula VI:

   Formula VI in which
GpR, GpA, GpC and r have the definitions given above.

4. The composition according to claim 1, wherein the co-polyamino acid bearing carboxylate charges and hydrophobic radicals is selected from the co-polyamino acids having the following formula VII:

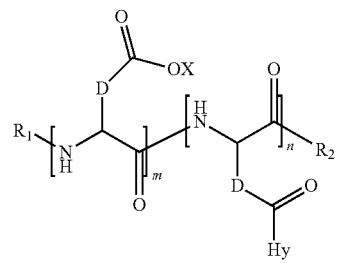

in which,
D represents, independently, either a —CH$_2$— group (aspartic unit) or a —CH$_2$—CH$_2$— group (glutamic unit), Hy is a hydrophobic radical selected from the hydrophobic radicals of formula I, V or VI in which r=1 and GpR is a radical of formula II, R$_1$ is a hydrophobic radical selected from the hydrophobic radicals of formula I, V or VI in which r=0 or r=1 and GpR is a radical of formula II', or a radical selected from the group consisting of an H, a linear C2 to C10 acyl group, a branched C3 to C10 acyl group, benzyl, a terminal "amino acid" unit, and a pyroglutamate, R$_2$ is a hydrophobic radical selected from the hydrophobic radicals of formula I, V or VI in which r=1 and GpR is a radical of formula II, or a —NR'R'' radical, R' and R'', which may be identical or different, being selected from the group consisting of H, the linear or branched or cyclic C2 to C10 alkyls, benzyl, and said alkyls R' and R'' optionally forming together one or more saturated, unsaturated and/or aromatic carbon rings and/or optionally comprising heteroatoms selected from the group consisting of O, N and S, X represents an H or a cationic entity selected from the group comprising the metal cations; and n+m represents the degree of polymerization DP of the co-polyamino acid, that is to say the average number of monomeric units per co-polyamino acid chain, and $5 \leq n+m \leq 250$.

5. The composition according to claim 4, wherein the co-polyamino acid bearing carboxylate charges and hydrophobic radicals is selected from the co-polyamino acids of formula VII in which R$_1$=R'$_1$ and R$_2$=R'$_2$, having the following formula VIIa:

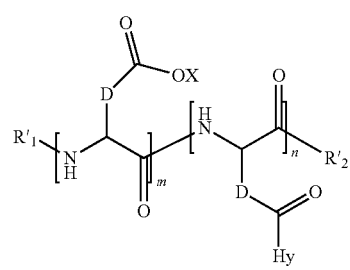

in which,
m, n, X, D and Hy have the definitions given above;
R'$_1$ is a radical selected from the group consisting of an H, a linear C2 to C10 acyl group, a branched C3 to C10 acyl group, benzyl, a terminal "amino acid" unit, and a pyroglutamate;

R'$_2$ is a —NR'R" radical, R' and R", which may be identical or different, being selected from the group consisting of H, the linear or branched or cyclic C2 to C10 alkyls, benzyl, and said alkyls R' and R" optionally forming together one or more saturated, unsaturated and/or aromatic carbon rings and/or optionally comprising heteroatoms selected from the group consisting of O, N and S.

6. The composition according to claim 4, wherein the co-polyamino acid bearing carboxylate charges and hydrophobic radicals is selected from the co-polyamino acids of formula VII in which n=0, having the following formula VIIb:

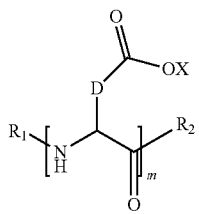

in which m, X, D, R$_1$ and R$_2$ have the definitions given above and at least R$_1$ or R$_2$ is a hydrophobic radical of formula I, V or VI.

7. The composition according to claim 1, wherein a molar ratio of co-polyamino acid/amylin or pramlintide is greater or equal to 1.

8. The composition according to claim 1, comprising amylin.

9. The composition according to claim 1, comprising pramlintide.

10. The composition according to claim 1, wherein the composition further comprises a prandial insulin.

11. The composition according to claim 1, wherein a molar ratio of co-polyamino acid/insulin is greater than or equal to 1.

12. The composition according to claim 1, wherein said composition has a stability measured by ThT which is greater than the stability of a reference composition comprising amylin or pramlintide, but not comprising any co-polyamino acid bearing carboxylate charges and hydrophobic radicals Hy.

* * * * *